United States Patent
Fürstner et al.

(10) Patent No.: US 9,751,843 B2
(45) Date of Patent: Sep. 5, 2017

(54) SUBSTITUTED URACILS AND USE THEREOF

(71) Applicant: Bayer Pharma Aktiengesellschaft, Berlin (DE)

(72) Inventors: Chantal Fürstner, Mülheim/Ruhr (DE); Jens Ackerstaff, Düsseldorf (DE); Alexander Straub, Wuppertal (DE); Heinrich Meier, Wuppertal (DE); Hanna Tinel, Wuppertal (DE); Katja Zimmermann, Düsseldorf (DE); Adrian Tersteegen, Wuppertal (DE); Dmitry Zubov, Remscheid (DE); Raimund Kast, Wuppertal (DE); Jens Schamberger, Velbert-Langenberg (DE); Martina Schäfer, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/034,499

(22) PCT Filed: Nov. 5, 2014

(86) PCT No.: PCT/EP2014/073760
§ 371 (c)(1),
(2) Date: May 4, 2016

(87) PCT Pub. No.: WO2015/067630
PCT Pub. Date: May 14, 2015

(65) Prior Publication Data
US 2016/0297771 A1    Oct. 13, 2016

(30) Foreign Application Priority Data
Nov. 8, 2013 (EP) ..................... 13192181

(51) Int. Cl.
| | | |
|---|---|---|
| C07D 239/557 | (2006.01) | |
| C07D 413/14 | (2006.01) | |
| C07D 403/10 | (2006.01) | |
| C07D 413/10 | (2006.01) | |
| A61K 31/513 | (2006.01) | |
| C07D 409/06 | (2006.01) | |
| C07D 417/10 | (2006.01) | |

(52) U.S. Cl.
CPC ........ *C07D 239/557* (2013.01); *A61K 31/513* (2013.01); *C07D 403/10* (2013.01); *C07D 409/06* (2013.01); *C07D 413/10* (2013.01); *C07D 413/14* (2013.01); *C07D 417/10* (2013.01)

(58) Field of Classification Search
None
See application file for complete search history.

(56) References Cited

U.S. PATENT DOCUMENTS

| | | |
|---|---|---|
| 2004/0087582 A1 | 5/2004 | Dorsch et al. |
| 2004/0102494 A1 | 5/2004 | Selvakumar et al. |
| 2008/0255230 A1 | 10/2008 | Chow et al. |

FOREIGN PATENT DOCUMENTS

| | | |
|---|---|---|
| DE | 2812578 | 1/1978 |
| DE | 10 2008 030091 | 12/2009 |
| WO | 00/06568 | 2/2000 |
| WO | 00/06569 | 2/2000 |
| WO | 00/37463 | 6/2000 |
| WO | 01/19355 | 3/2001 |
| WO | 01/19776 | 3/2001 |
| WO | 01/19778 | 3/2001 |
| WO | 01/19780 | 3/2001 |
| WO | 02/42301 | 5/2002 |
| WO | 02/070462 | 9/2002 |
| WO | 02/070510 | 9/2002 |
| WO | 03/095451 | 11/2003 |
| WO | 2004/052858 | 6/2004 |
| WO | 2005/026135 | 3/2005 |
| WO | 2005/054238 | 6/2005 |
| WO | 2007/053094 | 5/2007 |
| WO | 2007/150011 | 12/2007 |
| WO | 2008/009881 | 1/2008 |

(Continued)

OTHER PUBLICATIONS

Artico, et al., "Research on Compounds with Antiblastic Activity", Farmaco Sci. Ed.179, 1969, 15 pages.
Bacani, et al., "Chymase: A New Pharmacologic Target in Cardiovascular Disease", Cardiology in Review, 14(4), Jul./Aug. 2006, pp. 187-193.
Dogrell, "Therapeutic Potential of Non-peptide Chymase Inhibitors", Expert Opin. Ther. Patents 18, 2008, pp. 485-499.

(Continued)

*Primary Examiner* — Bong-Sook Baek
(74) *Attorney, Agent, or Firm* — Morrison & Foerster LLP

(57) ABSTRACT

Substituted uracil derivatives of the compound of Formula (I), processes for their preparation, their use alone or in combinations for treatment and/or prophylaxis of diseases, and their use for preparing medicaments for treatment and/or prophylaxis of diseases.

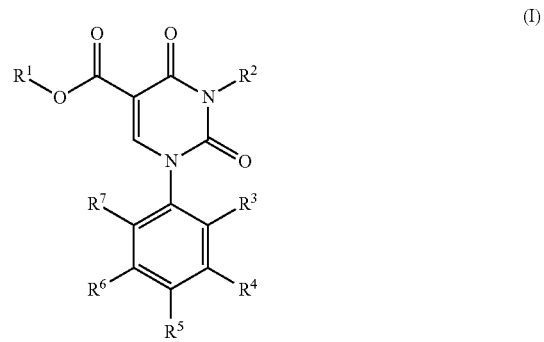

10 Claims, No Drawings

(56) References Cited

FOREIGN PATENT DOCUMENTS

| WO | 2008/056257 | 5/2008 |
|---|---|---|
| WO | 2008/103277 | 8/2008 |
| WO | 2009/049112 | 4/2009 |
| WO | 2009/064835 | 5/2009 |
| WO | 2009/156182 | 12/2009 |
| WO | 2010/019903 | 2/2010 |
| WO | 2013/167495 | 11/2013 |

OTHER PUBLICATIONS

European Patent Office, Written Opinion for International Patent Application No. PCT/EP2014/073760, May 14, 2015, 7 pages.
European Patent Office, International Search Report for International Patent Application No. PCT/EP2014/073760, Jan. 8, 2015, 8 pages.
Fleming, "Signaling by the Angiotensin-Converting Enzyme", Circulation Research, Apr. 14, 2006, pp. 887-896.
Gregory, et al., "Antibacterials. Synthesis and structure-activity studies of 3-aryl-2-oxooxazolidines. 2. The "A" group," Journal of Medicinal chemistry, 33 (9), 1990, pp. 2569-2578.
Huang, et al., "Chymase Is Upregulated in Diabetic Nephropathy: Implications for an Alternative Pathway of Angiotensin II-Mediated Diabetic Renal and Vascular Disease", Journal of the American Society of Nephrology, 14, 2003, pp. 1738-1747.
Hughes, "Progress in the Mitsunobu Reaction. A Review", Organic Preparations and Procedures International: The New Journal for Organic Synthesis, 28(2), 1996, pp. 127-164.
Hughes, "The Mitsunobu Reaction", Chapter 2, Organic Reactions, 42, 1992, pp. 335-656.
International Bureau of WIPO, International Preliminary Report on Patentability for International Patent Application No. PCT/EP2014/073760, May 10, 2016, 8 pages.
Jin, et al., "An Antiarrhythmic Effect of a Chymase Inhibitor After Myocardial Infarction", Pharmacol. Exp. Ther. 309, 2004, pp. 409-417.
Jin, et al., "Beneficial effects of cardiac chymase inhibition during the acute phase of myocardial infarction", Life Sciences, 71, 2002, pp. 437-446.

Kovanen, et al., "Infiltrates of Activated Mast Cells at the Site of Coronary Atheromatous Erosion or Rupture in Myocardial Infarction", Circulation, 92(5), Sep. 1, 1995, pp. 1084-1088.
Libby, et al., "Mast Cells as Mediators and Modulators of Atherogenesis", Circulation 115, 2007, pp. 2555-2558.
Lucero, et al., "Synthesis and anti-HSV-1 activity of quinolonic acyclovir analogues", Bioorg. Med. Chem. Lett., 16(4), 2006, pp. 1010-1013.
Matsumoto, et al., "Chymase Inhibition Prevents Cardiac Fibrosis and Improves Diastolic Dysfunction in the Progression of Heart Failure", Circulation, May 27, 2003, pp. 2555-2558.
McPherson, et al., "Chymase-like Angiotensin II-Generating Activity in End-Stage Human Autosomal Dominant Polycystic Kidney Disease", Journal of the American Society of Nephrology, 15, 2004, pp. 493-500.
Miyazaki, et al., "Pathological roles of angiotensin II produced by mast cell chymase and the effects of chymase inhibition in animal models", Pharmacology & Therapeutics, 112, 2006, pp. 668-676.
Mulvany, et al., "Contractile Properties of Small Arterial Resistance Vessels in Spontaneously Hypertensive and Normotensive Rats", Circulation Research, 41(1), Jul. 1977, pp. 19-26.
Nicolaou, et al., "New Uses for the Burgess Reagent in Chemical Synthesis: Methods for the Facile and Stereoselective Formation of Sulfamidates, Glycosylamines, and Sulfamides", Chem. Eur. J., 10, 2004, pp. 5581-5606.
Senda, et al., "Pyrimidine Derivatives and Related Compounds. XVI.1) Synthesis of 1,3-Disubstituted5-Cyanouracil Derivatives and Related Compounds", Chem. Pharm. Bull., vol. 20(7), 1972, pp. 1380-1388.
Shiota, et al., "Cardiac mast cells in the transition to heart failure: innocent bystanders or key actors?", Journal of Hypertension, 21, 2003, pp. 1823-1825.
Stabile, et al., "Mild, convenient and versatile Cu-mediated synthesis of N-aryl-2-imidazolidinones", Tetrahedron Letters, 51(24), 2010, pp. 3232-3235.
Takai, et al., "An Orally Active Chymase Inhibitor, BCEAB, Suppresses Heart Chymase Activity in the Hamster", Japanese Journal of Pharmacology, 86, 2001, pp. 124-126.
Taylor, et al., "Discovery of Potent, Selective Chymase Inhibitors via Fragment Linking Strategies", Journal of Medical Chemistry, vol. 56, No. 11, Jun. 13, 2013, pp. 4465-4481.
Zanini, et al., "Chymase-positive mast cells play a role in the vascular component of airway remodeling in asthma", Journal of Allergy Clinical Immunology, 120(2), Aug. 2007, pp. 329-333.

SUBSTITUTED URACILS AND USE THEREOF

CROSS-REFERENCE TO RELATED APPLICATIONS

This application is a U.S. national phase application of International Patent Application No. PCT/EP2014/073760, filed Nov. 5, 2014 and titled SUBSTITUTED URACILS AND USE THEREOF, which claims priority to European Patent Application No. 13192181.9, filed Nov. 8, 2013 and titled SUBSTITUTED URACILS AND USE THEREOF, the contents of both of which are incorporated herein by reference in their entirety.

The present application relates to novel substituted uracil derivatives, to processes for their preparation, to their use alone or in combinations for treatment and/or prophylaxis of diseases, and to their use for preparing medicaments for treatment and/or prophylaxis of diseases.

Chymase is a chymotrypsin-like serine protease which is stored as a macromolecular complex with heparin proteoglycans in secretory vesicles of mast cells. After activation of the mast cells, chymase is released into the extracellular matrix and activated.

Activated mast cells play an important role in healing wounds and in inflammatory processes, for example fibrosis of wounds, angiogenesis and cardiac remodeling (Miyazaki et al., *Pharmacol. Ther.* 112 (2006), 668-676; Shiota et al.; *J. Hypertens.* 21 (2003), 1823-1825). An increase in the number of mast cells has been observed in the event of heart failure, myocardial infarction and ischemia, in human atherosclerotic plaques and in abdominal aortic aneurysms (Kovanen et al., *Circulation* 92 (1995), 1084-1088; Libby and Shi, *Circulation* 115 (2007), 2555-2558; Bacani and Frishman, *Cardiol. Rev.* 14(4) (2006), 187-193). Chymase-positive mast cells can also play an important role in the vascular remodeling of the respiratory pathways in the event of asthma and chronic obstructive pulmonary diseases. An increased number of mast cells has been found in endobronchial biopsies of asthma patients (Zanini et al., *J. Allergy Clin. Immunol.* 120 (2007), 329-333). Moreover, chymase is suspected of being partly responsible for the genesis of many renal disorders, such as diabetic nephropathy and polycystic kidney disease (Huang et al., *J. Am. Soc. Nephrol.* 14(7) (2003), 1738-1747; McPherson et al., *J. Am. Soc. Nephrol.* 15(2) (2004), 493-500).

Chymase is predominantly involved in the production of angiotensin II in the heart, in the artery wall and in the lung, whereas the angiotensin-converting enzyme is responsible for the formation of the peptide in the circulation system (Fleming I., *Circ. Res.* 98 (2006), 887-896). In addition, chymase cleaves a number of other substrates of pathological significance. Chymase leads to degradation of extracellular matrix proteins, such as fibronectin, procollagen and vitronectin, and to the breakoff of focal adhesions. It brings about activation and release of TGFβ from its latent form, which plays an important role in the genesis of cardiac hypertrophy and cardiac fibrosis. The enzyme has atherogenic action, by degrading apolipoproteins and preventing the absorption of cholesterol by HDL. The action of chymase leads to release and activation of the cytokine interleukin 1 with its pro-inflammatory properties. Furthermore, it contributes to production of endothelin 1 (Bacani and Frishman, *Cardiol. Rev.* 14(4) (2006), 187-193). An accumulation of chymase-positive mast cells has been found in biopsies of patients having atopic dermatitis, Crohn's disease, chronic hepatitis and hepatic cirrhosis, and also idiopathic interstitial pneumonia (Dogrell S. A., *Expert Opin. Ther. Patents* 18 (2008), 485-499).

The possibility of using chymase inhibitors for the treatment of different diseases has been demonstrated in numerous studies involving animal experimentation. Inhibition of chymase can be useful for the treatment of myocardial infarction. Jin et al. (*Pharmacol. Exp. Ther.* 309 (2004), 409-417) showed that a ligature of the coronary artery in dogs led to ventricular arrhythmias and elevated production of angiotensin II and chymase activity in the heart. Intravenous administration of the chymase inhibitor TY-501076 reduced chymase activity and the angiotensin II concentration in the plasma, and suppressed the occurrence of arrhythmias. A positive effect of chymase inhibition was shown in an in vivo model for myocardial infarction in hamsters. Treatment of the animals with the chymase inhibitor BCEAB reduced chymase activity, improved hemodynamics and reduced mortality (Jin et al., *Life Sci.* 71 (2002), 437-446). In the cardiomyopathic Syrian hamster, where the number of mast cells in the heart is elevated, oral treatment of the animals with the chymase inhibitor reduced cardiac fibrosis by 50% (Takai et al., *Jpn. J. Pharmacol.* 86 (2001), 124-126). In a tachycardia-induced heart failure model in dogs, chymase inhibition with SUN-C82257 led to reduction in the number of mast cells and in fibrosis in the heart. In addition, the diastolic function of the heart was improved after the treatment (Matsumoto et al., *Circulation* 107 (2003), 2555-2558).

Inhibition of chymase thus constitutes an effective principle in the treatment of cardiovascular disorders, inflammatory and allergic disorders, and various fibrotic disorders.

WO 2007/150011 and WO 2009/049112 disclose a process for preparing pyrimidinetriones with glycine substituents. WO 2008/056257 describes triazinediones as GABA-B receptor modulators for treatment of CNS disorders. WO 2008/103277 discloses various nitrogen heterocycles for treatment of cancer. WO 2009/156182 describes uracil derivatives for suppression or reduction of resistance development in the course of cytostatic treatment.

It was an object of the present invention to provide novel substances which act as inhibitors of chymase and are suitable as such for treatment and/or prophylaxis of disorders, especially cardiovascular disorders.

The present invention relates to compounds of the general formula (I)

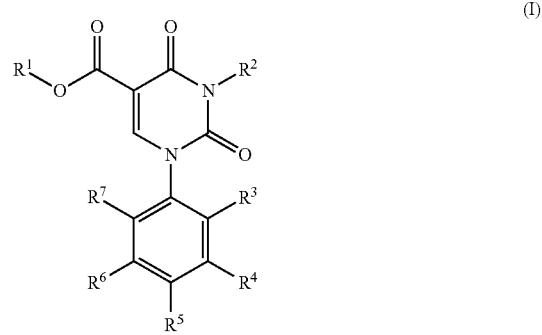

in which $R^1$ represents hydrogen or $(C_1-C_4)$-alkyl, $R^2$ represents a group of the formula

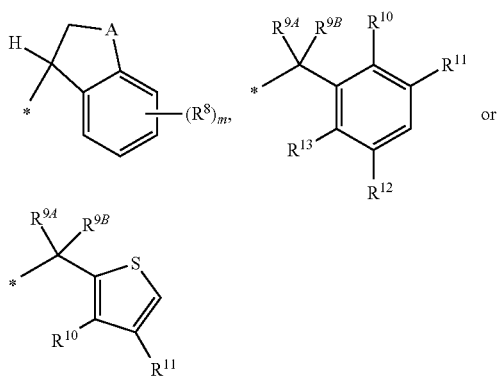

where
* represents the point of attachment to the uracil nitrogen atom,
A represents —CH$_2$—, —CH$_2$—CH$_2$—, —O—CH$_2$-## or oxygen,
  in which ## represents the point of attachment to the phenyl ring,
m represents a number 0, 1 or 2,
$R^8$ represents hydrogen, halogen, difluoromethyl, trifluoromethyl, (C$_1$-C$_4$)-alkyl, difluoromethoxy, trifluoromethoxy or (C$_1$-C$_4$)-alkoxy,
$R^{9A}$ represents hydrogen or deuterium,
$R^{9B}$ represents hydrogen, deuterium or (C$_1$-C$_4$)-alkyl,
$R^{10}$ represents hydrogen, halogen, (C$_1$-C$_4$)-alkyl, difluoromethyl, trifluoromethyl, nitro or (C$_1$-C$_4$)-alkylthio,
$R^{11}$ represents hydrogen, halogen, (C$_1$-C$_4$)-alkyl, difluoromethyl, trifluoromethyl, nitro or (C$_1$-C$_4$)-alkylthio,
$R^{12}$ represents hydrogen or halogen,
$R^{13}$ represents hydrogen or halogen,
$R^3$ represents hydrogen,
$R^4$ represents hydrogen, halogen, (C$_1$-C$_4$)-alkyl or (C$_1$-C$_4$)-alkoxy,
$R^5$ represents (C$_1$-C$_4$)-alkyl, (C$_1$-C$_4$)-alkoxy, (C$_1$-C$_4$)-alkylthio, (C$_1$-C$_4$)-alkylsulfinyl, (C$_1$-C$_4$)-alkylsulfonyl or —N(R$^{14}$R$^{15}$),
  where (C$_1$-C$_4$)-alkyl may be substituted by 1 or 2 substituents independently of one another selected from the group consisting of halogen, hydroxy, 4- to 7-membered heterocyclyl, (C$_1$-C$_4$)-alkoxy, hydroxycarbonyl, (C$_1$-C$_4$)-alkoxycarbonyl, aminocarbonyl, mono-(C$_1$-C$_4$)-alkylaminocarbonyl and di-(C$_1$-C$_4$)-alkylaminocarbonyl,
    in which 4- to 7-membered heterocyclyl may be substituted by 1 or 2 halogen or oxo substituents,
  where (C$_1$-C$_4$)-alkoxy may be substituted by a substituent independently of one another selected from the group consisting of hydroxy, (C$_1$-C$_4$)-alkoxycarbonyl, amino, mono-(C$_1$-C$_4$)-alkylamino, di-(C$_1$-C$_4$)-alkylamino, aminocarbonyl, mono-(C$_1$-C$_4$)-alkylaminocarbonyl and di-(C$_1$-C$_4$)-alkylaminocarbonyl,
  where
    $R^{14}$ represents (C$_1$-C$_4$)-alkyl, (C$_1$-C$_4$)-alkoxycarbonyl or (C$_1$-C$_4$)-alkylaminocarbonyl,
      in which (C$_1$-C$_4$)-alkyl may be substituted by hydroxy or (C$_1$-C$_4$)-alkoxy,
    and
      in which (C$_1$-C$_4$)-alkylaminocarbonyl may be substituted by hydroxy or (C$_1$-C$_4$)-alkoxy,
    $R^{15}$ represents hydrogen or (C$_1$-C$_4$)-alkyl,
or
$R^5$ represents 4- to 7-membered heterocyclyl or 5- to 6-membered heteroaryl,
  where 4- to 7-membered heterocyclyl may be substituted by 1 to 3 substituents independently of one another selected from the group consisting of halogen, trifluoromethyl, (C$_1$-C$_4$)-alkyl, hydroxy, oxo, amino and (C$_1$-C$_4$)-alkoxycarbonyl,
    in which (C$_1$-C$_4$)-alkyl may be substituted by 1 or 2 substituents independently of one another selected from the group consisting of halogen, hydroxy and —N(R$^{16}$R$^{17}$),
      in which R$^{16}$ represents hydrogen, (C$_1$-C$_4$)-alkyl or (C$_1$-C$_4$)-alkylcarbonyl,
      in which R$^{17}$ represents hydrogen or (C$_1$-C$_4$)-alkyl,
  where 5- to 6-membered heteroaryl may be substituted by 1 or 2 substituents independently of one another selected from the group consisting of halogen, trifluoromethyl, (C$_1$-C$_4$)-alkyl, hydroxy, amino and (C$_1$-C$_4$)-alkoxycarbonyl,
    in which (C$_1$-C$_4$)-alkyl may be substituted by 1 or 2 substituents independently of one another selected from the group consisting of halogen, hydroxy and —N(R$^{16}$R$^{17}$),
      in which R$^{16}$ represents hydrogen, (C$_1$-C$_4$)-alkyl or (C$_1$-C$_4$)-alkylcarbonyl,
      in which R$^{17}$ represents hydrogen or (C$_1$-C$_4$)-alkyl,
$R^6$ represents hydrogen, halogen, cyano, (C$_1$-C$_4$)-alkyl or (C$_1$-C$_4$)-alkoxy,
$R^7$ represents hydrogen, halogen, (C$_1$-C$_4$)-alkyl or (C$_1$-C$_4$)-alkoxy,
and the salts, solvates and solvates of the salts thereof.

The present invention relates to compounds of the general formula (I)
in which
$R^1$ represents hydrogen or (C$_1$-C$_4$)-alkyl,
$R^2$ represents a group of the formula

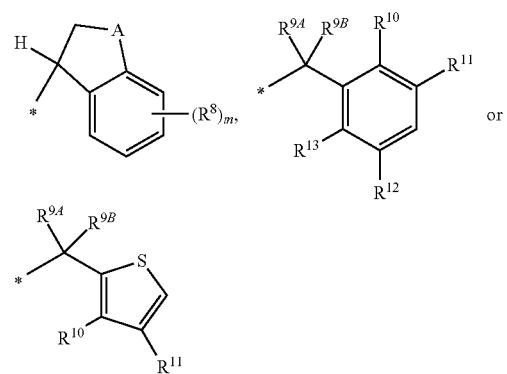

where
* represents the point of attachment to the uracil nitrogen atom,
A represents —CH$_2$—, —CH$_2$—CH$_2$—, —O—CH$_2$-## or oxygen,
  in which ## represents the point of attachment to the phenyl ring,
m represents a number 0, 1 or 2,
$R^8$ represents hydrogen, halogen, difluoromethyl, trifluoromethyl, (C$_1$-C$_4$)-alkyl, difluoromethoxy, trifluoromethoxy or (C$_1$-C$_4$)-alkoxy, $R^{9A}$ represents hydrogen or deuterium, $R^{9B}$ represents hydrogen, deuterium or $(C_1-C_4)$-alkyl, $R^{10}$ represents hydrogen, halogen, $(C_1-C_4)$-alkyl, difluoromethyl, trifluoromethyl, nitro or $(C_1-C_4)$-alkylthio, $R^{11}$ represents hydrogen, halogen, $(C_1-C_4)$-alkyl, difluoromethyl, trifluoromethyl, nitro or $(C_1-C_4)$-alkylthio, $R^{12}$ represents hydrogen or halogen, $R^{13}$ represents hydrogen or halogen, $R^3$ represents hydrogen, $R^4$ represents hydrogen, halogen, $(C_1-C_4)$-alkyl or $(C_1-C_4)$-alkoxy, $R^5$ represents $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl or $-N(R^{14}R^{15})$, where $(C_1-C_4)$-alkyl may be substituted by 1 or 2 substituents independently of one another selected from the group consisting of halogen, hydroxy, 4- to 7-membered heterocyclyl, $(C_1-C_4)$-alkoxy, hydroxycarbonyl, $(C_1-C_4)$-alkoxycarbonyl, aminocarbonyl, mono-$(C_1-C_4)$-alkylaminocarbonyl and di-$(C_1-C_4)$-alkylaminocarbonyl, in which 4- to 7-membered heterocyclyl may be substituted by 1 or 2 halogen or oxo substituents, where $(C_1-C_4)$-alkoxy may be substituted by a substituent independently of one another selected from the group consisting of hydroxy, $(C_1-C_4)$-alkoxycarbonyl, amino, mono-$(C_1-C_4)$-alkylamino, di-$(C_1-C_4)$-alkylamino, aminocarbonyl, mono-$(C_1-C_4)$-alkylaminocarbonyl and di-$(C_1-C_4)$-alkylaminocarbonyl, where $R^{14}$ represents $(C_1-C_4)$-alkyl, $(C_1-C_4)$-alkoxycarbonyl or $(C_1-C_4)$-alkylaminocarbonyl, in which $(C_1-C_4)$-alkylaminocarbonyl may be substituted by hydroxy or $(C_1-C_4)$-alkoxy, $R^{15}$ represents hydrogen or $(C_1-C_4)$-alkyl, or $R^5$ represents 4- to 7-membered heterocyclyl or 5- to 6-membered heteroaryl, where 4- to 7-membered heterocyclyl may be substituted by 1 to 3 substituents independently of one another selected from the group consisting of halogen, trifluoromethyl, $(C_1-C_4)$-alkyl, hydroxy, oxo, amino and $(C_1-C_4)$-alkoxycarbonyl, in which $(C_1-C_4)$-alkyl may be substituted by 1 or 2 substituents independently of one another selected from the group consisting of halogen, hydroxy and $-N(R^{16}R^{17})$, in which $R^{16}$ represents hydrogen, $(C_1-C_4)$-alkyl or $(C_1-C_4)$-alkylcarbonyl, in which $R^{17}$ represents hydrogen or $(C_1-C_4)$-alkyl, where 5- to 6-membered heteroaryl may be substituted by 1 or 2 substituents independently of one another selected from the group consisting of halogen, trifluoromethyl, $(C_1-C_4)$-alkyl, hydroxy, amino and $(C_1-C_4)$-alkoxycarbonyl, in which $(C_1-C_4)$-alkyl may be substituted by 1 or 2 substituents independently of one another selected from the group consisting of halogen, hydroxy and $-N(R^{16}R^{17})$, in which $R^{16}$ represents hydrogen, $(C_1-C_4)$-alkyl or $(C_1-C_4)$-alkylcarbonyl, in which $R^{17}$ represents hydrogen or $(C_1-C_4)$-alkyl, $R^6$ represents hydrogen, halogen, cyano, $(C_1-C_4)$-alkyl or $(C_1-C_4)$-alkoxy, $R^7$ represents hydrogen, halogen, $(C_1-C_4)$-alkyl or $(C_1-C_4)$-alkoxy, and the salts, solvates and solvates of the salts thereof.

Compounds of the invention are the compounds of the formula (I) and the salts, solvates and solvates of the salts thereof, the compounds that are encompassed by formula (I) and are of the formulae given below and the salts, solvates and solvates of the salts thereof and the compounds that are encompassed by formula (I) and are mentioned below as embodiments and the salts, solvates and solvates of the salts thereof if the compounds that are encompassed by formula (I) and are mentioned below are not already salts, solvates and solvates of the salts.

The compounds of the invention may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers and the respective mixtures thereof. It is possible to isolate the stereoisomerically homogeneous constituents from such mixtures of enantiomers and/or diastereomers in a known manner.

If the compounds of the invention can occur in tautomeric forms, the present invention encompasses all the tautomeric forms.

Preferred salts in the context of the present invention are physiologically acceptable salts of the compounds according to the invention. Also encompassed are salts which are not themselves suitable for pharmaceutical applications but can be used, for example, for isolation or purification of the compounds of the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

In the context of the present invention, unless specified otherwise, the substituents are defined as follows:

Alkyl in the context of the invention is a straight-chain or branched alkyl radical having 1 to 4 carbon atoms. The following may be mentioned by way of example and by way of preference: methyl, ethyl, n-propyl, isopropyl, n-butyl, isobutyl, sec-butyl and tert-butyl.

Alkylcarbonyloxy in the context of the invention is a straight-chain or branched alkylcarbonyl radical which is attached via an oxygen atom and carries 1 to 4 carbon atoms in the alkyl chain. The following may be mentioned by way of example and by way of preference: methylcarbonyloxy, ethylcarbonyloxy, n-propylcarbonyloxy, isopropylcarbonyloxy, n-butylcarbonyloxy, isobutylcarbonyloxy and tert-butylcarbonyloxy.

Alkoxy in the context of the invention is a straight-chain or branched alkoxy radical 1 to 4 carbon atoms. The following may be mentioned by way of example and by way of preference: methoxy, ethoxy, n-propoxy, isopropoxy, n-butoxy and tert-butoxy.

Alkoxycarbonyl in the context of the invention is a straight-chain or branched alkoxy radical having 1 to 4 carbon atoms and a carbonyl group attached to the oxygen. Preference is given to a straight-chain or branched alkoxycarbonyl radical having 1 to 4 carbon atoms in the alkoxy group. The following may be mentioned by way of example and by way of preference: methoxycarbonyl, ethoxycarbonyl, n-propoxycarbonyl, isopropoxycarbonyl and tert-butoxycarbonyl.

Alkoxycarbonylamino in the context of the invention is an amino group having a straight-chain or branched alkoxycarbonyl substituent which has 1 to 4 carbon atoms in the alkyl chain and is attached to the nitrogen atom via the carbonyl group. The following may be mentioned by way of example and by way of preference: methoxycarbonylamino, ethoxycarbonylamino, propoxycarbonylamino, n-butoxycarbonylamino, isobutoxycarbonylamino and tert-butoxycarbonylamino.

Alkylthio in the context of the invention is a straight-chain or branched alkyl radical having 1 to 4 carbon atoms which is attached via a sulfur atom. The following may be mentioned by way of example and by way of preference: methylthio, ethylthio, n-propylthio, isopropylthio, 1-methylpropylthio, n-butylthio, isobutylthio and tert-butylthio.

Alkylsulfinyl in the context of the invention is a straight-chain or branched alkyl radical having 1 to 4 carbon atoms which is attached via a sulfoxide group. The following may be mentioned by way of example and by way of preference: methylsulfinyl, ethylsulfinyl, n-propylsulfinyl, isopropylsulfinyl, n-butylsulfinyl and tert-butylsulfinyl.

Alkylsulfonyl in the context of the invention is a straight-chain or branched alkyl radical having 1 to 4 carbon atoms which is attached via a sulfonyl group. The following may be mentioned by way of example and by way of preference: methylsulfonyl, ethylsulfonyl, n-propylsulfonyl, isopropylsulfonyl, n-butylsulfonyl and tert-butylsulfonyl.

Monoalkylamino in the context of the invention is an amino group having a straight-chain or branched alkyl substituent having 1 to 4 carbon atoms. The following may be mentioned by way of example and by way of preference: methylamino, ethylamino, n-propylamino, isopropylamino and tert-butylamino.

Dialkylamino in the context of the invention is an amino group having two identical or different, straight-chain or branched alkyl substituents each having 1 to 4 carbon atoms. The following may be mentioned by way of example and by way of preference: N,N-dimethylamino, N,N-diethylamino, N-ethyl-N-methylamino, N-methyl-N-n-propylamino, N-isopropyl-N-n-propylamino and N-tert-butyl-N-methylamino.

Monoalkylaminocarbonyl in the context of the invention is an amino group which is attached via a carbonyl group and has a straight-chain or branched alkyl substituent having 1 to 4 carbon atoms. The following may be mentioned by way of example and by way of preference: methylaminocarbonyl, ethylaminocarbonyl, n-propylaminocarbonyl, isopropylaminocarbonyl, n-butylaminocarbonyl and tert-butylaminocarbonyl.

Dialkylaminocarbonyl in the context of the invention is an amino group which is attached via a carbonyl group and has two identical or different, straight-chain or branched alkyl substituents each having 1 to 4 carbon atoms. The following may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Monoalkylaminocarbonylamino in the context of the invention is an amino group which carries a straight-chain or branched alkylaminocarbonyl substituent which has 1 to 4 carbon atoms in the alkyl chain and is attached via the carbonyl group. The following may be mentioned by way of example and by way of preference: methylaminocarbonylamino, ethylaminocarbonylamino, n-propylaminocarbonylamino, isopropylaminocarbonylamino, n-butylaminocarbonylamino and tert-butylaminocarbonylamino.

Dialkylaminocarbonylamino in the context of the invention is an amino group which carries a straight-chain or branched dialkylaminocarbonyl substituent which has in each case 1 to 4 carbon atoms in the alkyl chain which may be identical or different and is attached via the carbonyl group. The following may be mentioned by way of example and by way of preference: N,N-dimethylaminocarbonylamino, N,N-diethylaminocarbonylamino, N-ethyl-N-methylaminocarbonylamino, N-methyl-N-n-propylaminocarbonylamino, N-n-butyl-N-methylaminocarbonylamino and N-tert-butyl-N-methylaminocarbonylamino.

Heterocyclyl or Heterocycle in the context of the invention is a saturated or partially unsaturated heterocycle having a total of 4 to 7 ring atoms which contains 1 to 3 ring heteroatoms from the group consisting of N, O and S and is attached via a ring carbon atom or optionally a ring nitrogen atom. The following may be mentioned by way of example: azetidinyl, pyrrolidinyl, tetrahydrofuranyl, imidazolidinyl, dihydroimidazolyl, pyrazolidinyl, dihydrotriazolyl, oxazolidinyl, dihydrooxazolyl, thiazolidinyl, dihydrooxadiazolyl, piperidinyl, piperazinyl, tetrahydropyranyl, oxazinanyl, hexahydropyrimidinyl, morpholinyl, thiomorpholinyl and azepanyl. Preference is given to 5- or 6-membered heterocyclyl radicals having 1 to 3 ring heteroatoms. The following may be mentioned by way of example and by way of preference: imidazolidinyl, dihydroimidazolyl, pyrazolidinyl, dihydrotriazolyl, oxazolidinyl, dihydrooxazolyl, piperazinyl and morpholinyl.

Heteroaryl in the context of the invention is a monocyclic aromatic heterocycle (heteroaromatic) which has a total of 5 or 6 ring atoms, contains up to three identical or different ring heteroatoms from the group of N, O and/or S and is attached via a ring carbon atom or via any ring nitrogen atom. The following may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to monocyclic 5-membered heteroaryl radicals having two or three ring heteroatoms from the group consisting of N, O and S, for example thiazolyl, oxazolyl, isothiazolyl, isoxazolyl, pyrazolyl, imidazolyl, triazolyl, oxadiazolyl and thiadiazolyl.

Halogen in the context of the invention includes fluorine, chlorine, bromine and iodine. Preference is given to chlorine or fluorine.

An oxo group in the context of the invention is an oxygen atom attached to a carbon atom via a double bond.

In the formulae of the group that A, $R^2$ and $R^5$ may represent, the end point of the line marked by a symbol * or ## or ### does not represent a carbon atom or a $CH_2$ group but is part of the bond to the respectively denoted atom to which A, $R^2$ and $R^5$ are attached.

When radicals in the compounds of the invention are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

Preference is given in the context of the present invention to compounds of the formula (I) in which
$R^1$ represents hydrogen, methyl or ethyl,
$R^2$ represents a group of the formula

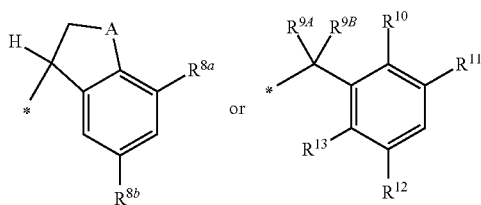

where
* represents the point of attachment to the uracil nitrogen atom,
A represents —$CH_2$—, —$CH_2$—$CH_2$— or oxygen,
$R^{8a}$ represents hydrogen, fluorine, chlorine, trifluoromethyl or methyl,
$R^{8b}$ represents hydrogen, fluorine, chlorine, trifluoromethyl or methyl,
$R^{9A}$ represents hydrogen,
$R^{9B}$ represents hydrogen, methyl or ethyl,
$R^{10}$ represents hydrogen, fluorine, chlorine, difluoromethyl, trifluoromethyl or methyl,
$R^{11}$ represents hydrogen, fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine, chlorine or methoxy,
$R^5$ represents ($C_1$-$C_4$)-alkoxy, 5- or 6-membered heterocyclyl or 5-membered heteroaryl,
where 5- to 6-membered heterocyclyl may be substituted by 1 or 2 substituents independently of one another selected from the group consisting of trifluoromethyl, methyl, ethyl, hydroxy, oxo and ($C_1$-$C_4$)-alkoxycarbonyl,
in which methyl and ethyl may be substituted by —$N(R^{16}R^{17})$,
in which $R^{16}$ represents ($C_1$-$C_4$)-alkylcarbonyl,
in which $R^{17}$ represents hydrogen,
where 5-membered heteroaryl may be substituted by fluorine, chlorine, trifluoromethyl, methyl, hydroxy, amino or ($C_1$-$C_4$)-alkoxycarbonyl,
in which methyl may be substituted by hydroxy,
$R^6$ represents hydrogen, fluorine, chlorine or methyl,
$R^7$ represents hydrogen, fluorine, chlorine or methyl,
and the salts, solvates and solvates of the salts thereof.

In the context of the present invention, preference is given to compounds of the formula (I) in which
$R^1$ represents hydrogen, methyl or ethyl,
$R^2$ represents a group of the formula

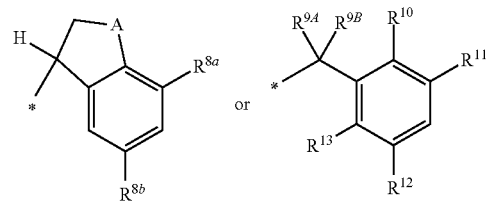

where
* represents the point of attachment to the uracil nitrogen atom,
A represents —$CH_2$— or —$CH_2$—$CH_2$—,
$R^{8a}$ represents hydrogen, chlorine, trifluoromethyl or methyl,
$R^{8b}$ represents hydrogen,
$R^{9A}$ represents hydrogen,
$R^{9B}$ represents hydrogen, methyl or ethyl,
$R^{10}$ represents hydrogen, chlorine, trifluoromethyl or methyl,
$R^{11}$ represents fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine, chlorine or methoxy,
$R^5$ represents 5- or 6-membered heterocyclyl or 5-membered heteroaryl,
where 5- to 6-membered heterocyclyl may be substituted by 1 or 2 methyl, ethyl or oxo substituents,
where 5-membered heteroaryl may be substituted by methyl or amino,
in which methyl may be substituted by hydroxy,
$R^6$ represents hydrogen, fluorine, chlorine or methyl,
$R^7$ represents hydrogen, fluorine or methyl,
and the salts, solvates and solvates of the salts thereof.

In the context of the present invention, preference is given to compounds of the formula (I) in which
$R^1$ represents hydrogen, methyl or ethyl,
$R^2$ represents a group of the formula

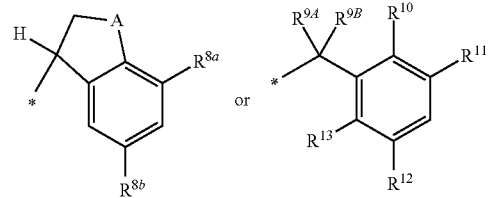

where
* represents the point of attachment to the uracil nitrogen atom,
A represents —$CH_2$— or —$CH_2$—$CH_2$—,
$R^{8a}$ represents chlorine or trifluoromethyl,
$R^{8b}$ represents hydrogen,
$R^{9A}$ represents hydrogen,
$R^{9B}$ represents hydrogen, $R^{10}$ represents chlorine, trifluoromethyl or methyl,
$R^{11}$ represents fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine or chlorine,
$R^5$ represents a group of the formula

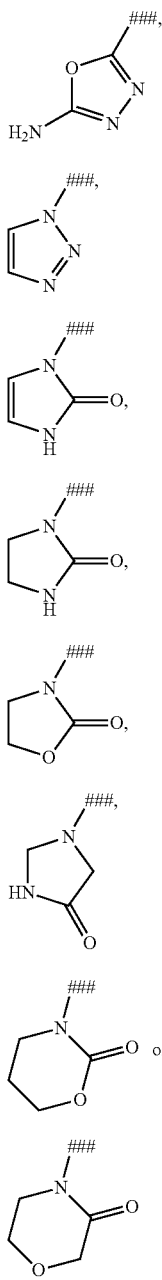

in which
represents the point of attachment to the phenyl ring,
$R^6$ represents hydrogen, fluorine, chlorine or methyl,
$R^7$ represents hydrogen, fluorine or methyl,
and the salts, solvates and solvates of the salts thereof.

In the context of the present invention, particular preference is given to compounds of the formula (I) in which
$R^1$ represents hydrogen, methyl or ethyl,
$R^2$ represents a group of the formula

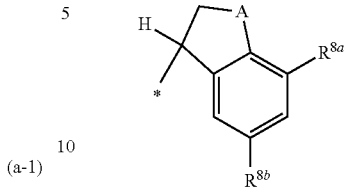

where
* represents the point of attachment to the uracil nitrogen atom,
A represents —CH$_2$— or —CH$_2$—CH$_2$—,
$R^{8a}$ represents chlorine or trifluoromethyl,
$R^{8b}$ represents hydrogen,
$R^3$ represents hydrogen,
$R^4$ represents hydrogen,
$R^5$ represents a group of the formula

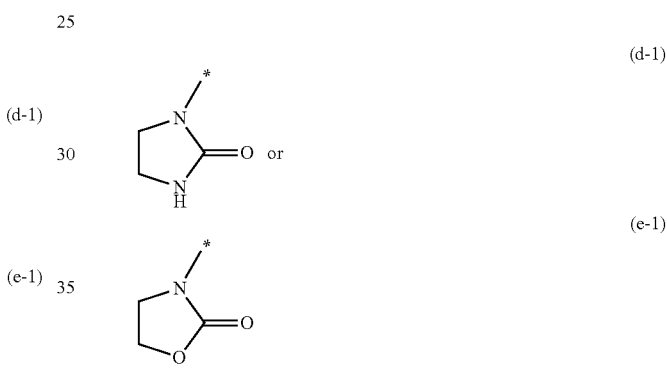

$R^6$ represents hydrogen,
$R^7$ represents hydrogen,
and the salts, solvates and solvates of the salts thereof.

In the context of the present invention, preference is also given to compounds of the formula (I) in which
$R^2$ represents a group of the formula

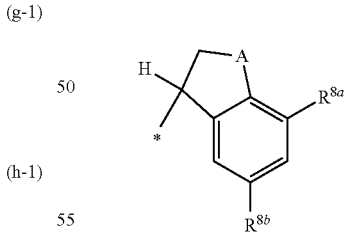

where
* represents the point of attachment to the uracil nitrogen atom,
A represents —CH$_2$— or —CH$_2$—CH$_2$—,
$R^{8a}$ represents chlorine or trifluoromethyl,
$R^{8b}$ represents hydrogen,
and the salts, solvates and solvates of the salts thereof.

In the context of the present invention, preference is also given to compounds of the formula (I) in which $R^5$ represents a group of the formula

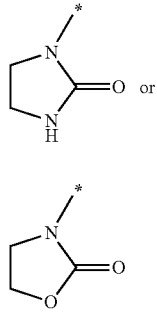

(d-1)

or (e-1)

and the salts, solvates and solvates of the salts thereof.

Irrespective of the particular combinations of the radicals specified, the individual radical definitions specified in the particular combinations or preferred combinations of radicals are also replaced as desired by radical definitions of other combinations.

Very particular preference is given to combinations of two or more of the abovementioned preferred ranges.

The invention further provides a process for preparing compounds of the formula (I) according to the invention, characterized in that

[A] a compound of the formula (II)

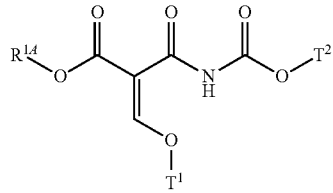

(II)

in which
$R^{14}$ represents $(C_1-C_4)$-alkyl,
$T^1$ represents $(C_1-C_4)$-alkyl,
$T^2$ represents $(C_1-C_4)$-alkyl,
is reacted in an inert solvent, optionally in the presence of a suitable base, with a compound of the formula (III)

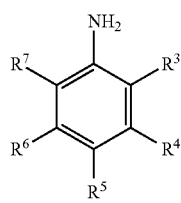

(III)

in which $R^3$, $R^4$, $R^5$, $R^6$ and $R^7$ have the meaning given above, to give a compound of the formula (IV)

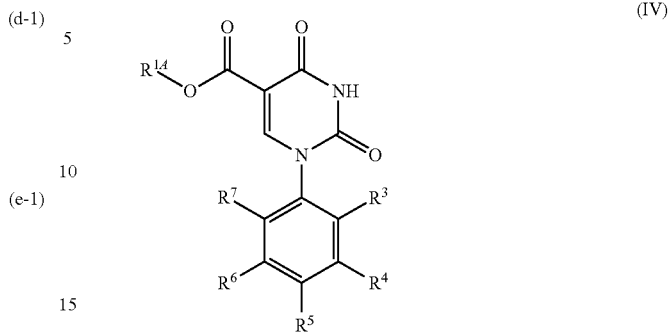

(IV)

in which $R^{14}$, $R^3$, $R^4$, $R^5$, $R^6$ and $R^7$ each have the meanings given above,
this is then reacted in an inert solvent, in the presence of a suitable base, with a compound of the formula (V)

$$X^1-R^2 \qquad (V)$$

in which $R^2$ has the meaning given above
and
$X^1$ represents hydroxy or a suitable leaving group, in particular chlorine, bromine or iodine,
to give a compound of the formula (I-1)

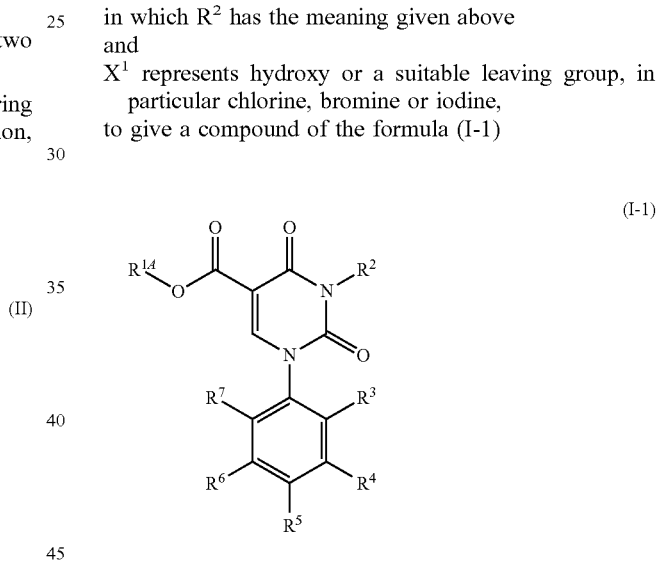

(I-1)

in which $R^{14}$, $R^2$, $R^3$, $R^4$, $R^5$, $R^6$ and $R^7$ each have the meanings given above,
or
[B] a compound of the formula (VI)

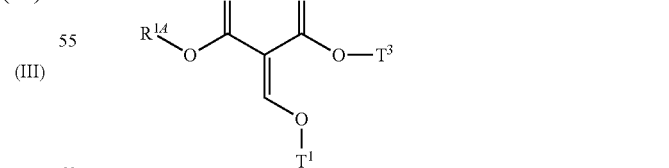

(VI)

in which $R^{14}$ and $T^1$ each have the meanings mentioned above and
$T^3$ represents $(C_1-C_4)$-alkyl,
is converted in an inert solvent or else without solvent with a compound of the formula (III) to a compound of the formula (VII)

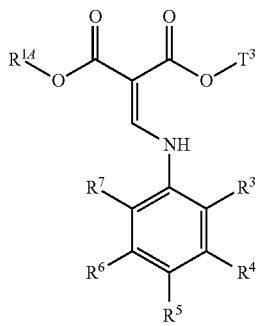

(VII)

in which $R^{1A}$, $R^3$, $R^4$, $R^5$, $R^6$, $R^7$ and $T^3$ each have the meanings given above, this is subsequently reacted in an inert solvent with chlorosulfonyl isocyanate to give a compound of the formula (IV) and this is subsequently converted analogously to process [A] to a compound of the formula (I-1), or

[C] a compound of the formula (VIII)

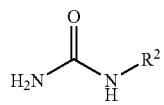

(VIII)

in which $R^2$ is as defined above is reacted in an inert solvent with a compound of the formula (IX)

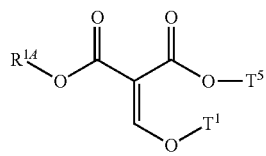

(IX)

in which $R^{1A}$ and $T^1$ each have the meanings given above and $T^5$ represents $(C_1-C_4)$-alkyl, and cyclized in the presence of a suitable base to give a compound of the formula (X)

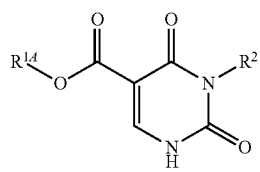

(X)

in which $R^1$ and $R^2$ each have the meanings mentioned above, and this is then reacted in an inert solvent in the presence of a suitable catalyst and a suitable base with a compound of the formula (XI)

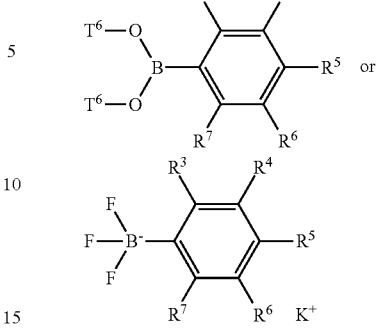

(XI)

in which $R^3$, $R^4$, $R^5$, $R^6$ and $R^7$ have the meaning given above and $T^6$ represents hydrogen, $(C_1-C_4)$-alkyl or the two radicals $T^6$ together form a $-C(CH_3)_2-C(CH_3)_2-$ bridge, to give a compound of the formula (I-1), or

[D] a compound of the formula (I-1) is hydrolyzed in an inert solvent in the presence of a suitable acid or base to give a compound of the formula (I-2)

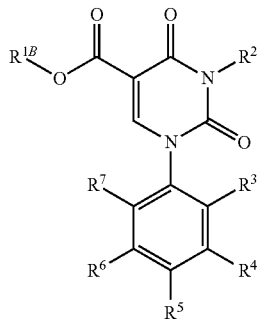

(I-2)

in which $R^2$, $R^3$, $R^4$, $R^5$, $R^6$ and $R^7$ each have the meanings mentioned above and $R^{1B}$ represents hydrogen, any protecting groups are detached and/or the compounds of the formulae (I-1) and (I-2) are, where appropriate, converted with the appropriate (i) solvents and/or (ii) bases or acids to the solvates, salts and/or solvates of the salts thereof.

The compounds of the formulae (I-1) and (I-2) together form the group of compounds of the formula (I) according to the invention.

Inert solvents for the process steps (II)+(III)→(IV), (VI)+(III)→(VII) and (VIII)+(IX)→(X) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, 1,2-dichloroethane, trichloroethylene or chlorobenzene, alcohols such as methanol, ethanol, n-propanol, isopropanol or n-butanol, or other solvents such as dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using ethanol.

Suitable bases for the process steps (II)+(III)→(IV) and (VIII)+(IX)→(X) are alkali metal alkoxides such as sodium or potassium methoxide, sodium or potassium ethoxide or sodium or potassium tert-butoxide, alkali metal hydrides such as sodium or potassium hydride, amides such as sodium amide, lithium or potassium bis(trimethylsilyl)amide or lithium diisopropylamide, or organic bases such as triethylamine, diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or phosphazene bases, for example 1-[N-tert-butyl-P,P-di(pyrrolidin-1-yl)phosphorimidoyl]pyrrolidine or N'''-tert-butyl-N,N,N',N'-tetramethyl-N''-[tris(dimethylamino)-lambda$^5$-phosphanylidene]phosphorimidetriamide Preference is given to sodium ethoxide and potassium tert-butoxide.

The base is generally used here in an amount of 1 to 5 mol, preferably in an amount of 1.2 to 3 mol, based on 1 mol of the compound of the formula (II) or (IX).

The conversions (II)+(III)→(IV), (VI)+(III)→(VII) and (VIII)+(IX)→(X) are generally carried out within a temperature range from 0° C. to +150° C., preferably at +20° C. to +120° C., optionally in a microwave. The reaction can be carried out under atmospheric, elevated or reduced pressure (for example from 0.5 to 5 bar). In general, the reactions are carried out at atmospheric pressure.

If $X^1$=OH, the conversion (IV)+(V)→(I-1) is carried out under Mitsunobu conditions [see: a) Hughes, D. L. "The Mitsunobu Reaction" *Organic Reactions*; John Wiley & Sons, Ltd, 1992, vol. 42, p. 335. b) Hughes, D. L. *Org. Prep. Proceed. Int.* 1996, 28, 127]. The Mitsunobu reaction is effected using triphenylphosphine, or tri-n-butylphosphine, 1,2-bis(diphenylphosphino)ethane (DPPE), diphenyl(2-pyridyl)phosphine (Ph2P-Py), (p-dimethylaminophenyl)diphenylphosphine (DAP-DP), tris(4-dimethylaminophenyl)phosphine (tris-DAP), and a suitable dialkyl azodicarboxylate, for example diethyl azodicarboxylate (DEAD), diisopropyl azodicarboxylate (DIAD), di-tert-butyl azodicarboxylate, N,N,N'N'-tetramethylazodicarboxamide (TMAD), 1,1'-(azodicarbonyl)dipiperidine (ADDP) or 4,7-dimethyl-3,5,7-hexahydro-1,2,4,7-tetrazocin-3,8-dione (DHTD). Preference is given to using triphenylphosphine and diisopropyl azodicarboxylate (DIAD).

Inert solvents for the Mitsunobu reaction (IV)+(V)→(I-1) are, for example, ethers such as tetrahydrofuran, diethyl ether, hydrocarbons such as benzene, toluene, xylene, halohydrocarbons such as dichloromethane, dichloroethane or other solvents such as acetonitrile or dimethylformamide (DMF). It is also possible to use mixtures of the solvents mentioned. Preference is given to using THF or a mixture of THF and DMF.

The Mitsunobu reaction (IV)+(V)→(I-1) is effected generally within a temperature range from −78° C. to +180° C., preferably at 0° C. to +50° C., optionally in a microwave. The conversions can be performed at atmospheric, elevated or reduced pressure (for example from 0.5 to 5 bar).

If $X^1$ represents a suitable leaving group, the conversion (IV)+(V)→(I-1) is carried out under conditions for a nucleophilic substitution. In that case, inert solvents for the process step (IV)+(V)→(I-1) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, 1,2-dichloroethane, trichloroethylene or chlorobenzene, or other solvents such as dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using acetonitrile, DMF or acetonitrile in a mixture with dimethylformamide.

Suitable bases for the process step (IV)+(V)→(I-1) are customary inorganic bases. These include in particular alkali metal or alkaline earth metal carbonates such as lithium carbonate, sodium carbonate, potassium carbonate, calcium carbonate or caesium carbonate, optionally with addition of an alkali metal iodide, for example potassium iodide, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide. Preference is given to using potassium carbonate with potassium iodide or sodium hydride.

The base is generally used here in an amount of 1 to 5 mol, preferably in an amount of 1.2 to 3 mol, based on 1 mol of the compound of the formula (IV).

The conversion (IV)+(V)→(I-1) is effected generally within a temperature range from 0° C. to +100° C., preferably at +20° C. to +80° C., optionally in a microwave. The reaction can be carried out under atmospheric, elevated or reduced pressure (for example from 0.5 to 5 bar). In general, the reactions are carried out at atmospheric pressure.

Inert solvents for the process step (VII)→(IV) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as chlorobenzene, dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using toluene.

The conversion (VII)→(IV) is effected generally within a temperature range from 0° C. to +150° C., preferably at +20° C. to +120° C., optionally in a microwave. The reaction can be carried out under atmospheric, elevated or reduced pressure (for example from 0.5 to 5 bar). In general, the reactions are carried out at atmospheric pressure.

The process step (X)+(XI)→(I-1) is similar to a conversion called the Chan-Lam coupling in the literature. Inert solvents for the process step (X)+(XI)→(I-1) are ethers such as 1,4-dioxane or tetrahydrofuran, halohydrocarbons such as dichloromethane, trichloromethane, 1,2-dichloroethane, or other solvents such as dimethylformamide (DMF), N-methylpyrrolidone (NMP), acetonitrile or dimethyl sulfoxide (DMSO). It is also possible to use mixtures of the solvents mentioned. Preference is given to a mixture of acetonitrile and DMSO when (XI) is a boronic ester or a trifluoroborate salt, or dichloromethane when (XI) is a boronic acid. In some cases, the addition of molecular sieve is advantageous.

Suitable bases for the process step (X)+(XI)→(I-1) are pyridine, pyridine derivatives, for example DMAP or organic tertiary amines, for example diisopropylethylamine or triethylamine Preference is given to triethylamine when (XI) is a boronic ester or a trifluoroborate salt, or pyridine when (XI) is a boronic acid.

Suitable catalysts for the process step (X)+(XI)→(I-1) are copper(II) salts, for example copper(II) acetate or copper(II) triflate, preference being given to copper(II) acetate.

The process step (X)+(XI)→(I-1) is performed under air or under an oxygenous atmosphere.

The reaction (X)+(XI)→(I-1) is generally performed within a temperature range from 0° C. to +150° C., preferably at +20° C. to +80° C.

The hydrolysis of the ester group $R^{1A}$ of the compound (I-1) to compounds of the formula (I-2) is effected by treating the esters in inert solvents with acids or bases, in which latter case the salts formed at first are converted to the free carboxylic acids by treating with acid. In general, the ester hydrolysis is preferably effected with acids.

Suitable inert solvents for these reactions are water, diethyl ether, tetrahydrofuran, dioxane or glycol dimethyl ether, or other solvents such as acetonitrile, acetic acid, dimethylformamide or dimethyl sulfoxide. It is also possible to use mixtures of the solvents mentioned. In the case of a basic ester hydrolysis, preference is given to using mixtures of water with dioxane, tetrahydrofuran or acetonitrile. For the hydrolysis of tert-butyl esters, the solvent used in the case of reaction with trifluoroacetic acid is preferably dichloromethane, and in the case of reaction with hydrogen chloride preferably tetrahydrofuran, diethyl ether or dioxane. For the hydrolysis of other esters under acidic conditions, preference is given to acetic acid or a mixture of acetic acid and water.

Suitable bases are the alkali metal or alkaline earth metal hydrogencarbonates such as sodium or potassium hydrogencarbonate. Preference is given to sodium hydrogencarbonate.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters, and to hydrochloric acid in a mixture with acetic acid, and to sulfuric acid in a mixture with acetic acid and water in the case of the methyl esters and ethyl esters.

The ester hydrolysis is generally carried out within a temperature range from 0° C. to 180° C., preferably at +20° C. to 120° C.

These conversions can be performed at atmospheric, elevated or reduced pressure (for example from 0.5 to 5 bar). In general, the reactions are in each case carried out at atmospheric pressure.

The preparation of the compounds according to the invention can be illustrated by way of example by the following synthesis schemes (Schemes 1 to 3):

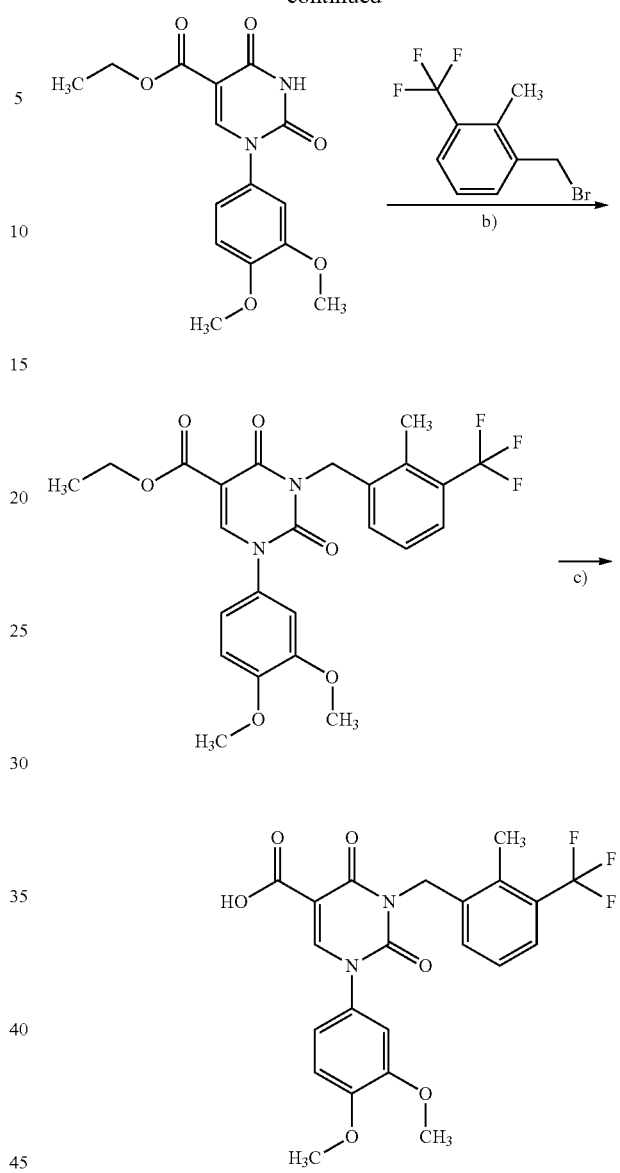

[a): 1) ethanol, reflux; 2) KOtBu, ethanol, reflux; b): K₂CO₃, KI, acetonitrile; c): acetic acid/hydrochloric acid (3:1); reflux].

Scheme 1:

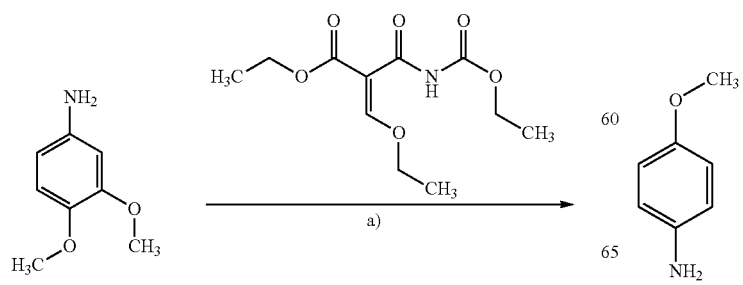

Scheme 2:

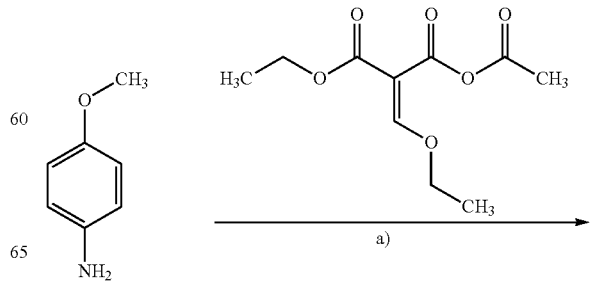

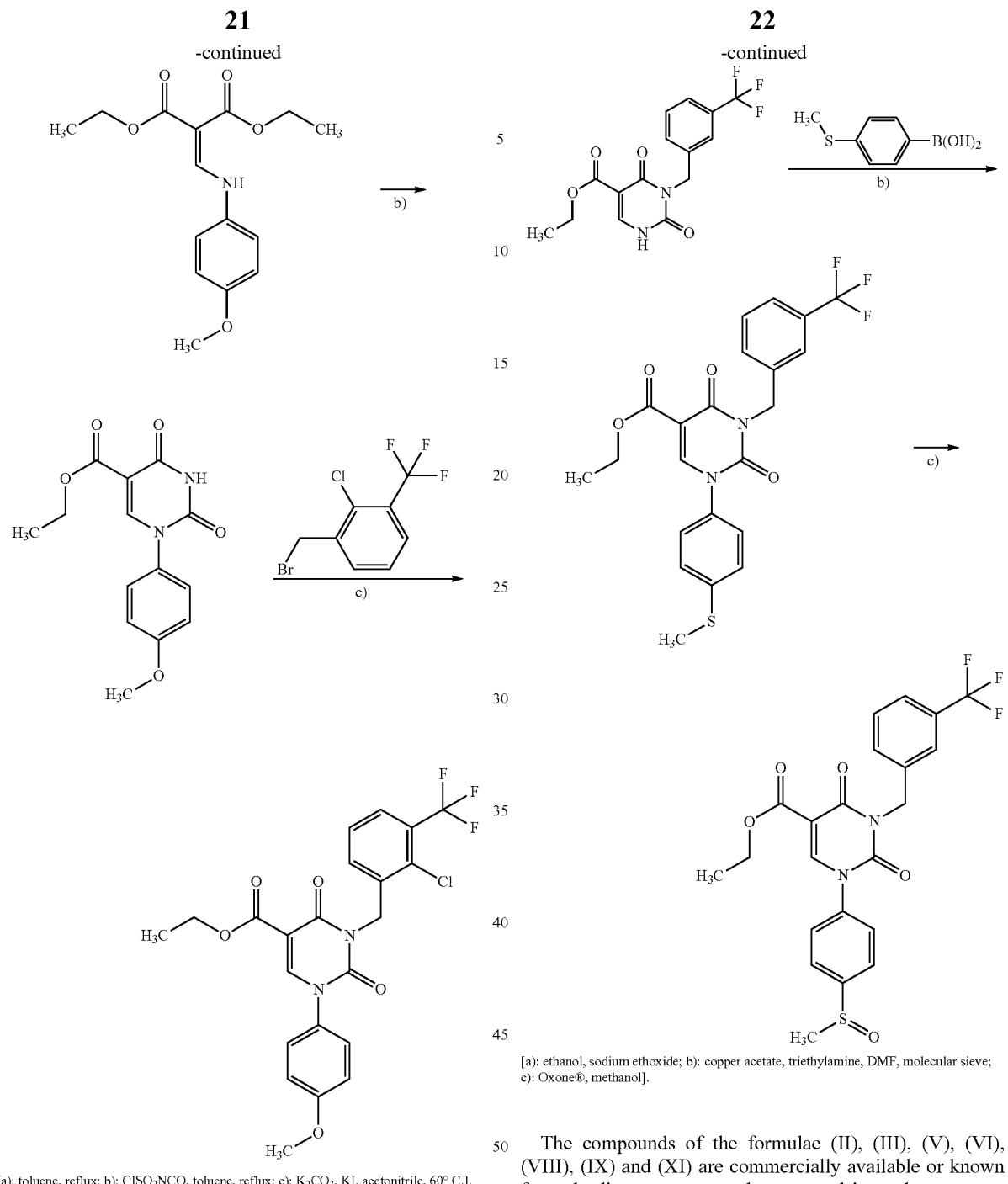

[a]: ethanol, sodium ethoxide; b): copper acetate, triethylamine, DMF, molecular sieve; c): Oxone®, methanol].

The compounds of the formulae (II), (III), (V), (VI), (VIII), (IX) and (XI) are commercially available or known from the literature, or can be prepared in analogy to processes known from the literature.

Further compounds of the invention can optionally also be prepared by conversions of functional groups of individual substituents, especially those listed for $R^5$, proceeding from the compounds of the formula (I) obtained by above processes. These conversions are performed as described in the present experimental section, by customary methods known to those skilled in the art and include, for example, reactions such as nucleophilic and electrophilic substitutions, oxidations, reductions, hydrogenations, transition metal-catalyzed coupling reactions, eliminations, alkylation, amination, esterification, ester hydrolysis, etherification, ether cleavage, formation of carbonamides, and introduction and removal of temporary protecting groups,

[a]: toluene, reflux; b): ClSO$_2$NCO, toluene, reflux; c): K$_2$CO$_3$, KI, acetonitrile, 60° C.].

Scheme 3:

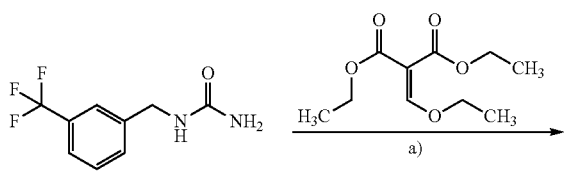

The compounds of the invention have valuable pharmacological properties and can be used for treatment and/or prophylaxis of diseases in humans and animals.

The compounds of the invention are chymase inhibitors and are therefore suitable for treatment and/or prophylaxis of cardiovascular, inflammatory, allergic and/or fibrotic disorders.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischemia, myocardial infarction, shock, atherosclerosis, cardiac hypertrophy, cardiac fibrosis, atrial and ventricular arrhythmias, transitory and ischemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, edema development, for example pulmonary edema, cerebral edema, renal edema or heart failure-related edema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, elevated levels of fibrinogen and of low-density LDL and elevated concentrations of plasminogen activator/inhibitor 1 (PAI-1).

In the context of the present invention, the term "heart failure" also includes more specific or related types of disease, such as acutely decompensated heart failure, right heart failure, left heart failure, global failure, ischemic cardiomyopathy, dilated cardiomyopathy, congenital heart defects, heart valve defects, heart failure associated with heart valve defects, mitral valve stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further suitable for the prophylaxis and/or treatment of polycystic kidney disease (PCKD) and of the syndrome of inappropriate ADH secretion (SIADH).

The compounds of the invention are also suitable for treatment and/or prophylaxis of kidney disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, hemolytic-uremic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphatemia and/or acute renal disorders which can be characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, renal artery thrombosis, renal vein thrombosis, analgesic nephropathy and renal tubular acidosis, and x-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal edema, hematuria, primary, secondary and chronic glomerulonephritis, membranous and membranoproliferative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphatemia and/or the need for dialysis, and in the event of renal cell carcinomas, after partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, and also renal artery stenosis, renal artery thrombosis, renal vein thrombosis, analgesic nephropathy and renal tubular acidosis. In addition, X-ray contrast agent- and medicament-induced chronic interstitial renal disorders, metabolic syndrome and dyslipidemia. The present invention also encompasses the use of the compounds of the invention for treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the compounds according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammations (myocarditis) and other autoimmune cardiac disorders (pericarditis, endocarditis, valvolitis, aortitis, cardiomyopathies), cardiogenic shock, aneurysms, sepsis (SIRS), multiple organ failure (MODS, MOF), inflammatory disorders of the kidney, chronic intestinal disorders (IBD, Crohn's Disease, UC), pancreatitis, peritonitis, rheumatoid disorders, inflammatory skin disorders and inflammatory eye disorders.

The compounds according to the invention can furthermore be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related diseases, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term "fibrotic disorders" encompasses particularly the following terms: hepatic fibrosis, cirrhosis of the liver, pulmonary fibrosis, endomyocardial fibrosis, cardiomyopathy, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), nevi, diabetic retinopathy and proliferative vitroretinopathy.

The compounds according to the invention are also suitable for controlling postoperative scarring, for example as a result of glaucoma operations.

Furthermore, the compounds according to the invention can also be used cosmetically for aging and keratinized skin.

In addition, the compounds of the invention can also be used for treatment and/or prophylaxis of dyslipidemias (hypercholesterolemia, hypertriglyceridemia, elevated concentrations of the postprandial plasma triglycerides, hypoalphalipoproteinemia, combined hyperlipidemias), nephropathy and neuropathy), cancers (skin cancer, brain tumors, breast cancer, bone marrow tumors, leukemias, liposarcomas, carcinomas of the gastrointestinal tract, of the liver, pancreas, lung, kidney, urinary tract, prostate and genital tract, and also malignant tumors in the lymphoproliferative system, for example Hodgkin's and non-Hodgkin's lymphoma), of disorders of the gastrointestinal tract and of the abdomen (glossitis, gingivitis, periodontitis, esophagitis, eosinophilic gastroenteritis, mastocytosis, Crohn's disease, colitis, proctitis, pruritus ani, diarrhea, celiac disease, hepatitis, chronic hepatitis, hepatic fibrosis, cirrhosis of the liver, pancreatitis and cholecystitis), skin disorders (allergic skin disorders, psoriasis, acne, eczema, neurodermitis, various forms of dermatitis, and also keratitis, bullosis, vasculitis, cellulitis, panniculitis, lupus erythematodes, erythema, lymphoma, skin cancer, Sweet's syndrome, Weber-Christian syndrome, scarring, warts, chillblains), of disorders of the skeletal bone and of the joints, and also of the skeletal muscle (various forms of arthritis, various forms of arthropathies, scleroderma and of further disorders with an inflammatory or immunological component, for example paraneoplastic syndrome, in the event of rejection reactions after organ transplants and for wound healing and angiogenesis, especially in the case of chronic wounds.

The compounds of the formula (I) according to the invention are additionally suitable for treatment and/or prophylaxis of ophthalmologic disorders, for example glaucoma, normotensive glaucoma, high intraocular pressure and combinations thereof, of age-related macular degeneration (AMD), of dry or non-exudative AMD, moist or exudative or neovascular AMD, choroidal neovascularization (CNV), detached retina, diabetic retinopathy, atrophic lesions to the retinal pigment epithelium (RPE), hypertrophic lesions to the retinal pigment epithelium (RPE), diabetic macular edema, retinal vein occlusion, choroidal retinal vein occlusion, macular edema, macular edema due to retinal vein occlusion, angiogenesis at the front of the eye, for example corneal angiogenesis, for example following keratitis, cornea transplant or keratoplasty, corneal angiogenesis due to hypoxia (extensive wearing of contact lenses), pterygium conjunctiva, subretinal edema and intraretinal edema.

In addition, the compounds of the formula (I) according to the invention are suitable for treatment and/or prophylaxis of elevated and high intraocular pressure resulting from traumatic hyphema, periorbital edema, postoperative viscoelastic retention, intraocular inflammation, use of corticosteroids, pupillary block or idiopathic causes, and of elevated intraocular pressure following trabeculectomy and due to pre-operative additions.

The present invention further provides for the use of the compounds according to the invention for treatment and/or prophylaxis of disorders, especially the disorders mentioned above.

The present invention further provides for the use of the compounds according to the invention for preparing a medicament for treatment and/or prophylaxis of disorders, especially the disorders mentioned above.

The present invention further provides the compounds according to the invention for use in a method for treatment and/or prophylaxis of heart failure, pulmonary hypertension, chronic obstructive pulmonary disease, asthma, kidney failure, nephropathy, fibrotic disorders of the internal organs and dermatological fibroses.

The compounds of the invention can be used alone or, if required, in combination with other active ingredients. Accordingly, the present invention further provides medicaments comprising at least one of the compounds according to the invention and one or more further active ingredients, especially for treatment and/or prophylaxis of the aforementioned disorders. Preferred examples of active ingredients suitable for combinations include:

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptor by way of example and with preference antagonists of the 5-$HT_{2b}$ receptor;

organic nitrates and NO donors, for example sodium nitroprusside, nitroglycerin, isosorbide mononitrate, isosorbide dinitrate, molsidomine or SIN-1, and inhaled NO;

NO-independent but hem-dependent stimulators of soluble guanylate cyclase, such as especially the compounds described in WO 00/06568, WO 00/06569, WO 02/42301 and WO 03/095451;

NO- and hem-independent activators of soluble guanylate cyclase, such as especially the compounds described in WO 01/19355, WO 01/19776, WO 01/19778, WO 01/19780, WO 02/070462 and WO 02/070510;

prostacyclin analogues, by way of example and with preference iloprost, beraprost, treprostinil or epoprostenol;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active ingredients, for example and with preference from the group of calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, rho-kinase inhibitors and the diuretics;

vasopressin receptor antagonists, for example and with preference conivaptan, tolvaptan, lixivaptan, mozavaptan, satavaptan, SR-121463, RWJ 676070 or BAY 86-8050;

bronchodilatory agents, by way of example and with preference from the group of the beta-adrenergic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone; and/or active ingredients altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

In a preferred embodiment of the invention, the compounds according to the invention are used in combination with a kinase inhibitor, by way of example and with preference bortezomib, canertinib, erlotinib, gefitinib, imatinib, lapatinib, lestaurtinib, lonafarnib, pegaptinib, pelitinib, semaxanib, sorafenib, regorafenib, sunitinib, tandutinib, tipifarnib, vatalanib, fasudil, lonidamine, leflunomide, BMS-3354825 or Y-27632.

In a preferred embodiment of the invention, the compounds according to the invention are used in combination with a serotonin receptor antagonist, by way of example and with preference PRX-08066.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, DU-176b, fidexaban, razaxaban, fondaparinux, idraparinux, PMD-3112, YM-150, KFA-1982, EMD-503982, MCM-17, mLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic, by way of example and with preference furosemide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorbent, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein (a) antagonist, by way of example and with preference gemcabene calcium (CI-1027) or nicotinic acid.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers, aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and inhalative administration.

The compounds of the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions, unless indicated otherwise, are based in each case on volume.

A. EXAMPLES

Abbreviations:
Ac acetyl
aq. aqueous, aqueous solution
br. broad
c concentration
cat. catalytic
TLC thin-layer chromatography
DCI direct chemical ionization (in MS)
dist. distilled
DIEA N,N-diisopropylethylamine
DMAP 4-N,N-dimethylaminopyridine
DMF dimethylformamide
DMSO dimethyl sulfoxide
EDC N'-(3-dimethylaminopropyl)-N-ethylcarbodiimide hydrochloride
ee enantiomeric excess
ent enantiomerically pure, enantiomer
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
conc. concentrated
LC-MS liquid chromatography-coupled mass spectrometry
Me methyl
min minute(s)
MS mass spectrometry
MTBE methyl tert-butyl ether
NMR nuclear magnetic resonance spectrometry
Pd/C palladium on activated carbon
Ph phenyl
PyBOP benzotriazol-1-yloxytris(pyrrolidino)phosphonium hexafluorophosphate
quant. quantitative (in yield)
rac racemic, racemate
RT room temperature
$R_t$ retention time (in HPLC)
m.p. melting point
tBu tert-butyl
tert. tertiary
TFA trifluoroacetic acid
TFAA trifluoroacetic anhydride
THF tetrahydrofuran
UV ultraviolet spectrometry
cf. see
v/v volume to volume ratio (of a solution)
HPLC, GC-MS and LC-MS Methods:

Method 1 (LC-MS): instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 2 (LC-MS): instrument: Waters (Micromass) Quattro Micro MS with HPLC Agilent Series 1100; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 3 (LC-MS): instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient 0.0 min 90% A→1.2 min 5% A→2.0 min 5% A; oven: 50° C.; flow rate: 0.40 ml/min; UV detection: 210-400 nm.

Method 4 (LC-MS): MS instrument type: Waters ZQ; HPLC instrument type: Agilent 1100 Series; UV DAD; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% flow rate: 2.5 ml/min, oven: 55° C.; flow rate 2/ml; UV detection: 210 nm.

Method 5a (preparative HPLC): column: Reprosil C18 10 µm, 250×30; flow rate 50 ml/min; runtime: 18 min; detection at 210 nm; injection after a runtime of 3 min; mobile phase: water+0.1% formic acid (A), methanol (B); gradient: to 4.25 min 40% B, 4.50 min 60% B, 11.50 min 80% B, 12.00-14.50 min 100% B, 14.75-18.00 min 40% B.

Method 5b (preparative HPLC): as Method 5a, but using the following mobile phase: water (A), methanol (B); gradient: to 4.25 min 50% B, 4.50 min 70% B, 11.50 min 90% B, 12.00-14.50 min 100% B, 14.75-18.00 min 50% B.

Method 6a (preparative HPLC): column: Reprosil C18 10 μm, 250×30, flow rate 50 ml/min, runtime: 38 min, detection at 210 nm, mobile phase acetonitrile (A), water (B); gradient: 3 min 10% A, 27 min 95% A, 34 min 95% A, 34-38 min 10% A.

Method 6b (preparative HPLC): as Method 6a, but mobile phase B is 0.1% formic acid in water.

Method 7a (preparative HPLC): column. Reprosil C18, 10 μm, 250 mm×30 mm. Mobile phase A: formic acid 0.1% in water, mobile phase B: methanol; flow rate: 50 ml/min; program: 0 to 4.25 min: 60% A/40% B; 4.25 to 4.50 min: gradient to 60% B; 4.50 min to 17 min gradient to 100% B; 17 min to 19.50 min 100% B; 19.50 min to 19.75 min gradient to 40% B; 19.75 to 22 min (end): 60% A/40% B.

Method 7b (preparative HPLC): as Method 7a, but using the following gradient: 0 to 7.25 min: 60% A/40% B; 7.25 to 7.50 min: gradient to 60% B; 7.50 min to 20 min gradient to 100% B; 20 min to 32.50 min 100% B; 32.50 min to 32.75 min gradient to 40% B; 32.75 to 35 min (end): 60% A/40% B.

Method 7c (preparative HPLC): similar to Method 7a, but using pure water as mobile phase A Method 8 (preparative HPLC): column: Reprosil C18, 10 μm, 250 mm×30 mm. Mobile phase A: formic acid 0.1% in water, mobile phase B: acetonitrile; flow rate: 50 ml/min; program: 0 to 6 min: 90% A/10% B; 6 min to 27 min: gradient to 95% B; 27 min to 38 min 95% B; 38 min to 39 min gradient to 10% B; 39 min to 43 min (end): 60% A/40% B. Slight variations in the gradient are possible.

Method 9 (preparative HPLC): column: Grom-Sil 120 ODS-4HE, 10 μm, SNo. 3331, 250 mm×30 mm. Mobile phase A: TFA 0.1% in water, mobile phase B: acetonitrile; flow rate: 50 ml/min program: 0-1 min: 10% B; 1-25 min: gradient to 95% B; 25-39 min: 95% B; 39-45 min: 10% B.

Method 10 (GC-MS): instrument: Micromass GCT, GC6890; column: Restek RTX-35, 15 m×200 μm×0.33 μm; constant flow rate of helium: 0.88 ml/min; oven: 70° C.; inlet: 250° C.; gradient: 70° C., 30° C./min→310° C. (hold for 3 min)

Method 11 (LC-MS): instrument: Waters ACQUITY SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient 0.0 min 90% A→1.2 min 5% A→2.0 min 5% A; oven: 50° C.; flow rate: 0.60 ml/min; UV detection: 208-400 nm.

Method 12 (chiral analytical HPLC): stationary phase Daicel Chiralpak AD-H 5 μm, column: 250 mm×4.6 mm; temperature: 30° C.; UV detection: 220 nm. Mobile phase: isohexane/2-propanol 95:5 (v/v); flow rate: 1 ml/min.

Method 13 (preparative HPLC): column: Kromasil C18 5 μm, 250×20 mm, mobile phase: methanol (B)/water+0.1% TFA (A), gradient: 0 to 4.25 min 60% A, 4.5 min 40% A, 11.5 min 20% A, 12 min 0% A, 14.5 min 0% A, 14.75 min 60% A, 18 min 60% A, flow rate: 25 ml/min, detection: 210 nm.

Method 14 (preparative HPLC): as Method 8, but using the Chromatorex C18 5 μm, 250×20 mm column.

Starting Materials and Intermediates

Example 1A 1-(2-Chloroethyl)-3-(2-fluoro-4-nitrophenyl)urea

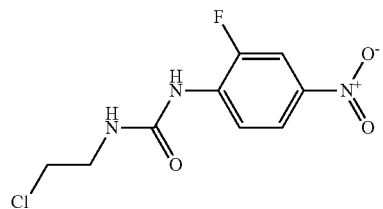 [SMILES: O=C(NCCCl)Nc1ccc([N+](=O)[O-])cc1F]

5 ml of 2-chloroethyl isocyanate were added to 10 g (64 mmol) of 2-fluoro-4-nitroaniline in 44.2 ml of 1,2-dimethoxyethane. The mixture was heated under reflux for 1.5 hours, a further 2 ml of 2-chloroethyl isocyanate were added and the mixture was then heated under reflux for a further 1.5 h. Another 1.6 ml of 2-chloroethyl isocyanate were added. Thus, in total 8.79 g (83 mmol) of 2-chloroethyl isocyanate were added. After 1.5 h of heating at reflux, the mixture was cooled and filtered and the filtrate was concentrated under reduced pressure. The residue was then co-evaporated with toluene, water was then added, the mixture was extracted with ethyl acetate and the organic extract was concentrated. The residue was stirred with diethyl ether and filtered off with suction. This gave 10.16 g (61% of theory) of the title compound.

LC-MS (Method 1): $R_t$=1.01 min; m/z=262 (M+H)$^+$.

$^1$H-NMR (400 MHz, DMSO-d$_6$): δ=3.47 (m, 2H), 3.70 (m, 2H), 7.20 (m, 1H), 7.20 (t, 1H), 8.08 (dd, 1H), 8.12 (dd, 1H), 8.48 (t, 1H), 9.18 (s, 1H).

Example 2A 1-(2-Fluoro-4-nitrophenyl)imidazolidin-2-one

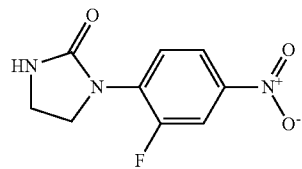 [SMILES: O=C1NCCN1c1ccc([N+](=O)[O-])cc1F]

10 g (38.2 mmol) of 1-(2-chloroethyl)-3-(2-fluoro-4-nitrophenyl)urea from Example 1A were dissolved in 84.5 ml of dioxane, 2.45 g (61.2 mmol) of 60% sodium hydride in paraffin were added under an argon protective atmosphere and the mixture was stirred at 20° C. for two hours. 800 ml of water were then added to the reaction mixture and the solid formed was filtered off with suction.

The solid was washed with water and subsequently dried under high vacuum. This gave 8.69 g (quantitative yield) of the target compound.

LC-MS (Method 1): $R_t$=0.79 min; m/z=226 (M+H)$^+$.

Example 3A 1-tert-Butyl-3-(2,6-difluoro-4-nitrophenyl)imidazolidin-2-one

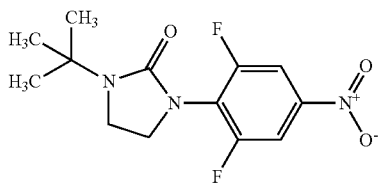 [SMILES: CC(C)(C)N1CCN(c2c(F)cc([N+](=O)[O-])cc2F)C1=O]

At 0° C., 4.20 g (29.5 mmol) of 1-tert-butylimidazolidin-2-one were added to 2.71 g (67.9 mmol) of 60% sodium hydride in paraffin in 105 ml of tetrahydrofuran, and the mixture was then stirred at RT for 20 min. At 0° C., 5.23 g (29.5 mmol) of 1,2,3-trifluoro-5-nitrobenzene in 7 ml of tetrahydrofuran were added and the mixture was stirred at this temperature for a further 20 min. The reaction mixture was quenched with water and then extracted with ethyl acetate and the organic phase was washed with saturated aqueous sodium chloride solution, dried over sodium sulfate, concentrated, and dried under reduced pressure. This gave 10.9 g (75% of theory, purity 75%) of the target compound.

LC-MS (Method 3): $R_t$=1.06 min; m/z=300 (M+H)$^+$.

$^1$H-NMR (400 MHz, DMSO-d$_6$): δ=1.34 (s, 9H), 3.55-3.62 (m, 2H), 3.65-3.72 (m, 2H), 8.11-8.18 (m, 2H).

Example 4A 1-(2,6-Difluoro-4-nitrophenyl)imidazolidin-2-one

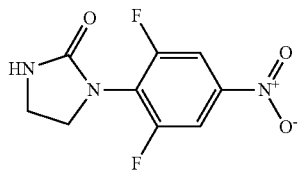 [SMILES: O=C1NCCN1c1c(F)cc([N+](=O)[O-])cc1F]

10.9 g (27.3 mmol, purity 75%) of 1-tert-butyl-3-(2,6-difluoro-4-nitrophenyl)imidazolidin-2-one from Example 3A in 100 ml of semiconcentrated aqueous hydrochloric acid were stirred at 80° C. for 5 h. The reaction mixture was neutralized with aqueous sodium hydroxide solution and extracted three times with dichloromethane, the combined organic phases were dried over sodium sulfate and filtered, and the solvent was removed under reduced pressure. The residue was purified by chromatography on silica gel using dichloromethane/methanol mixtures (first 100:1, then 50:1). This gave, after concentration of the appropriate fractions and drying under reduced pressure, 3.87 g (58% of theory) of the target compound.

LC-MS (Method 4): $R_t$=1.43 min; m/z=244 (M+H)$^+$.

$^1$H-NMR (400 MHz, DMSO-d$_6$): δ=3.48-3.55 (m, 2H), 3.81-3.88 (m, 2H), 7.21 (br. s, 1H), 8.12-8.19 (m, 2H).

Example 5A 1-(2-Fluoro-4-nitrophenyl)-3-(2-methoxyethyl)urea

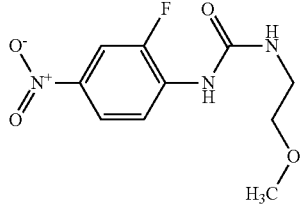 [SMILES: COCCNC(=O)Nc1ccc([N+](=O)[O-])cc1F]

25.14 g (96 mmol) of 1-(2-chloroethyl)-3-(2-fluoro-4-nitrophenyl)urea from Example 1A were dissolved in 150 ml of methanol and 37 ml of DMF and filtered, a solution of 8.3 g (153.7 mmol) of sodium methoxide in 62.5 ml of methanol was added under an atmosphere of argon and the mixture was heated at reflux with stirring for two hours. At 20° C., 300 ml of water were then added, the mixture was stirred and the solid was filtered off with suction. The solid was then washed first with 150 ml of a methanol/water mixture (1:1), then with 100 ml of water and finally with 100 ml of ethanol and dried under high vacuum. This gave 17.9 g (72% of theory) of the target compound.

LC-MS (Method 3): $R_t$=0.82 min; m/z=258 (M+H)$^+$.

$^1$H-NMR (400 MHz, DMSO-d$_6$): δ=3.12-3.20 (m, 2H), 3.28-3.35 (m, 2H), 3.52 (s, 3H), 6.88 (t, 1H), 7.08 (br. m, 1H), 7.26 (br. m, 1H), 7.91 (dd, 1H), 7.95 (dd, 1H).

Example 6A tert-Butyl 3-(4-nitrophenyl)-1H-pyrazole-1-carboxylate

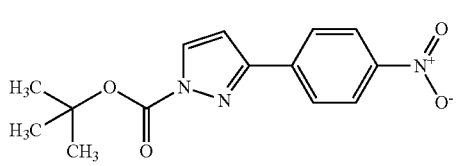 [SMILES: CC(C)(C)OC(=O)n1ccc(-c2ccc([N+](=O)[O-])cc2)n1]

5 g (26.43 mmol) of 3-(4-nitrophenyl)-1H-pyrazole, 7.5 g (34.4 mmol) of di-tert-butyl carbonate, 1.13 g (9.25 mmol) of 4-dimethylaminopyridine and 3.21 g (31.72 mmol) of triethylamine in 70.4 ml of THF were stirred at 20° C. for four hours. After addition of water and ethyl acetate, the organic phase was separated off, washed with saturated aqueous ammonium chloride solution and saturated aqueous sodium chloride solution, dried with sodium sulfate and, after filtration, concentrated under reduced pressure. Drying of the residue under high vacuum gave 8.05 g of the title compound in quantitative yield.

LC-MS (Method 3): $R_t$=1.16 min; m/z=290 (M+H)$^+$.

$^1$H-NMR (400 MHz, DMSO-d$_6$): δ=1.62 (s, 9H), 7.28 (d, 1H), 8.19 (d, 2H), 8.34 (d, 2H), 8.42 (d, 1H).

Example 7A tert-Butyl 5-(4-nitrophenyl)-1,2,5-thiadiazolidine-2-carboxylate 1,1-dioxide

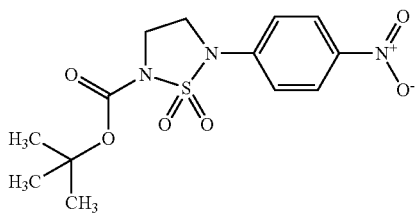 [SMILES: CC(C)(C)OC(=O)N1CCN(c2ccc([N+](=O)[O-])cc2)S1(=O)=O]

The preparation was carried out analogously to the literature (see Example 132 of Nicolaou, K. C. et al. Chem. Eur. J. (2004), 10, 5581-5606) from 2 g (11 mmol) of 2-[(4-nitrophenyl)amino]ethanol and 7.4 g (26 mmol) of 1-(tert-butoxycarbonyl)-3,3,3-triethyldiazathian-3-ium-1-ide 2,2-dioxide.

Yield: 1.2 g (29% of theory)
LC-MS (Method 3): $R_t$=1.08 min; m/z=361 (M+NH$_4$)$^+$.
$^1$H-NMR (400 MHz, DMSO-d$_6$): δ=1.50 (s, 9H), 4.00-4.06 (m, 4H), 7.51 (d, 2H), 8.35 (d, 2H).

Example 8A tert-Butyl 4-(4-nitrophenyl)-5-oxo-4,5-dihydro-1H-1,2,4-triazole-1-carboxylate

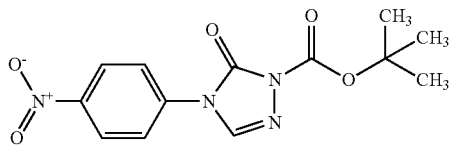 [SMILES: CC(C)(C)OC(=O)n1ncn(-c2ccc([N+](=O)[O-])cc2)c1=O]

4.75 g (23 mmol) of 4-(4-nitrophenyl)-2,4-dihydro-3H-1,2,4-triazol-3-one (preparation: WO 2000037463, page 18), 6.54 g (30 mmol) of di-tert-butyl carbonate, 0.99 g (8.1 mmol) of 4-dimethylaminopyridine and 2.8 g (27.7 mmol) of triethylamine in 61.4 ml of THF were stirred at 20° C. for four hours. After addition of water, the solid formed was filtered off with suction, washed first with water and then with diethyl ether and dried under high vacuum. This gave 7.2 g of the target compound in quantitative yield.

LC-MS (Method 3): $R_t$=0.93 min; m/z=307 (M+H)$^+$.
$^1$H-NMR (400 MHz, DMSO-d$_6$): δ=1.59 (s, 9H), 8.0 (d, 2H), 8.4 (d, 2H), 8.78 (s, 1H).

Example 9A 1-(4-Amino-2-fluorophenyl)imidazolidin-2-one

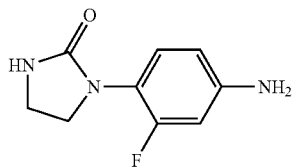

8.6 g (38.2 mmol) of 1-(2-fluoro-4-nitrophenyl)imidazolidin-2-one from Example 2A were dissolved in 152 ml of THF and 84 ml of DMF, 0.813 g of 10% palladium on carbon was added and the mixture was hydrogenated at 20° C. and under at standard pressure for 24 hours. The catalyst was filtered off over kieselguhr and the filtrate was concentrated under reduced pressure, giving 7.71 g of the target compound in quantitative yield.

LC-MS (Method 3): $R_t$=0.34 min; m/z=195 (M+H)$^+$.

Example 10A 1-(4-Amino-2,6-difluorophenyl)imidazolidin-2-one

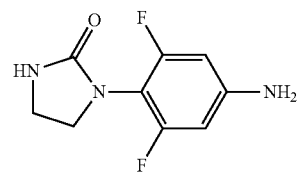 [SMILES: Nc1cc(F)c(N2CCNC2=O)c(F)c1]

4.29 g (17.6 mmol) of 1-(2,6-difluoro-4-nitrophenyl)imidazolidin-2-one from Example 4A were dissolved in 50 ml of ethanol and hydrogenated in a continuous flow hydrogenation apparatus ("H-Cube" from Thales Nano, Budapest, Hungary) under the following conditions: cartridge palladium on carbon 10% (Thales THS01111), 1 bar hydrogen pressure, temperature 20° C., flow rate 1 ml/min. The eluate was concentrated under reduced pressure and dried. This gave 3.71 g (99% of theory) of the target compound.

LC-MS (Method 4): $R_t$=1.14 min; m/z=214 (M+H)$^+$.
$^1$H-NMR (400 MHz, DMSO-d$_6$): δ=3.35-3.42 (m, 2H), 3.52-3.59 (m, 2H), 5.74 (s, 2H), 6.18-6.26 (m, 2H), 6.65 (s, 1H).

Example 11A tert-Butyl 4-(4-aminophenyl)-5-oxo-4,5-dihydro-1H-1,2,4-triazole-1-carboxylate

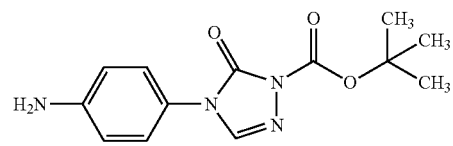 [SMILES: CC(C)(C)OC(=O)n1ncn(-c2ccc(N)cc2)c1=O]

7.2 g (23.51 mmol) of tert-butyl 4-(4-nitrophenyl)-5-oxo-4,5-dihydro-1H-1,2,4-triazole-1-carboxylate from Example 8A were hydrogenated using 0.5 g of 10% palladium on carbon in 94 ml of THF and 52 ml of DMF at standard pressure under a hydrogen atmosphere for 24 hours. The catalyst was subsequently filtered off and the filtrate was concentrated under reduced pressure. This gave 6.74 g of the target compound in quantitative yield.

LC-MS (Method 3): $R_t$=1.08 min; m/z=361 (M+NH$_4$)$^+$.
$^1$H-NMR (400 MHz, DMSO-d$_6$): δ=1.52 (s, 9H), 5.39 (s, 2H), 6.6 (d, 2H), 7.12 (d, 2H), 8.30 (s, 1H).

Example 12A tert-Butyl 5-(4-aminophenyl)-1,2,5-thiadiazolidine-2-carboxylate 1,1-dioxide

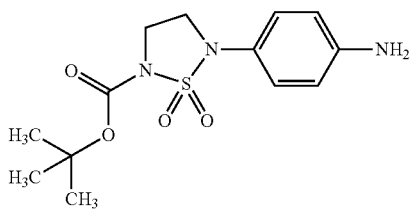 [SMILES: CC(C)(C)OC(=O)N1CCN(c2ccc(N)cc2)S1(=O)=O]

1.2 g (3.5 mmol) of tert-butyl 5-(4-nitrophenyl)-1,2,5-thiadiazolidine-2-carboxylate 1,1-dioxide from Example 7A were hydrogenated using 0.074 g of 10% palladium on carbon in 20 ml of THF and 10 ml of DMF at standard pressure under a hydrogen atmosphere for 48 hours. The catalyst was subsequently filtered off and the filtrate was concentrated under reduced pressure. This gave 1.11 g of the target compound, which was converted further without purification.

LC-MS (Method 3): $R_t$=0.86 min; m/z=314 (M+H)$^+$.

$^1$H-NMR (400 MHz, DMSO-d$_6$): δ=1.48 (s, 9H), 3.68 (t, 2H), 3.82 (t, 2H), 5.3 (br. s, 2H), 6.6 (d, 2H), 7.02 (d, 2H).

Example 13A 1-(4-Amino-2-fluorophenyl)-3-(2-methoxyethyl)urea

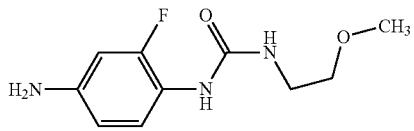

17.9 g (69.6 mmol) of 1-(2-fluoro-4-nitrophenyl)-3-(2-methoxyethyl)urea from Example 5A were dissolved in 326 ml of THF and 163 ml of DMF, 2.96 g of 5% palladium on carbon were added and the mixture was hydrogenated at 20° C. under standard pressure for 24 hours. The catalyst was filtered off with suction over kieselguhr and the filtrate was concentrated under reduced pressure, giving 18.34 g of the target compound in quantitative yield.

$^1$H-NMR (400 MHz, DMSO-d$_6$): δ=3.12-3.20 (m, 2H), 3.09-3.20 (m, 2H), 3.51 (s, 3H), 4.42 (br. m, 1H), 4.53 (s, 2H), 6.25 (dd, 1H), 6.34 (dd, 1H), 6.5 (t, 1H), 7.13-7.23 (m, 1H).

Example 14A tert-Butyl 3-(4-aminophenyl)-1H-pyrazole-1-carboxylate

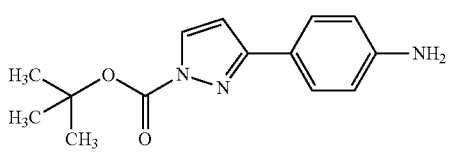 [SMILES: CC(C)(C)OC(=O)n1ccc(-c2ccc(N)cc2)n1]

8.05 g (27.83 mmol) of tert-butyl 3-(4-nitrophenyl)-1H-pyrazole-1-carboxylate from Example 6A were dissolved in 111 ml of THF and 62 ml of DMF, 0.59 g of 10% palladium on carbon were added and the mixture was hydrogenated at 20° C. under standard pressure in a hydrogen atmosphere for 24 hours. The catalyst was filtered off with suction over kieselguhr and the filtrate was concentrated under reduced pressure, giving 8.82 g of the target compound in quantitative yield.

LC-MS (Method 3): $R_t$=0.91 min; m/z=260 (M+H)$^+$.

$^1$H-NMR (400 MHz, DMSO-d$_6$): δ=1.6 (s, 9H), 5.38 (br. s, 2H), 6.50 (d, 2H), 6.82 (d, 1H), 7.54 (d, 2H), 8.2 (d, 1H).

Example 15A

Ethyl 2,4-dioxo-1-[4-(2-oxoimidazolidin-1-yl)phenyl]-1,2,3,4-tetrahydropyrimidine-5-carboxylate

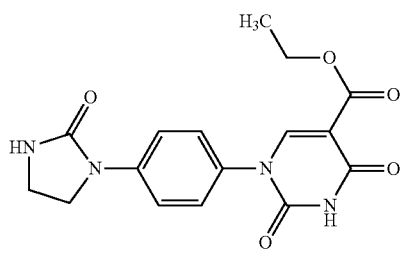 [SMILES: CCOC(=O)c1cn(-c2ccc(N3CCNC3=O)cc2)c(=O)[nH]c1=O]

15.96 g (61.6 mmol) of ethyl 3-ethoxy-2-[(ethoxycarbonyl)carbamoyl]acrylate (preparation see: Senda, Shigeo; Hirota, Kosaku; Notani, Jiyoji, Chemical & Pharmaceutical Bulletin (1972), 20(7), 1380-8) and 12.0 g (67.7 mmol) of 1-(4-aminophenyl)imidazolidin-2-one (preparation see: P. Stabile et al., Tetrahedron Letters 2010, 51 (24), 3232-3235) in 724 ml of ethanol were heated at reflux with stirring for two hours. The mixture was allowed to cool to 20° C., 6.91 g (61.6 mmol) of potassium tert-butoxide were added and the mixture was stirred at 20° C. for a further 18 hours. 1000 ml of water were added and the mixture was acidified to pH 3 with 1 N aqueous hydrochloric acid. The solid formed was filtered off, washed with water (200 ml), ethyl acetate (100 ml) and diethyl ether (100 ml) and dried under high vacuum. This gave 13.54 g (54% of theory) of the title compound.

LC-MS (Method 3): $R_t$=0.62 min; m/z=345 (M+H)$^+$.

$^1$H-NMR (400 MHz, DMSO-d$_6$): δ=1.21 (t, 3H), 3.44 (m, 2H), 3.88 (m, 2H), 4.19 (q, 2H), 7.10 (s, 1H), 7.40 (d, 2H), 7.65 (d, 2H), 8.23 (s, 1H), 11.65 (br. s, 1H).

Analogously to Example 15A, the following substances were prepared from the anilines mentioned in each case. In some cases, after the addition of potassium tert-butoxide the reaction mixture was slightly heated (50° C.) for a few hours to improve the conversion. In some cases, the product was obtained by extracting the acidified mixture with ethyl acetate, drying the organic phases over sodium sulfate and concentrating under reduced pressure.

Example 16A

Ethyl 2,4-dioxo-1-[4-(2-oxotetrahydropyrimidin-1(2H)-yl)phenyl]-1,2,3,4-tetrahydropyrimidine-5-carboxylate

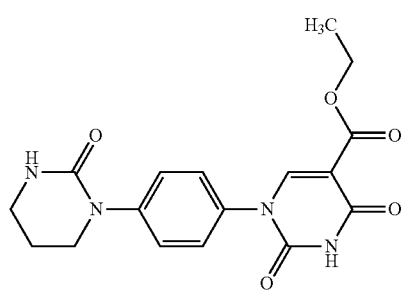 [SMILES: CCOC(=O)c1cn(-c2ccc(N3CCCNC3=O)cc2)c(=O)[nH]c1=O]

The preparation and purification were carried out analogously to Example 15A from 4.0 g (20.92 mmol) of 1-(4-aminophenyl)tetrahydropyrimidin-2(1H)-one (preparation: see WO 2007/053094, page 57) and 4.93 g (19.02 mmol) of ethyl 3-ethoxy-2-[(ethoxycarbonyl)carbamoyl]acrylate. Yield: 5.88 g (68% of theory, purity: 86%).

LC-MS (Method 2): $R_t$=1.30 min; m/z=359 (M+H)$^+$.

$^1$H-NMR (400 MHz, DMSO-d$_6$): δ=1.22 (t, 3H), 1.98 (m, 2H), 3.22 (m, 2H), 3.66 (m, 2H), 4.18 (q, 2H), 6.69 (s, 1H), 7.38-7.45 (m, 4H), 8.24 (s, 1H), 11.64 (s, 1H).

Example 17A

Ethyl 2,4-dioxo-1-[4-(4-oxoimidazolidin-1-yl)phenyl]-1,2,3,4-tetrahydropyrimidine-5-carboxylate

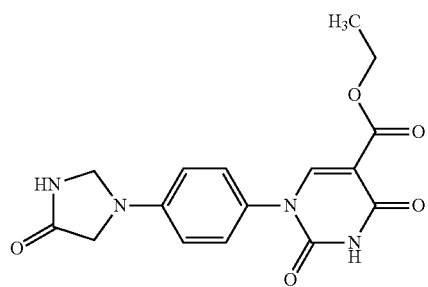 [SMILES: CCOC(=O)c1cn(-c2ccc(N3CNC(=O)C3)cc2)c(=O)[nH]c1=O]

The preparation and purification were carried out analogously to Example 15A from 4.91 g (22.2 mmol, purity 80%) of 1-(4-aminophenyl)imidazolidin-4-one (preparation: see US 2004/0102494, Example 2; preparation 26). Yield: 4.59 g (46% of theory, purity: 77%).

LC-MS (Method 2): $R_t$=1.25 min; m/z=345 (M+H)$^+$.

$^1$H-NMR (400 MHz, DMSO-d$_6$): δ=1.22 (t, 3H), 3.78 (s, 2H), 4.18 (q, 2H), 4.70 (s, 2H), 6.63 (d, 2H), 7.31 (d, 2H), 8.18 (s, 1H), 8.71 (s, 1H), 11.60 (s, 1H).

Example 18A

Ethyl 2,4-dioxo-1-[4-(2-oxo-2,3-dihydro-1H-imidazol-1-yl)phenyl]-1,2,3,4-tetrahydropyrimidine-5-carboxylate The preparation and purification were carried out analogously to Example 15A from 4 g (22.8 mmol) of 1-(4-aminophenyl)-1,3-dihydro-2H-imidazol-2-one (UkrOrgSynthesis Building Blocks, Cat. No. BBV-057991). Yield: 1.68 g (20% of theory, purity: 93%).

LC-MS (Method 2): $R_t$=1.93 min; m/z=389 (M+H)$^+$.

$^1$H-NMR (400 MHz, DMSO-d$_6$): δ=1.20 (t, 3H), 4.12 (q, 2H), 6.61 (m, 1H), 7.71 (m, 1H), 7.47 (d, 2H), 7.82 (d, 2H), 8.18 (s, 1H).

Example 19A

Ethyl 1-[3-fluoro-4-(2-oxoimidazolidin-1-yl)phenyl]-2,4-dioxo-1,2,3,4-tetrahydropyrimidine-5-carboxylate The preparation and purification were carried out analogously to Example 15A from 4 g (20.5 mmol) of 1-(4-amino-2-fluorophenyl)imidazolidin-2-one (Example 9A). Yield: 3.96 g (53% of theory).

LC-MS (Method 3): $R_t$=0.62 min; m/z=363 (M+H)$^+$.

$^1$H-NMR (400 MHz, DMSO-d$_6$): δ=1.20 (t, 3H), 3.44 (m, 2H), 3.83 (m, 2H), 4.09 (q, 2H), 6.93 (s, 1H), 7.15 (dd, 1H), 7.32 (dd, 1H), 7.50 (t, 1H), 7.95 (s, 1H).

Example 20A

Ethyl 2,4-dioxo-1-[4-(3-oxomorpholin-4-yl)phenyl]-1,2,3,4-tetrahydropyrimidine-5-carboxylate

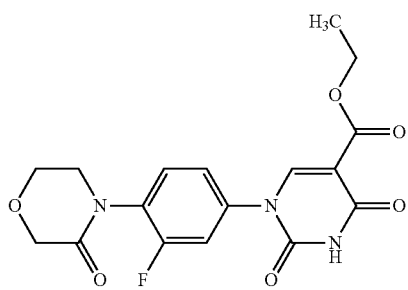 [SMILES: CCOC(=O)c1cn(-c2ccc(N3CCOCC3=O)c(F)c2)c(=O)[nH]c1=O]

The preparation and purification were carried out analogously to Example 15A from 1 g (5.2 mmol) of 4-(4-aminophenyl)morpholin-3-one (WO 2005/026135, p. 7). Yield: 1.72 g (43% of theory).

LC-MS (Method 3): Rt=0.96 min; m/z=406 (M+H)⁺.

¹H-NMR (400 MHz, DMSO-d₆): δ=1.22 (t, 3H), 3.78 (m, 2H), 4.00 (m, 2H), 4.18 (q, 2H), 4.22 (s, 2H), 7.5-7.6 (m, 4H), 8.30 (s, 1H), 11.70 (s, 1H).

Example 21A

Ethyl 2,4-dioxo-1-[4-(2-oxo-1,3-oxazolidin-3-yl)phenyl]-1,2,3,4-tetrahydropyrimidine-5-carboxylate

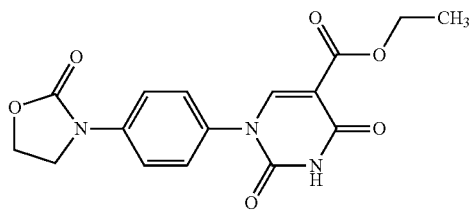 [SMILES: CCOC(=O)c1cn(-c2ccc(N3CCOC3=O)cc2)c(=O)[nH]c1=O]

3.02 g (17 mmol) of 3-(4-aminophenyl)-1,3-oxazolidin-2-one (preparation: see WO2010/019903, p. 222, Method 38; or Farmaco Sci. Ed. (1969), 179) and 4.0 g (15.4 mmol) of ethyl 3-ethoxy-2-[(ethoxycarbonyl)carbamoyl]acrylate (preparation see: Senda, Shigeo; Hirota, Kosaku; Notani, Jiyoji, Chemical & Pharmaceutical Bulletin (1972), 20(7), 1380-8) in 170 ml of ethanol were heated at reflux for 2 h. After cooling to RT, 1.73 g (15.4 mmol) of potassium tert-butoxide were added and the mixture was stirred first at RT overnight and then at 50° C. for 5 h. The reaction mixture was poured into 1.4 l of 1N aqueous hydrochloric acid and the solid formed was isolated by filtration. The solid was stirred with diethyl ether and then dried under high vacuum. This gave 4.2 g (66% of theory, purity 92%) of the title compound.

LC-MS (Method 3): Rt=0.59 min; m/z=346 (M+H)⁺.

¹H-NMR (400 MHz, DMSO-d₆): δ=1.22 (t, 3H), 4.06-4.14 (m, 2H), 4.17 (q, 2H), 4.43-4.51 (m, 2H), 7.51 (d, 2H), 7.68 (d, 2H), 8.26 (s, 1H), 11.69 (s, 1H).

Example 22A

Ethyl 2,4-dioxo-1-[4-(2-oxopyrrolidin-1-yl)phenyl]-1,2,3,4-tetrahydropyrimidine-5-carboxylate

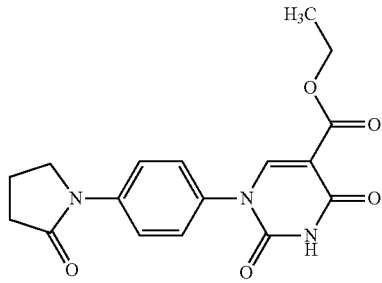 [SMILES: CCOC(=O)c1cn(-c2ccc(N3CCCC3=O)cc2)c(=O)[nH]c1=O]

The preparation and purification were carried out analogously to Example 15A from 1 g (5.68 mmol) of 1-(4-aminophenyl)pyrrolidin-2-one (Justus Liebigs Ann. Chem. (1955), 596). Yield: 0.58 g (28% of theory).

LC-MS (Method 3): Rt=0.69 min; m/z=344 (M+H)⁺.

¹H-NMR (400 MHz, DMSO-d₆): δ=1.20 (t, 3H), 2.08 (m, 2H), 3.43 (m, 2H), 3.85 (m, 2H), 4.11 (q, 2H), 7.36 (d, 2H), 7.70 (d, 2H), 8.01 (s, 1H).

Example 23A (3-Chloro-4-methyl-2-thienyl)methanol

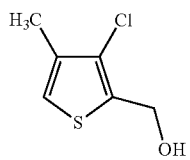

At RT and under argon, 200 mg (1.13 mmol) of 3-chloro-4-methylthiophene-2-carboxylic acid were added a little at a time to 3.40 ml (3.40 mmol) of a 1M borane/tetrahydrofuran complex, and the reaction mixture was stirred at RT for 1 h. 1N aqueous hydrochloric acid was then added carefully until the evolution of gas had ended. The whole mixture was separated by preparative HPLC (Method 7a). This gave 115 mg (62% of theory) of the title compound.

GC-MS (Method 10): Rt=4.00 min; EI: m/z=162 (M)⁺

¹H-NMR (400 MHz, DMSO-d₆): δ [ppm]=2.12 (s, 3H), 4.58 (d, 2H), 5.57 (t, 1H), 7.25 (s, 1H).

Example 24A

1-[3-(Trifluoromethyl)benzyl]urea

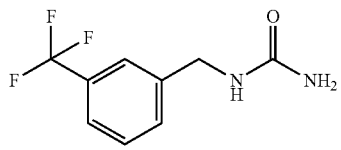 [SMILES: NC(=O)NCc1cccc(C(F)(F)F)c1]

3.9 g (39.5 mmol) of conc. hydrochloric acid were added dropwise to 54 g (308 mmol) of 3-(trifluoromethyl)benzylamine and 74 g (1.23 mol) of urea in 124 ml of water, and the mixture was heated at reflux for three hours. The mixture was then allowed to cool to 20° C. and the solid formed was filtered off with suction. The solid was washed with water and then dried under reduced pressure. This gave 66.6 g (95% of theory) of the target compound.

LC-MS (Method 3): $R_t$=0.73 min; m/z=219 (M+H)$^+$.

Example 25A

Ethyl 2,4-dioxo-3-[3-(trifluoromethyl)benzyl]-1,2,3,4-tetrahydropyrimidine-5-carboxylate

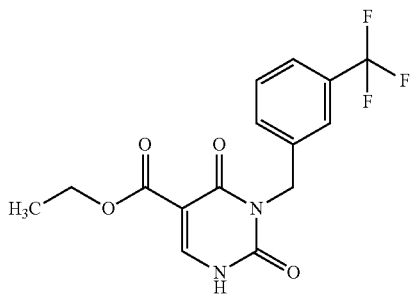 [SMILES: CCOC(=O)c1c[nH]c(=O)n(Cc2cccc(C(F)(F)F)c2)c1=O]

A mixture of 66.66 g (305.5 mmol) of 1-[3-(trifluoromethyl)benzyl]urea from Example 24A and 66.1 g (305.5 mmol) of diethyl (ethoxymethylene)malonate was stirred at 120° C. for 24 h. The mixture was allowed to cool, 611 ml of ethanol and 20.8 g (305.5 mmol) of sodium ethoxide were then added and the mixture was stirred at 20° C. for 24 hours. Another 6 g of sodium ethoxide were then added and the mixture was stirred for a further 24 h. The mixture was concentrated under reduced pressure, 305 ml of water and 305 g of ice were added, the pH was adjusted to 1 using hydrochloric acid and the mixture was extracted with ethyl acetate. The organic phase was dried with sodium sulfate, concentrated under reduced pressure and dried under high vacuum. Ten times, the residue was stirred with diethyl ether and the liquid was decanted off. Drying of the residue under high vacuum gave 47.8 g (39% of theory, purity 84%) of the target compound.

LC-MS (Method 2): $R_t$=1.96 min; m/z=343 (M+H)$^+$.

Example 26A

Ethyl 1-[4-(methylsulfanyl)phenyl]-2,4-dioxo-3-[3-(trifluoromethyl)benzyl]-1,2,3,4-tetrahydropyrimidine-5-carboxylate

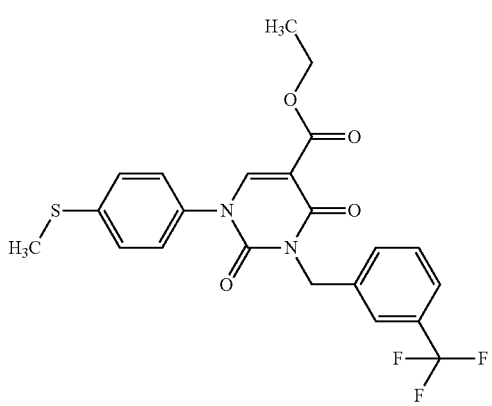 [SMILES: CCOC(=O)c1cn(-c2ccc(SC)cc2)c(=O)n(Cc2cccc(C(F)(F)F)c2)c1=O]

800 mg (2.34 mmol) of ethyl 2,4-dioxo-3-[3-(trifluoromethyl)benzyl]-1,2,3,4-tetrahydropyrimidine-5-carboxylate from Example 25A, 785.4 mg (4.68 mmol) of 4-(methylthio)phenylboronic acid, 424.5 mg (2.34 mmol) of anhydrous copper(II) acetate, 185 mg (2.34 mmol) of pyridine, 237 mg (2.34 mmol) of triethylamine and 1.4 g of molecular sieve (3 Å) in 80 ml of dichloroethane were stirred at 20° C. and exposed to the air for one day. The mixture was subsequently filtered off and the filtrate was concentrated under reduced pressure. Purification by preparative HPLC (Method 6b) gave 583 mg (40% of theory) of the target compound.

LC-MS (Method 3): $R_t$=1.24 min; m/z=465 (M+H)$^+$.

$^1$H-NMR (400 MHz, DMSO-d$_6$): δ=1.22 (t, 3H), 3.25 (s, 3H), 4.19 (q, 2H), 5.09 (s, 2H), 7.38 (d, 2H), 7.45 (d, 2H), 7.55 (t, 1H), 7.60-7.68 (m, 2H), 7.71 (s, 1H), 8.35 (s, 1H).

Example 27A

Ethyl 1-[3,5-difluoro-4-(2-oxoimidazolidin-1-yl)phenyl]-2,4-dioxo-1,2,3,4-tetrahydropyrimidine-5-carboxylate

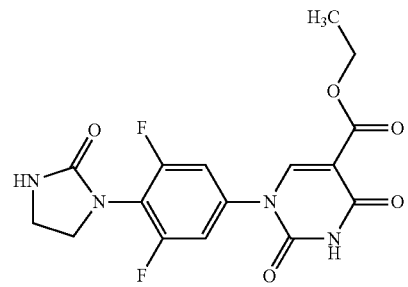 [SMILES: CCOC(=O)c1cn(-c2cc(F)c(N3CCNC3=O)c(F)c2)c(=O)[nH]c1=O]

3.70 g (17.4 mmol) of 1-(4-amino-2,6-difluorophenyl)imidazolidin-2-one from Example 10A and 4.09 g (15.8 mmol) of ethyl 3-ethoxy-2-[(ethoxycarbonyl)carbamoyl]acrylate in 250 ml of ethanol were heated under reflux for 3.25 h. After cooling to RT, 1.77 g (15.8 mmol) of potassium tert-butoxide were added and the reaction mixture was stirred at 50° C. overnight. The mixture was then diluted with water and acidified with 1N aqueous hydrochloric acid. The solid formed was filtered off and dried under reduced pressure. This gave 3.27 g (39% of theory, purity 79%) of the target compound.

LC-MS (Method 4): $R_t$=1.33 min; m/z=381 (M+H)$^+$.

$^1$H-NMR (400 MHz, DMSO-d$_6$): δ=1.23 (t, 3H), 3.46-3.54 (m, 2H), 3.72-3.79 (m, 2H), 4.18 (q, 2H), 7.02 (s, 1H), 7.47-7.53 (m, 2H), 8.39 (s, 1H), 11.79 (s, 1H).

Example 28A

Ethyl 1-[4-(2-amino-2-oxoethoxy)phenyl]-2,4-dioxo-1,2,3,4-tetrahydropyrimidine-5-carboxylate

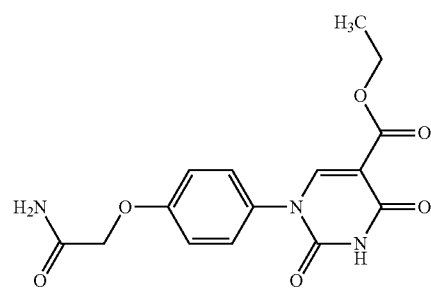 [SMILES: CCOC(=O)c1cn(-c2ccc(OCC(N)=O)cc2)c(=O)[nH]c1=O]

With stirring, 1 g (6.02 mmol) of 2-(4-aminophenoxy)acetamide and 1.34 g (5.47 mmol) of ethyl 3-ethoxy-2-

[(ethoxycarbonyl)carbamoyl]acrylate in 50 ml of ethanol were heated at reflux for two hours. After cooling to 20° C., 20 ml of ethanol and 0.614 g (5.47 mmol) of potassium tert-butoxide were added to the suspension and the mixture was stirred at 20° C. for 18 hours. 300 ml of water were added, and the mixture was acidified slightly with 1 N aqueous hydrochloric acid and extracted three times with ethyl acetate. The combined organic phases were dried over sodium sulfate, filtered and concentrated under reduced pressure. This gave 0.98 g (44% of theory, purity 90%) of the title compound.

LC-MS (Method 3): $R_t$=0.53 min; m/z=334 (M+H)$^+$.

$^1$H-NMR (400 MHz, DMSO-d$_6$): δ=1.21 (t, 3H), 4.18 (q, 2H), 7.05 (d, 2H), 7.38-7.45 (m, 3H), 7.54 (br. s, 1H), 8.20 (s, 1H), 11.63 (s, 1H).

Example 29A

Ethyl 1-(3-fluoro-4-{[(2-methoxyethyl)carbamoyl]amino}phenyl)-2,4-dioxo-1,2,3,4-tetrahydropyrimidine-5-carboxylate

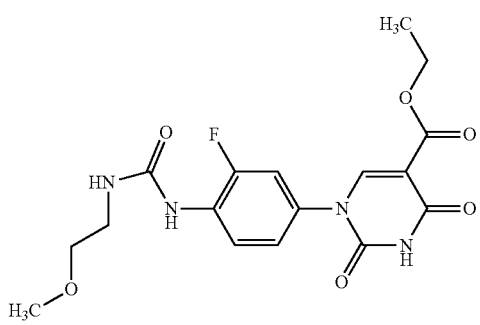 [SMILES: CCOC(=O)c1cn(-c2ccc(NC(=O)NCCOC)c(F)c2)c(=O)[nH]c1=O]

With stirring, 4 g (17.6 mmol) of 1-(4-amino-2-fluorophenyl)-3-(2-methoxyethyl)urea (Example 13A) and 4.15 g (16 mmol) of ethyl 3-ethoxy-2-[(ethoxycarbonyl)carbamoyl]acrylate in 188 ml of ethanol were heated at reflux for two hours. After cooling to 20° C., 1.8 g (16 mmol) of potassium tert-butoxide were added to the suspension and the mixture was stirred at 20° C. for 4 hours. 1 l of water was added, and the mixture was acidified slightly with 1 N aqueous hydrochloric acid. The solid was filtered off, washed with 50 ml of ethyl acetate and dried under high vacuum. This gave 4.73 g (66% of theory) of the title compound.

LC-MS (Method 3): $R_t$=0.74 min; m/z=394 (M+H)$^+$.

$^1$H-NMR (400 MHz, DMSO-d$_6$): δ=1.20 (t, 3H), 3.1-3.23 (m, 4H), 3.51 (s, 3H), 4.15 (q, 2H), 5.80-5.88 (br. t, 1H), 6.78-6.85 (m, 1H), 7.1 (d, 1H), 7.23 (m, 2H), 8.20 (s, 1H).

The following were prepared analogously to Example 29A:

Example 30A

Ethyl 1-[4-(2-hydroxyethoxy)phenyl]-2,4-dioxo-1,2,3,4-tetrahydropyrimidine-5-carboxylate

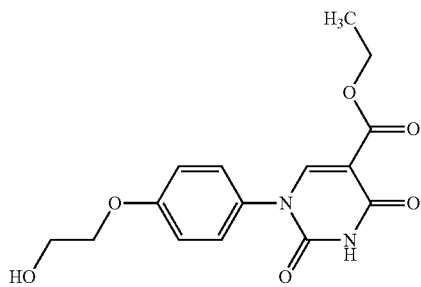 [SMILES: CCOC(=O)c1cn(-c2ccc(OCCO)cc2)c(=O)[nH]c1=O]

The preparation and purification were carried out analogously to Example 29A from 1.88 g (12.27 mmol) of 2-(4-aminophenoxy)ethanol and 2.89 g (11.16 mmol) of ethyl 3-ethoxy-2-[(ethoxycarbonyl)carbamoyl]acrylate. Yield: 2.15 g (55% of theory).

LC-MS (Method 3): $R_t$=0.59 min; m/z=321 (M+H)$^+$.

$^1$H-NMR (400 MHz, DMSO-d$_6$): δ=1.20 (t, 3H), 3.68-3.78 (m, 2H), 4.01 (m, 2H), 4.15 (q, 2H), 4.9 (t, 1H), 7.02 (d, 2H), 7.38 (d, 2H), 8.20 (s, 1H), 11.62 (s, 1H).

Example 31A

Ethyl 1-{4-[(2-hydroxyethyl)amino]phenyl}-2,4-dioxo-1,2,3,4-tetrahydropyrimidine-5-carboxylate

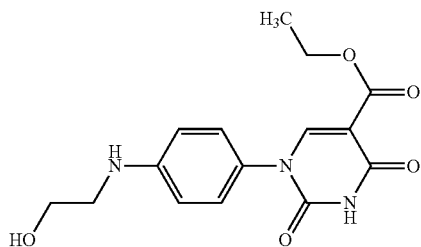 [SMILES: CCOC(=O)c1cn(-c2ccc(NCCO)cc2)c(=O)[nH]c1=O]

The preparation and purification were carried out analogously to Example 29A from 1.88 g (12.35 mmol) of 2-[(4-aminophenyl)amino]ethanol. Yield: 2.15 g (55% of theory).

LC-MS (Method 1): $R_t$=0.68 min; m/z=320 (M+H)$^+$.

$^1$H-NMR (400 MHz, DMSO-d$_6$): δ=1.20 (t, 3H), 3.05-3.16 (m, 2H), 3.54 (m, 2H), 4.12 (q, 2H), 5.9 (t, 1H), 6.60 (d, 2H), 7.10 (d, 2H), 8.12 (s, 1H), 11.5 (br. s, 1H).

Example 32A

Ethyl 2,4-dioxo-1-[4-(5-oxopyrrolidin-2-yl)phenyl]-1,2,3,4-tetrahydropyrimidine-5-carboxylate

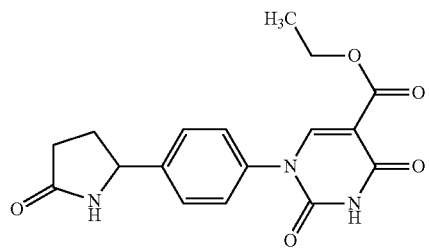 [SMILES: CCOC(=O)c1cn(-c2ccc(C3CCC(=O)N3)cc2)c(=O)[nH]c1=O]

The preparation and purification were carried out analogously to Example 29A from 1 g (5.68 mmol) of 5-(4-aminophenyl)pyrrolidin-2-one (Liebigs Ann. Chem. (1955), 596, 158). Yield: 2.16 g (82% of theory, purity: 74%).

LC-MS (Method 1): $R_t$=0.71 min; m/z=344 (M+H)$^+$.

Example 33A

Ethyl 1-{4-[1-(tert-butoxycarbonyl)-1H-pyrazol-3-yl]phenyl)-2,4-dioxo-1,2,3,4-tetrahydropyrimidine-5-carboxylate

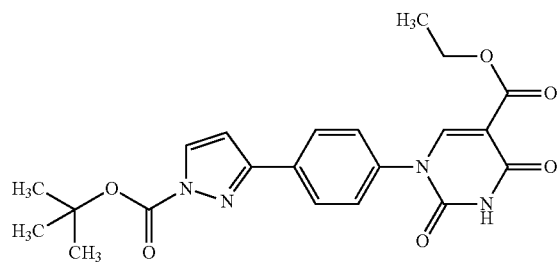 [SMILES: CCOC(=O)c1cn(-c2ccc(-c3ccn(C(=O)OC(C)(C)C)n3)cc2)c(=O)[nH]c1=O]

The preparation and purification were carried out analogously to Example 29A from 4.41 g (17 mmol) of tert-butyl 3-(4-aminophenyl)-1H-pyrazole-1-carboxylate (Example 14A). Yield: 1.97 g (13% of theory, purity: 48%).

LC-MS (Method 3): $R_t$=0.98 min; m/z=427 (M+H)$^+$.

Example 34A

Ethyl 1-{4-[5-(tert-butoxycarbonyl)-1,1-dioxido-1,2,5-thiadiazolidin-2-yl]phenyl}-2,4-dioxo-1,2,3,4-tetrahydropyrimidine-5-carboxylate

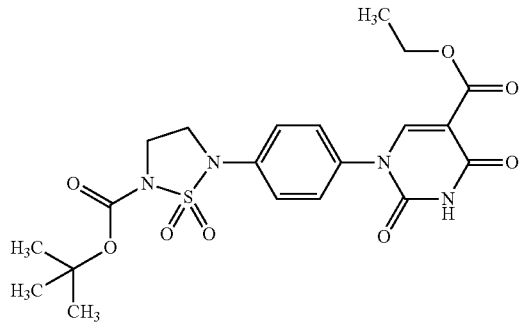 [SMILES: CCOC(=O)c1cn(-c2ccc(N3CCN(C(=O)OC(C)(C)C)S3(=O)=O)cc2)c(=O)[nH]c1=O]

The preparation and purification were carried out analogously to Example 29A from 1.11 g (3.54 mmol) of tert-butyl 5-(4-aminophenyl)-1,2,5-thiadiazolidine-2-carboxylate 1,1-dioxide (Example 12A). Yield: 0.72 g (33% of theory, purity: 79%).

LC-MS (Method 1): $R_t$=1.07 min; m/z=481 (M+H)$^+$.

$^1$H-NMR (400 MHz, DMSO-d$_6$): δ=1.22 (t, 3H), 1.50 (s, 9H), 3.90-4.00 (m, 4H), 4.16 (q, 2H), 7.45 (d, 2H), 7.58 (d, 2H), 8.30 (s, 1H), 11.70 (s, 1H).

Example 35A

Ethyl 2,4-dioxo-1-[4-(5-oxo-1,5-dihydro-4H-1,2,4-triazol-4-yl)phenyl]-1,2,3,4-tetrahydropyrimidine-5-carboxylate

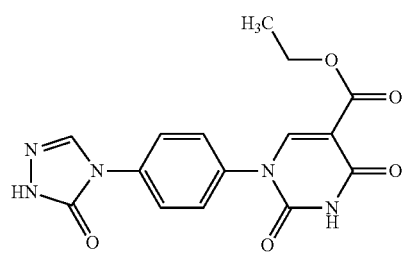 [SMILES: CCOC(=O)c1cn(-c2ccc(-n3cn[nH]c3=O)cc2)c(=O)[nH]c1=O]

The preparation and purification were carried out analogously to Example 29A from 3.37 g (12.2 mmol) of tert-butyl 4-(4-aminophenyl)-5-oxo-4,5-dihydro-1H-1,2,4-triazole-1-carboxylate (Example 11A). Yield: 1.66 g (40% of theory, purity: 72%).

LC-MS (Method 3): $R_t$=0.5 min; m/z=344 (M+H)$^+$.

Example 36A

Ethyl 1-(4-azidophenyl)-2,4-dioxo-1,2,3,4-tetrahydropyrimidine-5-carboxylate

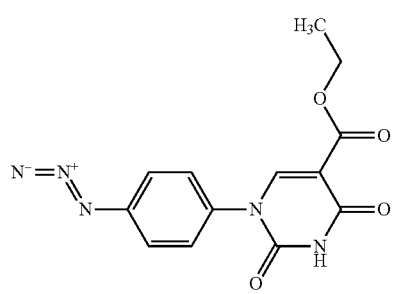 [SMILES: CCOC(=O)c1cn(-c2ccc(N=[N+]=[N-])cc2)c(=O)[nH]c1=O]

The preparation and purification were carried out analogously to Example 29A from 4 g (23.5 mmol) of 4-azidoaniline. Yield: 7.90 g (100% of theory, purity: 90%).

LC-MS (Method 3): $R_t$=0.80 min; m/z=302 (M+H)$^+$.

$^1$H-NMR (400 MHz, DMSO-d$_6$): δ=1.22 (t, 3H), 4.19 (q, 2H), 7.26 (d, 2H), 7.52 (d, 2H), 8.28 (s, 1H), 11.70 (s, 1H).

Example 37A

Ethyl 2,4-dioxo-1-[4-(2-oxo-1,3-oxazinan-3-yl)phenyl]-1,2,3,4-tetrahydropyrimidine-5-carboxylate

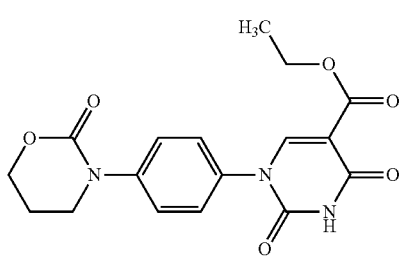 [SMILES: CCOC(=O)c1cn(-c2ccc(N3CCCOC3=O)cc2)c(=O)[nH]c1=O]

The preparation and purification were carried out analogously to Example 29A from 2.16 g (11.24 mmol) of 3-(4-aminophenyl)-1,3-oxazinan-2-one (WO 2009/064835, p. 85). Yield: 2.06 g (41% of theory, purity: 80%).

LC-MS (Method 1): $R_t$=0.68 min; m/z=360 (M+H)$^+$.

$^1$H-NMR (400 MHz, DMSO-d$_6$): δ=1.21 (t, 3H), 2.08-2.17 (m, 2H), 3.67-3.72 (m, 2H), 4.17 (q, 2H), 4.33-4.39 (m, 2H), 7.50 (s, 4H), 8.30 (s, 1H), 11.70 (s, 1H).

Example 38A

Ethyl 1-(4-methoxyphenyl)-2,4-dioxo-1,2,3,4-tetrahydropyrimidine-5-carboxylate

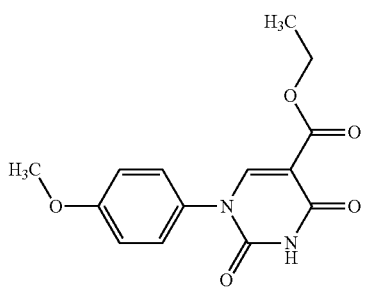 [SMILES: CCOC(=O)c1cn(-c2ccc(OC)cc2)c(=O)[nH]c1=O]

5.00 g (17.0 mmol) of diethyl {[(4-methoxyphenyl)amino]methylene}malonate (prepared according to Bioorg. Med. Chem. Lett., 16(4) 1010-1013; 2006) and 2.65 g (18.8 mmol) of chlorosulfonyl isocyanate in 30 ml of toluene were stirred in a microwave apparatus (CEM Discover, initial irradiation power 200 W, target temperature 120° C.) for 45 min. After concentration, the crude mixture was separated by chromatography on silica gel using dichloromethane/methanol mixtures with increasing methanol content (50:1-30:1-10:1). This gave, after concentration and drying of the appropriate fractions under reduced pressure, 1.14 g (23% of theory) of the target compound.

LC-MS (Method 1): $R_t$=0.86 min; m/z=291 (M+H)$^+$.

$^1$H-NMR (400 MHz, DMSO-d$_6$): δ=1.22 (t, 3H), 3.80 (s, 3H), 4.17 (q, 2H), 7.01-7.07 (m, 2H), 7.38-7.44 (m, 2H), 8.22 (s, 1H), 11.63 (br. s, 1H).

Example 39A

Ethyl 1-(3,4-dimethoxyphenyl)-2,4-dioxo-1,2,3,4-tetrahydropyrimidine-5-carboxylate

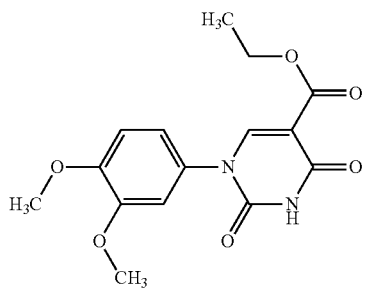 [SMILES: CCOC(=O)c1cn(-c2ccc(OC)c(OC)c2)c(=O)[nH]c1=O]

1 g (6.53 mmol) of 3,4-dimethoxyaniline and 1.54 g (5.9 mmol) of ethyl 3-ethoxy-2-[(ethoxycarbonyl)carbamoyl]acrylate in 20 ml of ethanol were heated at reflux for one hour and then concentrated under reduced pressure. 0.5 g of the resulting residue in 40 ml of ethanol was stirred with 0.153 g of potassium tert-butoxide at 20° C. for two hours, 100 ml of water were added, and the mixture was acidified with 1N aqueous hydrochloric acid and extracted three times with ethyl acetate. The combined organic phases were dried over sodium sulfate, filtered, concentrated under reduced pressure and dried under high vacuum. This gave 262 mg (60% of theory) of the target compound.

LC-MS (Method 1): $R_t$=0.78 min; m/z=321 (M+H)$^+$.

$^1$H-NMR (400 MHz, DMSO-d$_6$): δ=1.21 (t, 3H), 3.75 (s, 3H), 3.80 (s, 3H), 4.19 (q, 2H), 6.98-7.08 (m, 2H), 7.12 (d, 1H), 8.20 (s, 1H), 11.61 (s, 1H).

Example 40A

Diethyl {[(4-ethoxyphenyl)amino]methylene}malonate

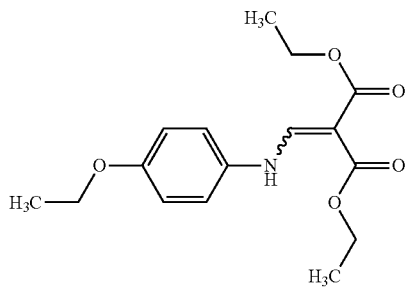 [SMILES: CCOC(=O)C(=CNc1ccc(OCC)cc1)C(=O)OCC]

With stirring, 20 g (145.8 mmol) of 4-ethoxyaniline and 31.53 g (145.8 mmol) of diethyl 2-(ethoxymethylene)malonate were heated at reflux for 18 hours. The reaction was cooled to 20° C. and concentrated under reduced pressure, and the residue was taken up in ethyl acetate, applied to silica gel, concentrated under reduced pressure and then purified by flash chromatography eluting with a cyclohexane/ethyl acetate mixture (5:1). The product-containing fractions were combined and concentrated. This gave 41.8 g (93% of theory) of the title compound.

LC-MS (Method 2): $R_t$=2.4 min; m/z=308 (M+H)$^+$.

¹H-NMR (400 MHz, DMSO-d₆): δ=1.19-1.28 (m, 6H), 1.3 (t, 3H), 4.0 (q, 2H), 4.1 (q, 2H), 4.18 (q, 2H), 7.92 (d, 2H), 7.30 (d, 2H), 8.3 (d, 1H), 10.70 (d, 1H).

Example 41A

Ethyl 1-(4-ethoxyphenyl)-2,4-dioxo-1,2,3,4-tetrahydropyrimidine-5-carboxylate

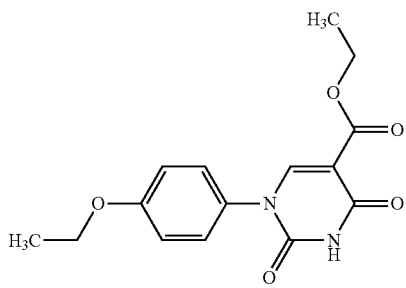 [SMILES: CCOC(=O)c1cn(-c2ccc(OCC)cc2)c(=O)[nH]c1=O]

21.19 g of chlorosulfonyl isocyanate were added to 41.83 g (136.1 mmol) of diethyl {[(4-ethoxyphenyl)amino]methylene}malonate from Example 40A in 200 ml of toluene, and the mixture was stirred at 120° C. for 19 hours. The reaction was cooled to 20° C., concentrated under reduced pressure and then purified by flash chromatography eluting with an ethyl acetate/methanol mixture (100:0, then 20:1). The product-containing fractions were combined and concentrated. This gave 15.23 g (37% of theory) of the title compound.

LC-MS (Method 2): $R_t$=1.74 min; m/z=305 (M+H)⁺.
¹H-NMR (400 MHz, DMSO-d₆): δ=1.20 (t, 3H), 1.32 (t, 3H), 4.08 (q, 2H), 4.17 (q, 2H), 7.01 (d, 2H), 7.40 (d, 2H), 8.22 (s, 1H).

Example 42A

Ethyl 1-(4-azidophenyl)-3-[2-methyl-3-(trifluoromethyl)benzyl]-2,4-dioxo-1,2,3,4-tetrahydropyrimidine-5-carboxylate

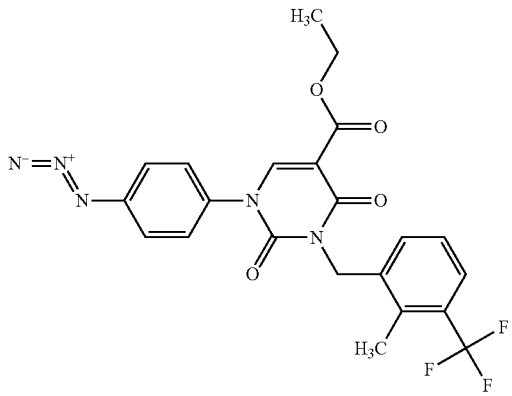 [SMILES: CCOC(=O)c1cn(-c2ccc(N=[N+]=[N-])cc2)c(=O)n(Cc2cccc(C(F)(F)F)c2C)c1=O]

The preparation was carried out analogously to Example 3 from 7.9 g (26.2 mmol) of ethyl 1-(4-azidophenyl)-2,4-dioxo-1,2,3,4-tetrahydropyrimidine-5-carboxylate from Example 36A and 6.6 g (26.2 mmol) of 2-methyl-3-(trifluoromethyl)benzyl bromide. Yield: 8.07 g (61% of theory, purity: 93%).

LC-MS (Method 1): $R_t$=1.42 min; m/z=474 (M+H)⁺.

¹H-NMR (400 MHz, DMSO-d₆): δ=1.22 (t, 1H), 2.45 (s, 3H), 4.18 (q, 2H), 5.05 (s, 2H), 7.28 (d, 2H), 7.30-7.40 (m, 2H), 7.55-7.62 (m, 3H), 8.42 (s, 1H).

Example 43A 1-(4-Azidophenyl)-3-[2-methyl-3-(trifluoromethyl)benzyl]-2,4-dioxo-1,2,3,4-tetrahydropyrimidine-5-carboxylic acid

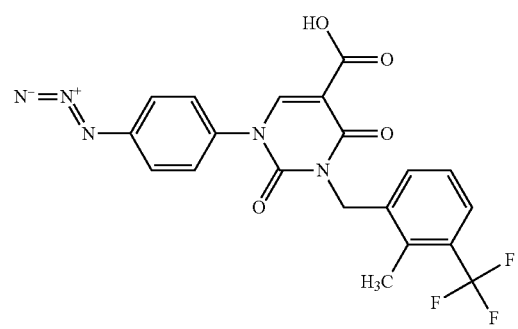 [SMILES: Cc1c(Cn2c(=O)c(C(=O)O)cn(-c3ccc(N=[N+]=[N-])cc3)c2=O)cccc1C(F)(F)F]

8.07 g (17 mmol) of ethyl 1-(4-azidophenyl)-3-[2-methyl-3-(trifluoromethyl)benzyl]-2,4-dioxo-1,2,3,4-tetrahydropyrimidine-5-carboxylate from Example 42A in 240 ml of glacial acetic acid/conc. hydrochloric acid 2:1 were heated at 60° C. for 6 h. The mixture was diluted with 700 ml of water. The solid formed was filtered off with suction, stirred with acetonitrile, once more filtered off with suction and then dried under high vacuum. This gave 4.97 g (62% of theory, purity 94%) of the title compound.

LC-MS (Method 1): $R_t$=1.37 min; m/z=446 (M+H)⁺.
¹H-NMR (400 MHz, DMSO-d₆): δ=2.45 (s, 3H), 5.10 (s, 2H), 7.29 (d, 2H), 7.30-7.42 (m, 2H), 7.55-7.63 (m, 3H), 8.45 (s, 1H), 12.72 (br. s, 1H).

Example 44A

1-Chloro-3-(chloromethyl)-2-[(2-nitrophenyl)disulfanyl]benzene

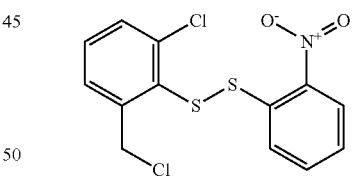

30.66 g (93.5 mmol) of {3-chloro-2-[(2-nitrophenyl)disulfanyl]phenyl}methanol in 361 ml of toluene together with 23.37 g (196.4 mmol) of thionyl chloride and a drop of DMF were heated at reflux for four hours. After addition of a further molar equivalent of thionyl chloride, the mixture was heated at reflux for another four hours and, after cooling to 20° C., concentrated under reduced pressure. Chromatography on silica gel (mobile phase: dichloromethane) gave 5.75 g of a mixture of the title compound and the dimer 1,1'-disulfanediylbis[2-chloro-6-(chloromethyl)benzene] in a ratio of 53:26. The mixture was directly reacted further.

DCI-MS (NH₃): m/z=363 (M+NH₄)⁺.
¹H-NMR (400 MHz, DMSO-d₆): δ=4.98 (s, 2H), 7.48 (t, 1H), 7.52-7.65 (m, 3H), 7.9 (t, 1H), 8.18 (d, 1H), 8.36 (d, 1H).

Example 45A

Ethyl 3-{3-chloro-2-[(2-nitrophenyl)disulfanyl]benzyl}-1-(3,4-dimethoxyphenyl)-2,4-dioxo-1,2,3,4-tetrahydropyrimidine-5-carboxylate

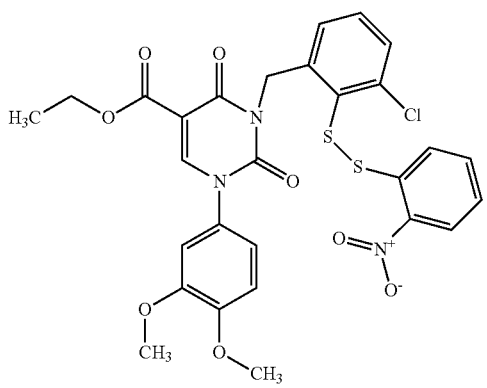 [SMILES: CCOC(=O)c1cn(-c2ccc(OC)c(OC)c2)c(=O)n(Cc2cccc(Cl)c2SSc2ccccc2[N+](=O)[O-])c1=O]

1.47 g of the mixture of 1-chloro-3-(chloromethyl)-2-[(2-nitrophenyl)disulfanyl]benzene and 1,1'-disulfanediylbis[2-chloro-6-(chloromethyl)benzene] from Example 44A (3.25 mmol, purity: 76.7%), 1.8 g (13 mmol) of potassium carbonate and 1.08 g (6.51 mmol) of potassium iodide were added to 1.04 g (3.25 mmol) of ethyl 1-(3,4-dimethoxyphenyl)-2,4-dioxo-1,2,3,4-tetrahydropyrimidine-5-carboxylate from Example 39A in 28.3 ml of acetonitrile, and the mixture was stirred at 60° C. for 2 h. The mixture was concentrated under reduced pressure, the residue was taken up in 50 ml of water and the mixture was extracted three times with ethyl acetate. The combined extracts were dried and then concentrated under reduced pressure. This gave 2.33 g of a mixture of the title compound and diethyl 3,3'-{disulfanediylbis[(3-chlorobenzene-2,1-diyl)methylene]}bis[1-(3,4-dimethoxyphenyl)-2,4-dioxo-1,2,3,4-tetrahydropyrimidine-5-carboxylate, which was reacted further as a crude product.

LC-MS (Method 1): $R_t$=1.40 min mit m/z=630 (M+H)$^+$ und $R_t$=1.43 min mit m/z=951 (M+H)$^+$.

Example 46A

1-[4-(Methylsulfanyl)phenyl]-2,4-dioxo-3-[3-(trifluoromethyl)benzyl]-1,2,3,4-tetrahydropyrimidine-5-carboxylic acid

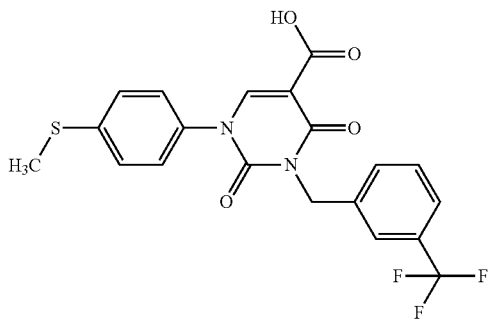 [SMILES: CSc1ccc(-n2cc(C(=O)O)c(=O)n(Cc3cccc(C(F)(F)F)c3)c2=O)cc1]

In a mixture of 8.2 ml of glacial acetic acid and 4.1 ml of conc. hydrochloric acid, 483.1 mg (about 0.944 mmol) of ethyl 1-[4-(methylsulfanyl)phenyl]-2,4-dioxo-3-[3-(trifluoromethyl)benzyl]-1,2,3,4-tetrahydropyrimidine-5-carboxylate from Example 26A were heated at 70° C. for 1.5 h, and the mixture was then allowed to cool to RT and diluted with 100 ml of water. The solid formed was filtered off, washed with water and dried under high vacuum. This gave 383 mg (85% of theory, purity 92%) of the title compound.

LC-MS (Method 1): $R_t$=1.32 min; m/z=437 (M+H)$^+$.
$^1$H-NMR (400 MHz, DMSO-d$_6$): δ=2.52 (s, 3H), 5.10 (s, 2H), 7.38 (d, 2H), 7.45 (d, 2H), 7.58 (t, 1H), 7.61-7.68 (m, 2H), 7.72 (s, 1H), 8.38 (s, 1H), 12.70 (br. s, 1H).

Example 47A

1-[2-Chloro-3-(trifluoromethyl)benzyl]urea

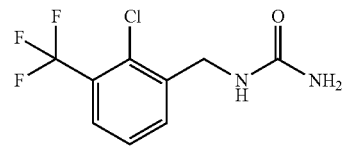 [SMILES: NC(=O)NCc1cccc(C(F)(F)F)c1Cl]

At RT, 4.00 g (19.2 mmol) of 2-chloro-3-(trifluoromethyl)benzaldehyde and 23.0 g (383.6 mmol) of urea were initially charged in 250 ml of acetic acid, and 2.50 g (2.92 ml, 23.0 mmol) of chlorotrimethylsilane were added. The mixture was stirred at RT for 1 h, 871 mg (23.0 mmol) of sodium borohydride were then added and stirring was continued overnight. Since, according to HPLC, the reaction was still incomplete, another 581 mg (15.4 mmol) of sodium borohydride were added and the reaction was stirred at RT for another 2 h. The reaction mixture was concentrated to a residual volume of about 100 ml on a rotary evaporator and then poured into 600 ml of an ice/water mixture. The solid formed was isolated by filtration, washed twice with water and twice with diethyl ether and then dried under high vacuum. This gave 3.91 g (79% of theory) of the title compound.

LC/MS (Method 3): $R_t$=0.79 min; m/z=253 (M+H)$^+$
$^1$H-NMR (400 MHz, DMSO-d$_6$): δ [ppm]=4.31 (d, 2H), 5.71 (s, 2H), 6.57 (t, 1H), 7.52-7.59 (m, 1H), 7.60-7.66 (m, 1H), 7.76 (d, 1H).

Example 48A

1-[2-Methyl-3-(trifluoromethyl)benzyl]urea

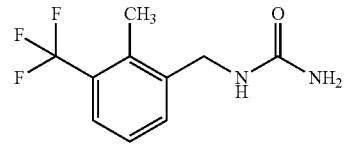 [SMILES: Cc1c(CNC(N)=O)cccc1C(F)(F)F]

Analogously to Example 47A, 10.00 g (53.1 mmol) of 2-methyl-3-(trifluoromethyl)benzaldehyde and 63.8 g (1.06 mol) of urea gave 10.18 g of the title compound (73% of theory, purity about 89%).

LC/MS (Method 3): $R_t$=0.78 min; m/z=233 (M+H)$^+$ $^1$H-NMR (400 MHz, DMSO-d$_6$): δ [ppm]=2.36 (s, 3H), 4.24 (d, 2H), 5.57 (s, 2H), 6.42 (t, 1H), 7.37 (t, 1H), 7.51 (d, 1H), 7.57 (d, 1H).

Example 49A 1-(2,3-Dichlorobenzyl)urea

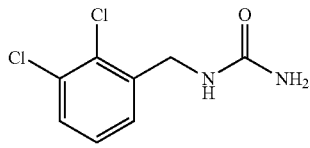 [SMILES: NC(=O)NCc1cccc(Cl)c1Cl]

Analogously to Example 47A, 4.00 g (22.9 mmol) of 2,3-dichlorobenzaldehyde gave 3.50 g of the title compound (49% of theory, purity 70%).

LC/MS (Method 3): R$_t$=0.74 min; m/z=219 (M+H)$^+$ $^1$H-NMR (400 MHz, DMSO-d$_6$): δ [ppm]=4.26 (d, 2H), 5.67 (s, 2H), 6.54 (t, 1H), 7.30 (d, 1H), 7.36 (t, 1H), 7.53 (d, 1H).

Example 50A

Ethyl 3-[2-chloro-3-(trifluoromethyl)benzyl]-2,4-dioxo-1,2,3,4-tetrahydropyrimidine-5-carboxylate

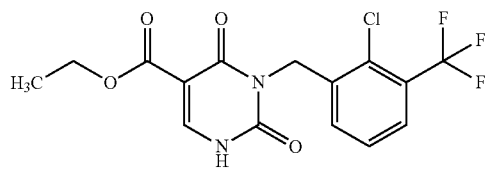 [SMILES: CCOC(=O)c1c[nH]c(=O)n(Cc2cccc(C(F)(F)F)c2Cl)c1=O]

A mixture of 3.9 g (15.5 mmol) of the compound from Example 47A and 6.7 g (31.0 mmol) of diethyl (ethoxymethylene)malonate was heated to 140° C. (bath temperature). After 10 h, the heating bath was removed and the mixture was allowed to cool. First 31 ml of ethanol and then 2.11 g (31 mmol) of sodium ethoxide were added. The mixture was heated and stirred at reflux for 1.5 h. After cooling to RT, the reaction content was added dropwise to 400 ml of ice-cooled 0.5 N aqueous hydrochloric acid. The solid formed was filtered off and washed with water and cyclohexane. It was then dissolved in 100 ml of a mixture of dichloromethane/methanol 10:1, this solution was dried over sodium sulfate and the solvents were removed on a rotary evaporator. The residue was stirred in 50 ml of diethyl ether for 1 h. The solid was filtered off, washed with a little diethyl ether and dried under high vacuum. This gave 3.09 g (50% of theory) of the title compound.

LC/MS (Method 1): R$_t$=1.12 min; m/z=377 (M+H)$^+$ $^1$H-NMR (400 MHz, DMSO-d$_6$): δ [ppm]=1.24 (t, 3H), 4.18 (q, 2H), 5.06 (s, 2H), 7.37 (d, 1H), 7.49 (t, 1H), 7.79 (d, 1H), 8.28 (s, 1H), 12.14 (s, 1H).

Example 51A

Ethyl 3-[2-methyl-3-(trifluoromethyl)benzyl]-2,4-dioxo-1,2,3,4-tetrahydropyrimidine-5-carboxylate

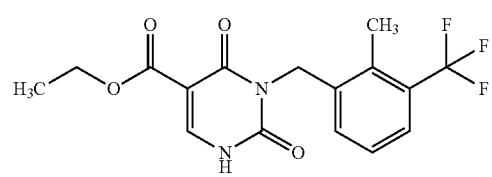 [SMILES: CCOC(=O)c1c[nH]c(=O)n(Cc2cccc(C(F)(F)F)c2C)c1=O]

A mixture of 10.18 g (43.8 mmol) of the compound from Example 48A and 23.7 g (109.6 mmol) of diethyl (ethoxymethylene)malonate was heated to 140° C. (bath temperature). After 6 h, the heating bath was removed and the mixture was allowed to cool. First 90 ml of ethanol and then 7.46 g (109.6 mmol) of sodium ethoxide were added, and the mixture was heated and, at reflux, stirred for another 1.5 h. After cooling to RT, the reaction content was added dropwise to 1 l of ice-cooled 0.5 N aqueous hydrochloric acid, resulting in the formation of a solid. The mixture was extracted three times with dichloromethane. The combined organic phases were dried over sodium sulfate and the solvent was removed on a rotary evaporator. The residue was stirred in 200 ml of diethyl ether for 1 h. The solid was filtered off, washed with a little diethyl ether and dried under high vacuum. This gave 15.6 g (59% of theory) of the title compound.

LC/MS (Method 3): R$_t$=0.95 min; m/z=357 (M+H)$^+$ $^1$H-NMR (400 MHz, DMSO-d$_6$): δ [ppm]=1.24 (t, 3H), 2.45 (s, 3H), 4.18 (q, 2H), 5.00 (s, 2H), 7.18 (d, 1H), 7.31 (t, 1H), 7.58 (d, 1H), 8.24-8.28 (m, 1H), 12.09 (d, 1H).

Example 52A

Ethyl 3-(2,3-dichlorobenzyl)-2,4-dioxo-1,2,3,4-tetrahydropyrimidine-5-carboxylate

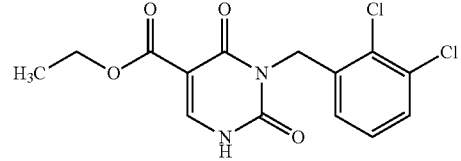 [SMILES: CCOC(=O)c1c[nH]c(=O)n(Cc2cccc(Cl)c2Cl)c1=O]

A mixture of 3.50 g (11.2 mmol, purity 70%) of the compound from Example 49A and 3.6 g (16.8 mmol) of diethyl (ethoxymethylene)malonate was heated to 140° C. (bath temperature). The mixture remained solid and unstirrable, even after addition of an additional 4.84 g (22.4 mmol) of diethyl (ethoxymethylene)malonate. At 140° C., 8 ml of polyethylene glycol were added, giving a stirrable suspension. After 10 h, the heating bath was removed and the mixture was allowed to cool. First 30 ml of ethanol and then 1.90 g (28.0 mmol) of sodium ethoxide were added, and the mixture was heated once more and, at reflux, stirred for another 1.5 h. After cooling to RT, the reaction content was added dropwise to 400 ml of ice-cooled 0.5 N aqueous hydrochloric acid. The mixture was extracted three times with dichloromethane. The combined organic phases were dried over sodium sulfate and the solvent was removed on a rotary evaporator. The residue was stirred in 30 ml of diethyl ether for 1 h. The solid was filtered off, washed with a little diethyl ether and dried under high vacuum. This gave 1.70 g (43% of theory) of the title compound.

LC/MS (Method 3): $R_t$=0.92 min; m/z=343 (M+H)$^+$ $^1$H-NMR (400 MHz, DMSO-d$_6$): δ [ppm]=1.24 (t, 3H), 4.18 (q, 2H), 5.02 (s, 2H), 7.01 (d, 1H), 7.29 (t, 1H), 7.57 (d, 1H), 8.27 (d, 1H), 12.12 (d, 1H).

Example 53A

Ethyl 1-[4-(tert-butoxycarbonyl)phenyl]-3-[2-chloro-3-(trifluoromethyl)benzyl]-2,4-dioxo-1,2,3,4-tetrahydropyrimidine-5-carboxylate

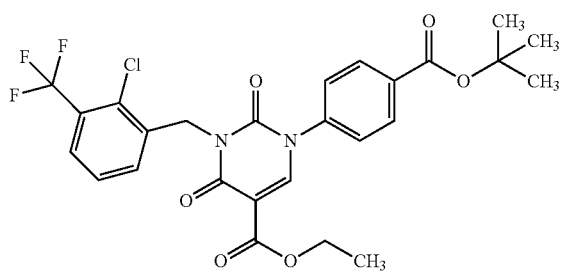 [SMILES: CCOC(=O)c1cn(-c2ccc(C(=O)OC(C)(C)C)cc2)c(=O)n(Cc2cccc(C(F)(F)F)c2Cl)c1=O]

A mixture of 286 mg (0.76 mmol) of the compound from Example 50A, 252 mg (1.14 mmol) of [4-(tert-butoxycarbonyl)phenyl]boronic acid, 207 mg (1.14 mmol) of copper (II) acetate, 184 (2.27 mmol) of pyridine and 675 mg of molecular sieve 3 Å in 8.1 ml of dichloromethane was, exposed to the air, stirred at RT for about 40 h and then filtered through kieselguhr. The filtrate was concentrated on a rotary evaporator and the residue was purified by preparative HPLC (Method 7b). This gave 260 mg (60% of theory) of the title compound.

LC/MS (Method 3): $R_t$=1.34 min; m/z=553 (M+H)$^+$ $^1$H-NMR (400 MHz, DMSO-d$_6$): δ [ppm]=1.24 (t, 3H), 1.57 (s, 9H), 4.21 (q, 2H), 5.14 (s, 2H), 7.52 (t, 1H), 7.61 (d, 1H), 7.68 (d, 2H), 7.80 (d, 1H), 8.04 (d, 2H), 8.51 (s, 1H).

Example 54A

Ethyl 1-[4-(tert-butoxycarbonyl)phenyl]-3-[2-methyl-3-(trifluoromethyl)benzyl]-2,4-dioxo-1,2,3,4-tetrahydropyrimidine-5-carboxylate

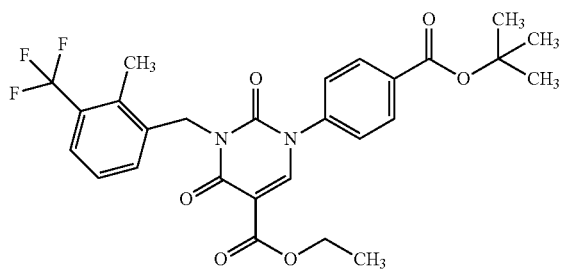 [SMILES: CCOC(=O)c1cn(-c2ccc(C(=O)OC(C)(C)C)cc2)c(=O)n(Cc2cccc(C(F)(F)F)c2C)c1=O]

Analogously to Example 53A, 200 mg (0.56 mmol) of the compound from Example 51A and 187 mg (0.84 mmol) of [4-(tert-butoxycarbonyl)phenyl]boronic acid gave 163 mg (55% of theory) of the title compound.

LC/MS (Method 3): $R_t$=1.33 min; m/z=533 (M+H)$^+$ $^1$H-NMR (400 MHz, DMSO-d$_6$): δ [ppm]=1.24 (t, 3H), 1.57 (s, 9H), 2.46 (s, 3H), 4.21 (q, 2H), 5.08 (s, 2H), 7.31-7.37 (m, 1H), 7.38-7.43 (m, 1H), 7.60 (d, 1H), 7.68 (d, 2H), 8.04 (d, 2H), 8.48 (s, 1H).

Example 55A

Ethyl 1-[4-(tert-butoxycarbonyl)phenyl]-3-(2,3-dichlorobenzyl)-2,4-dioxo-1,2,3,4-tetrahydropyrimidine-5-carboxylate

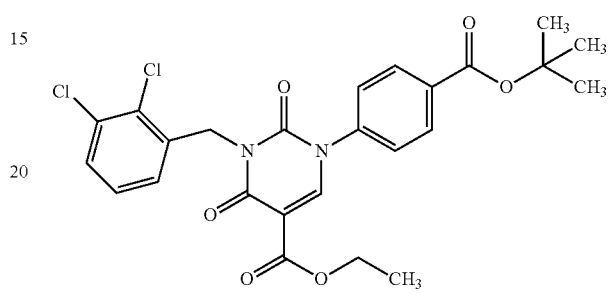

Analogously to Example 53A, 260 mg (0.76 mmol) of the compound from Example 52A gave 232 mg (59% of theory) of the title compound (purified according to Method 8 instead of Method 7b).

LC/MS (Method 3): $R_t$=1.32 min; m/z=519 (M+H)$^+$ $^1$H-NMR (400 MHz, DMSO-d$_6$): δ [ppm]=1.21-1.27 (m, 3H), 1.57 (s, 9H), 4.21 (q, 2H), 5.10 (s, 2H), 7.22-7.28 (m, 1H), 7.28-7.37 (m, 1H), 7.58 (d, 1H), 7.68 (d, 2H), 8.04 (d, 2H), 8.49 (s, 1H).

Example 56A

4-{3-[2-Chloro-3-(trifluoromethyl)benzyl]-5-(ethoxycarbonyl)-2,4-dioxo-3,4-dihydropyrimidin-1 (2H)-yl}benzoic acid

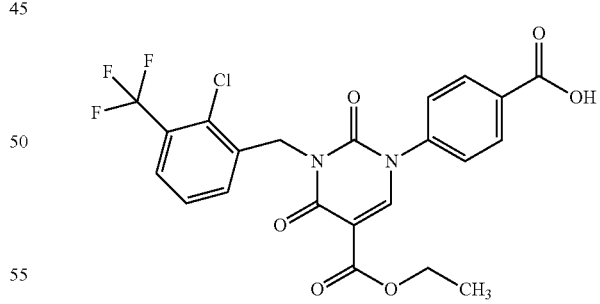

260 mg (0.46 mmol) of the compound from Example 53A were dissolved in 11.4 ml of a dichloromethane/trifluoroacetic acid mixture (1:1 v/v) and stirred at RT for 1 h. The volatile components were removed on a rotary evaporator and the oily residue was stirred with a little diethyl ether, resulting in the formation of a solid. The diethyl ether was removed on a rotary evaporator and the product was dried under high vacuum. This gave 214 mg (90% of theory) of the title compound.

LC/MS (Method 1): $R_t$=1.23 min; m/z=497 (M+H)$^+$

Example 57A

4-{3-[2-Methyl-3-(trifluoromethyl)benzyl]-5-(ethoxycarbonyl)-2,4-dioxo-3,4-dihydropyrimidin-1(2H)-yl}benzoic acid

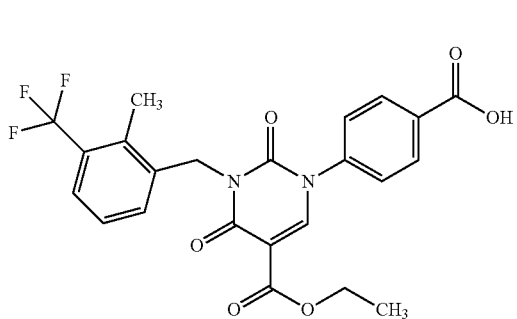 [SMILES: CCOC(=O)c1cn(-c2ccc(C(=O)O)cc2)c(=O)n(Cc2cccc(C(F)(F)F)c2C)c1=O]

Analogously to Example 56A, 220 mg (0.31 mmol) of the compound from Example 54A were treated with trifluoroacetic acid in dichloromethane. The solid which was formed by addition of ether was filtered off, washed with ether and dried under high vacuum. This gave 153 mg (78% of theory) of the title compound.

LC/MS (Method 3): $R_t$=1.01 min; m/z=477 (M+H)$^+$ $^1$H-NMR (400 MHz, DMSO-d$_6$): δ [ppm]=1.24 (t, 3H), 2.46 (s, 3H), 4.21 (q, 2H), 5.08 (s, 2H), 7.30-7.38 (m, 1H), 7.38-7.44 (m, 1H), 7.60 (d, 1H), 7.69 (s, 2H), 8.09 (s, 2H), 8.51 (s, 1H), 13.25 (br. s, 1H).

Example 58A

4-[3-(2,3-Dichlorobenzyl)-5-(ethoxycarbonyl)-2,4-dioxo-3,4-dihydropyrimidin-1(2H)-yl]benzoic acid

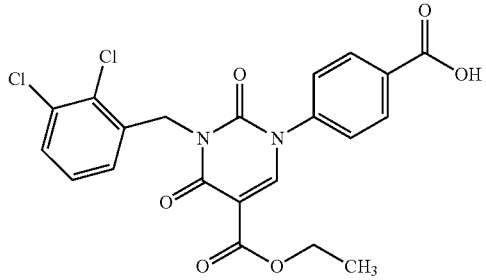 [SMILES: CCOC(=O)c1cn(-c2ccc(C(=O)O)cc2)c(=O)n(Cc2cccc(Cl)c2Cl)c1=O]

Analogously to Example 56A, 232 mg (0.45 mmol) of the compound from Example 55A gave 202 mg (97% of theory) of the title compound.

LC/MS (Method 1): $R_t$=1.19 min; m/z=463 (M+H)$^+$

Example 59A

Ethyl 3-[2-chloro-3-(trifluoromethyl)benzyl]-1-[4-(hydrazinocarbonyl)phenyl]-2,4-dioxo-1,2,3,4-tetrahydropyrimidine-5-carboxylate

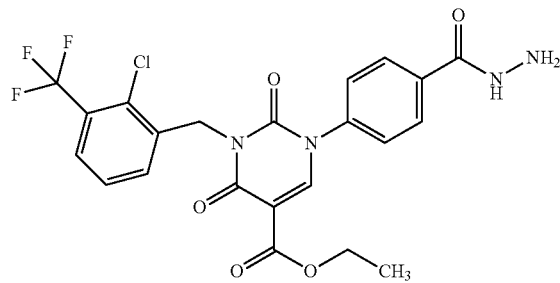 [SMILES: CCOC(=O)c1cn(-c2ccc(C(=O)NN)cc2)c(=O)n(Cc2cccc(C(F)(F)F)c2Cl)c1=O]

At RT, 105 mg (0.55 mmol) of EDC and 74 mg (0.55 mmol) of HOBt were added to a suspension of 210 mg (0.42 mmol) of the compound from Example 56A in 3 ml of acetonitrile, and the mixture was stirred at RT for 20 min. The resulting solution was cooled to 0° C., and 25 µl (0.51 mmol) of hydrazine hydrate were added. The reaction mixture was stirred at RT for a further 1 h, 30 ml of water were then added and the mixture was extracted three times with dichloromethane. The combined organic phases were dried over sodium sulfate and concentrated on a rotary evaporator. The residue was purified by preparative HPLC (Method 7a). This gave 137 mg (55% of theory, purity 87%) of the title compound.

LC/MS (Method 3): $R_t$=0.90 min; m/z=511 (M+H)$^+$

Example 60A

Ethyl 3-[2-methyl-3-(trifluoromethyl)benzyl]-1-[4-(hydrazinocarbonyl)phenyl]-2,4-dioxo-1,2,3,4-tetrahydropyrimidine-5-carboxylate

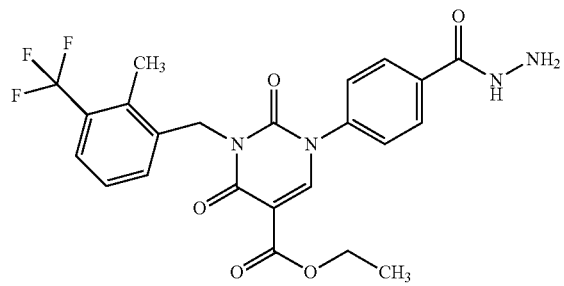

75 mg (0.40 mmol) of EDC and 53 mg (0.40 mmol) of HOBt were added to a suspension of 145 mg (0.30 mmol) of the compound from Example 57A in 3 ml of acetonitrile, and the mixture was stirred at RT for 20 min. The resulting solution was cooled to 0° C., and 18 al (0.37 mmol) of hydrazine hydrate were added. The reaction mixture was stirred at RT for a further 1 h, and 30 ml of water were then added. The solid formed was filtered off, washed with water, and dried in a vacuum drying cabinet at 50° C. This gave 138 mg (92% of theory) of the title compound.

LC/MS (Method 3): $R_t$=0.93 min; m/z=491 (M+H)$^+$

¹H-NMR (400 MHz, DMSO-d₆): δ [ppm]=1.24 (t, 3H), 2.46 (s, 3H), 4.20 (q, 2H), 4.55 (br. s., 2H), 5.08 (s, 2H), 7.30-7.42 (m, 2H), 7.60 (d, 1H), 7.63 (d, 2H), 7.95 (d, 2H), 8.48 (s, 1H), 9.91 (br. s, 1H).

Example 61A

Ethyl 3-(2,3-dichlorobenzyl)-1-[4-(hydrazinocarbonyl)phenyl]-2,4-dioxo-1,2,3,4-tetrahydropyrimidine-5-carboxylate

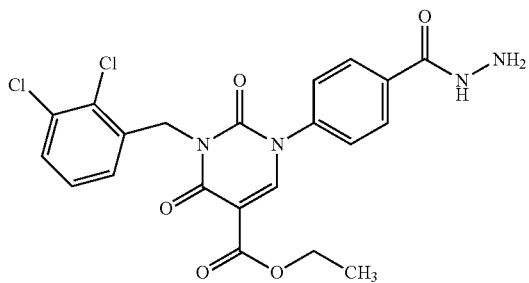 [SMILES: CCOC(=O)c1cn(-c2ccc(C(=O)NN)cc2)c(=O)n(Cc2cccc(Cl)c2Cl)c1=O]

Analogously to Example 59A, 200 mg (0.43 mmol) of the compound from Example 58A and 25 µl (0.51 mmol) of hydrazine hydrate gave 127 mg (60% of theory) of the title compound.

LC/MS (Method 3): R$_t$=0.86 min; m/z=477 (M+H)⁺

Example 62A

Ethyl 1-(4-cyanophenyl)-3-[2-methyl-3-(trifluoromethyl)benzyl]-2,4-dioxo-1,2,3,4-tetrahydropyrimidine-5-carboxylate

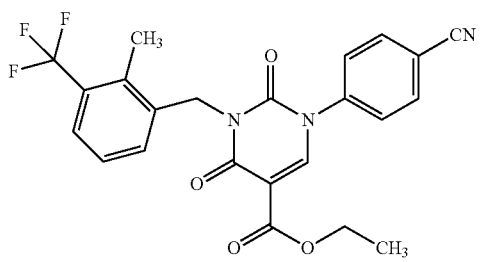 [SMILES: CCOC(=O)c1cn(-c2ccc(C#N)cc2)c(=O)n(Cc2cccc(C(F)(F)F)c2C)c1=O]

A mixture of 1.00 g (2.81 mmol) of the compound from Example 51A, 824 mg (5.6 mmol) of 4-cyanophenylboronic acid, 765 mg (4.21 mmol) of copper(II) acetate, 681 µl (8.42 mmol) of pyridine and 2.5 g mg of molecular sieve 3 Å in 30 ml of dichloromethane was, exposed to the air, stirred at RT for about 40 h. The reaction mixture was diluted with ethyl acetate and washed twice with 1M aqueous hydrochloric acid, then once with saturated aqueous sodium bicarbonate solution and once with saturated aqueous sodium chloride solution. The organic phase was dried over sodium sulfate and freed from the solvents on a rotary evaporator. The residue in 10 ml of methanol was stirred in an ultrasonic bath. The solid was filtered off, washed with a little methanol and dried under high vacuum. This gave 1.07 g (78% of theory) of the title compound.

LC/MS (Method 3): R$_t$=1.14 min; m/z=458 (M+H)⁺

¹H-NMR (400 MHz, DMSO-d₆): δ [ppm]=1.24 (t, 3H), 2.46 (s, 3H), 4.21 (q, 2H), 5.08 (s, 2H), 7.30-7.37 (m, 1H), 7.38-7.44 (m, 1H), 7.60 (d, 1H), 7.75-7.82 (m, 2H), 8.01-8.08 (m, 2H), 8.54 (s, 1H).

Example 63A

Ethyl 1-[4-(N'-hydroxycarbamimidoyl)phenyl]-3-[2-methyl-3-(trifluoromethyl)benzyl]-2,4-dioxo-1,2,3,4-tetrahydropyrimidine-5-carboxylate

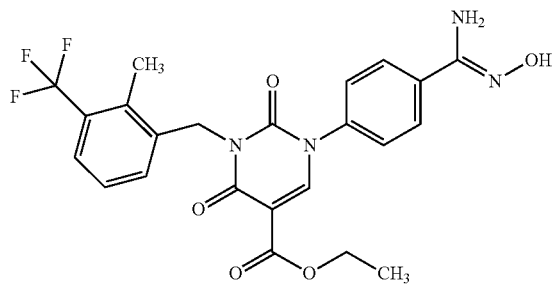 [SMILES: CCOC(=O)c1cn(-c2ccc(/C(N)=N/O)cc2)c(=O)n(Cc2cccc(C(F)(F)F)c2C)c1=O]

From 218 mg (3.14 mmol) of hydroxylamine hydrochloride in 7.8 ml of anhydrous DMSO, the base was released by addition of 430 µl (3.14 mmol) of triethylamine. After 10 min of stirring at RT, triethylamine hydrochloride was filtered off 287 mg (0.63 mmol) of the compound from Example 62A were added to the filtrate, and the mixture was stirred at 70° C. for 2 h. After cooling to RT, the reaction mixture was separated completely by preparative HPLC (Method 8). The product was dried under high vacuum. This gave 212 mg (69% of theory) of the title compound.

LC/MS (Method 1): R$_t$=1.08 min; m/z=491 (M+H)⁺
¹H-NMR (400 MHz, DMSO-d₆): δ [ppm]=1.24 (t, 3H), 2.46 (s, 3H), 4.20 (q, 2H), 5.08 (s, 2H), 5.93 (s, 2H), 7.29-7.42 (m, 2H), 7.55 (d, 2H), 7.60 (d, 1H), 7.81 (d, 2H), 8.46 (s, 1H), 9.79 (s, 1H).

Example 64A

Ethyl 1-[3-chloro-4-(2-oxo-1,3-oxazolidin-3-yl)phenyl]-2,4-dioxo-1,2,3,4-tetrahydropyrimidine-5-carboxylate

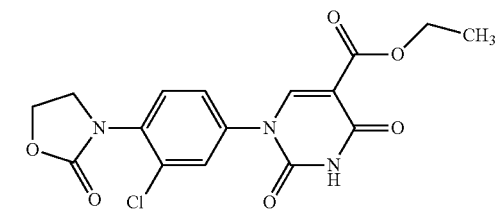 [SMILES: CCOC(=O)c1cn(-c2ccc(N3CCOC3=O)c(Cl)c2)c(=O)[nH]c1=O]

659.4 mg (3.10 mmol) of 3-(4-amino-2-chlorophenyl)-1,3-oxazolidin-2-one (described in: US2004/0087582 A1) and 804.0 mg (3.10 mmol) of ethyl 3-ethoxy-2-[(ethoxycarbonyl)carbamoyl]acrylate in 25 ml of ethanol were heated under reflux for 1.5 h. After cooling to RT, 348 mg (3.10 mmol) of potassium tert-butoxide were added and the reaction mixture was stirred first at RT for 16 h and then at reflux temperature for 2 h. For work-up, the cooled reaction mixture was acidified with 1 N aqueous hydrochloric acid and diluted with water. The mixture was concentrated on a rotary evaporator and the remaining suspension was filtered. The solid was washed with water and ethyl acetate, and dried under reduced pressure at 50° C. This gave 692.6 mg (41% of theory, purity 70%) of the title compound.

LC-MS (Method 11): $R_t$=0.62 min; m/z=379 (M+H)$^+$.

$^1$H-NMR (400 MHz, DMSO-$d_6$): δ=1.23 (t, 3H), 4.00 (br. t, 2H), 4.17 (q, 2H), 4.53 (t, 2H), 7.51 (d, 1H), 7.59 (d, 1H), 7.85 (s, 1H), 8.39 (s, 1H), 11.76 (s, 1H).

Example 65A 1-tert-Butyl-3-(2-chloro-4-nitrophenyl)imidazolidin-2-one

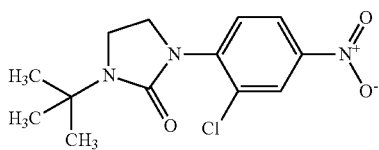

Under argon, a solution of 2.22 g (15.7 mmol) of 1-tert-butylimidazolidin-2-one in THF (20 ml) was cooled to 0° C., and 1.14 g (28.5 mmol) of 60% sodium hydride were then added a little at a time. The mixture was stirred at RT for 30 min, a solution of 2.50 g (14.2 mmol) of 2-chloro-1-fluoro-4-nitrobenzene dissolved in THF (6 ml) was then added and the mixture was stirred at 0° C. for 1 h. For work-up, the reaction mixture was diluted with water. The mixture was extracted three times with ethyl acetate. The combined organic phases were dried over magnesium sulfate and concentrated on a rotary evaporator. The residue was dissolved in ethyl acetate, absorbed on diatomaceous earth and purified by flash chromatography (cyclohexane/ethyl acetate 7:1→4:1). This gave 1.78 g (39% of theory) of the title compound.

LC-MS (Method 3): $R_t$=1.03 min; m/z=297 (M+H)$^+$.

$^1$H-NMR (400 MHz, DMSO-$d_6$): δ=1.36 (s, 9H), 3.55 (t, 2H), 3.75 (t, 2H), 7.70 (d, 1H), 8.21 (dd, 1H), 8.35 (d, 1H).

Example 66A 1-(4-Amino-2-chlorophenyl)-3-tert-butylimidazolidin-2-one

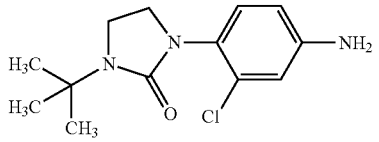 [SMILES: CC(C)(C)N1CCN(c2ccc(N)cc2Cl)C1=O]

3.33 g (11.2 mmol) of 1-tert-butyl 3-(2-chloro-4-nitrophenyl)imidazolidin-2-one from Example 65A were initially charged in THF/methanol 1:2 (75 ml), 332 mg (5.66 mmol) of Raney nickel were added and the mixture was hydrogenated at standard pressure for 3 h. For work-up, the reaction mixture was filtered through kieselguhr, washed with THF and concentrated. The residue was stirred in MTBE and the solid was filtered off and dried under reduced pressure at 50° C. This gave 2.24 g (74% of theory) of the title compound.

LC-MS (Method 3): $R_t$=0.89 min; m/z=268 (M+H)$^+$.

$^1$H-NMR (400 MHz, DMSO-$d_6$): δ=1.30 (s, 9H), 3.37-3.47 (m, 4H), 5.36-5.44 (m, 2H), 6.48 (dd, 1H), 6.63 (d, 1H), 6.92 (d, 1H).

Example 67A 1-(4-Amino-2-chlorophenyl)imidazolidin-2-one

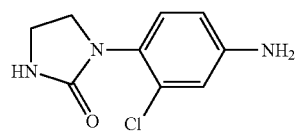 [SMILES: Nc1ccc(N2CCNC2=O)c(Cl)c1]

2.23 g (8.36 mmol) of 1-(4-amino-2-chlorophenyl)-3-tert-butylimidazolidin-2-one from Example 66A were initially charged in semi-concentrated hydrochloric acid (45 ml, 18.5% w/w), and the mixture was heated at 80° C. for 4 h. For work-up, the reaction mixture, cooled in an ice/water bath, was made basic using concentrated aqueous sodium hydroxide solution (pH 12). The solid formed was filtered off, washed with water and dichloromethane and dried under reduced pressure. This gave 1.28 g (72% of theory) of the title compound. Extractive work-up of the filtrate with dichloromethane gave an additional 453 mg of the title compound.

LC-MS (Method 2): $R_t$=1.08 min; m/z=212 (M+H)$^+$.

$^1$H-NMR (400 MHz, DMSO-$d_6$): δ=3.35-3.40 (m, 2H), 3.59 (t, 2H), 5.38-5.45 (m, 2H), 6.48 (dd, 1H), 6.54 (s, 1H), 6.64 (d, 1H), 6.96 (d, 1H).

Example 68A

Ethyl 1-[3-chloro-4-(2-oxoimidazolidin-1-yl)phenyl]-2,4-dioxo-1,2,3,4-tetrahydropyrimidine-5-carboxylate

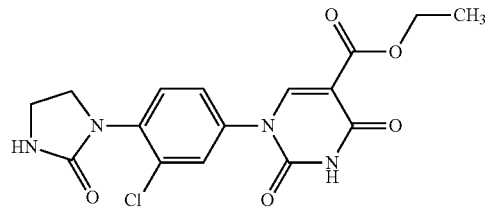 [SMILES: CCOC(=O)c1cn(-c2ccc(N3CCNC3=O)c(Cl)c2)c(=O)[nH]c1=O]

453 mg (2.14 mmol) of 1-(4-amino-2-chlorophenyl)imidazolidin-2-one from Example 67A and 555 mg (2.14 mmol) of ethyl 3-ethoxy-2-[(ethoxycarbonyl)carbamoyl]acrylate in 15 ml of ethanol were heated under reflux for 2 h. After cooling to RT, 240 mg (2.14 mmol) of potassium tert-butoxide were added and the reaction mixture was stirred at RT for 16 h and then heated at 60° C. for 3 h. For work-up, the cooled reaction mixture was acidified with 1 N aqueous hydrochloric acid and diluted with water. The solid was filtered off with suction, washed with water and dried under reduced pressure at 50° C. This gave 530 mg (62% of theory) of the title compound.

LC-MS (Method 11): $R_t$=0.57 min; m/z=379 (M+H)$^+$.

$^1$H-NMR (400 MHz, DMSO-$d_6$): δ=1.23 (t, 3H), 3.46 (t, 2H), 3.80 (t, 2H), 4.17 (q, 2H), 6.94 (s, 1H), 7.50 (dd, 1H), 7.55 (d, 1H), 7.76 (d, 1H), 8.35 (s, 1H), 11.74 (s, 1H).

Example 69A 1-tert-Butyl-3-(2,6-dichloro-4-nitrophenyl)imidazolidin-2-one

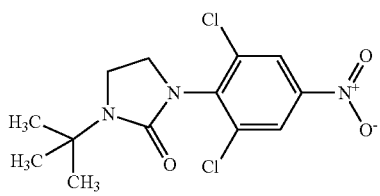

Under argon, a solution of 1.48 g (10.5 mmol) of 1-tert-butylimidazolidin-2-one in THF (10 ml) was cooled to 0° C., 1.60 g (14.3 mmol) of potassium tert-butoxide were added a little at a time and the mixture was stirred at RT for 30 min. A solution of 2.00 g (9.52 mmol) of 1,3-dichloro-2-fluoro-5-nitrobenzene in THF (7 ml) was added and the mixture was stirred at 0° C. for 2 h. For work-up, the reaction mixture was diluted with water. The mixture was extracted three times with ethyl acetate and the organic phase was dried with magnesium sulfate, filtered on a rotary evaporator and concentrated. The residue was dissolved in ethyl acetate, absorbed on diatomaceous earth and purified by flash chromatography (cyclohexane/ethyl acetate 9:1→7:1). This gave 1.18 g (37% of theory) of the title compound.

LC-MS (Method 3): $R_t$=1.11 min; m/z=332 (M+H)$^+$.

Example 70A 1-(4-Amino-2, 6-dichlorophenyl)-3-tert-butylimidazolidin-2-one

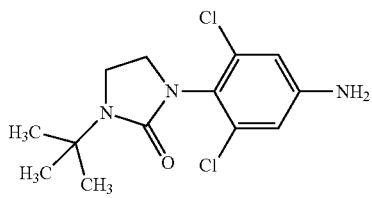 [SMILES: CC(C)(C)N1CCN(c2c(Cl)cc(N)cc2Cl)C1=O]

Preparation and purification of the title compound were carried out analogously to Example 66A. Starting with 1.40 g (4.22 mmol) of 1-tert-butyl 3-(2,6-dichloro-4-nitrophenyl)imidazolidin-2-one from Example 69A, 1.24 g (98% of theory) of the title compound were obtained.

LC-MS (Method 1): $R_t$=1.13 min; m/z=302 (M+H)$^+$.

$^1$H-NMR (400 MHz, DMSO-d$_6$): δ=1.30 (s, 9H), 3.38-3.51 (m, 4H), 5.71-5.77 (m, 2H), 6.62 (s, 2H).

Example 71A 1-(4-Amino-2,6-dichlorophenyl)imidazolidin-2-one

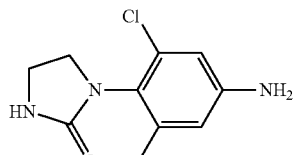

Preparation and purification of the title compound were carried out analogously to Example 67A using a reaction time of 3 h. Starting with 1.25 g (4.13 mmol) of 1-(4-amino-2,6-dichlorophenyl)-3-tert-butylimidazolidin-2-one from Example 70A, this gave 759 mg (74% of theory) of the title compound.

LC-MS (Method 1): $R_t$=0.71 min; m/z=246 (M+H)$^+$.

Example 72A

Ethyl 1-[3,5-dichloro-4-(2-oxoimidazolidin-1-yl)phenyl]-2,4-dioxo-1,2,3,4-tetrahydropyrimidine-5-carboxylate

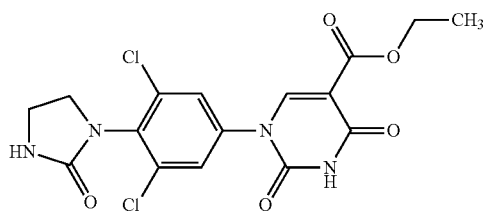 [SMILES: CCOC(=O)c1cn(-c2cc(Cl)c(N3CCNC3=O)c(Cl)c2)c(=O)[nH]c1=O]

758 mg (3.08 mmol) of 1-(4-amino-2,6-dichlorophenyl)imidazolidin-2-one from Example 71A and 799 mg (3.08 mmol) of ethyl 3-ethoxy-2-[(ethoxycarbonyl)carbamoyl]acrylate in 23 ml of ethanol were heated under reflux for 2 h. After cooling to RT, 346 mg (3.08 mmol) of potassium tert-butoxide were added and the reaction mixture was stirred at RT for 16 h and then heated at reflux for 1 h. For work-up, the cooled reaction mixture was acidified with 1 N aqueous hydrochloric acid and diluted with water. The solid was filtered off with suction, washed with a little ethyl acetate and dried under reduced pressure at 50° C. This gave 863 mg (67% of theory) of the title compound.

LC-MS (Method 3): $R_t$=0.80 min; m/z=413 (M+H)$^+$.

$^1$H-NMR (400 MHz, DMSO-d$_6$): δ=1.23 (t, 3H), 3.53 (t, 2H), 3.71 (t, 2H), 4.17 (q, 2H), 6.90 (s, 1H), 7.84 (s, 2H), 8.43 (s, 1H), 11.79 (s, 1H).

Example 73A

2-Chloroethyl (3-fluoro-4-nitrophenyl)carbamate

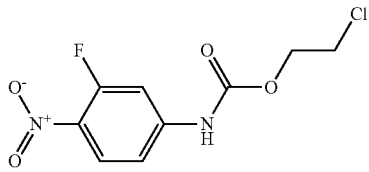 [SMILES: O=C(Nc1ccc([N+](=O)[O-])c(F)c1)OCCCl]

A solution of 2.00 g (12.8 mmol) of 3-fluoro-4-nitroaniline and 1.14 ml (14.1 mmol) of pyridine in 15 ml of THF was cooled to 0° C., and a solution of 1.45 ml (14.1 mmol) of 2-chloroethyl chloroformate in 5 ml of THF was added dropwise. The reaction mixture was stirred at RT for 0.5 h. For work-up, 20 ml of ethyl acetate and 50 ml of water were added to the reaction mixture. The phases were separated, the aqueous phase was extracted twice with 50 ml of ethyl acetate and the combined organic phases were washed once with water and once with saturated sodium chloride solution, dried over magnesium sulfate, filtered and concentrated on a rotary evaporator. This gave 3.36 g (98% of theory) of the title compound.

LC-MS (Method 3): $R_t$=0.97 min; m/z=263 (M+H)$^+$.

$^1$H-NMR (400 MHz, DMSO-d$_6$): δ=3.89-3.93 (m, 2H), 4.39-4.45 (m, 2H), 7.42 (dd, 1H), 7.64 (dd, 1H), 8.18 (t, 1H), 10.75 (s, 1H).

Example 74A 3-(3-Fluoro-4-nitrophenyl)-1,3-oxazolidin-2-one

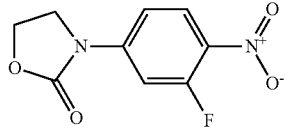 [SMILES: O=C1OCCN1c1ccc([N+](=O)[O-])c(F)c1]

3.36 g (12.8 mmol) of 2-chloroethyl (3-fluoro-4-nitrophenyl)carbamate from Example 73A were initially charged in 35 ml of acetonitrile, 2.12 g (15.4 mmol) of potassium carbonate were added and the reaction mixture was heated at reflux temperature for 45 min. For work-up, the cooled reaction mixture was concentrated and 20 ml of ethyl acetate and 50 ml of water were added. The phases were separated, the aqueous phase was extracted twice with 50 ml of ethyl acetate and the combined organic phases were washed once with water and once with saturated sodium chloride solution, dried over magnesium sulfate, filtered and concentrated. This gave 2.83 g (96% of theory) of the title compound.

LC-MS (Method 3): $R_t$=0.79 min; m/z=227 (M+H)$^+$.

$^1$H-NMR (400 MHz, DMSO-d$_6$): δ=4.10-4.17 (m, 2H), 4.47-4.54 (m, 2H), 7.61 (dd, 1H), 7.76 (dd, 1H), 8.24 (t, 1H).

Example 75A 3-(4-Amino-3-fluorophenyl)-1,3-oxazolidin-2-one

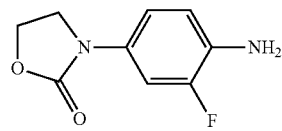 [SMILES: Nc1ccc(N2CCOC2=O)cc1F]

2.83 g (12.5 mmol) of 3-(3-fluoro-4-nitrophenyl)-1,3-oxazolidin-2-one from Example 74A were initially charged in THF/DMF 2:1 (75 ml), 1.33 g (1.25 mmol) of 10% palladium on activated carbon were added and the reaction mixture was hydrogenated at standard pressure for 16 h. For work-up, the reaction mixture was filtered through kieselguhr. The filter residue was washed with THF and the entire filtrate was concentrated. The residue was stirred with MTBE, and the solid was filtered off and dried at 50° C. under reduced pressure. The mother liquor was concentrated to half its original volume and the solid formed was filtered off and dried under reduced pressure. This gave a total yield of 2.22 g (88% of theory) of the title compound.

LC-MS (Method 3): $R_t$=0.44 min; m/z=197 (M+H)$^+$.

$^1$H-NMR (400 MHz, DMSO-d$_6$): δ=3.91-3.99 (m, 2H), 4.34-4.42 (m, 2H), 5.02 (s, 2H), 6.77 (t, 1H), 6.99 (dd, 1H), 7.32 (dd, 1H).

Example 76A

Ethyl 1-[2-fluoro-4-(2-oxo-1,3-oxazolidin-3-yl)phenyl]-2,4-dioxo-1,2,3,4-tetrahydropyrimidine-5-carboxylate

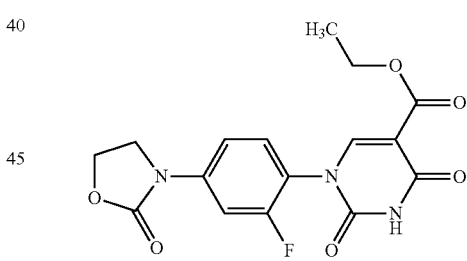

1.00 g (5.09 mmol) of 3-(4-amino-3-fluorophenyl)-1,3-oxazolidin-2-one from Example 75A and 1.32 g (5.09 mmol) of ethyl 3-ethoxy-2-[(ethoxycarbonyl)carbamoyl]acrylate in 40 ml of ethanol were heated under reflux for 1.5 h. After cooling to RT, 572 mg (5.09 mmol) of potassium tert-butoxide were added and the reaction mixture was heated at reflux for 4 h. For work-up, the cooled reaction mixture was acidified with 1 N aqueous hydrochloric acid and diluted with water. The ethanol was removed on a rotary evaporator. The solid formed in the aqueous phase that remained was filtered off with suction, washed with water and dried under reduced pressure at 30° C. This gave 1.27 g (67% of theory) of the title compound.

LC-MS (Method 3): $R_t$=0.68 min; m/z=364 (M+H)$^+$.

$^1$H-NMR (400 MHz, DMSO-d$_6$): δ=1.23 (t, 3H), 4.10 (t, 2H), 4.18 (q, 2H), 4.49 (t, 2H), 7.47 (dd, 1H), 7.64 (t, 1H), 7.71 (dd, 1H), 8.40 (s, 1H), 11.84 (s, 1H).

Example 77A 3-(2-Methyl-4-nitrophenyl)-1,3-oxazolidin-2-one

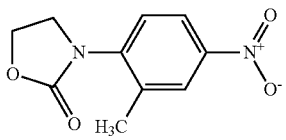

A mixture of 1.50 g (9.85 mmol) of 2-methyl-4-nitroaniline and 1.49 g (10.84 mmol) of potassium carbonate in 5 ml of THF was cooled to 0° C., and a solution of 1.12 ml (10.84 mmol) of 2-chloroethyl chloroformate in 5 ml of THF was added dropwise. The reaction mixture was stirred at RT for 11 h. 406 mg (2.95 mmol) of potassium carbonate and 305 µl (2.95 mmol) of 2-chloroethyl chloroformate were added and the mixture was heated at reflux for 2 h. 1.10 g (9.85 mmol) of potassium tert-butoxide were then added and the mixture was heated at reflux for 1 h. For work-up, the cooled reaction mixture was diluted with water and extracted twice with ethyl acetate. The combined organic phases were washed once with saturated aqueous sodium chloride solution, dried over magnesium sulfate and concentrated. This gave 2.20 g (96% of theory) of the title compound.

LC-MS (Method 1): $R_t$=0.83 min; m/z=223 (M+H)$^+$.

$^1$H-NMR (400 MHz, DMSO-$d_6$): δ=2.35 (s, 3H), 4.02-4.08 (m, 2H), 4.48-4.54 (m, 2H), 7.64 (d, 1H), 8.11 (dd, 1H), 8.21 (d, 1H).

Example 78A 3-(4-Amino-2-methylphenyl)-1,3-oxazolidin-2-one

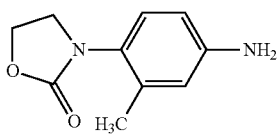

2.20 g (9.90 mmol) of 3-(2-methyl-4-nitrophenyl)-1,3-oxazolidin-2-one from Example 77A were initially charged in pyridine (50 ml), 1.05 g (0.99 mmol) of 10% palladium on activated carbon were added and the reaction mixture was hydrogenated at standard pressure for 16 h. For work-up, the reaction mixture was filtered through kieselguhr, the filter cake was washed with ethanol and the entire filtrate was concentrated. The residue was stirred with ethyl acetate. The solid was filtered off and dried under reduced pressure at 50° C. This gave 980 mg (51% of theory) of the title compound.

LC-MS (Method 1): $R_t$=0.26 min; m/z=193 (M+H)$^+$.

$^1$H-NMR (400 MHz, DMSO-$d_6$): δ=2.05 (s, 3H), 3.74-3.82 (m, 2H), 4.34-4.43 (m, 2H), 5.11 (s, 2H), 6.36-6.45 (m, 2H), 6.90 (d, 1H).

Example 79A

Ethyl 1-[3-methyl-4-(2-oxo-1,3-oxazolidin-3-yl)phenyl]-2,4-dioxo-1,2,3,4-tetrahydropyrimidine-5-carboxylate

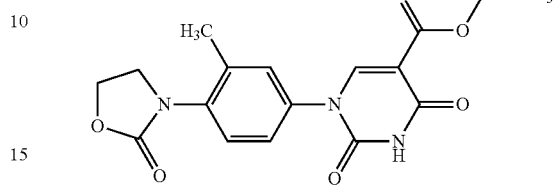

980 mg (5.09 mmol) of 3-(4-amino-2-methylphenyl)-1,3-oxazolidin-2-one from Example 78A and 1.32 g (5.09 mmol) of ethyl 3-ethoxy-2-[(ethoxycarbonyl)carbamoyl]acrylate in 50 ml of ethanol were heated under reflux for 30 min. After cooling to RT, 572 mg (5.09 mmol) of potassium tert-butoxide were added and the reaction mixture was stirred at RT for 16 h. For work-up, the cooled reaction mixture was partially concentrated, acidified with 1 N aqueous hydrochloric acid and diluted with water. The solid formed was filtered off with suction, washed with water and dried under reduced pressure at 30° C. The filtrate was partially concentrated, and the solid formed was filtered off with suction and washed with water and MTBE and dried under reduced pressure. This gave a total yield of 1.06 g (58% of theory) of the title compound.

LC-MS (Method 3): $R_t$=0.63 min; m/z=360 (M+H)$^+$.

$^1$H-NMR (400 MHz, DMSO-$d_6$): δ=1.23 (t, 3H), 2.27 (s, 3H), 3.98 (t, 2H), 4.16 (q, 2H), 4.50 (t, 2H), 7.39 (d, 1H), 7.45 (s, 1H), 7.50 (d, 1H), 8.30 (s, 1H), 11.71 (s, 1H).

Example 80A 3-(3-Methyl-4-nitrophenyl)-1,3-oxazolidin-2-one

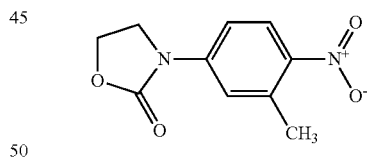

1.50 g (9.85 mmol) of 3-methyl-4-nitroaniline and 1.49 g (10.84 mmol) of potassium carbonate were initially charged in 5 ml of THF at 0° C., and a solution of 1.12 ml (10.84 mmol) of 2-chloroethyl chloroformate in 5 ml of THF was added dropwise. The reaction mixture was stirred at RT for 11 h. An additional 1.35 g (9.85 mmol) of potassium carbonate were added to the reaction mixture, and the mixture was heated at reflux for 12 h. 1.10 g (9.85 mmol) of potassium tert-butoxide were then added and the mixture was heated at reflux for 10 min. For work-up, the cooled reaction mixture was diluted with water and extracted twice with ethyl acetate. The combined organic phases were washed with saturated aqueous sodium chloride solution, dried over magnesium sulfate and concentrated. This gave 2.08 g (92% of theory) of the title compound.

LC-MS (Method 1): $R_t$=0.94 min; m/z=223 (M+H)$^+$.

¹H-NMR (400 MHz, DMSO-d₆): δ=2.58 (s, 3H), 4.10-4.16 (m, 2H), 4.45-4.52 (m, 2H), 7.59 (d, 1H), 7.73 (dd, 1H), 8.11 (d, 1H).

Example 81A 3-(4-Amino-3-methylphenyl)-1,3-oxazolidin-2-one

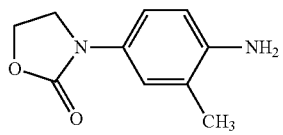

2.08 g (9.36 mmol) of 3-(3-methyl-4-nitrophenyl)-1,3-oxazolidin-2-one from Example 80A were initially charged in ethanol (25.81 ml), 996 mg (0.93 mmol) of 10% palladium on activated carbon were added and the reaction mixture was hydrogenated at standard pressure for 16 h. For work-up, the reaction mixture was filtered through kieselguhr, the filter cake was washed with ethanol and the entire filtrate was concentrated. The residue was stirred with ethyl acetate. The solid was filtered off and dried under reduced pressure at 50° C. This gave 767 mg (42% of theory) of the title compound.

LC-MS (Method 1): $R_t$=0.25 min; m/z=1923 (M+H)⁺.

¹H-NMR (400 MHz, DMSO-d₆): δ=2.05 (br. s., 3H), 3.93 (t, 2H), 4.36 (t, 2H), 4.66-4.83 (m, 2H), 6.60 (d, 1H), 7.03 (d, 1H), 7.10 (s, 1H).

Example 82A

Ethyl 2-[(ethoxycarbonyl)carbamoyl]-3-{[2-methyl-4-(2-oxo-1,3-oxazolidin-3-yl)phenyl]amino}acrylate

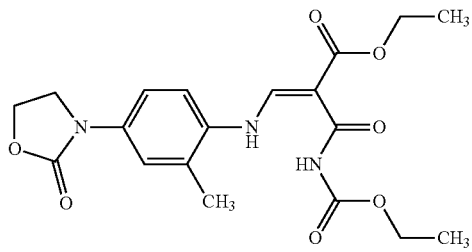 [SMILES: CCOC(=O)NC(=O)/C(=C\Nc1ccc(N2CCOC2=O)cc1C)C(=O)OCC]

767 mg (3.99 mmol) of 3-(4-amino-3-methylphenyl)-1,3-oxazolidin-2-one from Example 81A and 1.03 g (3.99 mmol) of ethyl 3-ethoxy-2-[(ethoxycarbonyl)carbamoyl]acrylate in 120 ml of ethanol were heated under reflux for 30 min. After cooling to RT, 448 mg (3.99 mmol) of potassium tert-butoxide were added and the reaction mixture was stirred at RT overnight. For work-up, the reaction mixture was partially concentrated, acidified with 1 N aqueous hydrochloric acid and diluted with water. The solid formed was filtered off with suction, washed with water and dried under reduced pressure at 30° C. This gave 715 mg (44% of theory) of the title compound.

LC-MS (Method 3): $R_t$=1.03 min; m/z=406 (M+H)⁺.

¹H-NMR (400 MHz, DMSO-d₆): δ=1.23 (t, 3H), 1.29 (t, 3H), 2.35 (s, 3H), 4.06 (t, 2H), 4.14 (q, 2H), 4.22 (q, 2H), 4.44 (t, 2H), 7.46-7.60 (m, 3H), 8.58 (d, 1H), 11.23 (s, 1H), 12.12 (d, 1H).

Example 83A

Ethyl 1-[2-methyl-4-(2-oxo-1,3-oxazolidin-3-yl)phenyl]-2,4-dioxo-1,2,3,4-tetrahydropyrimidine-5-carboxylate

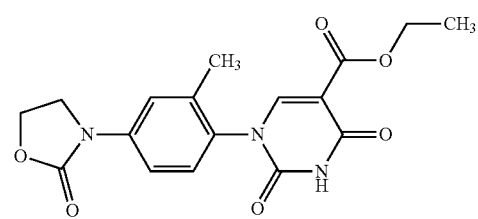 [SMILES: CCOC(=O)c1cn(-c2ccc(N3CCOC3=O)cc2C)c(=O)[nH]c1=O]

318.4 mg (2.84 mmol) of potassium tert-butoxide were added to 767 mg (1.89 mmol) of ethyl 2-[(ethoxycarbonyl)carbamoyl]-3-{[2-methyl-4-(2-oxo-1,3-oxazolidin-3-yl)phenyl]amino}acrylate from Example 82A in 50 ml of ethanol. The reaction mixture was stirred at RT for 2 days and then heated at 60° C. for 1 h. For work-up, the cooled reaction mixture was acidified with 1 N aqueous hydrochloric acid and concentrated almost completely. The remainder was diluted with water. The solid was filtered off with suction, washed repeatedly with water and dried under reduced pressure. This gave 502 mg (72% of theory) of the title compound.

LC-MS (Method 3): $R_t$=0.67 min; m/z=360 (M+H)⁺.

¹H-NMR (400 MHz, DMSO-d₆): δ=1.22 (t, 3H), 2.15 (s, 3H), 4.09 (t, 2H), 4.16 (q, 2H), 4.47 (t, 2H), 7.40-7.47 (m, 1H), 7.51-7.59 (m, 2H), 8.22 (s, 1H), 11.72 (s, 1H).

Example 84A 3-(2,6-Dichloro-4-nitrophenyl)-1,3-oxazolidin-2-one

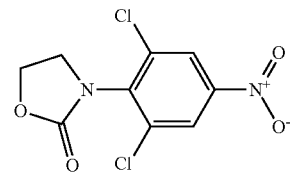 [SMILES: O=C1OCCN1c1c(Cl)cc([N+](=O)[O-])cc1Cl]

Preparation and purification of the title compound were carried out analogously to Example 69A using a reaction time of 1 h. Starting with 1.00 g (4.76 mmol) of 1,3-dichloro-2-fluoro-5-nitrobenzene and 456 mg (5.23 mmol) of 1,3-oxazolidin-2-one, purification by flash chromatography (cyclohexane/ethyl acetate 7:1→5:1) gave 928.6 mg (70% of theory) of the title compound.

LC-MS (Method 3): $R_t$=0.83 min; m/z=277 (M+H)⁺.

¹H-NMR (400 MHz, DMSO-d₆): δ=3.91-3.98 (m, 2H), 4.60-4.67 (m, 2H), 8.50 (s, 2H).

Example 85A 3-(4-Amino-2,6-dichlorophenyl)-1,3-oxazolidin-2-one

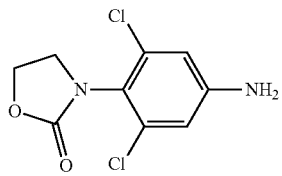 [SMILES: Nc1cc(Cl)c(N2CCOC2=O)c(Cl)c1]

Preparation and purification of the title compound were carried out analogously to Example 66A using a reaction time of 1 h. Starting with 928 mg (3.35 mmol) of 3-(2,6-dichloro-4-nitrophenyl)-1,3-oxazolidin-2-one from Example 84A, this gave 657.4 mg (79% of theory) of the title compound.

LC-MS (Method 1): $R_t$=0.75 min; m/z=247 (M+H)$^+$.

$^1$H-NMR (400 MHz, DMSO-d$_6$): δ=3.76 (t, 2H), 4.48 (t, 2H), 5.86-5.94 (m, 1H), 6.67 (s, 2H).

Example 86A

Ethyl 1-[3,5-dichloro-4-(2-oxo-1,3-oxazolidin-3-yl)phenyl]-2,4-dioxo-1,2,3,4-tetrahydropyrimidine-5-carboxylate

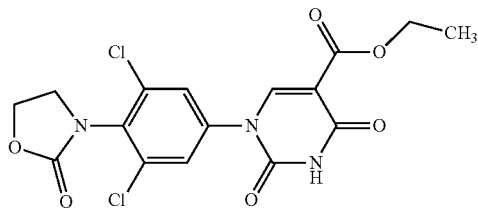 [SMILES: CCOC(=O)c1cn(-c2cc(Cl)c(N3CCOC3=O)c(Cl)c2)c(=O)[nH]c1=O]

657 mg (2.65 mmol) of 3-(4-amino-2,6-dichlorophenyl)-1,3-oxazolidin-2-one from Example 85A and 689.4 mg (2.65 mmol) of ethyl 3-ethoxy-2-[(ethoxycarbonyl)carbamoyl]acrylate in 20 ml of ethanol were heated under reflux for 2 h. After cooling to RT, 298 mg (2.65 mmol) of potassium tert-butoxide were added and the reaction mixture was stirred at RT for 16 h. For work-up, the reaction mixture was acidified with 1 N aqueous hydrochloric acid and diluted with water. The solid formed was filtered off with suction, washed with water and a little ethyl acetate/MTBE 1:1 and dried under reduced pressure. This gave 728.1 mg (66% of theory) of the title compound.

LC-MS (Method 3): $R_t$=0.75 min; m/z=415 (M+H)$^+$.

$^1$H-NMR (400 MHz, DMSO-d$_6$): δ=1.23 (t, 3H), 3.92 (t, 2H), 4.18 (q, 2H), 4.62 (t, 2H), 7.92 (s, 2H), 8.47 (s, 1H), 11.82 (s, 1H).

Example 87A

Ethyl 1-{4-[(5S)-5-(acetamidomethyl)-2-oxo-1,3-oxazolidin-3-yl]phenyl}-2,4-dioxo-1,2,3,4-tetrahydropyrimidine-5-carboxylate (S enantiomer)

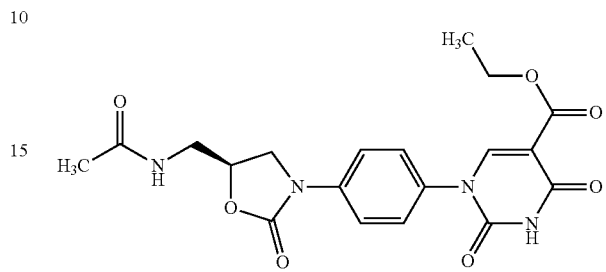

Preparation and purification of the title compound were analogous to Example 79A. Starting with 500 mg (2.00 mmol) of 3N-{[(5S)-3-(4-aminophenyl)-2-oxo-1,3-oxazolidin-5-yl]methyl}acetamide (described in: Journal of Medicinal Chemistry, 1990, 33 (9), 2569-2578) and 473 mg (1.82 mmol) of ethyl 3-ethoxy-2-[(ethoxycarbonyl)carbamoyl]acrylate, 469 mg (56% of theory) of the title compound were obtained.

LC-MS (Method 3): $R_t$=0.57 min; m/z=417 (M+H)$^+$.

$^1$H-NMR (400 MHz, DMSO-d$_6$): δ=1.23 (t, 3H), 1.84 (s, 3H), 3.43 (t, 2H), 3.75-3.82 (m, 1H), 4.12-4.22 (m, 3H), 4.71-4.80 (m, 1H), 7.49-7.54 (m, 2H), 7.63-7.69 (m, 2H), 8.23-8.29 (m, 2H), 11.68 (s, 1H).

Example 88A 1-(1-Hydroxy-2-methylpropan-2-yl)-3-(4-nitrophenyl)urea

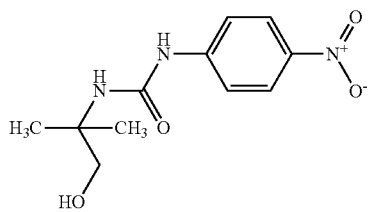 [SMILES: CC(C)(CO)NC(=O)Nc1ccc([N+](=O)[O-])cc1]

1.03 g (6.30 mmol) of 1-isocyanato-4-nitrobenzene and 0.59 g (6.61 mmol) of 2-amino-2-methyl-1-propanol were mixed in 19.2 ml of dichloromethane After a few minutes, a precipitate was formed. The suspension was stirred at RT for 5 h, and the solid formed was filtered off, washed with dichloromethane and dried under high vacuum. This gave 1.41 g (88% of theory) of the title compound.

LC-MS (Method 1): $R_t$=0.87 min; m/z=254 (M+H)$^+$.

$^1$H-NMR (400 MHz, DMSO-d$_6$): δ=1.24 (s, 6H), 3.36-3.41 (m, 2H), 4.95-5.06 (m, 1H), 6.18 (s, 1H), 7.57 (d, 2H), 8.12 (d, 2H), 9.27 (s, 1H).

Example 89A 4,4-Dimethyl-1-(4-nitrophenyl)imidazolidin-2-one

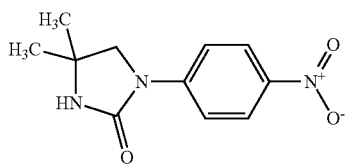 [SMILES: CC1(C)CN(c2ccc([N+](=O)[O-])cc2)C(=O)N1]

Under argon, 1.41 g (5.56 mmol) of 1-(1-hydroxy-2-methylpropan-2-yl)-3-(4-nitrophenyl)urea from Example 88A were initially charged in 59.5 ml of THF, and 1.46 g (5.56 mmol) of triphenylphosphine were added. The mixture was cooled to 0° C., a solution of 1.09 ml (5.56 mmol) of diisopropyl azodicarboxylate in 10 ml of THF was added dropwise and the mixture was stirred at RT for 16 h. Saturated aqueous sodium bicarbonate solution was added and the reaction mixture was extracted twice with ethyl acetate. The organic phase was washed with saturated aqueous sodium chloride solution, dried over magnesium sulfate and concentrated. The residue was stirred in MTBE. The solid formed was filtered off, washed with MTBE and dried under high vacuum. This gave 809.3 mg (52% of theory, purity 85%) of the title compound.

LC-MS (Method 1): $R_t$=0.96 min; m/z=236 (M+H)$^+$.

$^1$H-NMR (400 MHz, DMSO-d$_6$): δ=1.29 (s, 6H), 3.70 (s, 2H), 7.74-7.82 (m, 2H), 8.16-8.23 (m, 2H).

Example 90A 1-(4-Aminophenyl)-4,4-dimethylimidazolidin-2-one

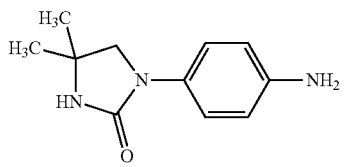

809 mg (3.43 mmol) of 4,4-dimethyl-1-(4-nitrophenyl)imidazolidin-2-one from Example 89A were initially charged in 23 ml of ethanol, 37 mg (0.03 mmol) of 10% palladium on activated carbon were added and the mixture was hydrogenated at standard pressure for 16 h. The reaction mixture was filtered through kieselguhr, washed with ethanol, and the entire filtrate was concentrated. The residue was stirred in MTBE. The solid formed was filtered off, washed with MTBE and dried under high vacuum. This gave 529 mg (74% of theory) of the title compound.

LC-MS (Method 3): $R_t$=0.27 min; m/z=206 (M+H)$^+$.

$^1$H-NMR (400 MHz, DMSO-d$_6$): δ=1.24 (s, 6H), 3.45 (s, 2H), 4.69-4.80 (m, 2H), 6.51 (d, 2H), 6.75 (s, 1H), 7.14 (d, 2H).

Example 91A

Ethyl 1-[4-(4,4-dimethyl-2-oxoimidazolidin-1-yl)phenyl]-2,4-dioxo-1,2,3,4-tetrahydropyrimidine-5-carboxylate

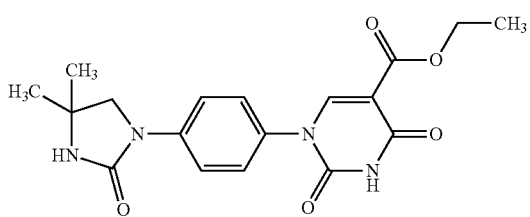 [SMILES: CCOC(=O)c1cn(-c2ccc(N3CC(C)(C)NC3=O)cc2)c(=O)[nH]c1=O]

Preparation and purification of the title compound were analogous to Example 79A. Starting with 529 mg (2.57 mmol) of 1-(4-aminophenyl)-4,4-dimethylimidazolidin-2-one from Example 90A and 668 mg (2.57 mmol) of ethyl 3-ethoxy-2-[(ethoxycarbonyl)carbamoyl]acrylate, 848 mg (88% of theory) of the title compound were obtained.

LC-MS (Method 3): $R_t$=0.71 min; m/z=373 (M+H)$^+$.

$^1$H-NMR (400 MHz, DMSO-d$_6$): δ=1.23 (t, 3H), 1.29 (s, 6H), 3.62 (s, 2H), 4.17 (q, 2H), 7.29 (s, 1H), 7.37-7.44 (m, 2H), 7.61-7.67 (m, 2H), 8.23 (s, 1H), 11.65 (s, 1H).

Example 92A

Ethyl 1-[4-(3-methyl-2-oxoimidazolidin-1-yl)phenyl]-2,4-dioxo-1,2,3,4-tetrahydropyrimidine-5-carboxylate

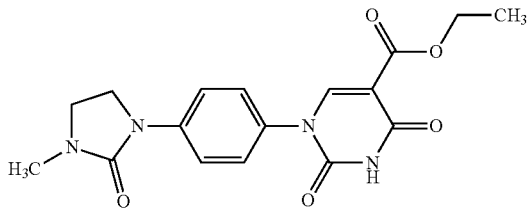 [SMILES: CCOC(=O)c1cn(-c2ccc(N3CCN(C)C3=O)cc2)c(=O)[nH]c1=O]

Preparation and purification of the title compound were analogous to Example 72A. Starting with 895 mg (4.68 mmol) of 1-(4-aminophenyl)-3-methylimidazolidin-2-one and 1.21 g (4.68 mmol) of ethyl 3-ethoxy-2-[(ethoxycarbonyl)carbamoyl]acrylate, 1.58 g (94% of theory) of the title compound were obtained.

LC-MS (Method 3): $R_t$=0.68 min; m/z=359 (M+H)$^+$.

$^1$H-NMR (400 MHz, DMSO-d$_6$): δ=1.22 (t, 3H), 2.79 (s, 3H), 3.47 (t, 2H), 3.82 (t, 3H), 4.17 (q, 2H), 7.42 (d, 2H), 7.67 (d, 2H), 8.24 (s, 1H), 11.65 (s, 1H).

Example 93A 1-(1-Hydroxypropan-2-yl)-3-(4-nitrophenyl)urea (racemate)

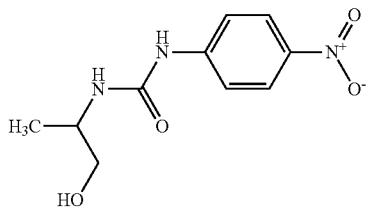 [SMILES: CC(CO)NC(=O)Nc1ccc([N+](=O)[O-])cc1]

Preparation and purification of the title compound were analogous to Example 88A. Starting with 1.79 g (10.90 mmol) of 1-isocyanato-4-nitrobenzene and 0.86 g (11.45 mmol) of 2-amino-1-propanol (racemate), this gave 2.39 g (91% of theory) of the title compound.

LC-MS (Method 1): $R_t$=0.76 min; m/z=240 (M+H)$^+$.

$^1$H-NMR (400 MHz, DMSO-d$_6$): δ=1.08 (d, 3H), 3.35-3.43 (m, 2H), 3.66-3.78 (m, 1H), 4.85 (t, 1H), 6.32 (d, 1H), 7.56-7.63 (m, 2H), 8.10-8.17 (m, 2H), 9.25 (s, 1H).

Example 94A

4-Methyl-1-(4-nitrophenyl)imidazolidin-2-one (racemate)

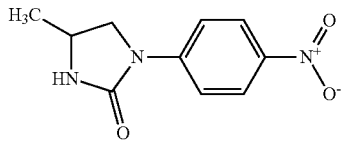 [SMILES: CC1CN(c2ccc([N+](=O)[O-])cc2)C(=O)N1]

Preparation and purification of the title compound were analogous to Example 89A. Starting with 2.39 g (9.99 mmol) of 1-(1-hydroxypropan-2-yl)-3-(4-nitrophenyl)urea from Example 93A, 2.62 g (9.99 mmol) of triphenylphosphine and 1.96 ml (9.99 mmol) of diisopropyl azodicarboxylate, 1.42 g (64% of theory) of the title compound were obtained.

LC-MS (Method 1): $R_t$=0.89 min; m/z=222 (M+H)$^+$.

$^1$H-NMR (400 MHz, DMSO-d$_6$): δ=1.22 (d, 3H), 3.46-3.52 (m, 1H), 3.80-3.91 (m, 1H), 4.07 (t, 1H), 7.63 (s, 1H), 7.75-7.81 (m, 2H), 8.16-8.23 (m, 2H).

Example 95A 1-(4-Aminophenyl)-4-methylimidazolidin-2-one (racemate)

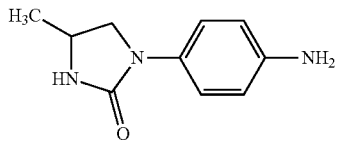

Preparation and purification of the title compound were analogous to Example 90A. Starting with 1.42 g (6.42 mmol) of 4-methyl-1-(4-nitrophenyl)imidazolidin-2-one from Example 94A, 1.13 g (92% of theory) of the title compound were obtained.

LC-MS (Method 3): $R_t$=0.21 min; m/z=192 (M+H)$^+$.

$^1$H-NMR (400 MHz, DMSO-d$_6$): δ=1.16 (d, 3H), 3.26 (dd, 1H), 3.67-3.77 (m, 1H), 3.81 (t, 1H), 4.70-4.82 (m, 2H), 6.48-6.55 (m, 2H), 6.73 (s, 1H), 7.11-7.18 (m, 2H).

Example 96A

Ethyl 1-[4-(4-methyl-2-oxoimidazolidin-1-yl)phenyl]-2,4-dioxo-1,2,3,4-tetrahydropyrimidine-5-carboxylate (racemate)

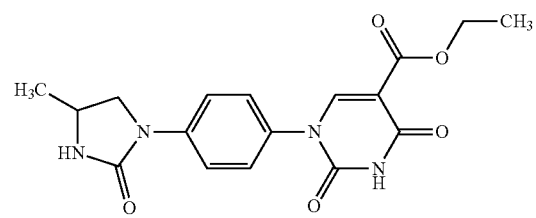 [SMILES: CCOC(=O)c1cn(-c2ccc(N3CC(C)NC3=O)cc2)c(=O)[nH]c1=O]

Preparation and purification of the title compound were analogous to Example 79A. Starting with 1.13 g (5.91 mmol) of 1-(4-aminophenyl)-4-methylimidazolidin-2-one from Example 95A and 1.53 g (5.91 mmol) of ethyl 3-ethoxy-2-[(ethoxycarbonyl)carbamoyl]acrylate, 1.64 g (77% of theory) of the title compound were obtained.

LC-MS (Method 3): $R_t$=0.66 min; m/z=359 (M+H)$^+$.

$^1$H-NMR (400 MHz, DMSO-d$_6$): δ=1.18-1.25 (m, 6H), 3.42 (dd, 1H), 3.77-3.88 (m, 1H), 4.00 (t, 1H), 4.17 (q, 2H), 7.25 (s, 1H), 7.37-7.43 (m, 2H), 7.61-7.67 (m, 2H), 8.23 (s, 1H), 11.65 (s, 1H).

Example 97A

Ethyl 2,4-dioxo-1-{4-[2-(2-oxo-1,3-oxazolidin-3-yl)ethyl]phenyl}-1,2,3,4-tetrahydropyrimidine-5-carboxylate

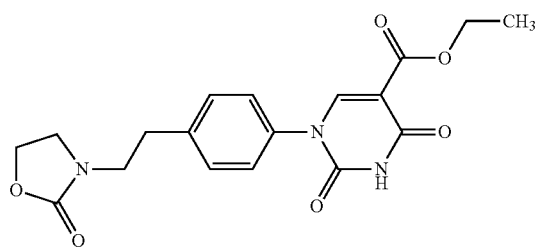 [SMILES: CCOC(=O)c1cn(-c2ccc(CCN3CCOC3=O)cc2)c(=O)[nH]c1=O]

996 mg (4.82 mmol) of 3-[2-(4-aminophenyl)ethyl]-1,3-oxazolidin-2-one and 1.25 g (4.82 mmol) of ethyl 3-ethoxy-2-[(ethoxycarbonyl)carbamoyl]acrylate in 100 ml of ethanol were heated under reflux for 1 h. After cooling to RT, 542 mg (4.82 mmol) of potassium tert-butoxide were added and the reaction mixture was stirred at RT for 16 h and at 60° C. for 5.5 h. For work-up, the cooled reaction mixture was acidified with 1 N aqueous hydrochloric acid and diluted with water. The solid formed was filtered off with suction, washed with water and ethyl acetate/MTBE 1:1 and dried under reduced pressure at 50° C. This gave 1.58 g (88% of theory) of the title compound.

LC-MS (Method 3): $R_t$=0.65 min; m/z=374 (M+H)$^+$.

$^1$H-NMR (400 MHz, DMSO-d$_6$): δ=1.22 (t, 3H), 2.87 (t, 2H), 3.43 (t, 2H), 3.54 (t, 2H), 4.17 (q, 2H), 4.23 (t, 2H), 7.36-7.45 (m, 4H), 8.24 (s, 1H), 11.68 (s, 1H).

Example 98A

Ethyl 2,4-dioxo-1-{4-[(2-oxo-1,3-oxazolidin-3-yl)methyl]phenyl}-1,2,3,4-tetrahydropyrimidine-5-carboxylate

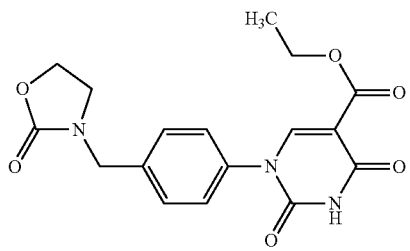 [SMILES: CCOC(=O)c1cn(-c2ccc(CN3CCOC3=O)cc2)c(=O)[nH]c1=O]

1.50 g (7.80 mmol) of 3-(4-aminobenzyl)-1,3-oxazolidin-2-one and 2.02 g (7.80 mmol) of ethyl 3-ethoxy-2-[(ethoxycarbonyl)carbamoyl]acrylate in 40 ml of ethanol were heated under reflux for 30 min. After cooling to RT, 876 mg (7.80 mmol) of potassium tert-butoxide were added and the reaction mixture was stirred at RT for 16 h and at 60° C. for 4.5 h. For work-up, the cooled reaction mixture was acidified with 1 N aqueous hydrochloric acid and diluted with water. The mixture was then partially concentrated and the solid formed was filtered off with suction, washed with water and dried under reduced pressure at 50° C. This gave 2.08 g (74% of theory) of the title compound.

LC-MS (Method 3): $R_t$=0.57 min; m/z=360 (M+H)$^+$.

$^1$H-NMR (400 MHz, DMSO-d$_6$): δ=1.22 (t, 3H), 3.48 (t, 2H), 4.17 (q, 2H), 4.30 (t, 2H), 4.41 (s, 2H), 7.37-7.54 (m, 4H), 8.27 (s, 1H), 11.70 (s, 1H).

Example 99A

Methyl methyl(4-nitrophenyl)carbamate

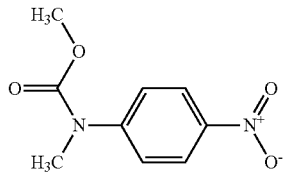

1.00 g (6.57 mmol) of N-methyl-4-nitroaniline were initially charged in THF (40 ml) and cooled to 0° C. 2.0 ml (24.7 mmol) of pyridine and 662 μl (7.88 mmol) of methyl chloroformate were slowly added dropwise and the reaction mixture was stirred at 0° C. for 1 h. At 0° C., 0.20 ml (2.47 ol) of methyl chloroformate was then added dropwise, and the mixture was stirred at RT for 1 h. For work-up, water was added and the reaction mixture was extracted three times with ethyl acetate. The combined organic phases were washed with saturated aqueous sodium chloride solution, dried over magnesium sulfate, filtered and concentrated. The residue was stirred with MTBE, and the solid was filtered off with suction, washed with MTBE and dried at 50° C. under reduced pressure. This gave 267 mg (19% of theory) of the title compound.

LC-MS (Method 3): $R_t$=0.81 min; m/z=211 (M+H)$^+$.

$^1$H-NMR (400 MHz, DMSO-d$_6$): δ=2.54 (s, 3H), 3.70 (s, 3H), 7.61-7.67 (m, 2H), 8.17-8.26 (m, 2H).

Example 100A

Methyl (4-aminophenyl)methylcarbamate

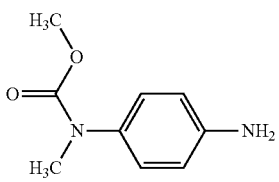

Preparation and purification of the title compound were analogous to Example 90A. Starting with 1.11 g (5.28 mmol) of methyl methyl(4-nitrophenyl)carbamate from Example 99A and after additional purification by flash chromatography (cyclohexane/ethyl acetate 5:1), 726 mg (76% of theory) of the title compound were obtained.

LC-MS (Method 2): $R_t$=0.94 min; m/z=181 (M+H)$^+$.

$^1$H-NMR (400 MHz, DMSO-d$_6$): δ=3.09 (s, 3H), 3.53 (br. s., 3H), 5.01-5.13 (m, 2H), 6.48-6.54 (m, 2H), 6.83-6.91 (m, 2H).

Example 101A

Ethyl 1-{4-[4(methoxycarbonyl)(methyl)amino]phenyl}-2,4-dioxo-1,2,3,4-tetrahydropyrimidine-5-carboxylate

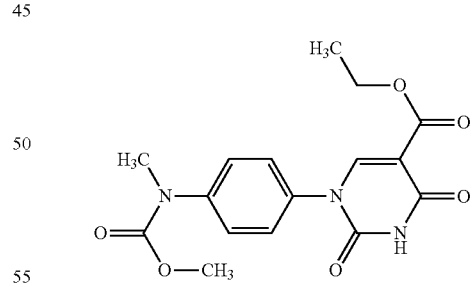

Preparation and purification of the title compound were analogous to Example 79A. Starting with 726 mg (4.03 mmol) of methyl (4-aminophenyl)methylcarbamate from Example 100A and 1.04 g (4.03 mmol) of ethyl 3-ethoxy-2-[(ethoxycarbonyl)carbamoyl]acrylate, 1.23 g (88% of theory) of the title compound were obtained.

LC-MS (Method 3): $R_t$=0.67 min; m/z=348 (M+H)$^+$.

$^1$H-NMR (400 MHz, DMSO-d$_6$): δ=1.23 (t, 3H), 3.26 (s, 3H), 3.64 (s, 3H), 4.17 (q, 2H), 7.42-7.52 (m, 4H), 8.29 (s, 1H), 11.70 (s, 1H).

Example 102A

Ethyl 1-(4-nitrophenyl)-2,4-dioxo-1,2,3,4-tetrahydropyrimidine-5-carboxylate

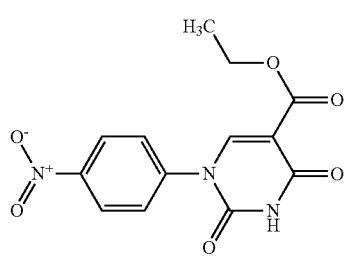 [SMILES: CCOC(=O)c1cn(-c2ccc([N+](=O)[O-])cc2)c(=O)[nH]c1=O]

2.00 g (14.48 mmol) of 4-nitroaniline and 3.75 g (14.48 mmol) of ethyl 3-ethoxy-2-[(ethoxycarbonyl)carbamoyl]acrylate in 109 ml of ethanol were heated under reflux for 2 h. After cooling to RT, 1.62 g (14.48 mmol) of potassium tert-butoxide were added and the reaction mixture was stirred at RT for 16 h and at reflux for 5 h. For work-up, the cooled reaction mixture was filtered and the filtrate was acidified with 1 N aqueous hydrochloric acid and diluted with water. The solid formed was filtered off with suction, washed with water and ethyl acetate and dried under reduced pressure at 50° C. The filtrate was stirred with MTBE/ethyl acetate, and the solid was filtered off with suction, washed with MTBE/ethyl acetate and dried under reduced pressure. This gave a total yield of 1.89 g (43% of theory) of the title compound.

LC-MS (Method 3): $R_t$=0.72 min; m/z=306 (M+H)$^+$.
$^1$H-NMR (400 MHz, DMSO-d$_6$): δ=1.24 (t, 3H), 4.19 (q, 2H), 7.78-7.84 (m, 2H), 8.34-8.42 (m, 3H), 11.81 (s, 1H).

Example 103A

Ethyl 3-[2-methyl-3-(trifluoromethyl)benzyl]-1-(4-nitrophenyl)-2,4-dioxo-1,2,3,4-tetrahydropyrimidine-5-carboxylate

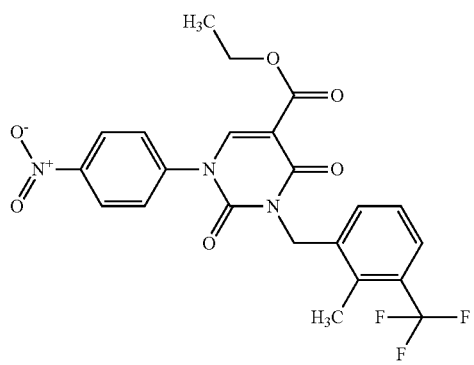 [SMILES: CCOC(=O)c1cn(-c2ccc([N+](=O)[O-])cc2)c(=O)n(Cc2cccc(C(F)(F)F)c2C)c1=O]

1.89 g (6.22 mmol) of ethyl 1-(4-nitrophenyl)-2,4-dioxo-1,2,3,4-tetrahydropyrimidine-5-carboxylate from Example 102A were initially charged in 20 ml of DMF. 1.73 g (6.84 mmol) of 2-methyl-3-(trifluoromethyl)benzyl bromide, 1.72 g (12.44 mmol) of potassium carbonate and 103 mg (0.62 mmol) of potassium iodide were added. The mixture was stirred at 60° C. for 5 h. Water was then added to the reaction mixture which had cooled to RT, and the solid formed was filtered off, washed with water and MTBE and dried under reduced pressure. The filtrate was stirred with ethanol, and the solid formed was filtered off with suction, washed with MTBE and dried under high vacuum. This gave a total yield of 2.02 g (68% of theory) of the title compound.

LC-MS (Method 3): $R_t$=1.15 min; m/z=478 (M+H)$^+$.
$^1$H-NMR (400 MHz, DMSO-d$_6$): δ=1.24 (t, 3H), 2.46 (s, 3H), 4.21 (q, 2H), 5.08 (s, 2H), 7.34 (t, 1H), 7.42 (d, 1H), 7.59 (d, 1H), 7.86 (d, 2H), 8.40 (d, 2H), 8.57 (s, 1H).

Example 104A

Ethyl 1-(4-aminophenyl)-3-[2-methyl-3-(trifluoromethyl)benzyl]-2,4-dioxo-1,2,3,4-tetrahydropyrimidine-5-carboxylate

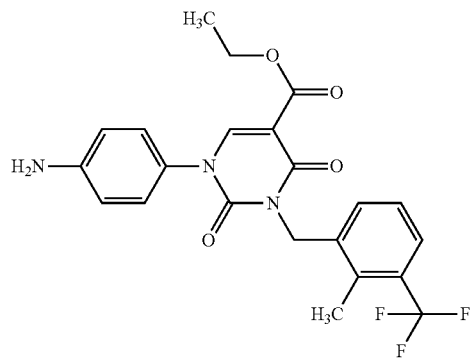 [SMILES: CCOC(=O)c1cn(-c2ccc(N)cc2)c(=O)n(Cc2cccc(C(F)(F)F)c2C)c1=O]

Under argon, 2.01 g (4.22 mmol) of ethyl 3-[2-methyl-3-(trifluoromethyl)benzyl]-1-(4-nitrophenyl)-2,4-dioxo-1,2,3,4-tetrahydropyrimidine-5-carboxylate from Example 103A were initially charged in 24 ml of THF/methanol (1:2). 45 mg (0.04 mmol) of 10% palladium on activated carbon were then added, and the mixture was hydrogenated at standard pressure for 4 h. The reaction mixture was diluted with dichloromethane and filtered through kieselguhr, and the filter cake was washed with dichloromethane/methanol. The filtrate was concentrated, the residue was stirred with ethyl acetate and the solid formed was filtered off with suction. The filter residue was washed with MTBE and dried under high vacuum. This gave 591 mg (27% of theory, purity 87%) of the title compound.

LC-MS (Method 3): $R_t$=1.05 min; m/z=448 (M+H)$^+$.
$^1$H-NMR (400 MHz, DMSO-d$_6$): δ=1.23 (t, 3H), 2.45 (s, 3H), 4.19 (q, 2H), 5.06 (s, 2H), 5.44 (s, 2H), 6.58-6.64 (m, 2H), 7.09-7.16 (m, 2H), 7.27-7.37 (m, 2H), 7.56-7.63 (m, 1H), 8.30 (s, 1H).

Example 105A

1-[3-(Difluoromethyl)-2-methylphenyl]methanamine

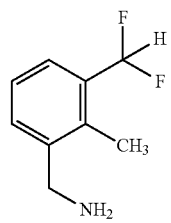

35.9 ml (35.89 mmol) of 1 M borane/THF complex were initially charged with ice cooling. Under argon, a solution of 2.00 g (11.96 mmol) of 3-(difluoromethyl)-2-methylbenzonitrile in THF (20 ml) was added dropwise, and the reaction mixture was heated at reflux for 3 h. The mixture was cooled to 0° C., 60 ml of 1 N aqueous hydrochloric acid were added and the mixture was concentrated. The residue was diluted with water and washed twice with dichloromethane. The aqueous phase was adjusted to pH 14 using 1N aqueous sodium hydroxide solution and extracted three times with dichloromethane. The combined organic phases were dried over sodium sulfate, filtered and concentrated. This gave 1.41 g (69% of theory) of the title compound.

$^1$H-NMR (400 MHz, DMSO-$d_6$): δ=1.64-1.88 (m, 2H), 2.31 (s, 3H), 3.72-3.78 (m, 2H), 7.25-7.32 (m, 1H), 7.38 (d, 1H), 7.53 (d, 1H).

Example 106A

1-[3-(Difluoromethyl)-2-methylbenzyl]urea

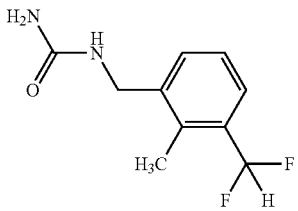

700 mg (4.08 mmol) of 1-[3-(difluoromethyl)-2-methylphenyl]methanamine from Example 105A and 982 mg (16.35 mmol) of urea were initially charged in 1.65 ml of water. 43 μl (0.52 mmol, purity 37%) of conc. hydrochloric acid were added dropwise, and the mixture was heated at reflux for 3 h. The cooled reaction mixture was diluted with water and stirred at RT for 30 min, the solid was filtered off with suction, washed with water and MTBE and dried under reduced pressure. This gave 719 mg (82% of theory) of the title compound.

LC-MS (Method 3): $R_t$=0.71 min; m/z=215 (M+H)$^+$.

$^1$H-NMR (400 MHz, DMSO-$d_6$): δ=2.31 (s, 3H), 4.21 (d, 2H), 5.53 (s, 2H), 6.35 (t, 1H), 7.03-7.22 (m, 1H), 7.25-7.34 (m, 1H), 7.36-7.46 (m, 2H).

Example 107A

Ethyl 3-[3-(difluoromethyl)-2-methylbenzyl]-2,4-dioxo-1,2,3,4-tetrahydropyrimidine-5-carboxylate

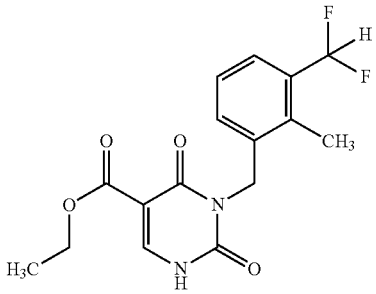 [SMILES: CCOC(=O)c1c[nH]c(=O)n(Cc2cccc(C(F)F)c2C)c1=O]

1.02 ml (5.03 mmol) of diethyl ethoxymethylenemalonate were added to 719 mg (3.35 mmol) of 1-[3-(difluoromethyl)-2-methylbenzyl]urea from Example 106A, and the mixture was stirred at 140° C. for 16 h. The cooled reaction mixture was diluted with 5 ml of ethanol, 343 mg (5.03 mmol) of sodium ethoxide were added and the mixture was stirred at reflux for 1 h. 200 ml of ice-cold 0.5 M aqueous hydrochloric acid were added to the cooled reaction mixture, and the reaction mixture was extracted twice with ethyl acetate. The combined organic phases were concentrated to half their original volume and the solid formed was filtered off, washed with MTBE and dried under reduced pressure. This gave 797 mg (70% of theory) of the title compound.

LC-MS (Method 3): $R_t$=0.98 min; m/z=339 (M+H)$^+$.

$^1$H-NMR (400 MHz, DMSO-$d_6$): δ=1.24 (t, 3H), 2.39 (s, 3H), 4.18 (q, 2H), 4.97 (s, 2H), 7.00-7.11 (m, 1H), 7.20-7.38 (m, 2H), 7.41 (d, 1H), 8.25 (s, 1H), 12.06 (s, 1H).

Example 108A 1-(2,3-Dihydro-1H-inden-1-yl)urea (racemate)

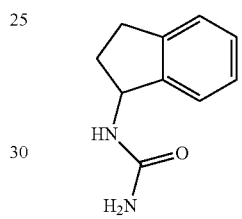

Preparation and purification of the title compound were carried out analogously to Example 106A using a reaction time of 2.5 h. Starting with 526 mg (3.95 mmol) of indane-1-amine (racemate) and 949 mg (15.79 mmol) of urea, this gave 563 mg (80% of theory) of the title compound.

LC-MS (Method 3): $R_t$=0.62 min; m/z=177 (M+H)$^+$.

$^1$H-NMR (400 MHz, DMSO-$d_6$): δ=1.57-1.74 (m, 1H), 2.30-2.42 (m, 1H), 2.68-2.80 (m, 1H), 2.82-2.94 (m, 1H), 5.05 (q, 1H), 5.46 (br. s., 2H), 6.28 (d, 1H), 7.14-7.27 (m, 4H).

Example 109A

Ethyl 3-(2,3-dihydro-1H-inden-1-yl)-2,4-dioxo-1,2,3,4-tetrahydropyrimidine-5-carboxylate (racemate)

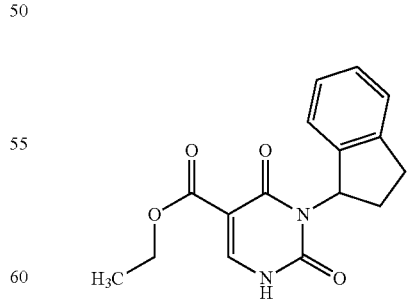

Preparation and purification of the title compound were analogous to Example 107A. Starting with 563 mg (3.19 mmol) of 1-(2,3-dihydro-1H-inden-1-yl)urea from Example 108A and 0.96 ml (4.78 mmol) of diethyl ethoxymethylenemalonate, after additional purification by flash chromatography (dichloromethane/methanol 99:1→4:1), 420 mg (43% of theory) of the title compound were obtained.

LC-MS (Method 3): $R_t$=0.84 min; m/z=301 (M+H)$^+$.

$^1$H-NMR (400 MHz, DMSO-d$_6$): δ=1.23 (t, 3H), 2.26-2.40 (m, 2H), 2.85-2.97 (m, 1H), 3.10-3.20 (m, 1H), 4.16 (q, 2H), 6.34 (t, 1H), 7.01 (d, 1H), 7.09 (t, 1H), 7.16 (t, 1H), 7.22 (d, 1H), 8.14 (s, 1H), 11.79 (br. s, 1H).

Example 110A 1-(3-Chloro-2-methylbenzyl)urea

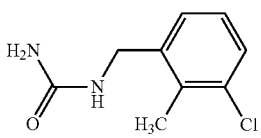

Preparation and purification of the title compound were carried out analogously to Example 106A using a reaction time of 6 h. Starting with 2.00 g (12.85 mmol) of 3-chloro-2-methylbenzylamine and 3.08 g (51.40 mmol) of urea, this gave 2.36 g (92% of theory) of the title compound.

LC-MS (Method 3): $R_t$=0.72 min; m/z=199 (M+H)$^+$.

$^1$H-NMR (400 MHz, DMSO-d$_6$): δ=2.29 (s, 3H), 4.19 (d, 2H), 5.53 (s, 2H), 6.36 (t, 1H), 7.14-7.22 (m, 2H), 7.28-7.35 (m, 1H).

Example 111A

Ethyl 3-(3-chloro-2-methylbenzyl)-2,4-dioxo-1,2,3,4-tetrahydropyrimidine-5-carboxylate

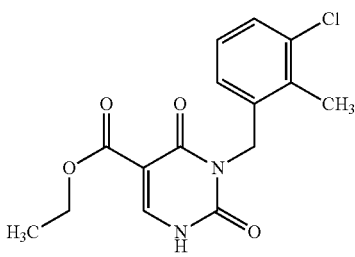

Preparation and purification of the title compound were analogous to Example 107A. Starting with 2.36 g (11.88 mmol) of 1-(3-chloro-2-methylbenzyl)urea from Example 110A and 3.60 ml (17.82 mmol) of diethyl ethoxymethylenemalonate, this gave 2.20 g (57% of theory) of the title compound.

LC-MS (Method 3): $R_t$=0.90 min; m/z=323 (M+H)$^+$.

$^1$H-NMR (400 MHz, DMSO-d$_6$): δ=1.24 (t, 3H), 2.40 (s, 3H), 4.17 (q, 2H), 4.96 (s, 2H), 6.85 (d, 1H), 7.13 (t, 1H), 7.33 (d, 1H), 8.25 (s, 1H), 12.06 (br. s, 1H).

Example 112A 1-(3-Fluoro-2-methylbenzyl)urea

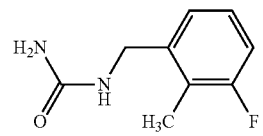

Preparation and purification of the title compound were carried out analogously to Example 106A using a reaction time of 2.5 h. Starting with 1.27 g (9.15 mmol) of 3-fluoro-2-methylbenzylamine and 2.74 g (45.76 mmol) of urea, this gave 1.40 g (84% of theory) of the title compound.

LC-MS (Method 3): $R_t$=0.59 min; m/z=183 (M+H)$^+$.

$^1$H-NMR (400 MHz, DMSO-d$_6$): δ=2.16 (s, 3H), 4.18 (d, 2H), 5.53 (br. s., 2H), 6.34 (t, 1H), 6.99-7.09 (m, 2H), 7.13-7.22 (m, 1H).

Example 113A

Ethyl 3-(3-fluoro-2-methylbenzyl)-2,4-dioxo-1,2,3,4-tetrahydropyrimidine-5-carboxylate

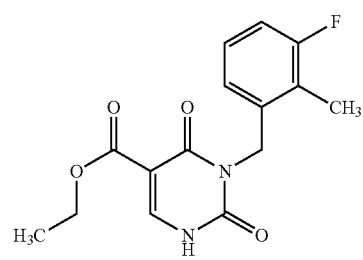 [SMILES: CCOC(=O)c1c[nH]c(=O)n(Cc2cccc(F)c2C)c1=O]

Preparation and purification of the title compound were analogous to Example 107A. Starting with 1.40 g (7.72 mmol) of 1-(3-fluoro-2-methylbenzyl)urea from Example 112A and 2.34 ml (11.58 mmol) of diethyl ethoxymethylenemalonate, this gave 1.35 g (57% of theory) of the title compound.

LC-MS (Method 3): $R_t$=0.84 min; m/z=307 (M+H)$^+$.

$^1$H-NMR (400 MHz, DMSO-d$_6$): δ=1.24 (t, 3H), 2.26 (s, 3H), 4.17 (q, 2H), 4.94 (s, 2H), 6.73 (d, 1H), 7.04 (t, 1H), 7.13 (q, 1H), 8.24 (s, 1H), 12.05 (s, 1H).

Example 114A

1-{1-[3-(Trifluoromethyl)phenyl]propyl}urea (racemate)

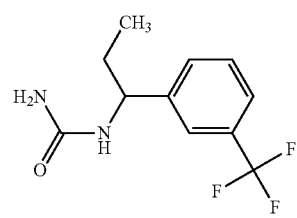 [SMILES: CCC(NC(N)=O)c1cccc(C(F)(F)F)c1]

Preparation and purification of the title compound were carried out analogously to Example 106A using a reaction time of 2.5 h. Starting with 1.10 g (5.42 mmol) of 1-[3-(trifluoromethyl)phenyl]propylamine (racemate) and 1.62 g (27.09 mmol) of urea, this gave 910 mg (68% of theory) of the title compound.

LC-MS (Method 3): $R_t$=0.79 min; m/z=247 (M+H)$^+$.

$^1$H-NMR (400 MHz, DMSO-d$_6$): δ=0.82 (t, 3H), 1.58-1.70 (m, 2H), 4.58 (q, 1H), 5.47 (s, 2H), 6.57 (d, 1H), 7.52-7.61 (m, 4H).

Example 115A

Ethyl 2,4-dioxo-3-{1-[3-(trifluoromethyl)phenyl]propyl}-1,2,3,4-tetrahydropyrimidine-5-carboxylate (racemate)

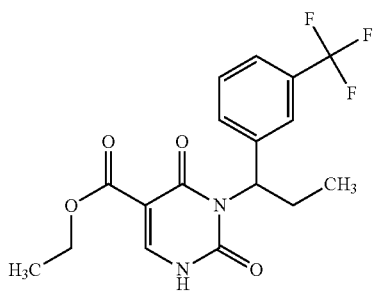 [SMILES: CCOC(=O)c1c[nH]c(=O)n(C(CC)c2cccc(C(F)(F)F)c2)c1=O]

Preparation and purification of the title compound were analogous to Example 107A. Starting with 910 mg (3.69 mmol) of 1-{1-[3-(trifluoromethyl)phenyl]propyl}urea from Example 114A and 1.12 ml (5.54 mmol) of diethyl ethoxymethylenemalonate, after two purifications by flash chromatography (dichloromethane/methanol 98:2 99:1), 300 mg (22% of theory) of the title compound were obtained.

LC-MS (Method 3): $R_t$=0.97 min; m/z=371 (M+H)$^+$.

$^1$H-NMR (400 MHz, DMSO-d$_6$): δ=0.86 (t, 3H), 1.23 (t, 3H), 2.25-2.35 (m, 1H), 2.36-2.47 (m, 1H), 4.16 (q, 2H), 5.87-5.97 (m, 1H), 7.52-7.58 (m, 1H), 7.60-7.66 (m, 3H), 8.17 (s, 1H), 11.83-11.93 (m, 1H).

Example 116A 1-(4-Methyl-2,3-dihydro-1H-inden-1-yl)urea (racemate)

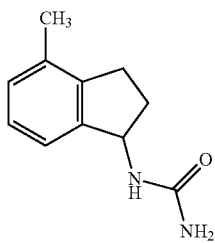

Preparation and purification of the title compound were carried out analogously to Example 106A using a reaction time of 3 h. Starting with 220 mg (0.89 mmol, purity 60%) of 4-methylindane-1-amine (racemate) [described in: WO2008/9881 A1, 2008, p. 65] and 269 mg (4.48 mmol) of urea, this gave 124 mg (72% of theory) of the title compound.

LC-MS (Method 1): $R_t$=0.87 min; m/z=191 (M+H)$^+$.

$^1$H-NMR (400 MHz, DMSO-d$_6$): δ=1.58-1.72 (m, 1H), 2.21 (s, 3H), 2.31-2.43 (m, 1H), 2.59-2.69 (m, 1H), 2.77-2.88 (m, 1H), 5.04 (q, 1H), 5.45 (br. s., 2H), 6.24 (d, 1H), 6.98-7.13 (m, 3H).

Example 117A

Ethyl 3-(4-methyl-2,3-dihydro-1H-inden-1-yl)-2,4-dioxo-1,2,3,4-tetrahydropyrimidine-5-carboxylate (racemate)

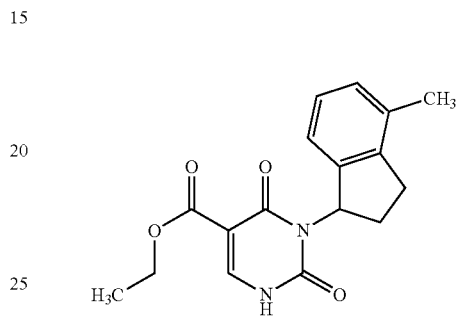

0.19 ml (0.94 mmol) of diethyl ethoxymethylenemalonate and 2 ml of ethanol were added to 120 mg (0.63 mmol) of 1-(4-methyl-2,3-dihydro-1H-inden-1-yl)urea from Example 116A. The reaction mixture was heated at 140° C. for 16 h. First 2 ml of ethanol and then 64 mg (0.94 mmol) of sodium ethoxide were added to the cooled reaction mixture, and the mixture was heated at reflux for 16 h. 64 mg (0.94 mmol) of sodium ethoxide were subsequently added to the cooled mixture, and the mixture was stirred under reflux for 1 h. The mixture was then cooled to RT and introduced into 100 ml of ice-cooled 0.5 M aqueous hydrochloric acid. The mixture was extracted three times with ethyl acetate and the combined organic phases were washed in each case once with water and saturated aqueous sodium chloride solution. The organic phases were concentrated and the residue was separated by preparative HPLC (Method 7a). The crude product was additionally purified by preparative HPLC (Method 8). This gave 70 mg (35% of theory) of the title compound.

LC-MS (Method 1): $R_t$=1.19 min; m/z=315 (M+H)$^+$.

$^1$H-NMR (400 MHz, DMSO-d$_6$): δ=1.22 (t, 3H), 2.23 (s, 3H), 2.27-2.38 (m, 2H), 2.76-2.87 (m, 1H), 3.00-3.12 (m, 1H), 4.15 (q, 2H), 6.25-6.41 (m, 1H), 6.82 (d, 1H), 6.95-7.05 (m, 2H), 8.13 (s, 1H), 11.63-11.98 (m, 1H).

Example 118A 1-(2-Chloro-3,6-difluorobenzyl)urea

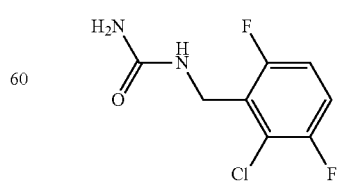

Preparation and purification of the title compound were carried out analogously to Example 106A using a reaction time of 3.5 h. Starting with 1.50 g (8.44 mmol) of 2-chloro-3,6-difluorobenzylamine and 2.02 g (33.78 mmol) of urea, this gave 1.15 g (62% of theory) of the title compound.

LC-MS (Method 1): R$_t$=0.79 min; m/z=221 (M+H)$^+$.

$^1$H-NMR (400 MHz, DMSO-d$_6$): δ=4.34 (dd, 2H), 5.51 (s, 2H), 6.36 (t, 1H), 7.26-7.34 (m, 1H), 7.39-7.48 (m, 1H).

Example 119A

Ethyl 3-(2-chloro-3,6-difluorobenzyl)-2,4-dioxo-1,2,3,4-tetrahydropyrimidine-5-carboxylate

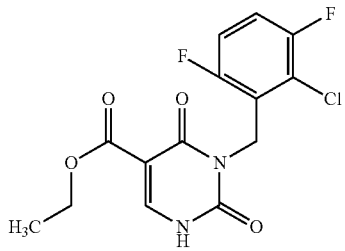 [SMILES: CCOC(=O)c1c[nH]c(=O)n(Cc2c(F)ccc(F)c2Cl)c1=O]

Preparation and purification of the title compound were analogous to Example 117A. Starting with 1.15 g (5.24 mmol) of 1-(2-chloro-3,6-difluorobenzyl)urea from Example 118A and 1.59 ml (7.86 mmol) of diethyl ethoxymethylenemalonate, this gave 851 mg (45% of theory) of the title compound.

LC-MS (Method 3): R$_t$=0.79 min; m/z=345 (M+H)$^+$.

$^1$H-NMR (400 MHz, DMSO-d$_6$): δ=1.22 (t, 3H), 4.16 (q, 2H), 5.13 (s, 2H), 7.20-7.29 (m, 1H), 7.38-7.46 (m, 1H), 8.20 (s, 1H), 11.94-12.05 (m, 1H).

Example 120A

1-[4-(Trifluoromethyl)-2,3-dihydro-1H-inden-1-yl]urea (racemate)

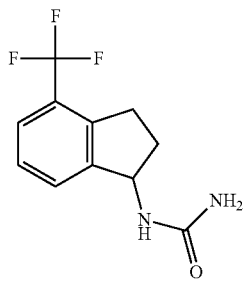 [SMILES: NC(=O)NC1CCc2c1cccc2C(F)(F)F]

Preparation and purification of the title compound were carried out analogously to Example 106A using a reaction time of 3 h. Starting with 774 mg (2.27 mmol, 59% pure) of 4-(trifluoromethyl)indane-1-amine (racemate) [described in: DE2812578, 1978; Chem. Abstr. Vol. 90, p. 54730] and 682 mg (11.35 mmol) of urea, 262 mg (47% of theory) of the title compound were obtained.

LC-MS (Method 3): R$_t$=0.81 min; m/z=245 (M+H)$^+$.

$^1$H-NMR (400 MHz, DMSO-d$_6$): δ=1.69-1.84 (m, 1H), 2.39-2.47 (m, 1H), 2.83-2.97 (m, 1H), 3.00-3.13 (m, 1H), 5.12 (q, 1H), 5.53 (br. s., 2H), 6.42 (d, 1H), 7.43 (t, 1H), 7.48-7.60 (m, 2H).

Example 121A

Ethyl 2,4-dioxo-3-[4-(trifluoromethyl)-2,3-dihydro-1H-inden-1-yl]-1,2,3,4-tetrahydropyrimidine-5-carboxylate (racemate)

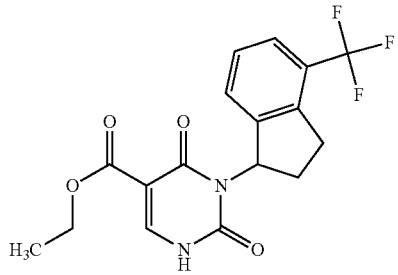 [SMILES: CCOC(=O)c1c[nH]c(=O)n(C2CCc3c2cccc3C(F)(F)F)c1=O]

Preparation and purification of the title compound were analogous to Example 107A. Starting with 3.00 g (12.28 mmol) of 1-[4-(trifluoromethyl)-2,3-dihydro-1H-inden-1-yl]urea from Example 120A and 3.72 ml (18.42 mmol) of diethyl ethoxymethylenemalonate, after additional purification by flash chromatography (dichloromethane/methanol 100:1→98:2), 1.03 g (18% of theory) of the title compound were obtained.

LC-MS (Method 3): R$_t$=0.94 min; m/z=369 (M+H)$^+$.

$^1$H-NMR (400 MHz, DMSO-d$_6$): δ=1.20-1.27 (m, 3H), 2.29-2.38 (m, 1H), 2.39-2.47 (m, 1H), 3.01-3.14 (m, 1H), 3.23-3.30 (m, 1H), 4.17 (q, 2H), 6.28-6.49 (m, 1H), 7.29-7.39 (m, 2H), 7.50-7.55 (m, 1H), 8.14-8.19 (m, 1H), 11.66-12.12 (m, 1H).

Example 122A 1-(4-Chloro-2,3-dihydro-1H-inden-1-yl)urea (racemate)

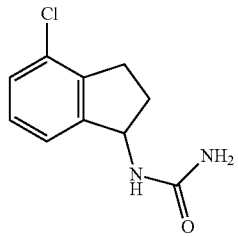 [SMILES: NC(=O)NC1CCc2c(Cl)cccc21]

Preparation and purification of the title compound were carried out analogously to Example 106A using a reaction time of 16 h. Starting with 3.02 g (5.95 mmol, purity 33%) of 4-chloroindane-1-amine (racemate) [described in: US 2008/255230 A1, 2008, p. 14] and 1.79 g (29.77 mmol) of urea, this gave, after additional purification by flash chromatography (dichloromethane/methanol 629:1→95:5), 629 mg (47% of theory) of the title compound.

LC-MS (Method 3): R$_t$=0.77 min; m/z=211 (M+H)$^+$.

$^1$H-NMR (400 MHz, DMSO-d$_6$): δ=1.66-1.79 (m, 1H), 2.35-2.46 (m, 1H), 2.71-2.82 (m, 1H), 2.87-2.98 (m, 1H), 5.13 (q, 1H), 5.51 (s, 2H), 6.39 (d, 1H), 7.16-7.30 (m, 3H).

Example 123A

Ethyl 3-(4-chloro-2,3-dihydro-1H-inden-1-yl)-2,4-dioxo-1,2,3,4-tetrahydropyrimidine-5-carboxylate (racemate)

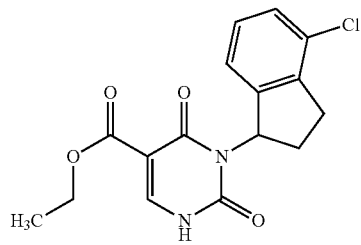 [SMILES: CCOC(=O)c1c[nH]c(=O)n(C2CCc3c(Cl)cccc32)c1=O]

820 mg (3.89 mmol) of 1-(4-chloro-2,3-dihydro-1H-inden-1-yl)urea (racemate) from Example 122A and 1.18 ml (5.84 mmol) of diethyl ethoxymethylenemalonate were stirred at 140° C. for 2 days. At RT, the reaction mixture was diluted with 9 ml of ethanol, 397 mg (5.84 mmol) of sodium ethoxide were then added and the mixture was stirred at reflux for a further 4 days. 1 M aqueous hydrochloric acid was added to the mixture which had cooled to RT, and the mixture was extracted three times with ethyl acetate. The combined organic phases were washed once each with water and saturated aqueous sodium chloride solution, dried over magnesium sulfate, filtered and concentrated. The residue was pre-purified by preparative HPLC (Method 7a) and the crude product was purified by flash chromatography (dichloromethane/methanol 98:2). This gave 294 mg (22% of theory) of the title compound.

LC-MS (Method 3): $R_t$=0.95 min; m/z=335 (M+H)$^+$.

$^1$H-NMR (400 MHz, DMSO-d$_6$): δ=1.23 (t, 3H), 2.26-2.35 (m, 1H), 2.36-2.46 (m, 1H), 2.88-2.98 (m, 1H), 3.08-3.19 (m, 1H), 4.15 (q, 2H), 6.30-6.51 (m, 1H), 7.02 (d, 1H), 7.14 (t, 1H), 7.25 (d, 1H), 8.15 (s, 1H), 11.69-12.03 (m, 1H).

Example 124A

1-[2,3-Bis(trifluoromethyl)phenyl]methanamine

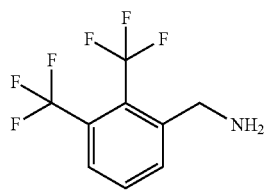 [SMILES: NCc1cccc(C(F)(F)F)c1C(F)(F)F]

Preparation and purification of the title compound were analogous to Example 105A. Starting with 5.53 g (23.12 mmol) of 2,3-bis(trifluoromethyl)benzonitrile, 4.07 g (70% of theory) of the title compound were obtained.

LC-MS (Method 3): $R_t$=0.49 min; m/z=244 (M+H)$^+$.

$^1$H-NMR (400 MHz, DMSO-d$_6$): δ=1.99 (br. s., 2H), 3.88-3.98 (m, 2H), 7.83-7.94 (m, 2H), 8.20 (d, 1H).

Example 125A

1-[2,3-Bis(trifluoromethyl)benzyl]urea

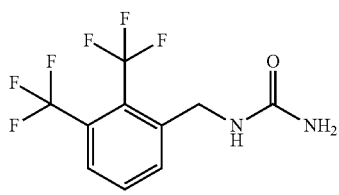 [SMILES: NC(=O)NCc1cccc(C(F)(F)F)c1C(F)(F)F]

Preparation and purification of the title compound were carried out analogously to Example 106A using a reaction time of 16 h. Starting with 4.07 g (16.73 mmol) of 1-[2,3-bis(trifluoromethyl)phenyl]methanamine and 4.02 g (66.95 mmol) of urea, this gave 2.01 g (42% of theory) of the title compound.

LC-MS (Method 3): $R_t$=0.79 min; m/z=287 (M+H)$^+$.

$^1$H-NMR (400 MHz, DMSO-d$_6$): δ=4.37-4.47 (m, 2H), 5.71 (s, 2H), 6.60 (t, 1H), 7.85-7.90 (m, 2H), 7.91-7.96 (m, 1H).

Example 126A

Ethyl 3-[2,3-bis(trifluoromethyl)benzyl]-2,4-dioxo-1,2,3,4-tetrahydropyrimidine-5-carboxylate

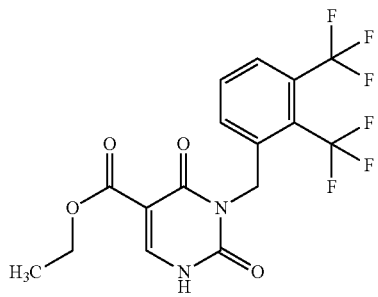 [SMILES: CCOC(=O)c1c[nH]c(=O)n(Cc2cccc(C(F)(F)F)c2C(F)(F)F)c1=O]

2.01 g (7.04 mmol) of 1-[2,3-bis(trifluoromethyl)benzyl]urea from Example 125A and 2.13 ml (10.56 mmol) of diethyl ethoxymethylenemalonate were stirred at 140° C. for 4 days. The cooled reaction mixture was diluted with 20 ml of ethanol, 719 mg (10.56 mmol) of sodium ethoxide were then added and the mixture was stirred at reflux for a further 2.5 h. The mixture, cooled to RT, was added dropwise to 400 ml of ice-cooled 0.5 M aqueous hydrochloric acid, and the solid formed was filtered off with suction, washed with MTBE and dried under reduced pressure. This gave 1.92 g (66% of theory) of the title compound.

LC-MS (Method 3): $R_t$=0.99 min; m/z=411 (M+H)$^+$.

$^1$H-NMR (400 MHz, DMSO-d$_6$): δ=1.24 (t, 3H), 4.18 (q, 2H), 5.17 (br. s., 2H), 7.53 (d, 1H), 7.79 (t, 1H), 7.94 (d, 1H), 8.29 (s, 1H), 12.15 (s, 1H).

Example 127A

Ethyl 1-[4-(3,5-dimethyl-1H-pyrazol-1-yl)phenyl]-2,4-dioxo-1,2,3,4-tetrahydropyrimidine-5-carboxylate

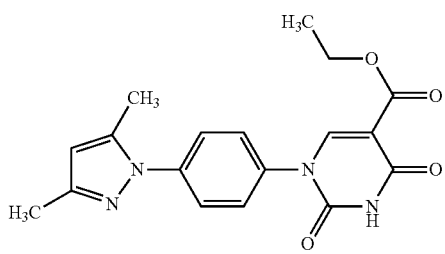 [SMILES: CCOC(=O)c1cn(-c2ccc(-n3nc(C)cc3C)cc2)c(=O)[nH]c1=O]

Preparation and purification of the title compound were analogous to Example 79A. Starting with 1 g (3.84 mmol) of 4-(3,5-dimethyl-1H-pyrazol-1-yl)aniline dihydrochloride and 997 mg (3.84 mmol) of ethyl 3-ethoxy-2-[(ethoxycarbonyl)carbamoyl]acrylate, after additional purification by flash chromatography (dichloromethane/methanol 24:1→9:1), 838 mg (46% of theory) of the title compound were obtained.

LC-MS (Method 1): $R_t$=0.93 min; m/z=355 (M+H)$^+$.

Example 128A (S)-4-Trifluoromethylindan-1-ol (S enantiomer)

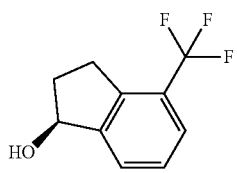 [SMILES: O[C@H]1CCc2c1cccc2C(F)(F)F]

A solution of 50.0 g (249.8 mmol) of 4-trifluoromethyl-1-indanone, 174 ml (1.249 mol) of triethylamine and 1.43 g (2.25 mmol) of (S,S)—N-(p-toluenesulfonyl)-1,2-diphenylethanediamine(chloro)[1-methyl-4-(propan-2-yl)benzene]ruthenium(II) [CASNo.: 192139-90-5; RuCl(p-cymene) [(S,S)-TsDPEN]] in 231 ml of dichloromethane was heated to 35° C. and, at this temperature, 47.1 ml (1.249 mol) of formic acid were added gradually (addition time about 40 min). During the addition, the temperature of the reaction mixture increased to 42° C. After the addition was complete, the mixture was stirred at 38° C. for a further 2 h. All volatile constituents were removed on a rotary evaporator and under high vacuum. Subsequently, the residue was dissolved in a little dichloromethane and purified on 1 kg of silica gel (mobile phase: first 2.5 l of cyclohexane/ethyl acetate 5:1, then 6 l of cyclohexane/ethyl acetate 1:1). The suitable fractions were concentrated on a rotary evaporator and the product was dried under high vacuum. This gave 45.0 g (89% of theory) of the title compound.

GC-MS (Method 10): $R_t$=3.43 min; MS (CI-pos): m/z=202 (M)$^+$.

$^1$H-NMR (400 MHz, DMSO-d$_6$): [ppm]=1.76-1.91 (m, 1H), 2.40 (ddt, 1H), 2.86 (dt, 1H), 3.01-3.13 (m, 1H), 5.09 (q, 1H), 5.45 (d, 1H), 7.38-7.48 (m, 1H), 7.55 (d, 1H), 7.62 (d, 1H).

Chiral analytical HPLC (Method 12): $R_t$=7.14 min; ee>99%.

Example 129A

3-[4-(4,4,5,5-Tetramethyl-1,3,2-dioxaborolan-2-yl)phenyl]-1,3-oxazolidin-2-one

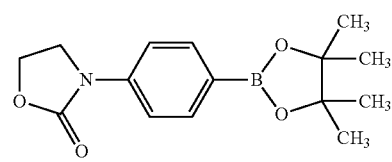 [SMILES: CC1(C)OB(c2ccc(N3CCOC3=O)cc2)OC1(C)C]

42.7 g (168.36 mmol) of 4,4,4',4',5,5,5',5'-octamethyl-2,2'-bi-1,3,2-dioxaborolane and 0.8 g (2.24 mmol, purity 70%) of dibenzoyl peroxide were initially charged in acetonitrile (160 ml), 20.0 g (112.24 mmol) of 3-(4-aminophenyl)-1,3-oxazolidin-2-one (described in: WO2005/54238 A1, 2005; page 105) and 19.3 g (168.36 mmol, 90% pure) of tert-butyl nitrite were added, and the reaction mixture was stirred at RT overnight. The reaction mixture was concentrated almost completely, the residue was stirred with MTBE and the solid was filtered off, washed with MTBE and dried under reduced pressure. This gave 21.4 g (61% of theory, purity 92%) of the target compound.

LC-MS (Method 11): $R_t$=1.03 min; MS (ESIpos): m/z=290 (M+H)$^+$.

$^1$H-NMR (400 MHz, DMSO-d$_6$): δ=1.29 (s, 12H), 4.07 (t, 2H), 4.44 (t, 2H), 7.59 (d, 2H), 7.68 (d, 2H).

Example 130A tert-Butyl 3-(4-nitrophenyl)-2-oxoimidazolidine-1-carboxylate

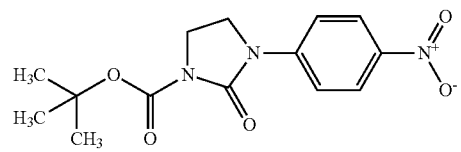 [SMILES: CC(C)(C)OC(=O)N1CCN(c2ccc([N+](=O)[O-])cc2)C1=O]

8.8 mg (72 μmol) of DMAP and 1.74 g (7.96 mmol) of di-tert-butyl dicarbonate were added to 2.0 g (7.24 mmol, purity 75%) of 1-(4-nitrophenyl)imidazolidin-2-one (preparation: see P. Stabile et al., Tetrahedron Letters (2010), 51(24), 3232) in 15 ml of DMF and 15 ml of THF. The suspension was stirred at RT overnight. 0.79 g of di-tert-butyl dicarbonate and 8.8 mg of DMAP were added, and the mixture was stirred for 24 h. For work-up, 50 ml of water were added and the solid was filtered off with suction. The solid was washed with 100 ml of water and then with 10 ml of MTBE and dried under high vacuum. This gave 2.49 g (95% of theory, purity 85%) of the title compound.

LC-MS (Method 3): $R_t$=1.02 min; MS (ESIpos): m/z=307 (M+H)$^+$, (ESIneg): m/z=205 (M–H)$^-$.

$^1$H-NMR (400 MHz, DMSO-d$_6$): δ [ppm]=1.49 (s, 9H), 3.80-3.87 (m, 2H), 3.87-3.94 (m, 2H), 7.81-7.87 (m, 2H), 8.23-8.28 (m, 2H).

Example 131A tert-Butyl 3-(4-aminophenyl)-2-oxoimidazolidine-1-carboxylate

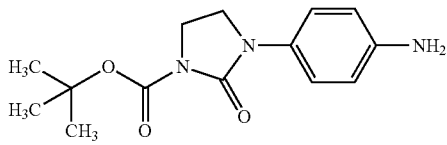 [SMILES: CC(C)(C)OC(=O)N1CCN(c2ccc(N)cc2)C1=O]

1.00 g (3.25 mmol) of the compound from Example 130A was hydrogenated in the presence of 35 mg of 10% palladium on carbon in 50 ml of THF at RT under standard hydrogen pressure. After completion of conversion (3 h), the catalyst was filtered off through kieselguhr. The filter was washed with 200 ml of THF and the entire filtrate was concentrated completely on a rotary evaporator. The solid that remained was dried under high vacuum. This gave 982 mg (98% of theory, purity 90%) of the title compound.

LC-MS (Method 3): $R_t$=0.66 min; MS (ESIpos): m/z=278 (M+H)$^+$.

$^1$H-NMR (400 MHz, DMSO-d$_6$): δ [ppm]=1.46 (s, 9H), 3.66-3.79 (m, 4H), 4.98 (s, 2H), 6.52-6.58 (m, 2H), 7.11-7.16 (m, 2H).

Example 132A

Ethyl 1-{4-[3-(tert-butoxycarbonyl)-2-oxoimidazolidin-1-yl]phenyl}-2,4-dioxo-1,2,3,4-tetrahydropyrimidine-5-carboxylate

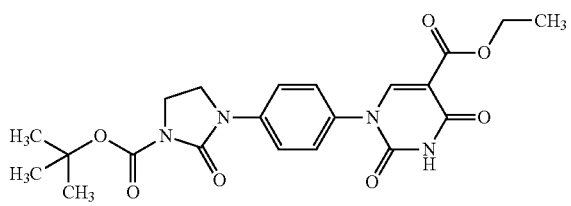 [SMILES: CCOC(=O)c1cn(-c2ccc(N3CCN(C(=O)OC(C)(C)C)C3=O)cc2)c(=O)[nH]c1=O]

980 mg (3.2 mmol) of the compound from Example 131A and 833 mg (3.21 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) in 30 ml of ethanol were heated at reflux for 1 h. After cooling to RT, 360 mg (3.21 mmol) of potassium tert-butoxide were added and the reaction mixture was stirred first at RT overnight and then at 60° C. for 7.5 h. After cooling to RT, the solution was acidified slightly (pH 6) by addition of 1N aqueous hydrochloric acid and diluted with 20 ml of water. The solid formed was filtered off with suction, washed three times with in each case 10 ml of water and dried overnight in a drying cabinet at 50° C. This gave 940 mg (54% of theory, purity 90%) of the title compound.

LC-MS (Method 3): $R_t$=0.86 min; MS (ESIpos): m/z=445 (M+H)$^+$.

$^1$H-NMR (400 MHz, DMSO-d$_6$): [ppm]=1.22 (t, 3H), 1.48 (s, 9H), 3.78-3.89 (m, 4H), 4.17 (q, 2H), 7.48 (d, 2H), 7.68 (d, 2H), 8.24 (s, 1H), 11.68 (br. s., 1H).

Example 133A

Ethyl 1-{4-[3-(tert-butoxycarbonyl)-2-oxoimidazolidin-1-yl]phenyl}-2,4-dioxo-3-[(1R)-4-(trifluoromethyl)-2,3-dihydro-1H-inden-1-yl]-1,2,3,4-tetrahydropyrimidine-5-carboxylate Under argon, 500 mg (1.13 mmol) of the compound from Example 132A and 885 mg (3.38 mmol) of triphenylphosphine were initially charged in 12 ml of THF/DMF 1:1. 455 mg (2.25 mmol) of diisopropyl azodicarboxylate and 273 mg (1.35 mmol) of the compound from Example 128A were added, and the mixture was stirred at RT overnight. For work-up, 1 ml of 1N aqueous hydrochloric acid and 50 ml of ethyl acetate were added. After stirring, the phases were separated. The organic phase was washed twice with 1N aqueous hydrochloric acid and once with a saturated sodium chloride solution, dried over magnesium sulfate and concentrated on a rotary evaporator. The residue was purified first by flash chromatography (mobile phase dichloromethane/methanol 99:1), then by preparative HPLC (Method 8). This gave 362 mg (40% of theory, purity 80%) of the title compound.

LC-MS (Method 3): $R_t$=1.26 min; MS (ESIpos): m/z=629 (M+H)$^+$.

$^1$H-NMR (400 MHz, CD$_2$Cl$_2$): δ [ppm]=1.23 (td, 3H), 1.37-1.50 (m, 9H), 2.27-2.43 (m, 1H), 2.43-2.59 (m, 1H), 2.97-3.15 (m, 1H), 3.30-3.46 (m, 1H), 3.67-3.90 (m, 4H), 4.20 (dq, 2H), 6.48-6.59 (m, 1H), 7.15-7.33 (m, 4H), 7.36-7.46 (m, 1H), 7.55-7.70 (m, 2H), 8.23 (s, 1H).

WORKING EXAMPLES

Example 1

Ethyl 3-(2,3-dichlorobenzyl)-1-(4-methoxyphenyl)-2,4-dioxo-1,2,3,4-tetrahydropyrimidine-5-carboxylate 95 mg (0.69 mmol) of potassium carbonate and 91 mg (0.38 mmol) of 2,3-dichlorobenzyl bromide were added to 100 mg (0.34 mmol) of ethyl 1-(4-methoxyphenyl)-2,4-dioxo-1,2,3,4-tetrahydropyrimidine-5-carboxylate from Example 38A in acetonitrile, and the reaction mixture was stirred at 60° C. overnight. The mixture was concentrated and the residue was purified by filtration through 500 mg of silica gel using cyclohexane/ethyl acetate in a ratio of 2:1. This gave, after concentration of the eluate and drying under reduced pressure, 137 mg (88% of theory) of the target compound.

LC-MS (Method 3): $R_t$=1.19 min; m/z=449 (M+H)$^+$.

$^1$H-NMR (400 MHz, DMSO-$d_6$): δ=1.23 (t, 3H), 3.81 (s, 3H), 4.20 (q, 2H), 5.09 (s, 2H), 7.04-7.09 (m, 2H), 7.21 (dd, 1H), 7.32 (t, 1H), 7.43-7.49 (m, 2H), 7.58 (dd, 1H), 8.39 (s, 1H).

Example 2

Ethyl 1-(4-methoxyphenyl)-3-[2-methyl-3-(trifluoromethyl)benzyl]-2,4-dioxo-1,2,3,4-tetrahydropyrimidine-5-carboxylate

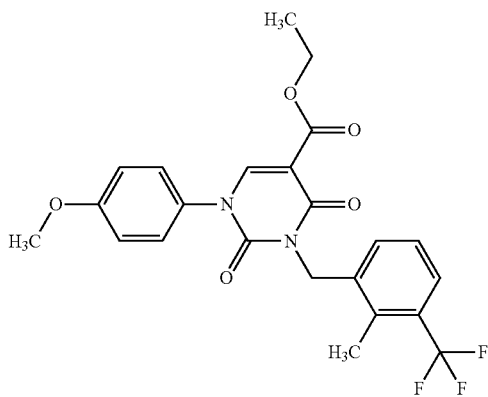 [SMILES: CCOC(=O)c1cn(-c2ccc(OC)cc2)c(=O)n(Cc2cccc(C(F)(F)F)c2C)c1=O]

190 mg (1.38 mmol) of potassium carbonate, 229 mg (1.38 mmol) of potassium iodide and 174 mg (0.69 mmol) of 2-methyl-3-(trifluoromethyl)benzyl bromide were added to 200 mg (0.69 mmol) of ethyl 1-(4-methoxyphenyl)-2,4-dioxo-1,2,3,4-tetrahydropyrimidine-5-carboxylate from Example 38A in 6 ml of acetonitrile, and the reaction mixture was stirred at 60° C. overnight. The mixture was concentrated and purified by preparative HPLC (Method 6a). This gave 211 mg (66% of theory) of the target compound.

LC-MS (Method 3): $R_t$=1.21 min; m/z=463 (M+H)$^+$.

$^1$H-NMR (400 MHz, DMSO-$d_6$): δ=1.22 (t, 3H), 2.45 (s, 3H), 3.80 (s, 3H), 4.19 (q, 2H), 5.08 (s, 2H), 7.05 (d, 2H), 7.30-7.40 (m, 2H), 7.45 (d, 2H), 7.60 (dd, 1H).

Example 3

Ethyl 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylate

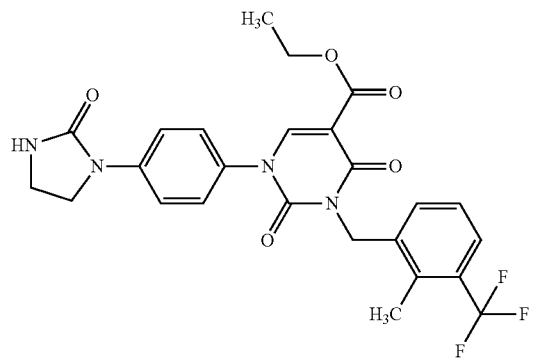 [SMILES: CCOC(=O)c1cn(-c2ccc(N3CCNC3=O)cc2)c(=O)n(Cc2cccc(C(F)(F)F)c2C)c1=O]

A mixture of 400 mg (1.16 mmol) of ethyl 2,4-dioxo-1-[4-(2-oxoimidazolidin-1-yl)phenyl]-1,2,3,4-tetrahydropyrimidine-5-carboxylate from Example 15A, 353 mg (1.39 mmol) of 2-methyl-3-(trifluoromethyl)benzyl bromide, 321 mg (2.32 mmol) of potassium carbonate and 193 mg (1.16 mmol) of potassium iodide in 16 ml of acetonitrile was stirred at 60° C. for 18 hours. The mixture was then cooled to 20° C., and 50 ml of water were added. The product formed was filtered off with suction, washed with a little diethyl ether and dried under high vacuum. 537 mg (89% of theory) of the target compound were obtained.

LC-MS (Method 3): $R_t$=1.05 min; m/z=517 (M+H)$^+$.

$^1$H-NMR (400 MHz, DMSO-$d_6$): δ=1.22 (t, 3H), 2.48 (s, 3H), 3.42 (m, 2H), 3.87 (m, 2H), 4.19 (q, 2H), 5.08 (s, 2H), 7.08 (s, 1H), 7.30-7.40 (m, 2H), 7.46 (d, 2H), 7.59 (d, 1H), 7.68 (d, 2H), 8.39 (s, 1H).

In analogy to Example 3, the above-described 1,2,3,4-tetrahydropyrimidine-2,4-dione-5-carboxylic esters (uracil-5-carboxylic esters) were used to obtain, by reaction with the respective benzyl chlorides or benzyl bromides in the presence of potassium carbonate and potassium iodide, the benzyl-substituted uracil compounds which follow. A difference is that 1-3 equivalents of potassium carbonate and 0.1 to 2 equivalents of potassium iodide may also be used. The solvent used was acetonitrile, to which dimethylformamide was added in the case of poorly soluble compounds.

Example 4

Ethyl 3-(2,3-dichlorobenzyl)-2,4-dioxo-1-[4-(2-oxoimidazolidin-1-yl)phenyl]-1,2,3,4-tetrahydropyrimidine-5-carboxylate

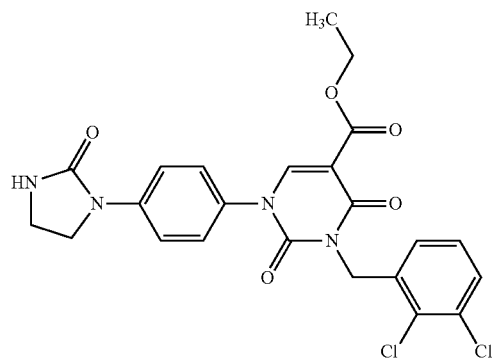 [SMILES: CCOC(=O)c1cn(-c2ccc(N3CCNC3=O)cc2)c(=O)n(Cc2cccc(Cl)c2Cl)c1=O]

The preparation was carried out analogously to Example 3 from 200 mg (0.58 mmol) of ethyl 2,4-dioxo-1-[4-(2-oxoimidazolidin-1-yl)phenyl]-1,2,3,4-tetrahydropyrimidine-5-carboxylate from Example 15A and 136.3 mg (0.70 mmol) of 2,3-dichlorobenzyl chloride. Yield: 78 mg (27% of theory).

LC-MS (Method 3): $R_t$=1.04 min; m/z=503 (M+H)$^+$.

$^1$H-NMR (400 MHz, DMSO-d$_6$): δ=1.22 (t, 3H), 3.42 (m, 2H), 3.89 (m, 2H), 4.20 (q, 2H), 5.1 (s, 2H), 7.09 (s, 1H), 7.21 (d, 1H), 7.32 (t, 1H), 7.48 (d, 2H), 7.58 (d, 1H), 7.68 (d, 2H), 8.40 (s, 1H).

Example 5

Ethyl 3-(2,3-dimethylbenzyl)-2,4-dioxo-1-[4-(2-oxoimidazolidin-1-yl)phenyl]-1,2,3,4-tetrahydropyrimidine-5-carboxylate

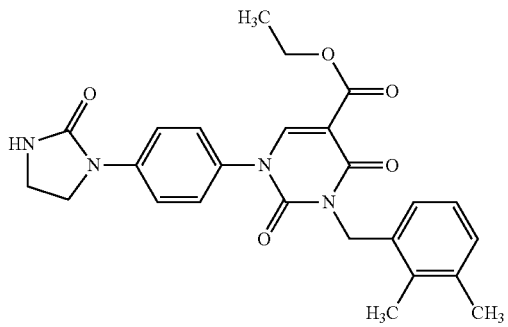 [SMILES: CCOC(=O)c1cn(-c2ccc(N3CCNC3=O)cc2)c(=O)n(Cc2cccc(C)c2C)c1=O]

The preparation was carried out analogously to Example 3 from 200 mg (0.58 mmol) of Example 15A and 90 mg (0.58 mmol) of 2,3-dimethylbenzyl chloride. Yield: 102 mg (38% of theory).

LC-MS (Method 3): $R_t$=1.01 min; m/z=463 (M+H)$^+$.

$^1$H-NMR (400 MHz, DMSO-d$_6$): δ=1.25 (t, 3H), 2.23 (s, 3H), 2.27 (s, 3H), 3.42 (m, 2H), 3.88 (m, 2H), 4.20 (q, 2H), 5.02 (s, 2H), 6.81 (d, 1H), 7.00 (t, 1H), 7.04 (s, 1H), 7.08 (d, 1H), 7.47 (d, 2H), 7.68 (d, 2H), 8.38 (s, 1H).

Example 6

Ethyl 3-(2,3-dichlorobenzyl)-2,4-dioxo-1-[4-(4-oxoimidazolidin-1-yl)phenyl]-1,2,3,4-tetrahydropyrimidine-5-carboxylate

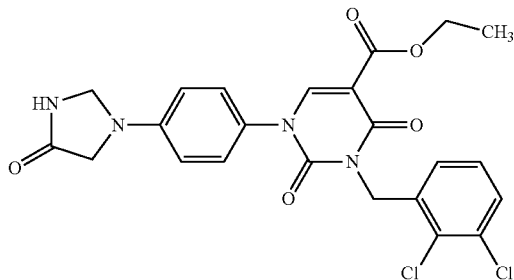 [SMILES: CCOC(=O)c1cn(-c2ccc(N3CNC(=O)C3)cc2)c(=O)n(Cc2cccc(Cl)c2Cl)c1=O]

The preparation was carried out analogously to Example 3 from 200 mg (0.58 mmol) of ethyl 2,4-dioxo-1-[4-(4-oxoimidazolidin-1-yl)phenyl]-1,2,3,4-tetrahydropyrimidine-5-carboxylate from Example 17A and 136.3 mg (0.70 mmol) of 2,3-dichlorobenzyl chloride. Yield: 45 mg (15% of theory).

LC-MS (Method 3): $R_t$=1.02 min; m/z=503 (M+H)$^+$.

$^1$H-NMR (400 MHz, DMSO-d$_6$): δ=1.23 (t, 3H), 3.80 (s, 2H), 4.18 (q, 2H), 4.72 (s, 2H), 5.10 (s, 2H), 6.65 (d, 2H), 7.20 (d, 1H), 7.31 (t, 1H), 7.38 (d, 2H), 7.66 (d, 1H), 8.32 (s, 1H), 8.70 (s, 1H).

Example 7

Ethyl 3-[3-fluoro-2-(trifluoromethyl)benzyl]-2,4-dioxo-1-[4-(4-oxoimidazolidin-1-yl)phenyl]-1,2,3,4-tetrahydropyrimidine-5-carboxylate

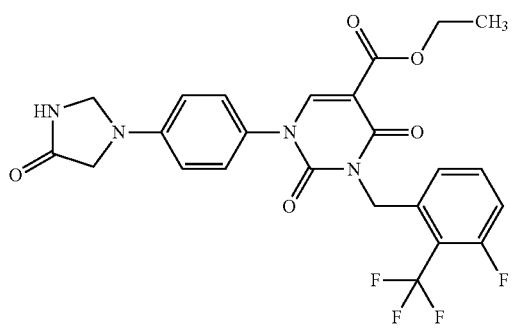 [SMILES: CCOC(=O)c1cn(-c2ccc(N3CNC(=O)C3)cc2)c(=O)n(Cc2cccc(F)c2C(F)(F)F)c1=O]

The preparation was carried out analogously to Example 3 from 200 mg (0.58 mmol) of ethyl 2,4-dioxo-1-[4-(4-oxoimidazolidin-1-yl)phenyl]-1,2,3,4-tetrahydropyrimidine-5-carboxylate from Example 17A and 179.2 mg (0.7 mmol) of 3-fluoro-2-(trifluoromethyl)benzyl bromide. Yield: 60 mg (20% of theory).

LC-MS (Method 1): $R_t$=1.12 min; m/z=521 (M+H)$^+$.

$^1$H-NMR (400 MHz, DMSO-d$_6$): δ=1.22 (t, 3H), 3.77 (s, 2H), 4.20 (q, 2H), 4.70 (s, 2H), 5.19 (s, 2H), 6.65 (d, 2H), 7.18 (d, 1H), 7.33-7.45 (m, 3H), 7.62 (m, 1H), 8.38 (s, 1H), 8.70 (s, 1H).

Example 8

Ethyl 3-[2-methyl-3-(trifluoromethyl)benzyl]-2,4-dioxo-1-[4-(4-oxoimidazolidin-1-yl)phenyl]-1,2,3,4-tetrahydropyrimidine-5-carboxylate

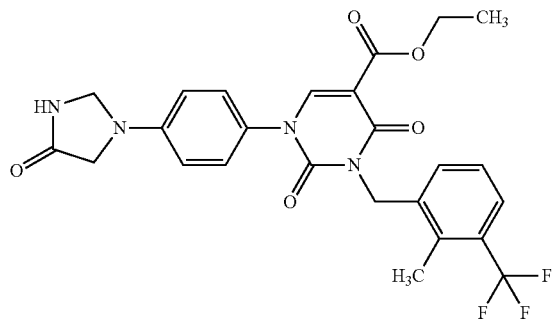 [SMILES: CCOC(=O)c1cn(-c2ccc(N3CNC(=O)C3)cc2)c(=O)n(Cc2cccc(C(F)(F)F)c2C)c1=O]

The preparation was carried out analogously to Example 3 from 200 mg (0.58 mmol) of ethyl 2,4-dioxo-1-[4-(4-oxoimidazolidin-1-yl)phenyl]-1,2,3,4-tetrahydropyrimididine-5-carboxylate from Example 17A and 176.4 mg (0.697 mmol) of 2-methyl-3-(trifluoromethyl)benzyl bromide. Yield: 74 mg (24% of theory).

LC-MS (Method 1): $R_t$=1.17 min; m/z=517 (M+H)$^+$.

$^1$H-NMR (400 MHz, DMSO-d$_6$): δ=1.22 (t, 3H), 2.48 (s, 1H), 3.80 (s, 2H), 4.20 (q, 2H), 4.71 (s, 2H), 5.08 (s, 2H), 6.68 (d, 2H), 7.30-7.41 (m, 4H), 7.61 (m, 1H), 8.32 (s, 1H), 8.70 (s, 1H).

Example 9

Ethyl 3-(2,3-dichlorobenzyl)-2,4-dioxo-1-[4-(2-oxo-tetrahydropyrimidin-1(2H)-yl)phenyl]-1,2,3,4-tetra-hydropyrimidine-5-carboxylate

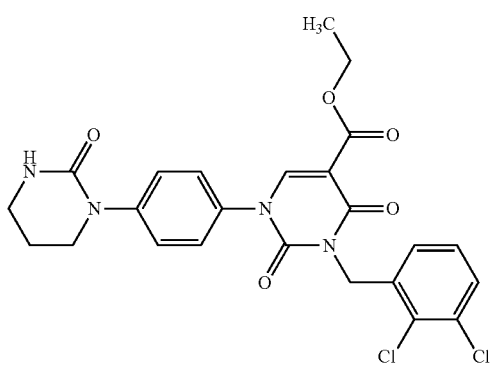 [SMILES: CCOC(=O)c1cn(-c2ccc(N3CCCNC3=O)cc2)c(=O)n(Cc2cccc(Cl)c2Cl)c1=O]

The preparation was carried out analogously to Example 3 from 200 mg (0.56 mmol) of ethyl 2,4-dioxo-1-[4-(2-oxotetrahydropyrimidin-1 (2H)-yl)phenyl]-1,2,3,4-tetrahydropyrimidine-5-carboxylate from Example 16A and 131 mg (0.67 mmol) of 2,3-dichlorobenzyl chloride. Yield: 240 mg (83% of theory).

LC-MS (Method 1): $R_t$=1.14 min; m/z=517 (M+H)$^+$.

$^1$H-NMR (400 MHz, DMSO-d$_6$): δ=1.22 (t, 3H), 1.97 (m, 2H), 3.24 (m, 2H), 3.69 (m, 2H), 4.20 (q, 2H), 5.10 (s, 2H), 6.71 (s, 1H), 7.23 (d, 1H), 7.32 (t, 1H), 7.47 (s, 4H), 7.58 (d, 1H), 8.42 (s, 1H).

Example 10

Ethyl 3-[3-fluoro-2-(trifluoromethyl)benzyl]-2,4-dioxo-1-[4-(2-oxotetrahydropyrimidin-1(2H)-yl)phenyl]-1,2,3,4-tetrahydropyrimidine-5-carboxylate

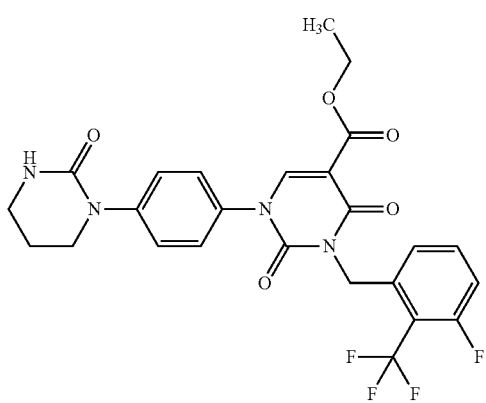 [SMILES: CCOC(=O)c1cn(-c2ccc(N3CCCNC3=O)cc2)c(=O)n(Cc2cccc(F)c2C(F)(F)F)c1=O]

The preparation was carried out analogously to Example 3 from 200 mg (0.56 mmol) of ethyl 2,4-dioxo-1-[4-(2-oxotetrahydropyrimidin-1(2H)-yl)phenyl]-1,2,3,4-tetrahydropyrimidine-5-carboxylate from Example 16A and 172.1 mg (0.67 mmol) of 3-fluoro-2-(trifluoromethyl)benzyl bromide. Yield: 75 mg (22% of theory, purity 88%).

LC-MS (Method 1): $R_t$=1.13 min; m/z=535 (M+H)$^+$.

$^1$H-NMR (400 MHz, DMSO-d$_6$): δ=1.22 (t, 3H), 1.98 (m, 2H), 3.23 (m, 2H), 3.68 (m, 2H), 4.20 (q, 2H), 5.20 (s, 2H), 6.70 (s, 1H), 7.20 (d, 1H), 7.36-7.50 (m, 5H), 7.65 (m, 1H), 8.45 (s, 1H).

Example 11

Ethyl 3-[2-methyl-3-(trifluoromethyl)benzyl]-2,4-dioxo-1-[4-(2-oxo-1,3-oxazinan-3-yl)phenyl]-1,2,3,4-tetrahydropyrimidine-5-carboxylate

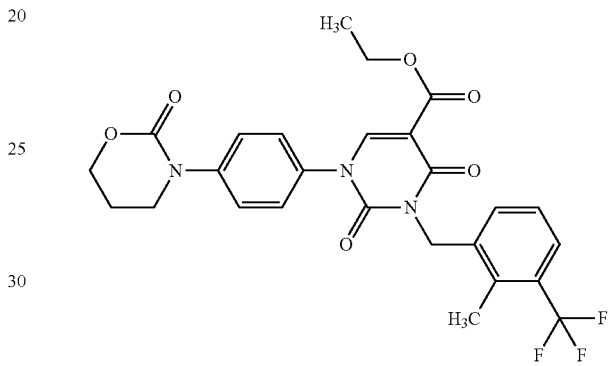

The preparation was carried out analogously to Example 3 from 250 mg (about 0.56 mmol) of ethyl 2,4-dioxo-1-[4-(2-oxo-1,3-oxazinan-3-yl)phenyl]-1,2,3,4-tetrahydropyrimidine-5-carboxylate from Example 37A and 140 mg (0.56 mmol) of 2-methyl-3-(trifluoromethyl)benzyl bromide. Yield: 184 mg (62% of theory).

LC-MS (Method 1): $R_t$=1.21 min; m/z=532 (M+H)$^+$.

$^1$H-NMR (400 MHz, DMSO-d$_6$): δ=1.22 (t, 3H), 2.08-2.17 (m, 2H), 2.47 (s, 3H), 3.67-3.72 (m, 2H), 4.20 (q, 2H), 4.32-4.40 (m, 2H), 5.08 (s, 2H), 7.30-7.41 (m, 2H), 7.48-7.62 (m, 5H), 8.42 (s, 1H).

Example 12

Ethyl 3-(2,3-dichlorobenzyl)-2,4-dioxo-1-[4-(2-oxo-1,3-oxazinan-3-yl)phenyl]-1,2,3,4-tetrahydropyrimidine-5-carboxylate

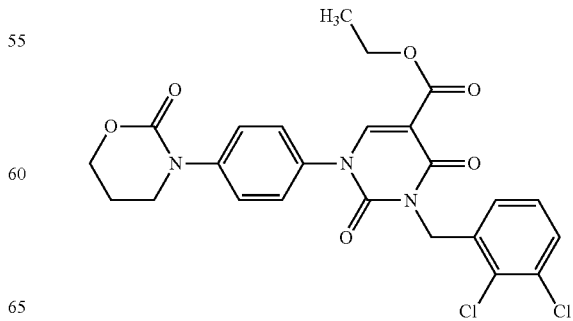

The preparation was carried out analogously to Example 3 from 250 mg (about 0.56 mmol) of ethyl 2,4-dioxo-1-[4-(2-oxo-1,3-oxazinan-3-yl)phenyl]-1,2,3,4-tetrahydropyrimidine-5-carboxylate from Example 37A and 109 mg (0.56 mmol) of 2,3-dichlorobenzyl chloride. Yield: 167 mg (58% of theory).

LC-MS (Method 1): $R_t$=1.17 min; m/z=518 (M+H)$^+$.

$^1$H-NMR (400 MHz, DMSO-d$_6$): δ=1.22 (t, 3H), 2.08-2.17 (m, 2H), 3.67-3.74 (m, 2H), 4.20 (q, 2H), 4.32-4.40 (m, 2H), 5.09 (s, 2H), 7.21 (d, 1H), 7.31 (t, 1H), 7.49-7.60 (m, 5H), 8.45 (s, 1H).

Example 13

Ethyl 3-(2,3-dichlorobenzyl)-2,4-dioxo-1-[4-(2-oxopyrrolidin-1-yl)phenyl]-1,2,3,4-tetrahydropyrimidine-5-carboxylate

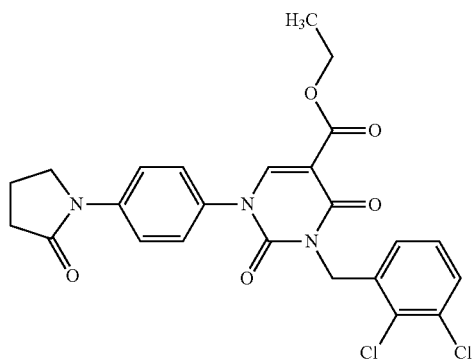 [SMILES: CCOC(=O)c1cn(-c2ccc(N3CCCC3=O)cc2)c(=O)n(Cc2cccc(Cl)c2Cl)c1=O]

The preparation was carried out analogously to Example 3 from 145 mg (0.42 mmol) of ethyl 2,4-dioxo-1-[4-(2-oxopyrrolidin-1-yl)phenyl]-1,2,3,4-tetrahydropyrimidine-5-carboxylate from Example 22A and 82.6 mg (0.42 mmol) of 2,3-dichlorobenzyl chloride. Yield: 143 mg (61% of theory).

LC-MS (Method 3): $R_t$=1.09 min; m/z=502 (M+H)$^+$.

$^1$H-NMR (400 MHz, DMSO-d$_6$): δ=1.25 (t, 3H), 2.09 (m, 2H), 2.50 (hidden by DMSO m), 3.88 (m, 2H), 4.20 (q, 2H), 5.07 (s, 2H), 7.22 (d, 1H), 7.32 (t, 1H), 7.55 (d, 2H), 7.58 (d, 1H), 7.80 (d, 2H), 8.43 (s, 1H).

Example 14

Ethyl 3-[3-fluoro-2-(trifluoromethyl)benzyl]-2,4-dioxo-1-[4-(2-oxopyrrolidin-1-yl)phenyl]-1,2,3,4-tetrahydropyrimidine-5-carboxylate

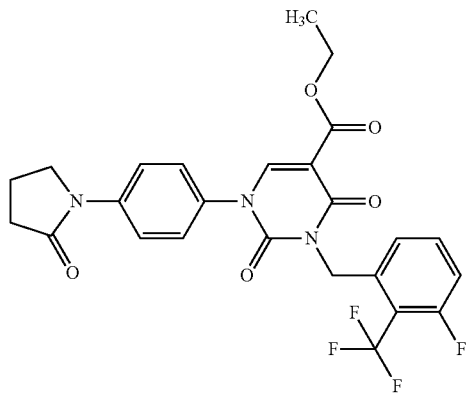 [SMILES: CCOC(=O)c1cn(-c2ccc(N3CCCC3=O)cc2)c(=O)n(Cc2cccc(F)c2C(F)(F)F)c1=O]

The preparation was carried out analogously to Example 3 from 145 mg (0.42 mmol) of ethyl 2,4-dioxo-1-[4-(2-oxopyrrolidin-1-yl)phenyl]-1,2,3,4-tetrahydropyrimidine-5-carboxylate from Example 22A and 108.6 mg (0.42 mmol) of 3-fluoro-2-(trifluoromethyl)benzyl bromide. Yield: 103 mg (45% of theory).

LC-MS (Method 4): $R_t$=2.30 min; m/z=520 (M+H)$^+$.

$^1$H-NMR (400 MHz, DMSO-d$_6$): δ=1.24 (t, 3H), 2.03-2.11 (m, 2H), 3.87 (m, 2H), 4.20 (q, 2H), 5.18 (s, 2H), 7.18 (d, 1H), 7.38 (m, 1H), 7.51 (d, 2H), 7.60-7.70 (m, 1H), 7.79 (d, 2H), 8.42 (s, 1H).

Example 15

Ethyl 1-(4-ethoxyphenyl)-3-[3-fluoro-2-(trifluoromethyl)benzyl]-2,4-dioxo-1,2,3,4-tetrahydropyrimidine-5-carboxylate

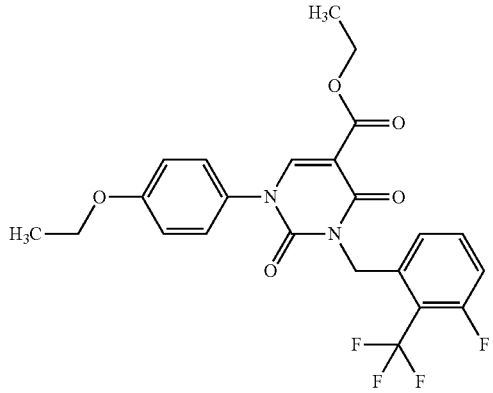 [SMILES: CCOC(=O)c1cn(-c2ccc(OCC)cc2)c(=O)n(Cc2cccc(F)c2C(F)(F)F)c1=O]

The preparation was carried out analogously to Example 3 from 200 mg (0.66 mmol) of ethyl 1-(4-ethoxyphenyl)-2,4-dioxo-1,2,3,4-tetrahydropyrimidine-5-carboxylate from Example 41A and 169 mg (0.66 mmol) of 3-fluoro-2-(trifluoromethyl)benzyl bromide. Yield: 195 mg (62% of theory).

LC-MS (Method 2): $R_t$=2.54 min; m/z=481 (M+H)$^+$.

$^1$H-NMR (400 MHz, DMSO-d$_6$): δ=1.22 (t, 3H), 1.32 (t, 3H), 4.05 (q, 2H), 4.18 (q, 2H), 5.19 (s, 2H), 7.05 (d, 2H), 7.18 (d, 1H), 7.40-7.45 (m, 3H), 7.63-7.66 (m, 1H), 8.41 (s, 1H).

Example 16

Ethyl 3-(2,3-dichlorobenzyl)-2,4-dioxo-1-[4-(2-oxo-2,3-dihydro-1H-imidazol-1-yl)phenyl]-1,2,3,4-tetrahydropyrimidine-5-carboxylate

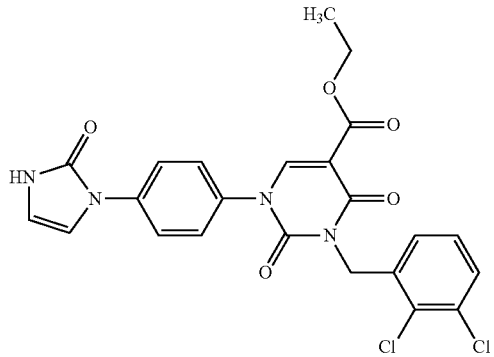 [SMILES: CCOC(=O)c1cn(-c2ccc(-n3cc[nH]c3=O)cc2)c(=O)n(Cc2cccc(Cl)c2Cl)c1=O]

The preparation was carried out analogously to Example 3 from 200 mg (0.58 mmol) of ethyl 2,4-dioxo-1-[4-(2-oxo-2,3-dihydro-1H-imidazol-1-yl)phenyl]-1,2,3,4-tetrahydropyrimidine-5-carboxylate from Example 18A and 168.2 mg (0.70 mmol) of 2,3-dichlorobenzyl chloride. Yield: 126 mg (43% of theory).

LC-MS (Method 3): $R_t$=1.02 min; m/z=501 (M+H)$^+$.

$^1$H-NMR (400 MHz, DMSO-d$_6$): δ=1.22 (t, 3H), 4.20 (q, 2H), 5.10 (s, 2H), 6.64 (m, 1H), 7.03 (m, 1H), 7.22 (d, 1H), 7.32 (t, 1H), 7.55-7.63 (m, 3H), 7.9 (d, 2H), 8.45 (s, 1H), 10.4 (s, 1H).

Example 17

Ethyl 3-[2-methyl-3-(trifluoromethyl)benzyl]-2,4-dioxo-1-[4-(2-oxo-2,3-dihydro-1H-imidazol-1-yl)phenyl]-1,2,3,4-tetrahydropyrimidine-5-carboxylate

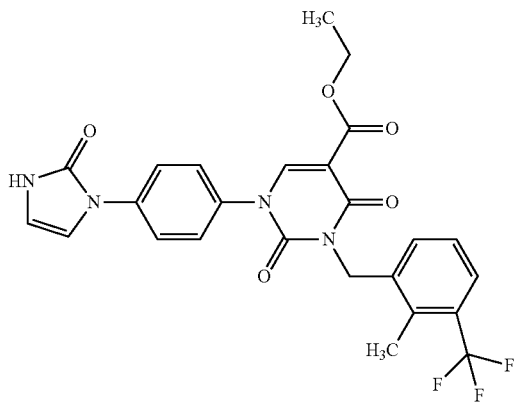 [SMILES: CCOC(=O)c1cn(-c2ccc(-n3cc[nH]c3=O)cc2)c(=O)n(Cc2cccc(C(F)(F)F)c2C)c1=O]

The preparation was carried out analogously to Example 3 from 200 mg (0.58 mmol) of ethyl 2,4-dioxo-1-[4-(2-oxo-2,3-dihydro-1H-imidazol-1-yl)phenyl]-1,2,3,4-tetrahydropyrimidine-5-carboxylate from Example 18A and 177.4 mg (0.7 mmol) of 2-methyl-3-(trifluoromethyl)benzyl bromide. Yield: 152 mg (51% of theory).

LC-MS (Method 3): $R_t$=1.04 min; m/z=515 (M+H)$^+$.

$^1$H-NMR (400 MHz, DMSO-d$_6$): δ=1.22 (t, 3H), 2.48 (s, 3H), 4.20 (q, 2H), 5.09 (s, 2H), 6.65 (m, 1H), 7.05 (m, 1H), 7.35 (t, 1H), 7.40 (d, 1H), 7.60 (d, 2H), 7.91 (d, 2H), 8.46 (s, 1H), 10.4 (s, 1H).

Example 18

Ethyl 1-[3-fluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate

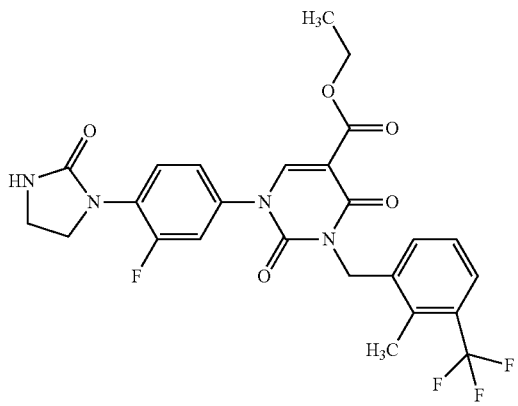 [SMILES: CCOC(=O)c1cn(-c2ccc(N3CCNC3=O)c(F)c2)c(=O)n(Cc2cccc(C(F)(F)F)c2C)c1=O]

The preparation was carried out analogously to Example 3 from 200 mg (0.55 mmol) of ethyl 1-[3-fluoro-4-(2-oxoimidazolidin-1-yl)phenyl]-2,4-dioxo-1,2,3,4-tetrahydropyrimidine-5-carboxylate from Example 19A and 167.6 mg (0.66 mmol) of 2-methyl-3-(trifluoromethyl)benzyl bromide. Yield: 145 mg (45% of theory, purity 93%).

LC-MS (Method 3): $R_t$=1.07 min; m/z=535 (M+H)$^+$.

$^1$H-NMR (400 MHz, DMSO-d$_6$): δ=1.26 (t, 3H), 2.45 (s, 3H), 3.45 (m, 2H), 3.87 (m, 2H), 4.18 (q, 2H), 5.10 (s, 2H), 7.01 (s, 1H), 7.30-7.44 (m, 3H), 7.52-7.62 (m, 2H), 7.68 (t, 1H), 8.5 (s, 1H).

Example 19

Ethyl 1-[3-fluoro-4-(2-oxoimidazolidin-1-yl)phenyl]-3-(2-methyl-3-nitrobenzyl)-2,4-dioxo-1,2,3,4-tetrahydropyrimidine-5-carboxylate

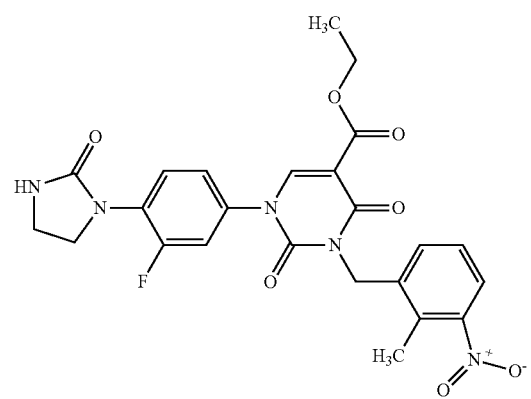

The preparation was carried out analogously to Example 3 from 200 mg (0.55 mmol) of ethyl 1-[3-fluoro-4-(2-oxoimidazolidin-1-yl)phenyl]-2,4-dioxo-1,2,3,4-tetrahydropyrimidine-5-carboxylate from Example 19A and 123 mg (0.66 mmol) of 2-methyl-3-nitrobenzyl chloride. Yield: 108 mg (35% of theory, purity 92%).

LC-MS (Method 3): $R_t$=0.96 min; m/z=512 (M+H)$^+$.

$^1$H-NMR (400 MHz, DMSO-d$_6$): δ=1.22 (t, 3H), 2.40 (s, 3H), 3.45 (m, 2H), 3.87 (m, 2H), 4.20 (q, 2H), 5.10 (s, 2H), 7.02 (s, 1H), 7.32-7.48 (m, 2H), 7.58 (dd, 1H), 7.67 (t, 1H), 7.72 (dd, 1H), 8.49 (s, 1H).

Example 20

Ethyl 3-(2,3-dichlorobenzyl)-1-[3-fluoro-4-(2-oxoimidazolidin-1-yl)phenyl]-2,4-dioxo-1,2,3,4-tetrahydropyrimidine-5-carboxylate

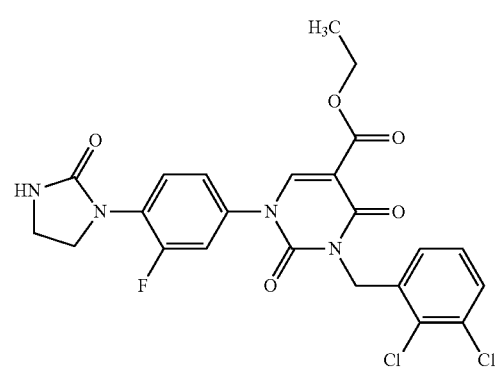 [SMILES: CCOC(=O)c1cn(-c2ccc(N3CCNC3=O)c(F)c2)c(=O)n(Cc2cccc(Cl)c2Cl)c1=O]

The preparation was carried out analogously to Example 3 from 200 mg (0.55 mmol) of ethyl 1-[3-fluoro-4-(2-oxoimidazolidin-1-yl)phenyl]-2,4-dioxo-1,2,3,4-tetrahydropyrimidine-5-carboxylate from Example 19A and 159 mg (0.66 mmol) of 2,3-dichlorobenzyl chloride. Yield: 75 mg (25% of theory).

LC-MS (Method 3): $R_t$=1.03 min; m/z=521 (M+H)$^+$.

$^1$H-NMR (400 MHz, DMSO-$d_6$): δ=1.22 (t, 3H), 3.45 (m, 2H), 3.87 (m, 2H), 4.20 (q, 2H), 5.10 (s, 2H), 7.02 (s, 1H), 7.21 (d, 1H), 7.31 (t, 1H), 7.38 (dd, 1H), 7.52-7.62 (m, 2H), 7.66 (t, 1H), 8.50 (s, 1H).

Example 21

Ethyl 3-(2,3-dichlorobenzyl)-2,4-dioxo-1-[4-(3-oxomorpholin-4-yl)phenyl]-1,2,3,4-tetrahydropyrimidine-5-carboxylate

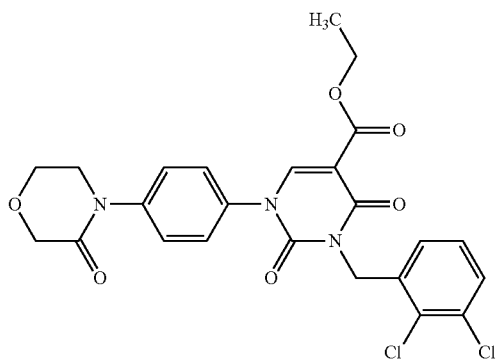 [SMILES: CCOC(=O)c1cn(-c2ccc(N3CCOCC3=O)cc2)c(=O)n(Cc2cccc(Cl)c2Cl)c1=O]

The preparation was carried out analogously to Example 3 from 200 mg (0.56 mmol) of ethyl 2,4-dioxo-1-[4-(3-oxomorpholin-4-yl)phenyl]-1,2,3,4-tetrahydropyrimidine-5-carboxylate from Example 20A and 217.6 mg (1.11 mmol) of 2,3-dichlorobenzyl chloride. Yield: 207 mg (70% of theory).

LC-MS (Method 3): $R_t$=1.04 min; m/z=518 (M+H)$^+$.

$^1$H-NMR (400 MHz, DMSO-$d_6$): δ=1.22 (t, 3H), 3.79 (m, 2H), 3.99 (m, 2H), 4.20 (q, 2H), 4.23 (s, 2H), 5.10 (s, 2H), 7.22 (d, 1H), 7.31 (t, 1H), 7.58 (m, 5H), 8.48 (s, 1H).

Example 22

Ethyl 3-[2-methyl-3-(trifluoromethyl)benzyl]-2,4-dioxo-1-[4-(3-oxomorpholin-4-yl)phenyl]-1,2,3,4-tetrahydropyrimidine-5-carboxylate

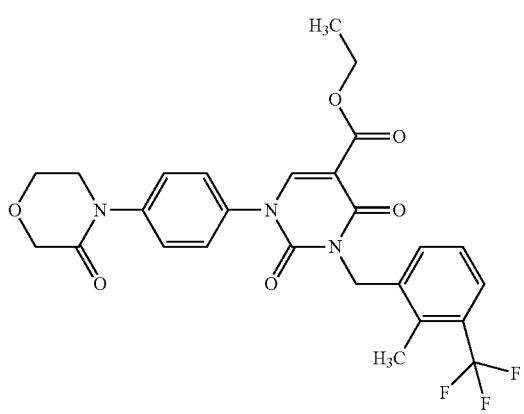 [SMILES: CCOC(=O)c1cn(-c2ccc(N3CCOCC3=O)cc2)c(=O)n(Cc2cccc(C(F)(F)F)c2C)c1=O]

The preparation was carried out analogously to Example 3 from 200 mg (0.56 mmol) of ethyl 2,4-dioxo-1-[4-(3-oxomorpholin-4-yl)phenyl]-1,2,3,4-tetrahydropyrimidine-5-carboxylate from Example 20A and 140.8 mg (0.56 mol) of 2-methyl-3-(trifluoromethyl)benzyl bromide. Yield: 228 mg (77% of theory).

LC-MS (Method 3): $R_t$=1.07 min; m/z=532 (M+H)$^+$.

$^1$H-NMR (400 MHz, DMSO-$d_6$): δ=1.22 (t, 3H), 2.45 (s, 3H), 3.79 (m, 2H), 4.00 (m, 2H), 4.20 (q, 2H), 4.22 (s, 2H), 5.09 (s, 2H), 7.32 (t, 1H), 7.39 (d, 1H), 7.55-7.62 (m, 5H), 8.45 (s, 1H).

Example 23

Ethyl 1-[3,5-difluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate

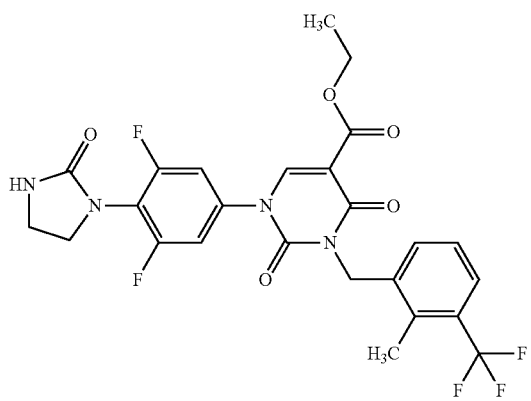 [SMILES: CCOC(=O)c1cn(-c2cc(F)c(N3CCNC3=O)c(F)c2)c(=O)n(Cc2cccc(C(F)(F)F)c2C)c1=O]

500 mg of ethyl 1-[3,5-difluoro-4-(2-oxoimidazolidin-1-yl)phenyl]-2,4-dioxo-1,2,3,4-tetrahydropyrimidine-5-carboxylate from Example 27A (1.04 mmol, purity 79%), 315 mg (1.25 mmol) of 2-methyl-3-(trifluoromethyl)benzyl bromide, 287 mg (2.08 mmol) of potassium carbonate and 86 mg (0.52 mmol) of potassium iodide in 10 ml of acetonitrile were stirred at 60° C. for 6 h and allowed to stand at RT overnight. The mixture was diluted with 20 ml of ethyl acetate. The organic phase was washed with water and saturated aqueous sodium chloride solution, dried over sodium sulfate and concentrated. The remaining crude product was purified by chromatography on silica gel using the mobile phase dichloromethane/methanol 80:1. This gave, after concentration of the appropriate fractions and drying under reduced pressure, 524 mg (91% of theory) of the target compound.

LC-MS (Method 3): $R_t$=1.06 min; m/z=553 (M+H)$^+$.

$^1$H-NMR (400 MHz, DMSO-$d_6$): δ=1.24 (t, 3H), 2.46 (s, 3H), 3.46-3.54 (m, 2H), 3.72-3.80 (m, 2H), 4.20 (q, 2H), 5.08 (s, 2H), 7.02 (s, 1H), 7.31-7.42 (m, 2H), 7.51-7.57 (m, 2H), 7.58-7.63 (m, 1H), 8.57 (s, 1H).

Example 24

Ethyl 3-(2,3-dichlorobenzyl)-1-[3,5-difluoro-4-(2-oxoimidazolidin-1-yl)phenyl]-2,4-dioxo-1,2,3,4-tetrahydropyrimidine-5-carboxylate

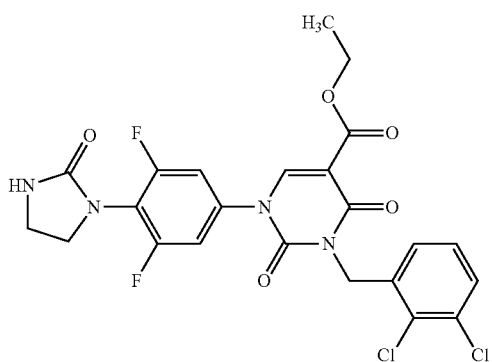 [SMILES: CCOC(=O)c1cn(-c2cc(F)c(N3CCNC3=O)c(F)c2)c(=O)n(Cc2cccc(Cl)c2Cl)c1=O]

150 mg of ethyl 1-[3,5-difluoro-4-(2-oxoimidazolidin-1-yl)phenyl]-2,4-dioxo-1,2,3,4-tetrahydropyrimidine-5-carboxylate (0.31 mmol, purity 79%) from Example 27A, 90 mg (0.37 mmol) of 2,3-dichlorobenzyl bromide, 86 mg (0.62 mmol) of potassium carbonate and 26 mg (0.16 mmol) of potassium iodide in 3 ml of acetonitrile were stirred at 60° C. for 4 h. Concentration of the reaction mixture under reduced pressure and purification of the crude product by chromatography on silica gel using dichloromethane/methanol mixtures (100:1 to 50:1) gave 133 mg (79% of theory) of the target compound.

LC-MS (Method 3): $R_t$=1.03 min; m/z=539 (M+H)$^+$.

$^1$H-NMR (400 MHz, DMSO-$d_6$): δ=1.24 (t, 3H), 3.47-3.54 (m, 2H), 3.73-3.80 (m, 2H), 4.20 (q, 2H), 5.10 (s, 2H), 7.02 (s, 1H), 7.23 (dd, 1H), 7.33 (t, 1H), 7.50-7.56 (m, 2H), 7.58 (dd, 1H), 8.59 (s, 1H).

Example 25

Ethyl 3-(2-chloro-3-(trifluoromethyl)benzyl)-1-[3,5-difluoro-4-(2-oxoimidazolidin-1-yl)phenyl]-2,4-dioxo-1,2,3,4-tetrahydropyrimidine-5-carboxylate

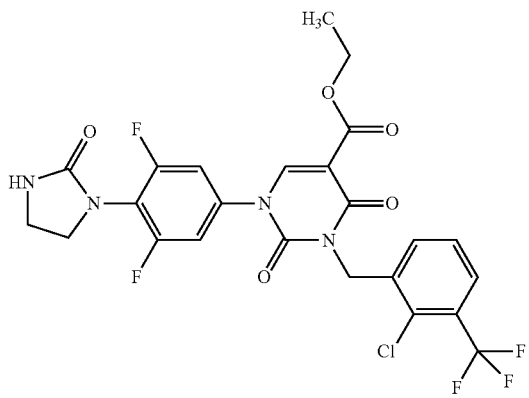 [SMILES: CCOC(=O)c1cn(-c2cc(F)c(N3CCNC3=O)c(F)c2)c(=O)n(Cc2cccc(C(F)(F)F)c2Cl)c1=O]

Preparation and purification of the title compound were carried out analogously to Example 24 using a reaction time of 5 h at 60° C. Starting from 150 mg of ethyl 1-[3,5-difluoro-4-(2-oxoimidazolidin-1-yl)phenyl]-2,4-dioxo-1,2,3,4-tetrahydropyrimidine-5-carboxylate (0.31 mmol, purity 79%) from Example 27A and 86 mg (0.37 mmol) of 2-chloro-3-(trifluoromethyl)benzyl bromide, 143 mg (76% of theory) of the target compound were obtained.

LC-MS (Method 3): $R_t$=1.07 min; m/z=573 (M+H)$^+$.

$^1$H-NMR (400 MHz, DMSO-$d_6$): δ=1.24 (t, 3H), 3.47-3.54 (m, 2H), 3.73-3.80 (m, 2H), 4.21 (s, 2H), 5.15 (s, 2H), 7.03 (br. s, 1H), 7.49-7.56 (m, 3H), 7.58 (br. d, 1H), 7.80 (br. d, 1H), 8.60 (s, 1H).

Example 26

Ethyl 1-[3,5-difluoro-4-(2-oxoimidazolidin-1-yl)phenyl]-3-[3-fluoro-2-(trifluoromethyl)benzyl]-2,4-dioxo-1,2,3,4-tetrahydropyrimidine-5-carboxylate

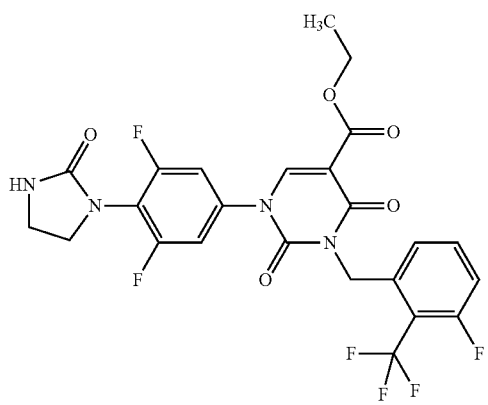 [SMILES: CCOC(=O)c1cn(-c2cc(F)c(N3CCNC3=O)c(F)c2)c(=O)n(Cc2cccc(F)c2C(F)(F)F)c1=O]

The preparation and purification of the title compound were carried out analogously to Example 24 using a reaction time of 6 h at 60° C. Starting from 150 mg of ethyl 1-[3,5-difluoro-4-(2-oxoimidazolidin-1-yl)phenyl]-2,4-dioxo-1,2,3,4-tetrahydropyrimidine-5-carboxylate (0.31 mmol, purity 79%) from Example 27A and 96 mg (0.37 mmol) of 3-fluoro-2-(trifluoromethyl)benzyl bromide, 127 mg (74% of theory) of the target compound were obtained.

LC-MS (Method 3): $R_t$=1.04 min; m/z=557 (M+H)$^+$.

$^1$H-NMR (400 MHz, DMSO-$d_6$): δ=1.24 (t, 3H), 3.47-3.54 (m, 2H), 3.73-3.80 (m, 2H), 4.21 (q, 2H), 5.19 (s, 2H), 7.03 (s, 1H), 7.20 (d, 1H), 7.41 (dd, 1H), 7.49-7.56 (m, 2H), 7.65 (td, 1H), 8.61 (s, 1H).

Example 27

Ethyl 3-(2-chloro-3-methylbenzyl)-1-[3,5-difluoro-4-(2-oxoimidazolidin-1-yl)phenyl]-2,4-dioxo-1,2,3,4-tetrahydropyrimidine-5-carboxylate

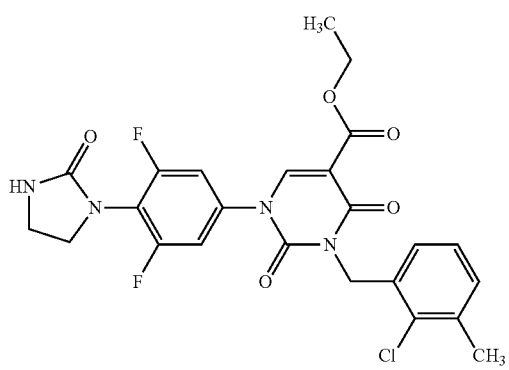 [SMILES: CCOC(=O)c1cn(-c2cc(F)c(N3CCNC3=O)c(F)c2)c(=O)n(Cc2cccc(C)c2Cl)c1=O]

Preparation and purification of the title compound were carried out analogously to Example 24, with a reaction time of 6 h at 60° C., where the mixture was subsequently allowed to stand at RT for another 3 days. Starting from 150 mg of ethyl 1-[3,5-difluoro-4-(2-oxoimidazolidin-1-yl)phenyl]-2,4-dioxo-1,2,3,4-tetrahydropyrimidine-5-carboxylate (0.31 mmol, purity 79%) from Example 27A and 82 mg (0.37 mmol) of 2-chloro-3-methylbenzyl bromide, 53 mg (32% of theory) of the target compound were obtained.

LC-MS (Method 4): $R_t$=2.20 min; m/z=519 (M+H)$^+$.
$^1$H-NMR (400 MHz, DMSO-d$_6$): δ=1.25 (t, 3H), 2.37 (s, 2H), 3.46-3.54 (m, 2H), 3.72-3.80 (m, 2H), 4.20 (q, 2H), 5.09 (s, 2H), 6.99-7.05 (m, 2H), 7.15-7.23 (m, 1H), 7.25-7.31 (m, 1H), 7.49-7.58 (m, 2H), 8.57 (s, 1H).

Example 28

Ethyl 3-[3-fluoro-2-(trifluoromethyl)benzyl]-2,4-dioxo-1-[4-(5-oxo-1,5-dihydro-4H-1,2,4-triazol-4-yl)phenyl]-1,2,3,4-tetrahydropyrimidine-5-carboxylate

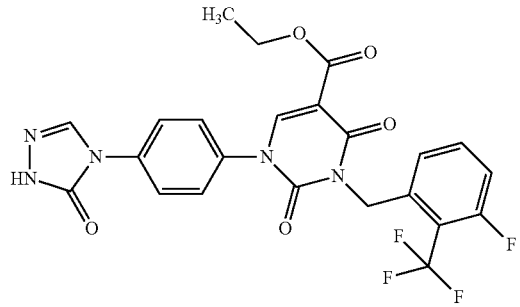 [SMILES: CCOC(=O)c1cn(-c2ccc(-n3cn[nH]c3=O)cc2)c(=O)n(Cc2cccc(F)c2C(F)(F)F)c1=O]

The preparation was carried out analogously to Example 3 from 200 mg (0.58 mmol) of ethyl 2,4-dioxo-1-[4-(5-oxo-1,5-dihydro-4H-1,2,4-triazol-4-yl)phenyl]-1,2,3,4-tetrahydropyrimidine-5-carboxylate from Example 35A and 150 mg (0.583 mmol) of 3-fluoro-2-(trifluoromethyl)benzyl bromide. Yield: 24 mg (8% of theory).

LC-MS (Method 3): $R_t$=0.96 min; m/z=520 (M+H)$^+$.
$^1$H-NMR (400 MHz, DMSO-d$_6$): δ=1.22 (t, 3H), 4.20 (q, 2H), 5.20 (s, 2H), 7.22 (d, 1H), 7.35-7.45 (m, 1H), 7.61-7.72 (m, 3H), 7.85 (d, 2H), 8.45 (s, 1H), 8.51 (s, 1H), 12.05 (br. s, 1H).

Example 29

Ethyl 1-{4-[1-(tert-butoxycarbonyl)-1H-pyrazol-3-yl]phenyl}-3-(2,3-dichlorobenzyl)-2,4-dioxo-1,2,3,4-tetrahydropyrimidine-5-carboxylate

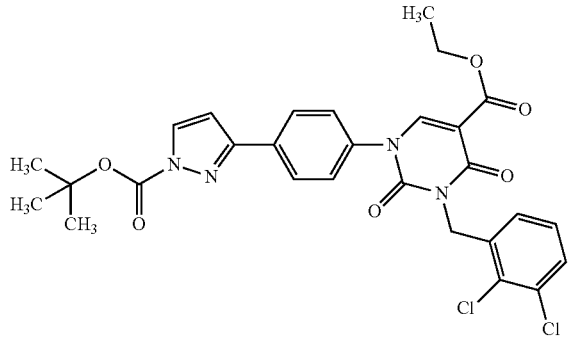 [SMILES: CCOC(=O)c1cn(-c2ccc(-c3ccn(C(=O)OC(C)(C)C)n3)cc2)c(=O)n(Cc2cccc(Cl)c2Cl)c1=O]

The preparation was carried out analogously to Example 3 from 200 mg (0.47 mmol) of ethyl 1-{4-[1-(tert-butoxycarbonyl)-1H-pyrazol-3-yl]phenyl}-2,4-dioxo-1,2,3,4-tetrahydropyrimidine-5-carboxylate from Example 33A and 110 mg (0.56 mmol) of 2,3-dichlorobenzyl chloride. Yield: 73 mg (25% of theory, purity 93%).

LC-MS (Method 2): $R_t$=2.74 min; m/z=585 (M+H)$^+$.
$^1$H-NMR (400 MHz, DMSO-d$_6$): δ=1.22 (t, 3H), 1.60 (s, 9H), 4.20 (q, 2H), 5.10 (s, 2H), 7.13 (d, 1H), 7.25 (d, 1H), 7.32 (t, 1H), 7.58 (d, 1H), 7.62 (d, 2H), 8.05 (d, 2H), 8.35 (d, 1H), 8.50 (s, 1H).

Example 30

Ethyl 1-{4-[1-(tert-butoxycarbonyl)-1H-pyrazol-3-yl]phenyl}-3-[2-methyl-3-(trifluoromethyl)benzyl]-2,4-dioxo-1,2,3,4-tetrahydropyrimidine-5-carboxylate

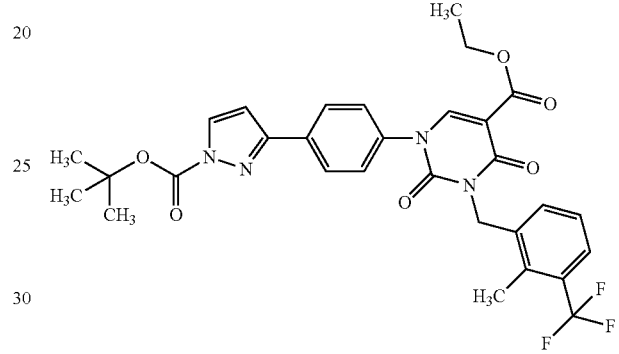

The preparation was carried out analogously to Example 3 from 200 mg (0.47 mmol) of ethyl 1-{4-[1-(tert-butoxycarbonyl)-1H-pyrazol-3-yl]phenyl}-2,4-dioxo-1,2,3,4-tetrahydropyrimidine-5-carboxylate from Example 33A and 142 mg (0.56 mmol) of 2-methyl-3-(trifluoromethyl)benzyl bromide. Yield: 67 mg (24% of theory).

LC-MS (Method 2): $R_t$=2.77 min; m/z=599 (M+H)$^+$.
$^1$H-NMR (400 MHz, DMSO-d$_6$): δ=1.23 (t, 3H), 1.61 (s, 9H), 2.45 (partially hidden by DMSO signal), 4.20 (q, 2H), 5.21 (s, 2H), 7.13 (d, 1H), 7.31-7.43 (m, 2H), 7.61 (d, 1H), 7.65 (d, 2H), 8.05 (d, 2H), 8.45 (d, 1H), 8.60 (s, 1H).

Example 31

Ethyl 3-(2-methyl-3-nitrobenzyl)-2,4-dioxo-1-[4-(2-oxo-1,3-oxazolidin-3-yl)phenyl]-1,2,3,4-tetrahydropyrimidine-5-carboxylate

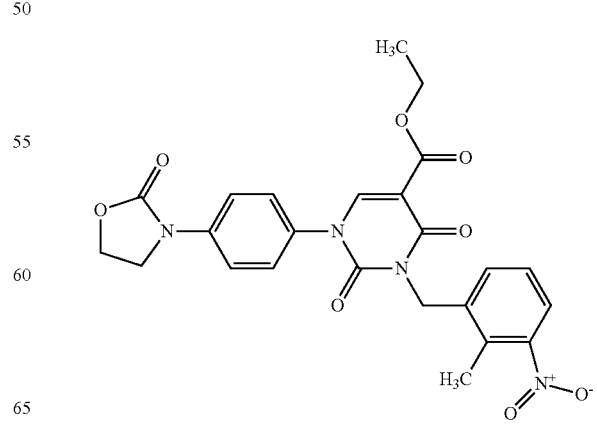

The preparation was carried out analogously to Example 3 from 200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 21A and 107.5 mg (0.58 mmol) of 2-methyl-3-nitrobenzyl chloride. Yield: 28 mg (10% of theory).

LC-MS (Method 3): $R_t$=0.99 min; m/z=494 (M+H)$^+$.

$^1$H-NMR (400 MHz, DMSO-d$_6$): δ=1.25 (t, 3H), 2.40 (s, 3H), 4.10 (m, 2H), 4.20 (q, 2H), 4.47 (m, 2H), 5.10 (s, 2H), 7.38 (t, 1H), 7.42 (d, 1H), 7.56 (d, 2H), 7.70 (d, 2H), 7.72 (d, 1H), 8.41 (s, 1H).

Example 32

Ethyl 3-[3-fluoro-2-(trifluoromethyl)benzyl]-2,4-dioxo-1-[4-(2-oxo-1,3-oxazolidin-3-yl)phenyl]-1,2,3,4-tetrahydropyrimidine-5-carboxylate

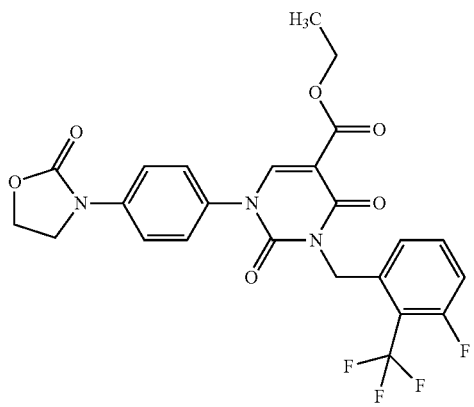 [SMILES: CCOC(=O)c1cn(-c2ccc(N3CCOC3=O)cc2)c(=O)n(Cc2cccc(F)c2C(F)(F)F)c1=O]

The preparation was carried out analogously to Example 3 from 200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 21A and 149 mg (0.58 mmol) of 3-fluoro-2-(trifluoromethyl)benzyl chloride. Yield: 86 mg (28% of theory).

LC-MS (Method 3): $R_t$=1.05 min; m/z=522 (M+H)$^+$.

$^1$H-NMR (400 MHz, DMSO-d$_6$): δ=1.22 (t, 3H), 4.10 (m, 2H), 4.20 (q, 2H), 4.49 (m, 2H), 5.20 (s, 2H), 7.20 (d, 1H), 7.40 (m, 1H), 7.52 (d, 2H), 7.65 (d, 1H), 7.70 (d, 2H), 8.45 (s, 1H).

Example 33

Ethyl 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylate

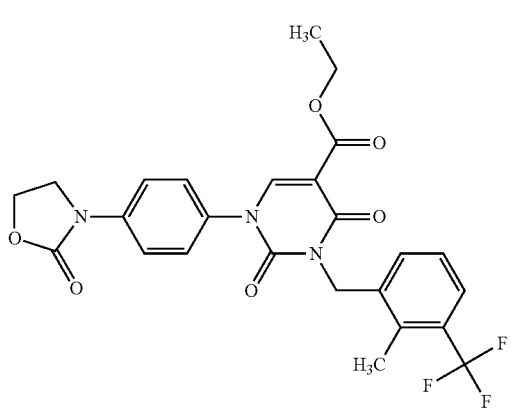 [SMILES: CCOC(=O)c1cn(-c2ccc(N3CCOC3=O)cc2)c(=O)n(Cc2cccc(C(F)(F)F)c2C)c1=O]

The preparation was carried out analogously to Example 3 from 200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 21A and 146.6 mg (0.58 mmol) of 2-methyl-3-(trifluoromethyl)benzyl bromide. Yield: 37 mg (12% of theory).

LC-MS (Method 4): $R_t$=2.36 min; m/z=518 (M+H)$^+$.

$^1$H-NMR (400 MHz, DMSO-d$_6$): δ=1.23 (t, 3H), 2.45 (s, 3H), 4.10 (m, 2H), 4.20 (q, 2H), 4.45 (m, 2H), 5.05 (s, 2H), 7.30-7.40 (m, 2H), 7.52-7.62 (m, 3H), 7.70 (d, 2H), 8.41 (s, 1H).

Example 34

Ethyl 3-(2,3-dichlorobenzyl)-2,4-dioxo-1-[4-(2-oxo-1,3-oxazolidin-3-yl)phenyl]-1,2,3,4-tetrahydropyrimidine-5-carboxylate

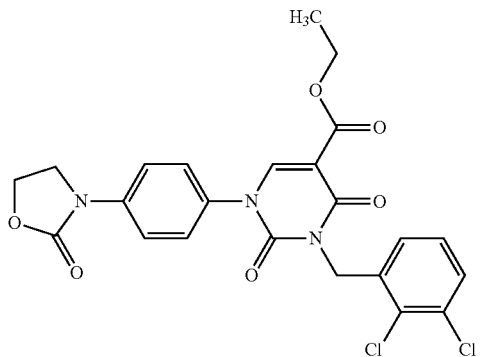 [SMILES: CCOC(=O)c1cn(-c2ccc(N3CCOC3=O)cc2)c(=O)n(Cc2cccc(Cl)c2Cl)c1=O]

The preparation was carried out analogously to Example 3 from 200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 21A and 113.2 mg (0.58 mmol) of 2,3-dichlorobenzyl chloride. Yield: 173 mg (56% of theory, purity 92%).

LC-MS (Method 4): $R_t$=2.31 min; m/z=504 (M+H)$^+$.

$^1$H-NMR (400 MHz, DMSO-d$_6$): δ=1.22 (t, 3H), 4.05-15 (m, 2H), 4.20 (q, 2H), 4.45 (m, 2H), 5.1 (s, 2H), 7.21 (d, 1H), 7.32 (t, 1H), 7.52-7.63 (m, 3H), 7.70 (d, 2H), 8.42 (s, 1H).

Example 35

Ethyl 3-(3-chloro-2-nitrobenzyl)-2,4-dioxo-1-[4-(2-oxo-1,3-oxazolidin-3-yl)phenyl]-1,2,3,4-tetrahydropyrimidine-5-carboxylate

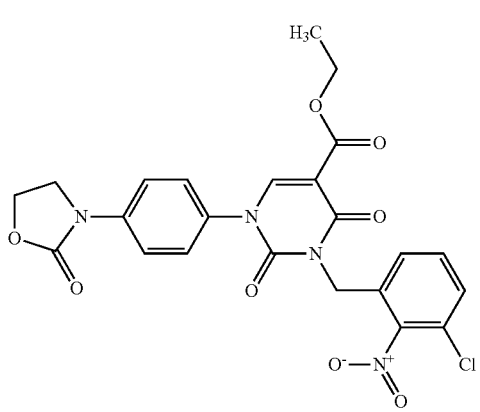 [SMILES: CCOC(=O)c1cn(-c2ccc(N3CCOC3=O)cc2)c(=O)n(Cc2cccc(Cl)c2[N+](=O)[O-])c1=O]

56.6 mg (0.48 mmol) of thionyl chloride and a drop of DMF were added to 81.9 mg (0.44 mmol) of 3-chloro-2-nitrophenyl)methanol in 5 ml of toluene, and the mixture was heated at reflux for three hours. The mixture was then partially concentrated on a rotary evaporator. The remaining solution was added to a mixture of 137 mg (0.40 mmol) from Example 21A, 109.7 mg (0.79 mmol) of potassium carbonate and 32.9 mg (0.198 mmol) of potassium iodide in 5 ml of DMF, and the mixture was stirred at 60° C. for 2 hours. The reaction was partially concentrated under reduced pressure and then purified by preparative HPLC (Method 5a, but using pure water as mobile phase A). The product fractions were combined, concentrated and dried under high vacuum. This gave 118 mg (56% of theory) of the title compound.

LC-MS (Method 3): $R_t$=1.04 min; m/z=515 (M+H)$^+$.

$^1$H-NMR (400 MHz, DMSO-d$_6$): δ=1.24 (t, 3H), 4.05-4.15 (m, 2H), 4.20 (q, 2H), 4.42-4.52 (m, 2H), 5.01 (s, 2H), 7.49-7.56 (m, 2H), 7.58-7.64 (m, 1H), 7.68-7.74 (m, 2H), 8.42 (s, 1H).

Example 36

Ethyl 1-[4-(2-amino-2-oxoethoxy)phenyl]-3-(2-methyl-3-nitrobenzyl)-2,4-dioxo-1,2,3,4-tetrahydropyrimidine-5-carboxylate

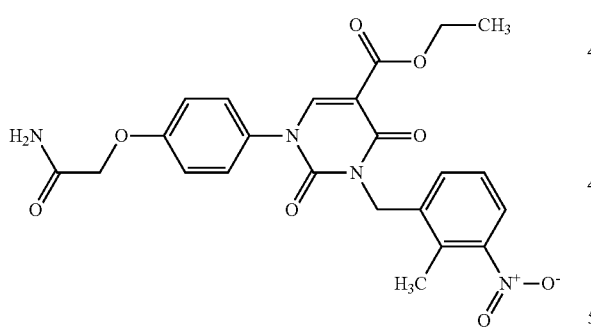

The preparation was carried out analogously to Example 3 from 200 mg (0.6 mmol) of ethyl 1-[4-(2-amino-2-oxoethoxy)phenyl]-2,4-dioxo-1,2,3,4-tetrahydropyrimidine-5-carboxylate from Example 28A and 111.4 mg (0.6 mmol) of 2-methyl-3-nitrobenzyl chloride. Yield: 204 mg (70% of theory).

LC-MS (Method 3): $R_t$=0.90 min; m/z=583 (M+H)$^+$.

$^1$H-NMR (400 MHz, DMSO-d$_6$): δ=1.22 (t, 3H), 2.40 (s, 3H), 4.20 (q, 2H), 4.50 (s, 2H), 5.09 (s, 2H), 7.05 (d, 2H), 7.31-7.42 (m, 3H), 7.48 (d, 2H), 7.50 (br. s, 1H), 7.71 (d, 1H), 8.38 (s, 1H).

Example 37

Ethyl 1-[4-(2-amino-2-oxoethoxy)phenyl]-3-(2,3-dichlorobenzyl)-2,4-dioxo-1,2,3,4-tetrahydropyrimidine-5-carboxylate

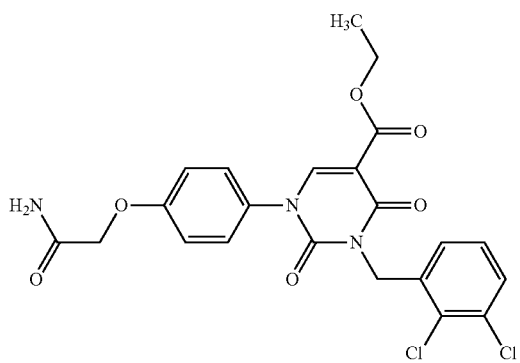 [SMILES: CCOC(=O)c1cn(-c2ccc(OCC(N)=O)cc2)c(=O)n(Cc2cccc(Cl)c2Cl)c1=O]

The preparation was carried out analogously to Example 3 from 200 mg (0.6 mmol) of ethyl 1-[4-(2-amino-2-oxoethoxy)phenyl]-2,4-dioxo-1,2,3,4-tetrahydropyrimidine-5-carboxylate from Example 28A and 234.6 mg (1.2 mmol) of 2,3-dichlorobenzyl chloride. Yield: 213 mg (70% of theory).

LC-MS (Method 3): $R_t$=0.98 min; m/z=492 (M+H)$^+$.

$^1$H-NMR (400 MHz, DMSO-d$_6$): δ=1.22 (t, 3H), 4.20 (q, 2H), 4.48 (s, 2H), 5.10 (s, 2H), 7.06 (d, 2H), 7.20 (d, 1H), 7.32 (t, 1H), 7.40 (br. s, 1H), 7.52-7.61 (m, 2H), 8.40 (s, 1H).

Example 38

Ethyl 1-(3-fluoro-4-{[(2-methoxyethyl)carbamoyl]amino}phenyl)-3-[2-methyl-3-(trifluoromethyl)benzyl]-2,4-dioxo-1,2,3,4-tetrahydropyrimidine-5-carboxylate

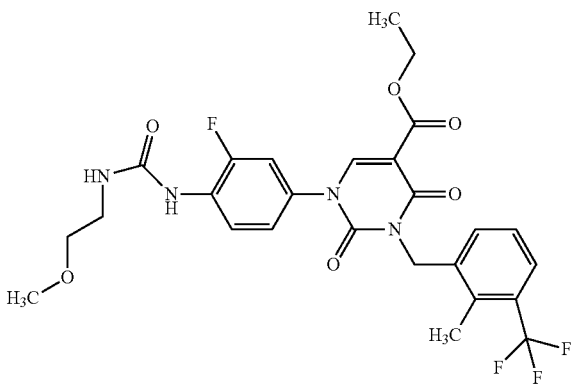 [SMILES: CCOC(=O)c1cn(-c2ccc(NC(=O)NCCOC)c(F)c2)c(=O)n(Cc2cccc(C(F)(F)F)c2C)c1=O]

The preparation was carried out analogously to Example 3 from 200 mg (0.51 mmol) of ethyl 1-(3-fluoro-4-{[(2-methoxyethyl)carbamoyl]amino}phenyl)-2,4-dioxo-1,2,3,4-tetrahydropyrimidine-5-carboxylate from Example 29A and 154 mg (0.61 mmol) of 2-methyl-3-(trifluoromethyl) benzyl bromide. Yield: 180 mg (62% of theory).

LC-MS (Method 2): $R_t$=2.37 min; m/z=567 (M+H)$^+$.

$^1$H-NMR (400 MHz, DMSO-d$_6$): δ=1.23 (t, 3H), 2.45 (s, 3H), 3.12-3.25 (m, 4H), 3.55 (s, 3H), 4.20 (q, 2H), 5.08 (s,

2H), 5.83-5.91 (m, 1H), 6.8-6.9 (m, 1H), 7.18 (dd, 1H), 7.21-7.38 (peak cluster, 4H), 7.58-7.62 (m, 1H), 8.35 (s, 1H).

Example 39

Ethyl 1-[4-(2-hydroxyethoxy)phenyl]-3-(2-methyl-3-nitrobenzyl)-2,4-dioxo-1,2,3,4-tetrahydropyrimidine-5-carboxylate

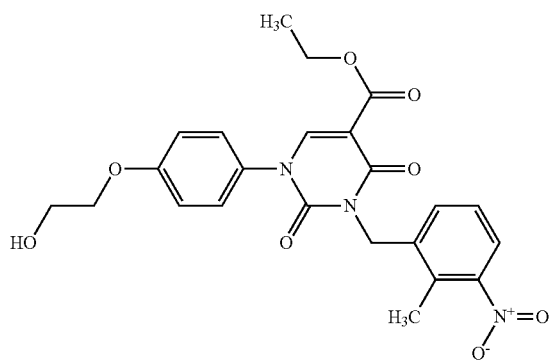 [SMILES: CCOC(=O)c1cn(-c2ccc(OCCO)cc2)c(=O)n(Cc2cccc([N+](=O)[O-])c2C)c1=O]

The preparation was carried out analogously to Example 3 from 200 mg (0.62 mmol) of ethyl 1-[4-(2-hydroxyethoxy)phenyl]-2,4-dioxo-1,2,3,4-tetrahydropyrimidine-5-carboxylate from Example 30A and 116 mg (0.62 mmol) of 2-methyl-3-nitrobenzyl chloride. Yield: 188 mg (64% of theory).

LC-MS (Method 4): $R_t$=2.03 min; m/z=470 (M+H)$^+$ $^1$H-NMR (400 MHz, DMSO-d$_6$): δ=1.22 (t, 3H), 2.40 (s, 3H), 3.70-3.75 (m, 2H), 4.00-4.08 (m, 2H), 4.18 (q, 2H), 4.90 (t, 1H), 5.08 (s, 2H), 7.05 (d, 2H), 7.32-7.48 (m, 4H), 7.71 (d, 1H), 8.37 (s, 1H).

Example 40

Ethyl 1-[4-(2-hydroxyethoxy)phenyl]-3-[2-methyl-3-(trifluoromethyl)benzyl]-2,4-dioxo-1,2,3,4-tetrahydropyrimidine-5-carboxylate

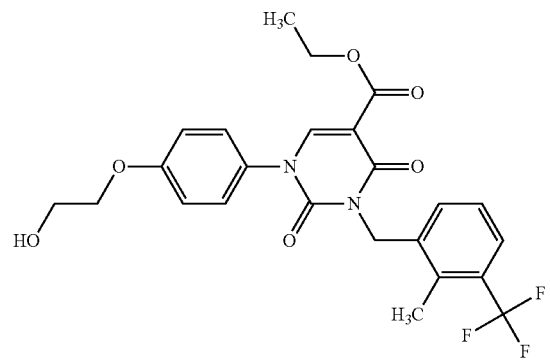 [SMILES: CCOC(=O)c1cn(-c2ccc(OCCO)cc2)c(=O)n(Cc2cccc(C(F)(F)F)c2C)c1=O]

The preparation was carried out analogously to Example 3 from 200 mg (0.62 mmol) of ethyl 1-[4-(2-hydroxyethoxy)phenyl]-2,4-dioxo-1,2,3,4-tetrahydropyrimidine-5-carboxylate from Example 30A and 158 mg (0.62 mmol) of 2-methyl-3-(trifluoromethyl)benzyl bromide. Yield: 197 mg (64% of theory).

LC-MS (Method 4): $R_t$=2.29 min; m/z=493 (M+H)$^+$.

$^1$H-NMR (400 MHz, DMSO-d$_6$): δ=1.22 (t, 3H), 2.45 (s, 3H), 3.70-3.78 (m, 2H), 4.00-4.08 (m, 2H), 4.20 (q, 2H), 4.90 (t, 1H), 5.05 (s, 2H), 7.05 (d, 2H), 7.30-7.40 (m, 2H), 7.45 (d, 2H), 7.60 (d, 1H), 8.37 (s, 1H).

Example 41

Ethyl 1-{4-[(2-hydroxyethyl)amino]phenyl}-3-[2-methyl-3-(trifluoromethyl)benzyl]-2,4-dioxo-1,2,3,4-tetrahydropyrimidine-5-carboxylate

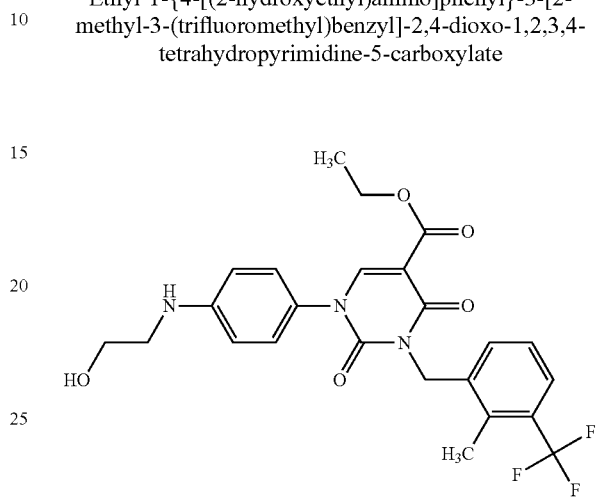

The preparation was carried out analogously to Example 3 from 200 mg (0.63 mmol) of ethyl 1-{4-[(2-hydroxyethyl)amino]phenyl}-2,4-dioxo-1,2,3,4-tetrahydropyrimidine-5-carboxylate from Example 31A and 159 mg (0.63 mmol) of 2-methyl-3-(trifluoromethyl)benzyl bromide. Yield: 107 mg (35% of theory).

LC-MS (Method 4): $R_t$=2.27 min; m/z=492 (M+H)$^+$.

$^1$H-NMR (400 MHz, DMSO-d$_6$): δ=1.22 (t, 3H), 2.45 (s, 3H), 3.09-3.16 (m, 2H), 3.50-3.60 (m, 2H), 4.20 (q, 2H), 4.70 (t, 1H), 5.05 (s, 2H), 5.92 (t, 1H), 6.62 (d, 2H), 7.18 (d, 2H), 7.31-7.36 (m, 2H), 7.55-7.61 (m, 1H), 8.32 (s, 1H).

Example 42

Ethyl 1-(3,4-dimethoxyphenyl)-3-[2-methyl-3-(trifluoromethyl)benzyl]-2,4-dioxo-1,2,3,4-tetrahydropyrimidine-5-carboxylate

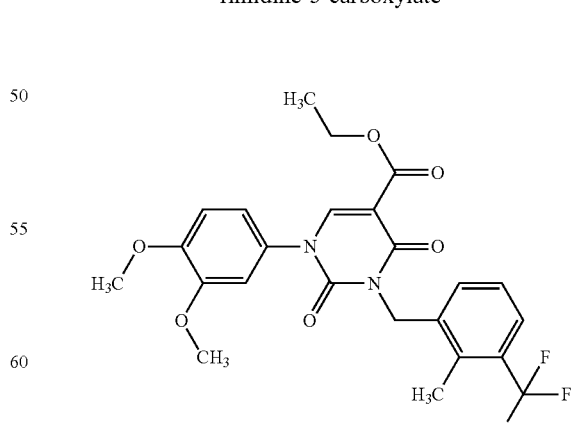

The preparation was carried out analogously to Example 3 from 200 mg (0.62 mmol) of ethyl 1-(3,4-dimethoxyphenyl)-2,4-dioxo-1,2,3,4-tetrahydropyrimidine-5-carboxylate from Example 39A and 189.6 mg (0.75 mmol) of 2-methyl-3-(trifluoromethyl)benzyl bromide. Yield: 252 mg (82% of theory).

LC-MS (Method 3): $R_t$=1.14 min; m/z=493 (M+H)$^+$.

$^1$H-NMR (400 MHz, DMSO-d$_6$): δ=1.21 (t, 3H), 2.45 (s, 3H), 3.75 (s, 3H), 3.80 (s, 3H), 4.19 (q, 2H), 5.08 (s, 2H), 7.02-7.1 (m, 2H), 7.20 (m, 1H), 7.30-7.40 (m, 2H), 7.6 (dd, 1H), 8.38 (s, 1H).

Example 43

Ethyl 3-[3-chloro-2-(methylsulfanyl)benzyl]-1-(3,4-dimethoxyphenyl)-2,4-dioxo-1,2,3,4-tetrahydropyrimidine-5-carboxylate

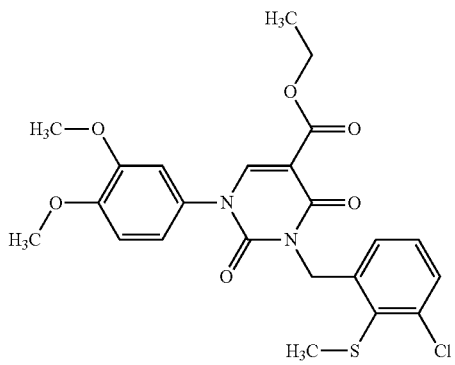 [SMILES: CCOC(=O)c1cn(-c2ccc(OC)c(OC)c2)c(=O)n(Cc2cccc(Cl)c2SC)c1=O]

27.9 mg (0.357 mmol) of 2-mercaptoethanol were added to 150 mg of the mixture of ethyl 3-{3-chloro-2-[(2-nitrophenyl)disulfanyl]benzyl}-1-(3,4-dimethoxyphenyl)-2,4-dioxo-1,2,3,4-tetrahydropyrimidine-5-carboxylate and diethyl 3,3'-{disulfanediylbis[(3-chlorobenzene-2,1-diyl)methylene]}bis[1-(3,4-dimethoxyphenyl)-2,4-dioxo-1,2,3,4-tetrahydropyrimidine-5-carboxylate from Example 45A in 2.38 ml of methanol, and the mixture was stirred at 20° C. for 2 hours. 169 mg (1.19 mmol) of methyl iodide and 64 mg (1.19 mmol) of sodium methoxide were then added and the mixture was stirred under reflux for one hour. After cooling of the mixture, the pH was adjusted to 6 using glacial acetic acid, and the mixture was concentrated and purified by preparative HPLC (Method 5b, but using 0.1% formic acid in water as mobile phase A). The product-containing fractions were combined and concentrated under reduced pressure. This gave 31.2 mg (26% of theory, purity 93%) of the target compound.

LC-MS (Method 3): $R_t$=1.11 min; m/z=477 (M+H)$^+$.

$^1$H-NMR (400 MHz, DMSO-d$_6$): δ=2.40 (s, 3H), 3.70, 3.75, 3.80 (3s, 3H), 5.32 (s, 2H), 7.06 (s, 2H), 7.1 (d, 1H), 7.18 (s, 1H), 7.32 (t, 1H), 7.5 (d, 1H), 8.38 (s, 1H).

Example 44

Ethyl 3-[2-methyl-3-(trifluoromethyl)benzyl]-2,4-dioxo-1-[4-(5-oxopyrrolidin-2-yl)phenyl]-1,2,3,4-tetrahydropyrimidine-5-carboxylate

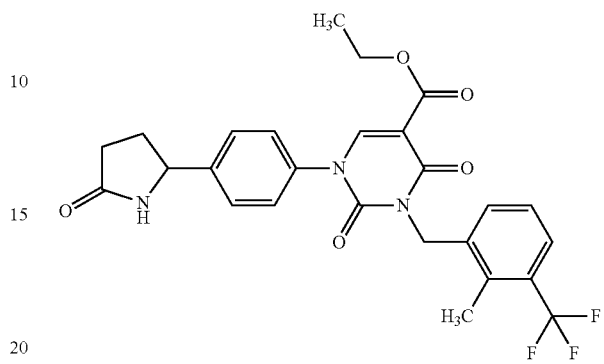

The preparation was carried out analogously to Example 3 from 250 mg (0.54 mmol, purity 74%) of ethyl 2,4-dioxo-1-[4-(5-oxopyrrolidin-2-yl)phenyl]-1,2,3,4-tetrahydropyrimidine-5-carboxylate Example 32A and 273 mg (1.08 mmol) of 2-methyl-3-(trifluoromethyl)benzyl bromide. Yield: 131 mg (47% of theory).

LC-MS (Method 1): $R_t$=1.18 min; m/z=516.0 (M+H)$^+$.

$^1$H-NMR (400 MHz, DMSO-d$_6$): δ=1.21 (t, 3H), 1.71-1.83 (m, 1H), 2.21-2.30 (m, 2H), 2.45 (s, 3H), 2.5 (m, partially hidden by DMSO signal), 4.18 (q, 2H), 4.71-4.78 (m, 1H), 5.05 (s, 2H), 7.30-7.40 (m, 2H), 7.45 (d, 2H), 7.52 (d, 2H), 8.15 (s, 1H), 8.41 (s, 1H).

Example 45

Ethyl 1-{4-[(methoxycarbonyl)amino]phenyl}-3-[2-methyl-3-(trifluoromethyl)benzyl]-2,4-dioxo-1,2,3,4-tetrahydropyrimidine-5-carboxylate

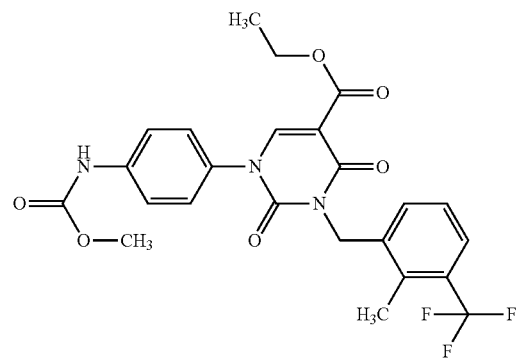 [SMILES: CCOC(=O)c1cn(-c2ccc(NC(=O)OC)cc2)c(=O)n(Cc2cccc(C(F)(F)F)c2C)c1=O]

Under argon, 200 mg (0.45 mmol) of ethyl 1-(4-aminophenyl)-3-[2-methyl-3-(trifluoromethyl)benzyl]-2,4-dioxo-1,2,3,4-tetrahydropyrimidine-5-carboxylate from Example 104A were initially charged in 5 ml of THF, the mixture was cooled to 0° C. and a solution of 75 μl (0.53 mmol) of triethylamine and 38 μl (0.45 mmol) of methyl chloroformate in 1 ml of THF was added dropwise. The mixture was stirred at 0° C. for 30 min and then at RT for 16 h. 1 ml of pyridine and 75 μl (0.88 mmol) of methyl chloroformate were then added. After 30 min at RT, water was added and the reaction mixture was extracted three times with ethyl acetate. The organic phase was washed with saturated aqueous sodium chloride solution, dried over magnesium sulfate and concentrated. The residue was stirred in ethanol, and the solid formed was filtered off, washed with a little ethanol and dried under reduced pressure. This gave 147.9 mg (65% of theory) of the title compound.

LC-MS (Method 3): $R_t$=1.07 min; m/z=506 (M+H)$^+$.

$^1$H-NMR (400 MHz, DMSO-d$_6$): δ=1.23 (t, 3H), 2.46 (s, 3H), 3.69 (s, 3H), 4.19 (q, 2H), 5.07 (s, 2H), 7.30-7.40 (m, 2H), 7.42-7.48 (m, 2H), 7.55-7.62 (m, 3H), 8.40 (s, 1H).

Example 46

1-[4-(Methylsulfinyl)phenyl]-2,4-dioxo-3-[3-(trifluoromethyl)benzyl]-1,2,3,4-tetrahydropyrimidine-5-carboxylic acid

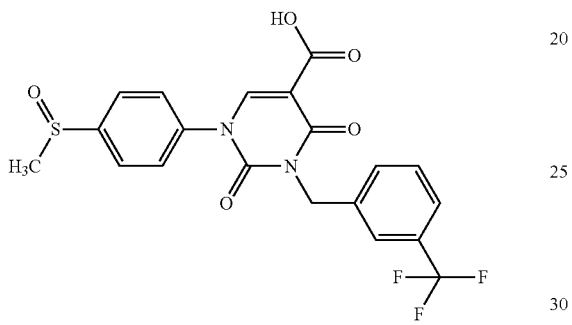

At 5° C., a solution of 77.6 mg of Oxone® in 1 ml of water was added over a period of 0.5 h to 100 mg (0.23 mmol) of 1-[4-(methylsulfanyl)phenyl]-2,4-dioxo-3-[3-(trifluoromethyl)benzyl]-1,2,3,4-tetrahydropyrimidine-5-carboxylic acid from Example 46A in 2 ml of methanol, and the mixture was stirred for 3 h. 33 mg of Oxone® were then added, followed after 1 h by another 33 mg of Oxone®. After 0.5 h, the mixture was concentrated and the residue was purified by preparative HPLC (Method 6b). This gave 22.1 mg (19% of theory, purity 91%) of the desired compound.

LC-MS (Method 3): $R_t$=0.93 min; m/z=453 (M+H)$^+$.

$^1$H-NMR (400 MHz, DMSO-d$_6$): δ=2.80 (s, 3H), 5.12 (s, 2H), 7.58 (t, 1H), 7.62-7.70 (m, 2H), 7.71-7.78 (m, 3H), 7.75 (d, 2H), 8.45 (s, 1H), 12.70 (br. s, 1H).

Example 47

Ethyl 1-{4-[5-(tert-butoxycarbonyl)-1,1-dioxido-1,2,5-thiadiazolidin-2-yl]phenyl}-3-(2-methyl-3-nitrobenzyl)-2,4-dioxo-1,2,3,4-tetrahydropyrimidine-5-carboxylate

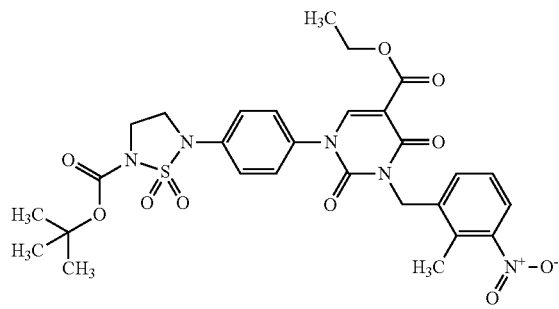 [SMILES: CCOC(=O)c1cn(-c2ccc(N3CCN(C(=O)OC(C)(C)C)S3(=O)=O)cc2)c(=O)n(Cc2cccc([N+](=O)[O-])c2C)c1=O]

The preparation was carried out analogously to Example 3 from 180 mg (0.375 mmol) of ethyl 1-{4-[5-(tert-butoxycarbonyl)-1,1-dioxido-1,2,5-thiadiazolidin-2-yl]phenyl}-2,4-dioxo-1,2,3,4-tetrahydropyrimidine-5-carboxylate from Example 34A and 69 mg (0.375 mmol) of 2-methyl-3-nitrobenzyl chloride. Yield: 156 mg (60% of theory, purity 91%).

LC-MS (Method 3): $R_t$=1.18 min; m/z=630 (M+H)$^+$.

$^1$H-NMR (400 MHz, DMSO-d$_6$): δ=1.22 (t, 3H), 1.5 (s, 9H), 2.40 (s, 3H), 3.90-4.00 (m, 4H), 4.20 (q, 2H), 5.09 (s, 2H), 7.35 (t, 1H), 7.43 (d, 1H), 7.48 (d, 2H), 7.63 (d, 2H), 7.72 (d, 1H), 8.48 (s, 1H).

Example 48

Ethyl 1-[4-(1,1-dioxido-1,2,5-thiadiazolidin-2-yl)phenyl]-3-(2-methyl-3-nitrobenzyl)-2,4-dioxo-1,2,3,4-tetrahydropyrimidine-5-carboxylate

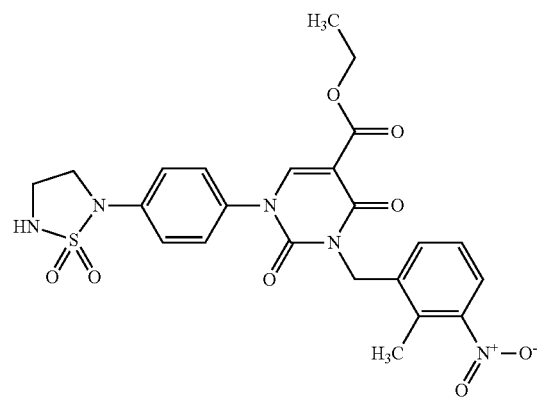 [SMILES: CCOC(=O)c1cn(-c2ccc(N3CCNS3(=O)=O)cc2)c(=O)n(Cc2cccc([N+](=O)[O-])c2C)c1=O]

118 mg (0.187 mmol) of ethyl 1-{4-[5-(tert-butoxycarbonyl)-1,1-dioxido-1,2,5-thiadiazolidin-2-yl]phenyl}-3-(2-methyl-3-nitrobenzyl)-2,4-dioxo-1,2,3,4-tetrahydropyrimidine-5-carboxylate from Example 47 in 2 ml of glacial acetic acid, 1 ml of concentrated hydrochloric acid and 1 ml of water were stirred at 60° C. for four hours. The mixture was diluted with 50 ml of water and the precipitate formed was filtered off with suction. The precipitate was washed with water and dried under high vacuum. This gave 31 mg (28% of theory, purity 91%) of the desired compound.

LC-MS (Method 3): $R_t$=0.99 min; m/z=530 (M+H)$^+$.

$^1$H-NMR (400 MHz, DMSO-d$_6$): δ=1.22 (t, 3H), 2.41 (s, 3H), 3.54 (m, 2H), 3.9 (m, 2H), 4.20 (q, 2H), 5.09 (s, 2H), 7.27 (d, 2H), 7.38 (t, 1H), 7.92 (d, 1H), 7.55 (d, 2H), 7.72 (d, 1H), 7.88 (t, 1H), 8.42 (s, 1H).

Example 49

3-[2-Chloro-3-(trifluoromethyl)benzyl]-1-(4-methoxyphenyl)-2,4-dioxo-1,2,3,4-tetrahydropyrimidine-5-carboxylic acid

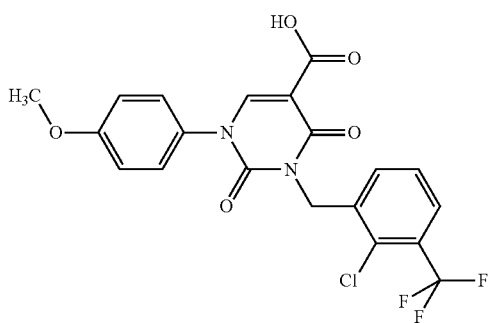 [SMILES: COc1ccc(-n2cc(C(=O)O)c(=O)n(Cc3cccc(C(F)(F)F)c3Cl)c2=O)cc1]

95 mg (0.69 mmol) of potassium carbonate, 63 mg (0.38 mmol) of potassium iodide and 87 mg (0.38 mmol) of 2-chloro-3-(trifluoromethyl)benzyl bromide were added to 100 mg (0.34 mmol) of ethyl 1-(4-methoxyphenyl)-2,4-dioxo-1,2,3,4-tetrahydropyrimidine-5-carboxylate from Example 38A in acetonitrile, and the reaction mixture was stirred at 60° C. overnight. The mixture was concentrated and filtered through 500 mg of silica gel using cyclohexane/ethyl acetate in a ratio of 2:1. Concentration of the mobile phase and drying under reduced pressure gave the ethyl ester of the target compound which was stirred without additional purification in a mixture of 2.00 ml of acetic acid and 1.00 ml of concentrated hydrochloric acid at reflux overnight. The mixture was concentrated under reduced pressure and purified by preparative HPLC (Method 9). Concentration of the appropriate fractions and drying under reduced pressure gave 55 mg (35% of theory over two steps) of the target compound.

LC-MS (Method 3): $R_t$=1.15 min; m/z=455 (M+H)$^+$.

$^1$H-NMR (400 MHz, DMSO-d$_6$): δ=3.81 (s, 3H), 5.16 (s, 2H), 7.03-7.10 (m, 2H), 7.43-7.49 (m, 2H), 7.52 (br. t, 1H), 7.59 (br. d, 1H), 7.80 (br. d, 1H), 8.42 (s, 1H), 12.68 (br. s, 1H).

Example 50

3-(2,3-Dichlorobenzyl)-1-(4-methoxyphenyl)-2,4-dioxo-1,2,3,4-tetrahydropyrimidine-5-carboxylic acid

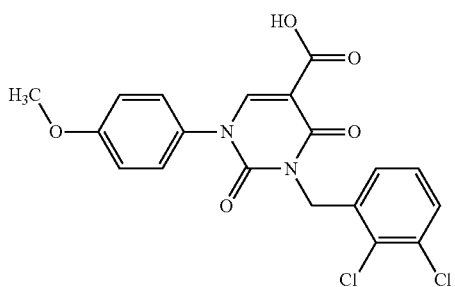 [SMILES: COc1ccc(-n2cc(C(=O)O)c(=O)n(Cc3cccc(Cl)c3Cl)c2=O)cc1]

135 mg (0.30 mmol) of ethyl 3-(2,3-dichlorobenzyl)-1-(4-methoxyphenyl)-2,4-dioxo-1,2,3,4-tetrahydropyrimidine-5-carboxylate from Example 1 in a mixture of 2.0 ml of acetic acid and 1.0 ml of concentrated hydrochloric acid were stirred at 110° C. overnight. Under reduced pressure, the reaction mixture was concentrated to about a third, and after addition of water a solid formed which was filtered off, washed with water and dried under reduced pressure. This gave 61 mg (48% of theory) of the target compound.

LC-MS (Method 1): $R_t$=1.28 min; m/z=421 (M+H)$^+$.

$^1$H-NMR (400 MHz, DMSO-d$_6$): δ=3.81 (s, 3H), 5.12 (s, 2H), 7.03-7.09 (m, 2H), 7.24 (dd, 1H), 7.33 (t, 1H), 7.43-7.49 (m, 2H), 7.58 (dd, 1H), 8.41 (s, 1H), 12.69 (br. s., 1H).

Example 51

3-[2-Methyl-3-(trifluoromethyl)benzyl]-2,4-dioxo-1-[4-(2-oxoimidazolidin-1-yl)phenyl]-1,2,3,4-tetrahydropyrimidine-5-carboxylic acid

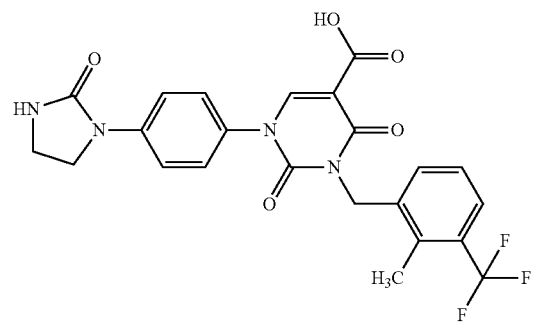 [SMILES: Cc1c(Cn2c(=O)c(C(=O)O)cn(-c3ccc(N4CCNC4=O)cc3)c2=O)cccc1C(F)(F)F]

532 mg (1.03 mmol) of ethyl 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylate from Example 3 were dissolved in 14 ml of glacial acetic acid and 7 ml of conc. hydrochloric acid, and the mixture was stirred at 60° C. After HPLC confirmed complete conversion of the reaction (reaction time 5.5 hours), the mixture was diluted with 30 ml of water and the precipitate formed was filtered off with suction. The mixture was then purified by preparative HPLC (Method 7c). This gave, after concentration of the product-containing fractions under reduced pressure, 338 mg (66% of theory) of the product.

LC-MS (Method 2): $R_t$=2.19 min; m/z=489 (M+H)$^+$.

$^1$H-NMR (400 MHz, DMSO-d$_6$): δ=2.45 (s, 3H), 3.44 (m, 2H), 3.9 (m, 2H), 5.1 (s, 2H), 7.08 (s, 1H), 7.32 (t, 1H), 7.38 (d, 1H), 7.45 (d, 2H), 7.60 (d, 1H), 7.65 (d, 2H), 8.42 (s, 1H), 12.70 (br. s, 1H).

The following carboxylic acids were prepared analogously to Example 51. In each case, the end of the reaction was confirmed by HPLC monitoring. Optionally, it is also possible to use reaction temperatures of up to 100° C. and longer reaction times. Moreover, it is also possible to use semi-concentrated hydrochloric acid instead of concentrated hydrochloric acid.

Example 52

3-(2,3-Dimethylbenzyl)-2,4-dioxo-1-[4-(2-oxoimidazolidin-1-yl)phenyl]-1,2,3,4-tetrahydropyrimidine-5-carboxylic acid

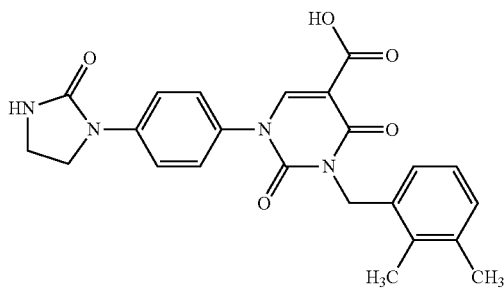 [SMILES: Cc1cccc(Cn2c(=O)c(C(=O)O)cn(-c3ccc(N4CCNC4=O)cc3)c2=O)c1C]

The preparation and purification were carried out analogously to Example 51 from 92 mg (0.2 mmol) of ethyl 3-(2,3-dimethylbenzyl)-2,4-dioxo-1-[4-(2-oxoimidazolidin-1-yl)phenyl]-1,2,3,4-tetrahydropyrimidine-5-carboxylate from Example 5. Yield: 67 mg (75% of theory).

LC-MS (Method 3): $R_t$=0.98 min; m/z=435 (M+H)$^+$.

$^1$H-NMR (400 MHz, DMSO-d$_6$): δ=2.23 (s, 3H), 2.28 (s, 3H), 3.42 (m, 2H), 3.90 (m, 2H), 5.08 (s, 2H), 6.88 (d, 1H), 7.01 (t, 1H), 7.06 (s, 1H), 7.09 (d, 1H), 7.48 (d, 2H), 7.69 (d, 2H), 8.42 (s, 1H), 12.70 (br. s, 1H).

Example 53

3-(2,3-Dichlorobenzyl)-2,4-dioxo-1-[4-(2-oxoimidazolidin-1-yl)phenyl]-1,2,3,4-tetrahydropyrimidine-5-carboxylic acid

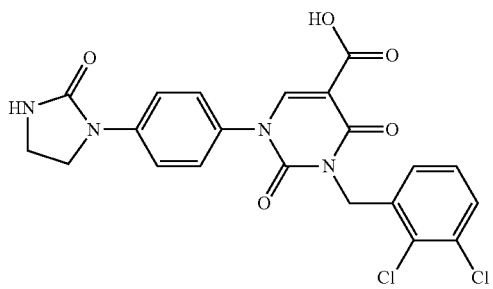 [SMILES: O=C(O)c1cn(-c2ccc(N3CCNC3=O)cc2)c(=O)n(Cc2cccc(Cl)c2Cl)c1=O]

The preparation and purification were carried out analogously to Example 51 from 75 mg (0.15 mmol) of ethyl 3-(2,3-dichlorobenzyl)-2,4-dioxo-1-[4-(2-oxoimidazolidin-1-yl)phenyl]-1,2,3,4-tetrahydropyrimidine-5-carboxylate from Example 4. Yield: 52 mg (68% of theory); purity: 93% (LC-MS).

LC-MS (Method 2): $R_t$=2.13 min; m/z=475 (M+H)$^+$.

$^1$H-NMR (400 MHz, DMSO-d$_6$): δ=3.40-3.46 (m, 2H), 3.85-3.91 (m, 2H), 5.12 (s, 2H), 7.1 (s, 1H), 7.25 (d, 1H), 7.33 (t, 1H), 7.48 (d, 2H), 7.59 (d, 1H), 7.68 (d, 2H), 8.42 (s, 1H), 12.69 (br. s, 1H).

Example 54

3-(2,3-Dichlorobenzyl)-2,4-dioxo-1-[4-(2-oxotetrahydropyrimidin-1(2H)-yl)phenyl]-1,2,3,4-tetrahydropyrimidine-5-carboxylic acid

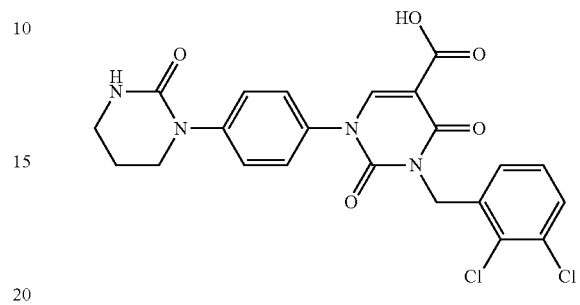

The preparation and purification were carried out analogously to Example 51 from 220 mg (0.43 mmol) of ethyl 3-(2,3-dichlorobenzyl)-2,4-dioxo-1-[4-(2-oxotetrahydropyrimidin-1 (2H)-yl)phenyl]-1,2,3,4-tetrahydropyrimidine-5-carboxylate from Example 9. Yield: 113 mg (53% of theory).

LC-MS (Method 3): $R_t$=0.98 min; m/z=589 (M+H)$^+$.

$^1$H-NMR (400 MHz, DMSO-d$_6$): δ=1.97 (m, 2H), 3.25 (m, 2H), 3.68 (m, 2H), 5.12 (s, 2H), 6.70 (s, 1H), 7.25 (d, 1H), 7.32 (t, 1H), 7.46 (s, 4H), 7.58 (d, 1H), 8.42 (s, 1H), 12.6 (br. s, 1H).

Example 55

3-[3-Fluoro-2-(trifluoromethyl)benzyl]-2,4-dioxo-1-[4-(2-oxotetrahydropyrimidin-1(2H)-yl)phenyl]-1,2,3,4-tetrahydropyrimidine-5-carboxylic acid

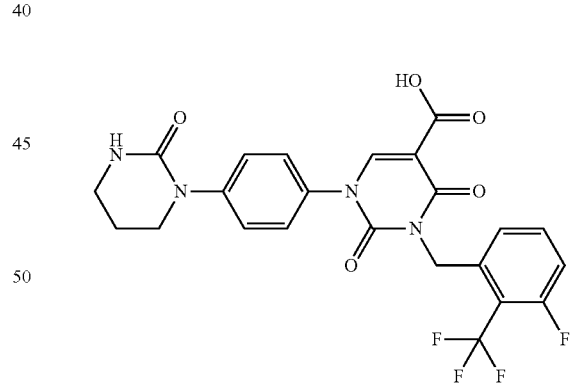

The preparation and purification were carried out analogously to Example 51 from 65 mg (0.13 mmol) of ethyl 3-[3-fluoro-2-(trifluoromethyl)benzyl]-2,4-dioxo-1-[4-(2-oxotetrahydropyrimidin-1(2H)-yl)phenyl]-1,2,3,4-tetrahydropyrimidine-5-carboxylate from Example 10. Yield: 57 mg (87% of theory).

LC-MS (Method 3): $R_t$=0.96 min; m/z=507 (M+H)$^+$.

$^1$H-NMR (400 MHz, DMSO-d$_6$): δ=1.95 (m, 2H), 3.22 (m, 2H), 3.67 (m, 2H), 5.21 (s, 2H), 6.70 (s, 1H), 7.20 (d, 1H), 7.40 (m, 1H), 7.45 (s, 4H), 7.65 (m, 1H), 8.43 (s, 1H), 12.68 (br. s, 1H).

Example 56

3-(2,3-Dichlorobenzyl)-1-[3-fluoro-4-(2-oxoimidazolidin-1-yl)phenyl]-2,4-dioxo-1,2,3,4-tetrahydropyrimidine-5-carboxylic acid

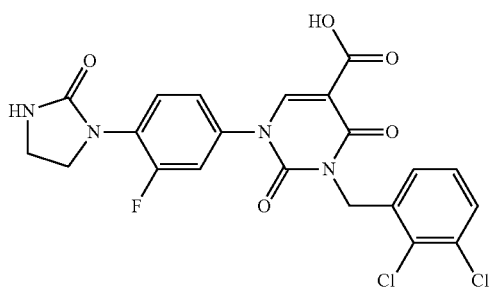 [SMILES: O=C(O)c1cn(-c2ccc(N3CCNC3=O)c(F)c2)c(=O)n(Cc2cccc(Cl)c2Cl)c1=O]

The preparation and purification were carried out analogously to Example 51 from 65 mg (0.13 mmol) of ethyl 3-(2,3-dichlorobenzyl)-1-[3-fluoro-4-(2-oxoimidazolidin-1-yl)phenyl]-2,4-dioxo-1,2,3,4-tetrahydropyrimidine-5-carboxylate from Example 20. Yield: 47 mg (76% of theory).

LC-MS (Method 3): $R_t$=1.02 min; m/z=493 (M+H)$^+$.

$^1$H-NMR (400 MHz, DMSO-d$_6$): δ=3.45 (m, 2H), 3.88 (m, 2H), 5.12 (s, 2H), 7.02 (s, 1H), 7.25 (d, 1H), 7.32 (t, 1H), 7.38 (dd, 1H), 7.52-7.61 (m, 2H), 7.68 (t, 1H), 8.5 (s, 1H), 12.65 (br. s, 1H).

Example 57

1-[3-Fluoro-4-(2-oxoimidazolidin-1-yl)phenyl]-3-(2-methyl-3-nitrobenzyl)-2,4-dioxo-1,2,3,4-tetrahydropyrimidine-5-carboxylic acid

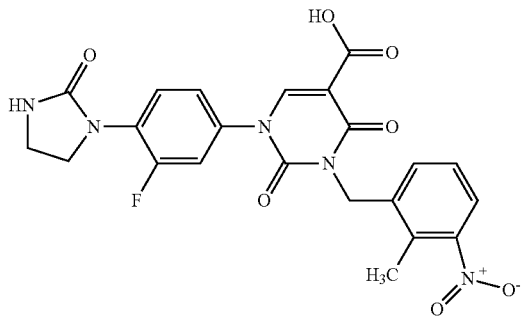

The preparation and purification were carried out analogously to Example 51 from 95 mg (0.19 mmol) of ethyl 1-[3-fluoro-4-(2-oxoimidazolidin-1-yl)phenyl]-3-(2-methyl-3-nitrobenzyl)-2,4-dioxo-1,2,3,4-tetrahydropyrimidine-5-carboxylate from Example 19. Yield: 74 mg (79% of theory).

LC-MS (Method 4): $R_t$=1.95 min; m/z=484 (M+H)$^+$.

$^1$H-NMR (400 MHz, DMSO-d$_6$): δ=2.40 (s, 3H), 3.45 (m, 2H), 3.87 (m, 2H), 5.10 (s, 2H), 7.02 (s, 1H), 7.35-7.40 (m, 2H), 7.45 (d, 1H), 7.55 (dd, 1H), 7.65 (t, 1H), 7.72 (dd, 1H), 8.50 (s, 1H), 12.70 (br. s, 1H).

Example 58

1-[3-Fluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylic acid

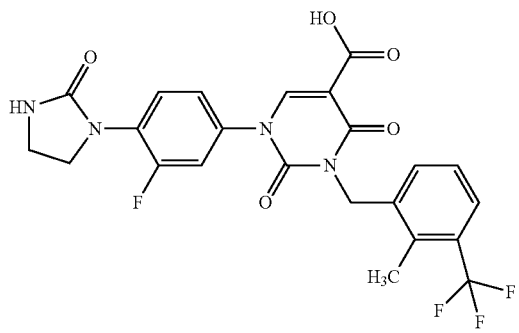 [SMILES: Cc1c(Cn2c(=O)c(C(=O)O)cn(-c3ccc(N4CCNC4=O)c(F)c3)c2=O)cccc1C(F)(F)F]

The preparation and purification were carried out analogously to Example 51 from 130 mg (0.23 mmol) of ethyl 1-[3-fluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate from Example 18. Yield: 96 mg (75% of theory).

LC-MS (Method 4): $R_t$=1.95 min; m/z=507 (M+H)$^+$.

$^1$H-NMR (400 MHz, DMSO-d$_6$): δ=2.48 (s, 3H), 3.45 (m, 2H), 3.87 (m, 2H), 5.08 (s, 2H), 7.02 (s, 1H), 7.30-7.45 (m, 3H), 7.52-7.62 (m, 2H), 7.68 (t, 1H), 8.50 (s, 1H), 12.72 (br. s, 1H).

Example 59

3-[2-Methyl-3-(trifluoromethyl)benzyl]-2,4-dioxo-1-[4-(2-oxo-2,3-dihydro-1H-imidazol-1-yl)phenyl]-1,2,3,4-tetrahydropyrimidine-5-carboxylic acid

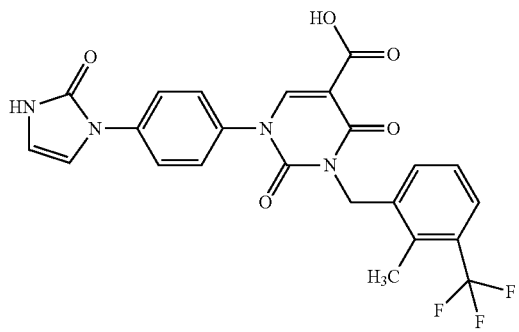 [SMILES: Cc1c(Cn2c(=O)c(C(=O)O)cn(-c3ccc(-n4cc[nH]c4=O)cc3)c2=O)cccc1C(F)(F)F]

The preparation and purification were carried out analogously to Example 51 from 140 mg (0.27 mmol) of ethyl 3-[2-methyl-3-(trifluoromethyl)benzyl]-2,4-dioxo-1-[4-(2-oxo-2,3-dihydro-1H-imidazol-1-yl)phenyl]-1,2,3,4-tetrahydropyrimidine-5-carboxylate from Example 17. Yield: 57 mg (41% of theory); purity: 94% (LC-MS).

LC-MS (Method 3): $R_t$=0.98 min; m/z=487 (M+H)$^+$.

$^1$H-NMR (400 MHz, DMSO-d$_6$): δ=2.48 (s, 3H), 5.12 (s, 2H), 6.65 (m, 1H), 7.05 (m, 1H), 7.35 (t, 1H), 7.45 (d, 1H), 7.61 (d, 2H), 7.90 (d, 2H), 8.49 (s, 1H), 10.40 (s, 1H), 12.70 (br. s, 1H).

Example 60

3-(2,3-Dichlorobenzyl)-2,4-dioxo-1-[4-(2-oxo-2,3-dihydro-1H-imidazol-1-yl)phenyl]-1,2,3,4-tetrahydropyrimidine-5-carboxylic acid

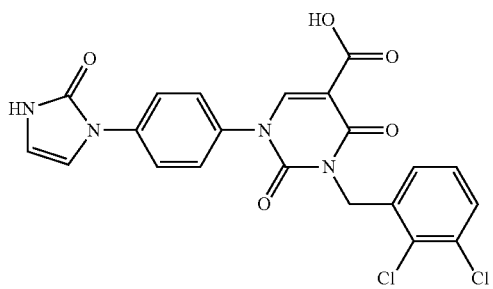 [SMILES: O=C(O)c1cn(-c2ccc(-n3cc[nH]c3=O)cc2)c(=O)n(Cc2cccc(Cl)c2Cl)c1=O]

The preparation and purification were carried out analogously to Example 51 from 110 mg (0.22 mmol) of ethyl 3-(2,3-dichlorobenzyl)-2,4-dioxo-1-[4-(2-oxo-2,3-dihydro-1H-imidazol-1-yl)phenyl]-1,2,3,4-tetrahydropyrimidine-5-carboxylate from Example 16. Yield: 37 mg (33% of theory); purity: 91% (LC-MS).

LC-MS (Method 3): $R_t$=0.96 min; m/z=473 (M+H)$^+$.

$^1$H-NMR (400 MHz, DMSO-d$_6$): δ=5.12 (s, 2H), 6.65 (m, 1H), 7.05 (m, 1H), 7.25 (d, 1H), 7.33 (t, 1H), 7.60 (d, 2H), 7.90 (d, 2H), 8.48 (s, 1H), 10.40 (s, 1H), 12.70 (br. s, 1H).

Example 61

3-(2,3-Dichlorobenzyl)-2,4-dioxo-1-[4-(2-oxopyrrolidin-1-yl)phenyl]-1,2,3,4-tetrahydropyrimidine-5-carboxylic acid

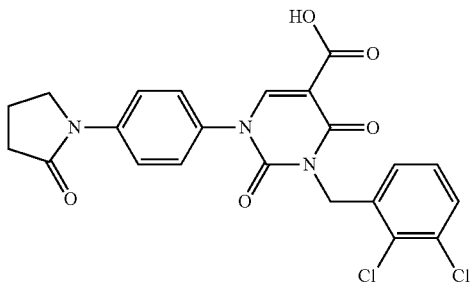 [SMILES: O=C(O)c1cn(-c2ccc(N3CCCC3=O)cc2)c(=O)n(Cc2cccc(Cl)c2Cl)c1=O]

The preparation and purification were carried out analogously to Example 51 from 100 mg (0.2 mmol) of ethyl 3-(2,3-dichlorobenzyl)-2,4-dioxo-1-[4-(2-oxopyrrolidin-1-yl)phenyl]-1,2,3,4-tetrahydropyrimidine-5-carboxylate from Example 13. Yield: 11 mg (12% of theory).

LC-MS (Method 3): $R_t$=1.06 min; m/z=474 (M+H)$^+$.

$^1$H-NMR (400 MHz, DMSO-d$_6$): δ=2.08 (m, 2H), 2.50 (m, hidden by DMSO signal), 3.87 (m, 2H), 5.10 (s, 2H), 7.23 (d, 1H), 7.32 (t, 1H), 7.52 (d, 2H), 7.58 (d, 2H), 7.81 (d, 2H), 8.49 (s, 1H), 12.71 (br. s, 1H).

Example 62

3-[3-Fluoro-2-(trifluoromethyl)benzyl]-2,4-dioxo-1-[4-(2-oxopyrrolidin-1-yl)phenyl]-1,2,3,4-tetrahydropyrimidine-5-carboxylic acid

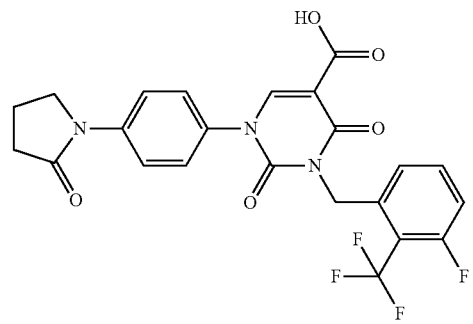 [SMILES: O=C(O)c1cn(-c2ccc(N3CCCC3=O)cc2)c(=O)n(Cc2cccc(F)c2C(F)(F)F)c1=O]

The preparation and purification were carried out analogously to Example 51 from 103 mg (0.2 mmol) of ethyl 3-[3-fluoro-2-(trifluoromethyl)benzyl]-2,4-dioxo-1-[4-(2-oxopyrrolidin-1-yl)phenyl]-1,2,3,4-tetrahydropyrimidine-5-carboxylate from Example 14. Yield: 28 mg (28% of theory).

LC-MS (Method 3): $R_t$=1.04 min; m/z=492 (M+H)$^+$.

$^1$H-NMR (400 MHz, DMSO-d$_6$): δ=2.08 (m, 2H), 2.50 (m, hidden by DMSO signal), 3.85 (m, 2H), 5.20 (s, 2H), 7.21 (d, 1H), 7.40 (dd, 1H), 7.51 (d, 2H), 7.60-7.70 (m, 1H), 7.80 (d, 2H), 8.45 (s, 1H), 12.70 (br. s, 1H).

Example 63

3-(2-Methyl-3-nitrobenzyl)-2,4-dioxo-1-[4-(2-oxo-1,3-oxazolidin-3-yl)phenyl]-1,2,3,4-tetrahydropyrimidine-5-carboxylic acid

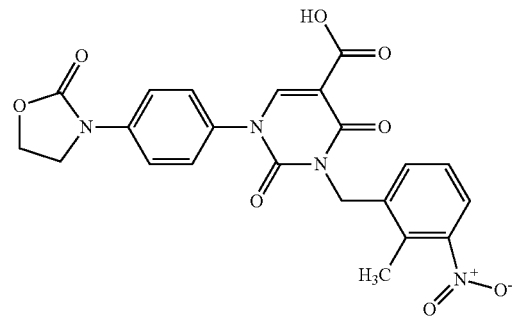

The preparation and purification were carried out analogously to Example 51 from 24 mg (0.05 mmol) of ethyl 3-(2-methyl-3-nitrobenzyl)-2,4-dioxo-1-[4-(2-oxo-1,3-oxazolidin-3-yl)phenyl]-1,2,3,4-tetrahydropyrimidine-5-carboxylate from Example 31. Yield: 3 mg (13% of theory).

LC-MS (Method 3): $R_t$=0.95 min; m/z=467 (M+H)$^+$.

$^1$H-NMR (400 MHz, DMSO-d$_6$): δ=2.40 (s, 3H), 4.10 (m, 2H), 4.45 (m, 2H), 5.10 (s, 2H), 7.38 (t, 1H), 7.45 (d, 1H), 7.52 (d, 2H), 7.68-7.78 (m, 3H), 8.45 (s, 1H), 12.7 (br. s, 1H).

Example 64

3-[3-Fluoro-2-(trifluoromethyl)benzyl]-2,4-dioxo-1-[4-(2-oxo-1,3-oxazolidin-3-yl)phenyl]-1,2,3,4-tetrahydropyrimidine-5-carboxylic acid

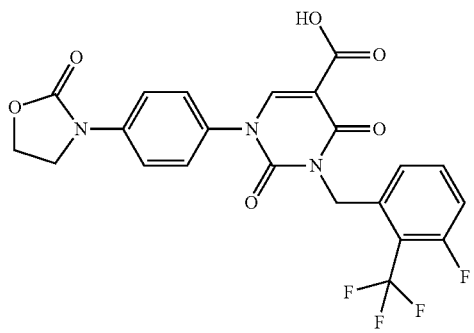 [SMILES: O=C(O)c1cn(-c2ccc(N3CCOC3=O)cc2)c(=O)n(Cc2cccc(F)c2C(F)(F)F)c1=O]

The preparation and purification were carried out analogously to Example 51 from 50 mg (0.1 mmol) of ethyl 3-[3-fluoro-2-(trifluoromethyl)benzyl]-2,4-dioxo-1-[4-(2-oxo-1,3-oxazolidin-3-yl)phenyl]-1,2,3,4-tetrahydropyrimidine-5-carboxylate from Example 32. Yield: 37 mg (77% of theory).

LC-MS (Method 3): $R_t$=1.03 min; m/z=494 (M+H)$^+$.

$^1$H-NMR (400 MHz, DMSO-d$_6$): δ=4.10 (m, 2H), 4.41 (m, 2H), 5.22 (s, 2H), 7.22 (d, 1H), 7.41 (dd, 1H), 7.55 (d, 2H), 7.66 (m, 1H), 7.71 (d, 2H), 8.48 (s, 1H), 12.7 (s, 1H).

Example 65

3-[2-Methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylic acid

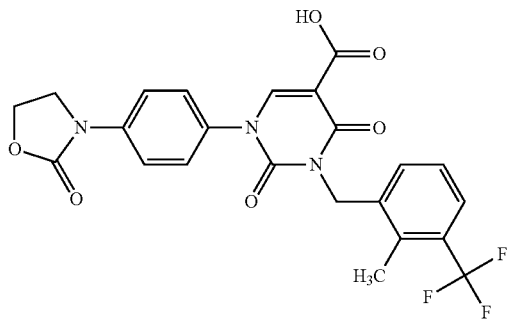 [SMILES: Cc1c(Cn2c(=O)c(C(=O)O)cn(-c3ccc(N4CCOC4=O)cc3)c2=O)cccc1C(F)(F)F]

The preparation and purification were carried out analogously to Example 51 from 37 mg (0.07 mmol) of ethyl 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylate from Example 33. Yield: 15 mg (42% of theory).

LC-MS (Method 3): $R_t$=1.08 min; m/z=490 (M+H)$^+$.

$^1$H-NMR (400 MHz, DMSO-d$_6$): δ=2.49 (s, 3H), 4.10 (m, 2H), 4.47 (m, 2H), 5.10 (s, 2H), 7.32 (t, 1H), 7.40 (d, 1H), 7.51-7.62 (m, 3H), 7.70 (d, 2H), 8.44 (s, 1H), 12.7 (br. s, 1H).

Example 66

3-(2,3-Dichlorobenzyl)-2,4-dioxo-1-[4-(2-oxo-1,3-oxazolidin-3-yl)phenyl]-1,2,3,4-tetrahydropyrimidine-5-carboxylic acid

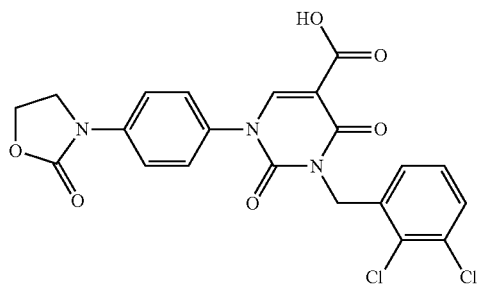 [SMILES: O=C(O)c1cn(-c2ccc(N3CCOC3=O)cc2)c(=O)n(Cc2cccc(Cl)c2Cl)c1=O]

The preparation and purification were carried out analogously to Example 51 from 173 mg (0.34 mmol) of ethyl 3-(2,3-dichlorobenzyl)-2,4-dioxo-1-[4-(2-oxo-1,3-oxazolidin-3-yl)phenyl]-1,2,3,4-tetrahydropyrimidine-5-carboxylate from Example 34. Yield: 59 mg (35% of theory).

LC-MS (Method 3): $R_t$=1.06 min; m/z=476 (M+H)$^+$.

$^1$H-NMR (400 MHz, DMSO-d$_6$): δ=4.10 (m, 2H), 4.45 (m, 2H), 5.11 (s, 2H), 7.24 (d, 1H), 7.31 (t, 1H), 7.51-7.60 (m, 3H), 7.70 (d, 2H), 8.45 (s, 1H), 12.7 (br. s, 1H).

Example 67

1-(4-Methoxyphenyl)-3-[2-methyl-3-(trifluoromethyl)benzyl]-2,4-dioxo-1,2,3,4-tetrahydropyrimidine-5-carboxylic acid

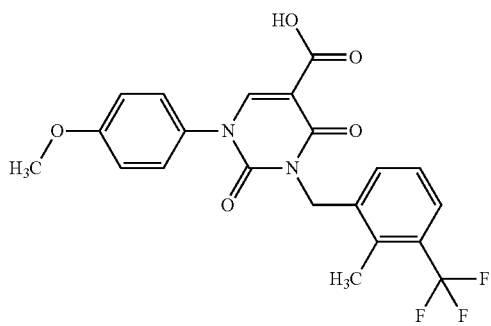 [SMILES: COc1ccc(-n2cc(C(=O)O)c(=O)n(Cc3cccc(C(F)(F)F)c3C)c2=O)cc1]

The preparation and purification were carried out analogously to Example 51 from 175 mg (0.38 mmol) of ethyl 1-(4-methoxyphenyl)-3-[2-methyl-3-(trifluoromethyl)benzyl]-2,4-dioxo-1,2,3,4-tetrahydropyrimidine-5-carboxylate from Example 2. Yield: 97 mg (58% of theory).

LC-MS (Method 2): $R_t$=2.45 min; m/z=435 (M+H)$^+$.

$^1$H-NMR (400 MHz, DMSO-d$_6$): δ=2.43 (s, 3H), 3.80 (s, 3H), 5.09 (s, 2H), 7.05 (d, 2H), 7.30-7.42 (m, 2H), 7.46 (d, 2H), 7.61 (d, 1H), 8.40 (s, 1H), 12.69 (br. s, 1H).

Example 68

1-(3,4-Dimethoxyphenyl)-3-[2-methyl-3-(trifluoromethyl)benzyl]-2,4-dioxo-1,2,3,4-tetrahydropyrimidine-5-carboxylic acid

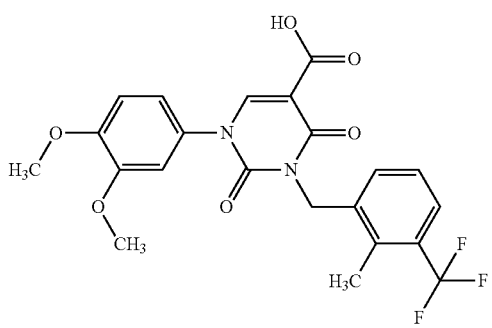 [SMILES: COc1ccc(-n2cc(C(=O)O)c(=O)n(Cc3cccc(C(F)(F)F)c3C)c2=O)cc1OC]

The preparation and purification were carried out analogously to Example 51 from 215 mg (0.44 mmol) of ethyl 1-(3,4-dimethoxyphenyl)-3-[2-methyl-3-(trifluoromethyl)benzyl]-2,4-dioxo-1,2,3,4-tetrahydropyrimidine-5-carboxylate from Example 42. Yield: 189 mg (93% of theory).

LC-MS (Method 2): $R_t$=2.37 min; m/z=465 (M+H)$^+$.

$^1$H-NMR (400 MHz, DMSO-d$_6$): δ=2.45 (s, 3H), 3.75 (s, 3H), 3.80 (s, 3H), 5.10 (s, 2H), 7.02-7.1 (m, 2H), 7.20 (s, 1H), 7.30-7.42 (m, 2H), 7.6 (d, 1H), 8.40 (s, 1H), 12.60 (br. s, 1H).

Example 69

1-(4-Ethoxyphenyl)-3-[3-fluoro-2-(trifluoromethyl)benzyl]-2,4-dioxo-1,2,3,4-tetrahydropyrimidine-5-carboxylic acid

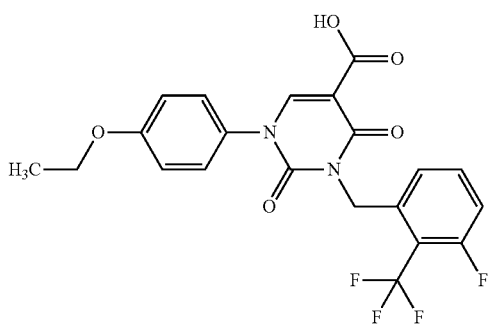 [SMILES: CCOc1ccc(-n2cc(C(=O)O)c(=O)n(Cc3cccc(F)c3C(F)(F)F)c2=O)cc1]

The preparation and purification were carried out analogously to Example 51 from 150 mg (0.31 mmol) of ethyl 1-(4-ethoxyphenyl)-3-[3-fluoro-2-(trifluoromethyl)benzyl]-2,4-dioxo-1,2,3,4-tetrahydropyrimidine-5-carboxylate from Example 15. Yield: 130 mg (89% of theory).

LC-MS (Method 1): $R_t$=1.31 min; m/z=453 (M+H)$^+$.

$^1$H-NMR (400 MHz, DMSO-d$_6$): δ=1.32 (t, 3H), 4.06 (q, 2H), 5.20 (s, 2H), 7.02 (d, 2H), 7.20 (d, 1H), 7.35-7.45 (m, 3H), 7.60-7.70 (m, 1H), 8.41 (s, 1H), 12.70 (br. s, 1H).

Example 70

3-[2-Methyl-3-(trifluoromethyl)benzyl]-2,4-dioxo-1-[4-(1H-pyrazol-3-yl)phenyl]-1,2,3,4-tetrahydropyrimidine-5-carboxylic acid

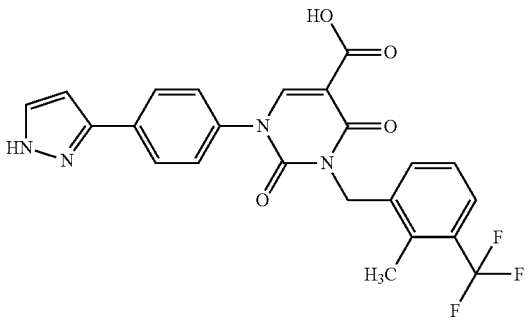 [SMILES: Cc1c(Cn2c(=O)c(C(=O)O)cn(-c3ccc(-c4cc[nH]n4)cc3)c2=O)cccc1C(F)(F)F]

The preparation and purification were carried out analogously to Example 51 from 60 mg (0.1 mmol) of ethyl 1-{4-[1-(tert-butoxycarbonyl)-1H-pyrazol-3-yl]phenyl}-3-[2-methyl-3-(trifluoromethyl)benzyl]-2,4-dioxo-1,2,3,4-tetrahydropyrimidine-5-carboxylate (Example 30) in glacial acetic acid/semi-concentrated hydrochloric acid (2:1). Yield: 29 mg (58% of theory); purity: 93% (HPLC).

LC-MS (Method 3): $R_t$=1.07 min; m/z=471 (M+H)$^+$.

$^1$H-NMR (400 MHz, DMSO-d$_6$): δ=2.45 (partially hidden by DMSO signal), 5.21 (s, 2H), 6.80 (d, 1H), 7.31-7.43 (m, 2H), 7.53-7.63 (m, 3H), 7.75 (s, 1H), 7.95 (d, 2H), 8.51 (s, 1H), 12.75 (br. s, 1H).

Example 71

3-(2,3-Dichlorobenzyl)-2,4-dioxo-1-[4-(1H-pyrazol-3-yl)phenyl]-1,2,3,4-tetrahydropyrimidine-5-carboxylic acid

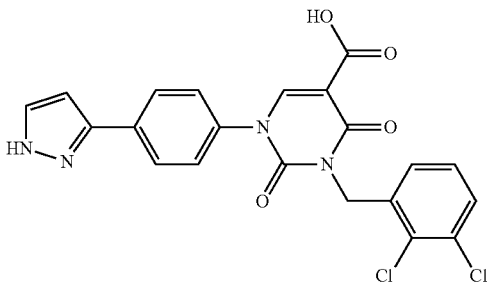 [SMILES: O=C(O)c1cn(-c2ccc(-c3cc[nH]n3)cc2)c(=O)n(Cc2cccc(Cl)c2Cl)c1=O]

The preparation and purification were carried out analogously to Example 51 from 65 mg (0.11 mmol) of ethyl 1-{4-[1-(tert-butoxycarbonyl)-1H-pyrazol-3-yl]phenyl}-3-(2,3-dichlorobenzyl)-2,4-dioxo-1,2,3,4-tetrahydropyrimidine-5-carboxylate (Example 29) in glacial acetic acid/semi-concentrated hydrochloric acid (2:1). Yield: 17 mg (32% of theory).

LC-MS (Method 3): $R_t$=1.06 min; m/z=457 (M+H)$^+$.

$^1$H-NMR (400 MHz, DMSO-d$_6$): δ=5.12 (s, 2H), 6.80 (d, 1H), 7.27 (d, 1H), 7.35 (t, 1H), 7.55-7.61 (m, 3H), 7.78 (br. s, 1H), 7.96 (d, 2H), 8.50 (s, 1H), 12.85 (br. s, 1H).

Example 72

3-[3-Fluoro-2-(trifluoromethyl)benzyl]-2,4-dioxo-1-[4-(5-oxo-1,5-dihydro-4H-1,2,4-triazol-4-yl)phenyl]-1,2,3,4-tetrahydropyrimidine-5-carboxylic acid

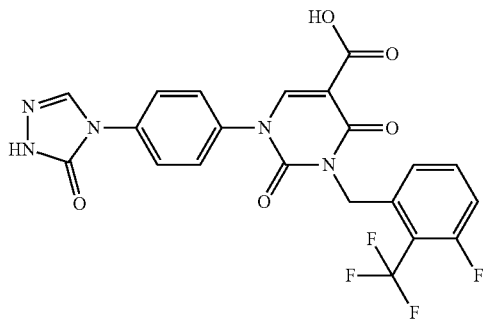 [SMILES: O=C(O)c1cn(-c2ccc(-n3cn[nH]c3=O)cc2)c(=O)n(Cc2cccc(F)c2C(F)(F)F)c1=O]

The preparation and purification were carried out analogously to Example 51 from 30 mg (0.058 mmol) of ethyl 3-[3-fluoro-2-(trifluoromethyl)benzyl]-2,4-dioxo-1-[4-(5-oxo-1,5-dihydro-4H-1,2,4-triazol-4-yl)phenyl]-1,2,3,4-tetrahydropyrimidine-5-carboxylate (Example 28) using glacial acetic acid/semi-concentrated hydrochloric acid (1:1). Yield: 8 mg (29% of theory).

LC-MS (Method 3): $R_t$=0.93 min; m/z=492 (M+H)$^+$.

$^1$H-NMR (400 MHz, DMSO-d$_6$): δ=5.20 (s, 2H), 7.10 (d, 1H), 7.35-7.45 (m, 1H), 7.61-7.72 (m, 3H), 7.85 (d, 2H), 8.45 (s, 1H), 8.51 (s, 1H), 12.08 (br. s, 1H), 12.72 (br. s, 1H).

Example 73

3-[2-Methyl-3-(trifluoromethyl)benzyl]-2,4-dioxo-1-[4-(2-oxo-1,3-oxazinan-3-yl)phenyl]-1,2,3,4-tetrahydropyrimidine-5-carboxylic acid

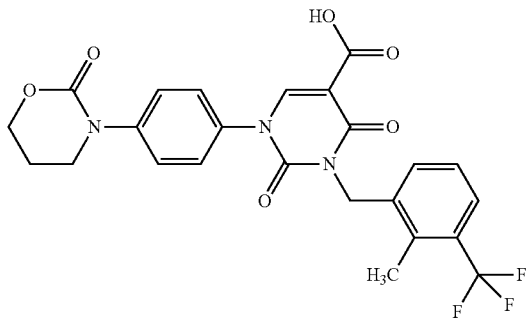 [SMILES: Cc1c(Cn2c(=O)c(C(=O)O)cn(-c3ccc(N4CCCOC4=O)cc3)c2=O)cccc1C(F)(F)F]

The preparation and purification were carried out analogously to Example 51 from 147 mg (0.23 mmol) of ethyl 3-[2-methyl-3-(trifluoromethyl)benzyl]-2,4-dioxo-1-[4-(2-oxo-1,3-oxazinan-3-yl)phenyl]-1,2,3,4-tetrahydropyrimidine-5-carboxylate from Example 11. Yield: 35 mg (8% of theory).

LC-MS (Method 1): $R_t$=1.17 min; m/z=504.0 (M+H)$^+$.

$^1$H-NMR (400 MHz, DMSO-d$_6$): δ=2.08-2.15 (m, 2H), 2.46 (s, 3H), 3.68-3.74 (m, 2H), 4.32-4.41 (m, 2H), 5.10 (s, 2H), 7.30-7.36 (m, 1H), 7.41 (d, 1H), 7.50-7.63 (m, 5H), 8.46 (s, 1H), 12.70 (br. s, 1H).

Example 74

3-(2,3-Dichlorobenzyl)-2,4-dioxo-1-[4-(2-oxo-1,3-oxazinan-3-yl)phenyl]-1,2,3,4-tetrahydropyrimidine-5-carboxylic acid

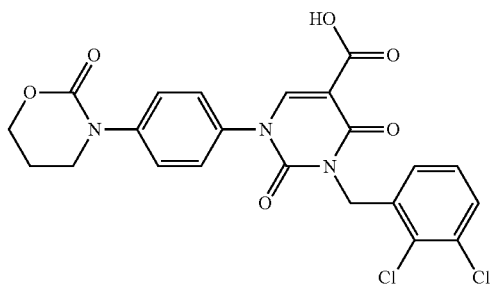 [SMILES: O=C(O)c1cn(-c2ccc(N3CCCOC3=O)cc2)c(=O)n(Cc2cccc(Cl)c2Cl)c1=O]

The preparation and purification were carried out analogously to Example 51 from 131 mg (0.25 mmol) of ethyl 3-(2,3-dichlorobenzyl)-2,4-dioxo-1-[4-(2-oxo-1,3-oxazinan-3-yl)phenyl]-1,2,3,4-tetrahydropyrimidine-5-carboxylate from Example 12. Yield: 9 mg (7% of theory).

LC-MS (Method 1): $R_t$=1.13 min; m/z=489.9 (M+H)$^+$.

$^1$H-NMR (400 MHz, DMSO-d$_6$): δ=2.06-2.15 (m, 2H), 3.68-3.74 (m, 2H), 4.32-4.40 (m, 2H), 5.12 (s, 2H), 7.25 (d, 1H), 7.32 (t, 1H), 7.50-7.61 (m, 5H), 8.42 (s, 1H), 12.70 (br. s, 1H).

Example 75

1-[3,5-Difluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylic acid

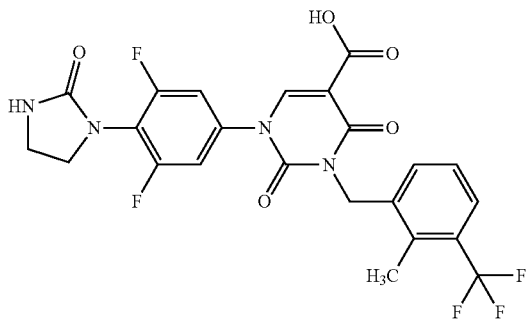 [SMILES: Cc1c(Cn2c(=O)c(C(=O)O)cn(-c3cc(F)c(N4CCNC4=O)c(F)c3)c2=O)cccc1C(F)(F)F]

480 mg (0.87 mmol) of ethyl 1-[3,5-difluoro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate from Example 23 in a mixture of 2.00 ml of acetic acid and 1.00 ml of concentrated hydrochloric acid were stirred under reflux for 4 h. After cooling to RT, a solid was precipitated out by addition of about 5 ml of water, and the solid was filtered off, washed with water and a little diethyl ether and dried under reduced pressure. This gave 361 mg (79% of theory) of the target compound.

LC-MS (Method 3): $R_t$=1.01 min; m/z=525 (M+H)$^+$.

$^1$H-NMR (400 MHz, DMSO-d$_6$): δ=2.46 (s, 3H), 3.47-3.54 (m, 2H), 3.72-3.80 (m, 2H), 5.08 (s, 2H), 7.03 (s, 1H), 7.31-7.38 (m, 1H), 7.38-7.43 (m, 1H), 7.50-7.57 (m, 2H), 7.58-7.63 (m, 1H), 8.58 (s, 1H), 12.75 (br. s, 1H).

Example 76

3-(2,3-Dichlorobenzyl)-1-[3,5-difluoro-4-(2-oxoimidazolidin-1-yl)phenyl]-2,4-dioxo-1,2,3,4-tetrahydropyrimidine-5-carboxylic acid

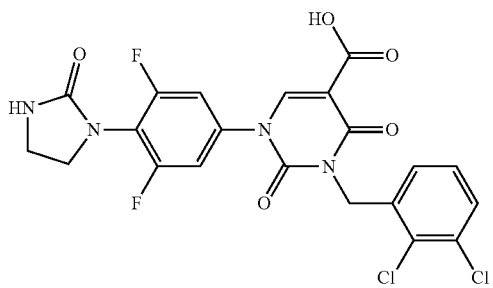 [SMILES: O=C(O)c1cn(-c2cc(F)c(N3CCNC3=O)c(F)c2)c(=O)n(Cc2cccc(Cl)c2Cl)c1=O]

Preparation and purification of the title compound were carried out analogously to Example 75 using a reaction time of 3 h. Starting with 90 mg (0.17 mmol) of ethyl 3-(2,3-dichlorobenzyl)-1-[3,5-difluoro-4-(2-oxoimidazolidin-1-yl)phenyl]-2,4-dioxo-1,2,3,4-tetrahydropyrimidine-5-carboxylate from Example 24, this gave the target compound in approximately quantitative yield (87 mg).

LC-MS (Method 3): $R_t$=1.00 min; m/z=511 (M+H)$^+$.

$^1$H-NMR (400 MHz, DMSO-d$_6$): δ=3.46-3.54 (m, 2H), 3.72-3.80 (m, 2H), 5.12 (s, 2H), 7.02 (s, 1H), 7.24 (br. d, 1H), 7.33 (t, 1H), 7.49-7.56 (m, 2H), 7.59 (br. d, 1H), 8.58 (s, 1H), 12.75 (br. s, 1H).

Example 77

3-(2-Chloro-3-(trifluoromethyl)benzyl)-1-[3,5-difluoro-4-(2-oxoimidazolidin-1-yl)phenyl]-2,4-dioxo-1,2,3,4-tetrahydropyrimidine-5-carboxylic acid

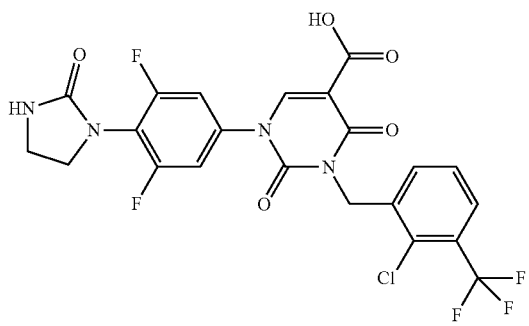 [SMILES: O=C(O)c1cn(-c2cc(F)c(N3CCNC3=O)c(F)c2)c(=O)n(Cc2cccc(C(F)(F)F)c2Cl)c1=O]

Preparation and purification of the title compound were carried out analogously to Example 75 using a reaction time of 2.5 h. Starting with 100 mg (0.18 mmol) of ethyl 3-(2-chloro-3-(trifluoromethyl)benzyl)-1-[3,5-difluoro-4-(2-oxoimidazolidin-1-yl)phenyl]-2,4-dioxo-1,2,3,4-tetrahydropyrimidine-5-carboxylate from Example 25, this gave 59 mg (62% of theory) of the target compound.

LC-MS (Method 4): $R_t$=2.22 min; m/z=545 (M+H)$^+$.

$^1$H-NMR (400 MHz, DMSO-d$_6$): δ=3.46-3.54 (m, 2H), 3.72-3.80 (m, 2H), 5.16 (s, 2H), 7.03 (s, 1H), 7.48-7.56 (m, 3H), 7.60 (d, 1H), 7.81 (d, 1H), 8.59 (s, 1H), 12.77 (br. s., 1H).

Example 78

1-[3,5-Difluoro-4-(2-oxoimidazolidin-1-yl)phenyl]-3-[3-fluoro-2-(trifluoromethyl)benzyl]-2,4-dioxo-1,2,3,4-tetrahydropyrimidine-5-carboxylic acid

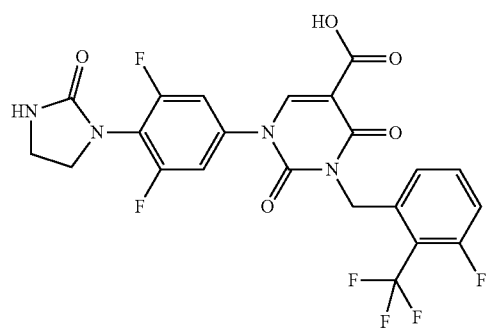 [SMILES: O=C(O)c1cn(-c2cc(F)c(N3CCNC3=O)c(F)c2)c(=O)n(Cc2cccc(F)c2C(F)(F)F)c1=O]

Preparation and purification of the title compound were carried out analogously to Example 75 using a reaction time of 2 h. Starting with 95 mg (0.17 mmol) of ethyl 1-[3,5-difluoro-4-(2-oxoimidazolidin-1-yl)phenyl]-3-[3-fluoro-2-(trifluoromethyl)benzyl]-2,4-dioxo-1,2,3,4-tetrahydropyrimidine-5-carboxylate from Example 26, this gave 65 mg (72% of theory) of the target compound.

LC-MS (Method 3): $R_t$=0.99 min; m/z=529 (M+H)$^+$.

$^1$H-NMR (400 MHz, DMSO-d$_6$): δ=3.46-3.54 (m, 2H), 3.72-3.80 (m, 2H), 5.20 (s, 2H), 7.03 (s, 1H), 7.20 (d, 1H), 7.41 (dd, 1H), 7.48-7.56 (m, 2H), 7.66 (td, 1H), 8.60 (s, 1H), 12.76 (br. s, 1H).

Example 79

3-(2-Chloro-3-methylbenzyl)-1-[3,5-difluoro-4-(2-oxoimidazolidin-1-yl)phenyl]-2,4-dioxo-1,2,3,4-tetrahydropyrimidine-5-carboxylic acid

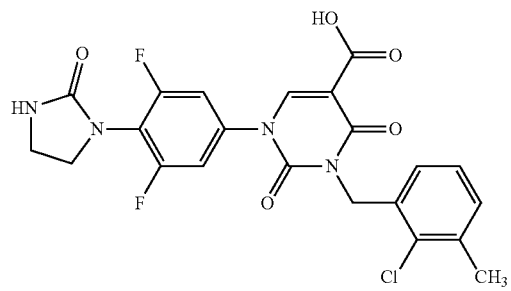 [SMILES: Cc1cccc(Cn2c(=O)c(C(=O)O)cn(-c3cc(F)c(N4CCNC4=O)c(F)c3)c2=O)c1Cl]

Reaction and work-up were carried out analogously to Example 75 using a reaction time of 4 h. The crude product obtained was purified by preparative HPLC (Method 13). Concentration and drying of the appropriate fractions under reduced pressure thus gave, starting from 50 mg (0.10 mmol) of ethyl 3-(2-chloro-3-methylbenzyl)-1-[3,5-difluoro-4-(2-oxoimidazolidin-1-yl)phenyl]-2,4-dioxo-1,2,3,4- tetrahydropyrimidine-5-carboxylate (from Example 27), 18 mg (38% of theory) of the target compound.

LC-MS (Method 3): $R_t$=1.01 min; m/z=491 (M+H)$^+$.

$^1$H-NMR (400 MHz, DMSO-d$_6$): δ=3.46-3.54 (m, 2H), 3.72-3.80 (m, 2H), 5.09 (s, 2H), 7.02 (s, 1H), 7.04 (d, 1H), 7.19 (t, 1H), 7.29 (d, 1H), 7.49-7.57 (m, 2H), 8.58 (s, 1H), 12.75 (br. s, 1H).

Example 80

3-[3-Chloro-2-(methylsulfanyl)benzyl]-1-(3,4-dimethoxyphenyl)-2,4-dioxo-1,2,3,4-tetrahydropyrimidine-5-carboxylic acid

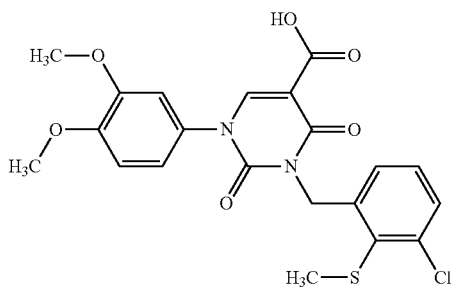 [SMILES: COc1ccc(-n2cc(C(=O)O)c(=O)n(Cc3cccc(Cl)c3SC)c2=O)cc1OC]

The preparation and purification were carried out analogously to Example 51 from 29 mg (0.06 mmol) of ethyl 3-[3-chloro-2-(methylsulfanyl)benzyl]-1-(3,4-dimethoxyphenyl)-2,4-dioxo-1,2,3,4-tetrahydropyrimidine-5-carboxylate from Example 43. The yield was 17 mg (61% of theory).

LC-MS (Method 3): $R_t$=1.13 min; m/z=463 (M+H)$^+$.

$^1$H-NMR (400 MHz, DMSO-d$_6$): δ=2.40 (s, 3H), 3.75, 3.80 (2s, 3H), 5.38 (s, 2H), 7.04 (s, 2H), 7.12 (d, 1H), 7.18 (s, 1H), 7.35 (t, 1H), 7.5 (d, 1H), 8.40 (s, 1H), 12.68 (br. s, 1H).

Example 81

3-[2-Methyl-3-(trifluoromethyl)benzyl]-2,4-dioxo-1-[4-(5-oxopyrrolidin-2-yl)phenyl]-1,2,3,4-tetrahydropyrimidine-5-carboxylic acid

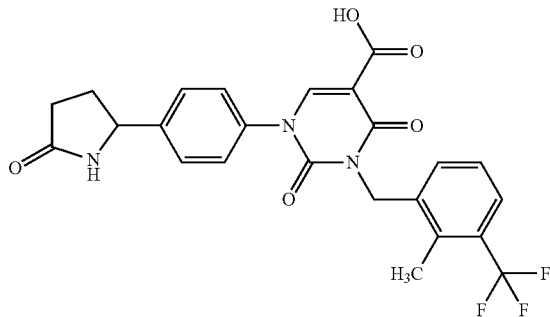 [SMILES: Cc1c(Cn2c(=O)c(C(=O)O)cn(-c3ccc(C4CCC(=O)N4)cc3)c2=O)cccc1C(F)(F)F]

The preparation was carried out analogously to Example 51 from 96 mg (0.19 mmol) of ethyl 3-[2-methyl-3-(trifluoromethyl)benzyl]-2,4-dioxo-1-[4-(5-oxopyrrolidin-2-yl)phenyl]-1,2,3,4-tetrahydropyrimidine-5-carboxylate (Example 44). Yield: 58 mg (62% of theory), purity: 97% (HPLC).

LC-MS (Method 2): $R_t$=2.13 min; m/z=488 (M+H)$^+$.

$^1$H-NMR (400 MHz, DMSO-d$_6$): δ=1.70-1.85 (m, 1H), 2.20-2.30 (m, 2H), 2.49 (s, 3H), 2.5 (m, partially hidden by DMSO signal), 4.70-4.78 (m, 1H), 5.10 (s, 2H), 7.32 (t, 1H), 7.38 (d, 1H), 7.45 (d, 2H), 7.52 (d, 2H), 7.60 (d, 1H), 8.18 (s, 1H), 8.42 (s, 1H), 12.5 (br. s, 1H).

Example 82

3-(3-Chloro-2-nitrobenzyl)-2,4-dioxo-1-[4-(2-oxo-1,3-oxazolidin-3-yl)phenyl]-1,2,3,4-tetrahydropyrimidine-5-carboxylic acid

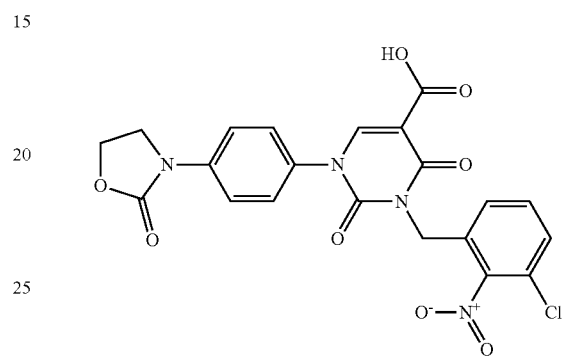

The preparation and purification were carried out analogously to Example 51 from 80 mg (0.16 mmol) of ethyl (3-chloro-2-nitrobenzyl)-2,4-dioxo-1-[4-(2-oxo-1,3-oxazolidin-3-yl)phenyl]-1,2,3,4-tetrahydropyrimidine-5-carboxylate from Example 35. Yield: 69 mg (88% of theory).

LC-MS (Method 3): $R_t$=0.97 min; m/z=487 (M+H)$^+$.

$^1$H-NMR (400 MHz, DMSO-d$_6$): δ=4.05-4.15 (m, 2H), 4.42-4.52 (m, 2H), 5.01 (s, 2H), 7.49-7.57 (m, 3H), 7.60 (t, 1H), 7.65-7.75 (m, 3H), 8.40 (s, 1H), 12.71 (br. s, 1H).

Example 83

1-[4-(2-Amino-2-oxoethoxy)phenyl]-3-(2-methyl-3-nitrobenzyl)-2,4-dioxo-1,2,3,4-tetrahydropyrimidine-5-carboxylic acid

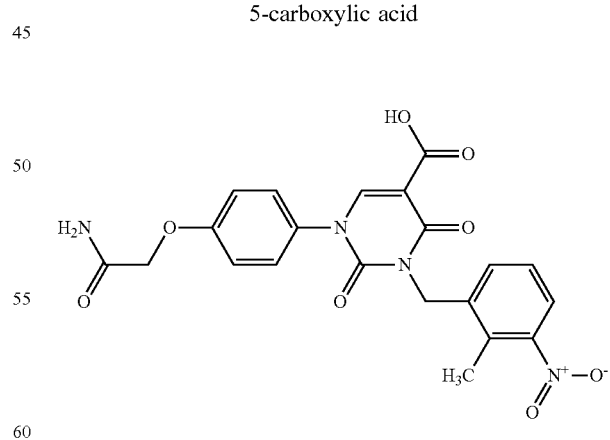

The preparation and purification were carried out analogously to Example 51 from 160 mg (0.33 mmol) of ethyl 1-[4-(2-amino-2-oxoethoxy)phenyl]-3-(2-methyl-3-nitrobenzyl)-2,4-dioxo-1,2,3,4-tetrahydropyrimidine-5-carboxylate from Example 36. Yield: 3 mg (2% of theory).

LC-MS (Method 4): $R_t$=1.88 min; m/z=455 (M+H)$^+$.

$^1$H-NMR (400 MHz, DMSO-d$_6$): δ=2.40 (s, 3H), 4.50 (s, 2H), 5.08 (s, 2H), 7.03 (d, 2H), 7.32-7.50 (m, 5H), 7.58 (br. s, 1H), 7.72 (d, 1H), 8.28 (s, 1H).

Example 84

1-[4-(2-Amino-2-oxoethoxy)phenyl]-3-(2,3-dichlorobenzyl)-2,4-dioxo-1,2,3,4-tetrahydropyrimidine-5-carboxylic acid

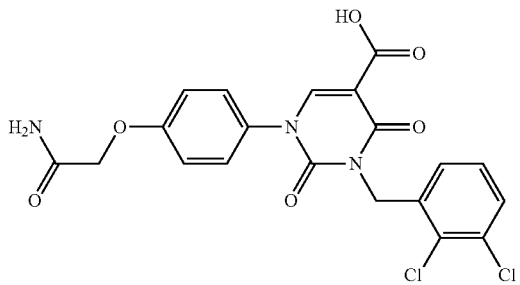 [SMILES: NC(=O)COc1ccc(-n2cc(C(=O)O)c(=O)n(Cc3cccc(Cl)c3Cl)c2=O)cc1]

The preparation and purification were carried out analogously to Example 51 from 155 mg (0.315 mmol) of ethyl 1-[4-(2-amino-2-oxoethoxy)phenyl]-3-(2,3-dichlorobenzyl)-2,4-dioxo-1,2,3,4-tetrahydropyrimidine-5-carboxylate from Example 37. Yield: 3 mg (2% of theory).

LC-MS (Method 4): R$_t$=2.09 min; m/z=464 (M+H)$^+$.

$^1$H-NMR (400 MHz, DMSO-d$_6$): δ=4.50 (s, 2H), 5.10 (s, 2H), 7.22 (d, 2H), 7.30 (t, 1H), 7.40-7.42 (m, 1H), 7.45 (d, 2H), 7.55-7.60 (m, 2H), 8.40 (s, 1H), 12.70 (br. s, 1H).

Example 85

1-(3-Fluoro-4-{[(2-methoxyethyl)carbamoyl]amino}phenyl)-3-[2-methyl-3-(trifluoromethyl)benzyl]-2,4-dioxo-1,2,3,4-tetrahydropyrimidine-5-carboxylic acid

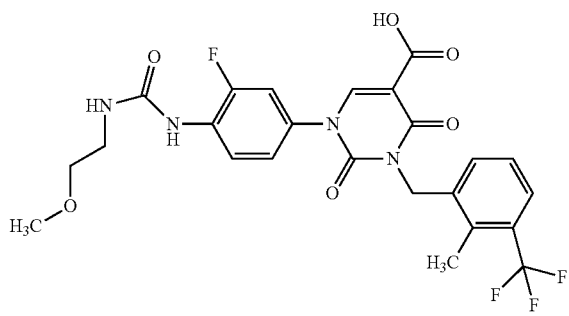 [SMILES: COCCNC(=O)Nc1ccc(-n2cc(C(=O)O)c(=O)n(Cc3cccc(C(F)(F)F)c3C)c2=O)cc1F]

The preparation and purification were carried out analogously to Example 51 from 50 mg (0.088 mmol) of ethyl 1-(3-fluoro-4-{[(2-methoxyethyl)carbamoyl]amino}phenyl)-3-[2-methyl-3-(trifluoromethyl)benzyl]-2,4-dioxo-1,2,3,4-tetrahydropyrimidine-5-carboxylate from Example 38. Yield: 34 mg (66% of theory); purity: 91% (LC-MS).

LC-MS (Method 1): R$_t$=1.27 min; m/z=539 (M+H)$^+$.

$^1$H-NMR (400 MHz, DMSO-d$_6$): δ=2.48 (s, 3H), 3.12-3.22 (m, 4H), 3.53 (s, 3H), 5.08 (s, 2H), 5.83-5.91 (m, 1H), 6.8-6.9 (m, 1H), 7.15 (dd, 1H), 7.21-7.40 (m, 4H), 7.60 (d, 1H), 8.40 (s, 1H), 12.69 (br. s, 1H).

Example 86

3-(2,3-Dichlorobenzyl)-2,4-dioxo-1-[4-(3-oxomorpholin-4-yl)phenyl]-1,2,3,4-tetrahydropyrimidine-5-carboxylic acid

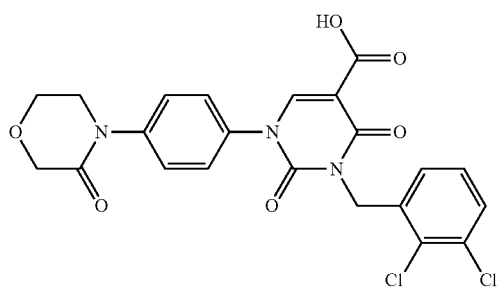 [SMILES: O=C(O)c1cn(-c2ccc(N3CCOCC3=O)cc2)c(=O)n(Cc2cccc(Cl)c2Cl)c1=O]

The preparation and purification were carried out analogously to Example 51 from 155 mg (0.3 mmol) of ethyl 3-(2,3-dichlorobenzyl)-2,4-dioxo-1-[4-(3-oxomorpholin-4-yl)phenyl]-1,2,3,4-tetrahydropyrimidine-5-carboxylate from Example 21. The reaction was purified by preparative HPLC (Method 5a). This gave 32 mg (22% of theory) of the title compound.

LC-MS (Method 4): R$_t$=2.13 min; m/z=490 (M+H)$^+$.

$^1$H-NMR (400 MHz, DMSO-d$_6$): δ=3.76-3.82 (m, 2H), 3.97-4.03 (m, 2H), 4.23 (s, 2H), 5.11 (s, 2H), 7.25 (d, 1H), 7.32 (t, 1H), 7.58 (s, 4H), 8.48 (s, 1H), 12.70 (br. s, 1H).

Example 87

3-[2-Methyl-3-(trifluoromethyl)benzyl]-2,4-dioxo-1-[4-(3-oxomorpholin-4-yl)phenyl]-1,2,3,4-tetrahydropyrimidine-5-carboxylic acid

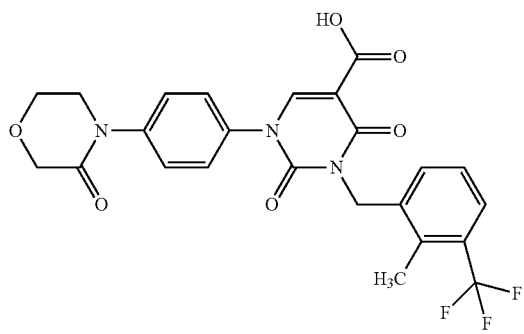 [SMILES: Cc1c(Cn2c(=O)c(C(=O)O)cn(-c3ccc(N4CCOCC4=O)cc3)c2=O)cccc1C(F)(F)F]

The preparation and purification were carried out analogously to Example 51 from 195 mg (0.37 mmol) of ethyl 3-[2-methyl-3-(trifluoromethyl)benzyl]-2,4-dioxo-1-[4-(3-oxomorpholin-4-yl)phenyl]-1,2,3,4-tetrahydropyrimidine-5-carboxylate from Example 22. The reaction was purified by preparative HPLC (Method 5a). This gave 12 mg (7% of theory) of the title compound.

LC-MS (Method 3): R$_t$=1.03 min; m/z=504 (M+H)$^+$.

¹H-NMR (400 MHz, DMSO-d₆): δ=2.48 (s, 3H), 3.77-3.81 (m, 2H), 3.98-4.02 (m, 2H), 4.22 (s, 2H), 5.10 (s, 2H), 7.35 (t, 1H), 7.40 (d, 1H), 7.60 (s, 4H), 7.61 (d, 1H), 8.48 (s, 1H), 12.70 (br. s, 1H).

Example 88

1-[4-(2-Hydroxyethoxy)phenyl]-3-(2-methyl-3-nitrobenzyl)-2,4-dioxo-1,2,3,4-tetrahydropyrimidine-5-carboxylic acid

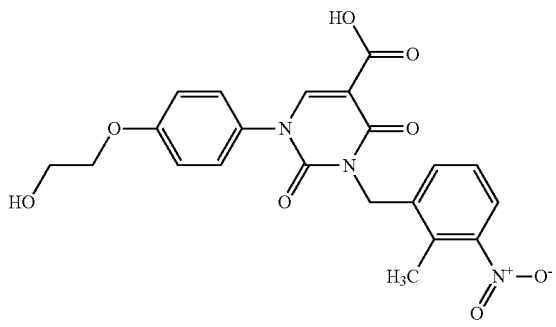 [SMILES: Cc1c(Cn2c(=O)c(C(=O)O)cn(-c3ccc(OCCO)cc3)c2=O)cccc1[N+](=O)[O-]]

The preparation and purification were carried out analogously to Example 51 from 155 mg (0.33 mmol) of ethyl 1-[4-(2-hydroxyethoxy)phenyl]-3-(2-methyl-3-nitrobenzyl)-2,4-dioxo-1,2,3,4-tetrahydropyrimidine-5-carboxylate from Example 39. This gave 33 mg (23% of theory) of the title compound.

LC-MS (Method 3): $R_t$=0.92 min; m/z=442 (M+H)⁺.

¹H-NMR (400 MHz, DMSO-d₆): δ=2.40 (s, 3H), 3.70-3.75 (m, 2H), 4.00-4.08 (m, 2H), 4.90 (t, 1H), 5.10 (s, 2H), 7.08 (d, 2H), 7.39 (t, 1H), 7.40-7.50 (m, 3H), 7.72 (d, 1H), 8.40 (s, 1H), 12.70 (br. s, 1H).

Example 89

1-[4-(2-Hydroxyethoxy)phenyl]-3-[2-methyl-3-(trifluoromethyl)benzyl]-2,4-dioxo-1,2,3,4-tetrahydropyrimidine-5-carboxylic acid

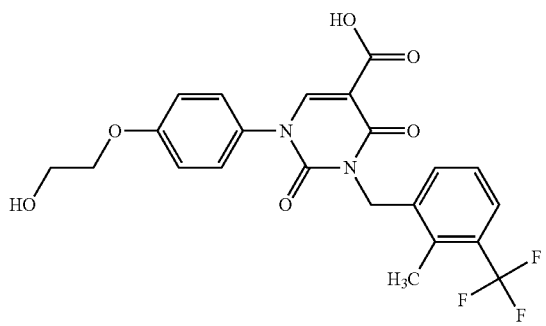 [SMILES: Cc1c(Cn2c(=O)c(C(=O)O)cn(-c3ccc(OCCO)cc3)c2=O)cccc1C(F)(F)F]

The preparation and purification were carried out analogously to Example 51 from 160 mg (0.33 mmol) of ethyl 1-[4-(2-hydroxyethoxy)phenyl]-3-[2-methyl-3-(trifluoromethyl)benzyl]-2,4-dioxo-1,2,3,4-tetrahydropyrimidine-5-carboxylate from Example 40. This gave 62 mg (41% of theory) of the title compound.

LC-MS (Method 3): $R_t$=1.04 min; m/z=465 (M+H)⁺.

¹H-NMR (400 MHz, DMSO-d₆): δ=2.46 (s, 3H), 3.68-3.78 (m, 2H), 4.00-4.08 (m, 2H), 4.90 (t, 1H), 5.10 (s, 2H), 7.03 (d, 2H), 7.31-7.49 (m, 4H), 7.60 (d, 1H), 8.41 (s, 1H), 12.71 (br. s, 1H).

Example 90

1-{4-[(2-Hydroxyethyl)amino]phenyl}-3-[2-methyl-3-(trifluoromethyl)benzyl]-2,4-dioxo-1,2,3,4-tetrahydropyrimidine-5-carboxylic acid

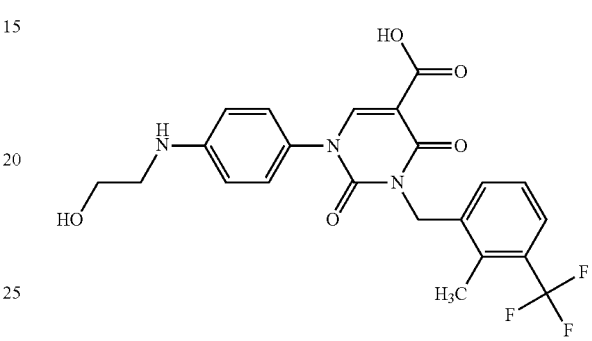

le;2qThe preparation and purification were carried out analogously to Example 51 from 75 mg (0.15 mmol) of ethyl 1-{4-[(2-hydroxyethyl)amino]phenyl}-3-[2-methyl-3-(trifluoromethyl)benzyl]-2,4-dioxo-1,2,3,4-tetrahydropyrimidine-5-carboxylate from Example 41. Yield: 46 mg (65% of theory).

LC-MS (Method 3): $R_t$=1.04 min; m/z=464 (M+H)⁺.

¹H-NMR (400 MHz, DMSO-d₆): δ=2.45 (s, 3H), 3.05-3.15 (m, 2H), 3.50-3.60 (m, 2H), 4.70 (t, 1H), 5.09 (s, 2H), 5.96 (t, 1H), 6.62 (d, 2H), 7.20 (d, 2H), 7.30-7.40 (m, 2H), 7.60 (d, 1H), 8.32 (s, 1H), 12.65 (br. s, 1H).

Example 91

1-{4-[4-(Hydroxymethyl)-1H-1,2,3-triazol-1-yl]phenyl}-3-[2-methyl-3-(trifluoromethyl)benzyl]-2,4-dioxo-1,2,3,4-tetrahydropyrimidine-5-carboxylic acid

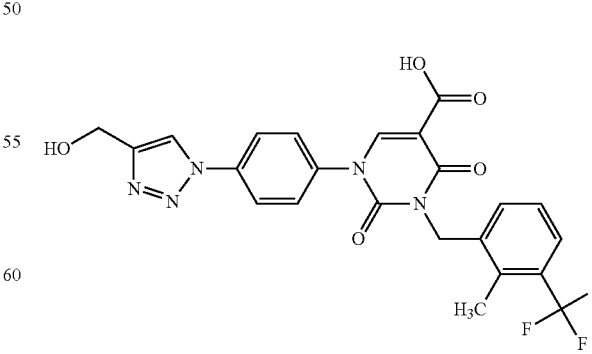

130 mg (0.29 mmol) of 1-(4-azidophenyl)-3-[2-methyl-3-(trifluoromethyl)benzyl]-2,4-dioxo-1,2,3,4-tetrahydropyrimidine-5-carboxylic acid from Example 43A and 17 mg (0.31 mmol) of prop-2-yn-1-ol were initially charged in 3 ml of a THF/water mixture (4:1), and 3.6 mg (15 µmol) of copper(II) sulfate pentahydrate and 6 mg (0.03 mmol) of (+)-sodium ascorbate were added. The mixture was then stirred at 20° C. for 24 h, diluted with a little DMF and chromatographed using preparative HPLC (Method 5b). The product-containing fractions were concentrated under reduced pressure. This gave 72 mg (49% of theory) of the title compound.

LC-MS (Method 3): $R_t$=0.99 min; m/z=502 (M+H)$^+$.

$^1$H-NMR (400 MHz, DMSO-d$_6$): δ=2.45 (s, 3H), 4.61 (d, 2H), 5.08 (s, 2H), 5.37 (t, 1H), 7.25-7.38 (m, 2H), 7.58 (d, 1H), 7.71 (d, 2H), 7.95 (s, 1H), 8.02 (d, 2H), 8.75 (s, 1H).

Example 92

3-[2-Methyl-3-(trifluoromethyl)benzyl]-2,4-dioxo-1-[4-(1H-1,2,3-triazol-1-yl)phenyl]-1,2,3,4-tetrahydropyrimidine-5-carboxylic acid

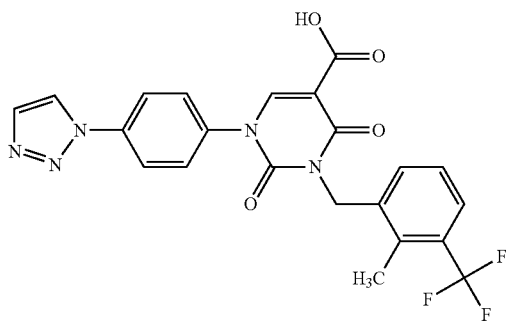 [SMILES: Cc1c(Cn2c(=O)c(C(=O)O)cn(-c3ccc(-n4ccnn4)cc3)c2=O)cccc1C(F)(F)F]

200 mg (0.45 mmol) of 1-(4-azidophenyl)-3-[2-methyl-3-(trifluoromethyl)benzyl]-2,4-dioxo-1,2,3,4-tetrahydropyrimidine-5-carboxylic acid from Example 43A and 273 mg (2.8 mmol) of trimethylsilylacetylene were initially charged in 2.5 ml of a methanol/water mixture (1:1), and 74.5 mg (0.54 mmol) of potassium carbonate, 22.4 mg (0.09 mmol) of copper(II) sulfate pentahydrate and 35.6 mg (0.18 mmol) of (+)-sodium ascorbate were added. The mixture was then stirred at 20° C. for 20 hours, another 5 equivalents of trimethylsilylacetylene were added and the mixture was stirred at 20° C. for 24 hours. After the reaction had gone to completion, 26 mg (0.54 mmol) of potassium fluoride and 2.13 g (6.74 mmol) of tetra-n-butylammonium fluoride were added and the mixture was stirred at 20° C. for 24 h. The reaction was added to water, acidified with 1 N hydrochloric acid and extracted twice with ethyl acetate. The combined organic phases were washed with water, concentrated under reduced pressure and chromatographed using preparative HPLC (Method 5b). The product-containing fractions were concentrated under reduced pressure. This gave 156 mg (70% of theory) of the title compound as a white solid.

LC-MS (Method 1): $R_t$=1.20 min; m/z=472 (M+H)$^+$.

$^1$H-NMR (400 MHz, DMSO-d$_6$): δ=2.45 (s, hidden by DMSO signal), 5.13 (s, 2H), 7.35 (t, 1H), 7.45 (d, 1H), 7.60 (d, 1H), 7.80 (d, 2H), 8.01 (s, 1H), 8.09 (d, 2H), 8.56 (s, 1H), 8.90 (s, 1H) 12.85 (br. s, 1H).

Example 93

Ethyl 1-[4-(5-amino-1,3,4-oxadiazol-2-yl)phenyl]-3-[2-chloro-3-(trifluoromethyl)benzyl]-2,4-dioxo-1,2,3,4-tetrahydropyrimidine-5-carboxylate

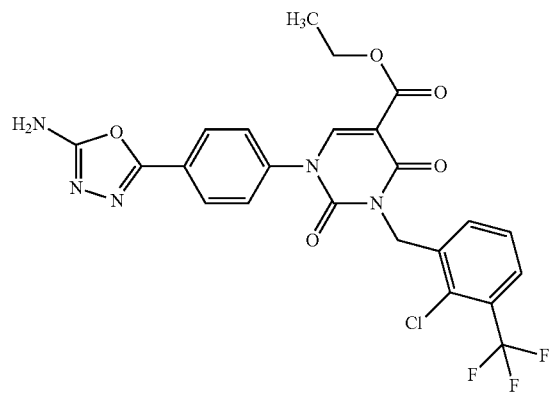 [SMILES: CCOC(=O)c1cn(-c2ccc(-c3nnc(C)o3)cc2)c(=O)n(Cc2cccc(C(F)(F)F)c2Cl)c1=O]

40 µl (120 µmol) of a solution of cyanogen bromide (3M in dichloromethane) were added to a solution of 47 mg (92 µmol) of the compound from Example 59A in 1.8 ml of methanol. The reaction mixture was stirred at 60° C. overnight and then allowed to cool to RT and concentrated on a rotary evaporator. The residue was dissolved in a little DMSO and purified by preparative HPLC (Method 8). This gave 32 mg (64% of theory) of the title compound.

LC/MS (Method 3): $R_t$=0.99 min; m/z=536 (M+H)$^+$ $^1$H-NMR (400 MHz, DMSO-d$_6$): δ [ppm]=1.24 (t, 3H), 4.21 (q, 2H), 5.15 (s, 2H), 7.35 (s, 2H), 7.52 (t, 1H), 7.62 (d, 1H), 7.71 (d, 2H), 7.80 (d, 1H), 7.94 (d, 2H), 8.55 (s, 1H).

Example 94

Ethyl 1-[4-(5-amino-1,3,4-oxadiazol-2-yl)phenyl]-3-[2-methyl-3-(trifluoromethyl)benzyl]-2,4-dioxo-1,2,3,4-tetrahydropyrimidine-5-carboxylate

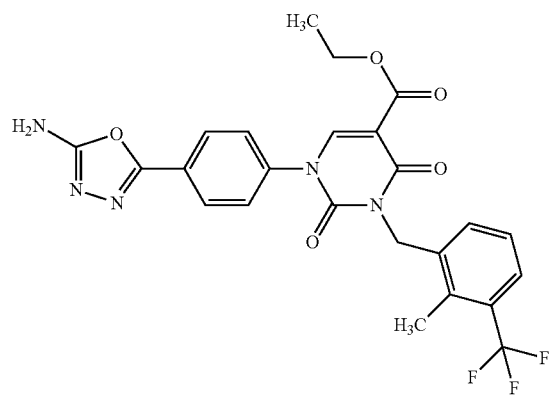 [SMILES: CCOC(=O)c1cn(-c2ccc(-c3nnc(C)o3)cc2)c(=O)n(Cc2cccc(C(F)(F)F)c2C)c1=O]

The title compound was prepared analogously to Example 93 from 57 mg (116 µmol) of the compound from Example 60A and 46 µl (139 µmol) of a solution of cyanogen bromide (3M in dichloromethane): yield 42 mg (70% of theory).

LC/MS (Method 3): $R_t$=0.98 min; m/z=516 (M+H)$^+$

¹H-NMR (400 MHz, DMSO-d₆): δ [ppm]=1.24 (t, 3H), 2.46 (s, 3H), 4.21 (q, 2H), 5.09 (s, 2H), 7.30-7.38 (m, 3H), 7.39-7.44 (m, 1H), 7.60 (d, 1H), 7.67-7.78 (m, 2H), 7.87-7.99 (m, 2H), 8.52 (s, 1H).

Example 95

Ethyl 1-[4-(5-amino-1,3,4-oxadiazol-2-yl)phenyl]-3-(2,3-dichlorobenzyl)-2,4-dioxo-1,2,3,4-tetrahydropyrimidine-5-carboxylate

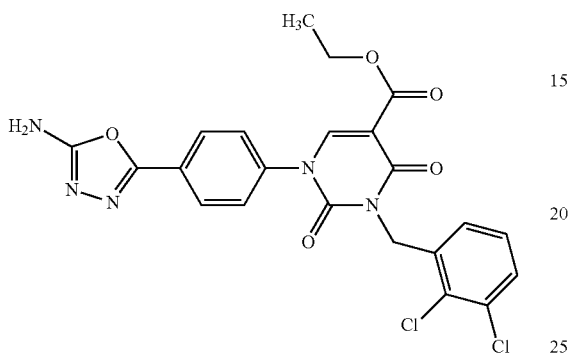

The title compound was prepared analogously to Example 93 from 44 mg (92 μmol) of the compound from Example 61A and 40 μl (120 μmol) of a solution of cyanogen bromide (3M in dichloromethane) yield 29 mg (63% of theory).

LC/MS (Method 3): R_t=0.96 min; m/z=502 (M+H)⁺
¹H-NMR (400 MHz, DMSO-d₆): δ [ppm]=1.24 (t, 3H), 4.21 (q, 2H), 5.11 (s, 2H), 7.26 (dd, 1H), 7.33 (t, 1H), 7.35 (br. s, 2H), 7.58 (dd, 1H), 7.67-7.73 (m, 2H), 7.90-7.97 (m, 2H), 8.53 (s, 1H).

Example 96

Ethyl 1-[4-(5-methyl-1,3,4-oxadiazol-2-yl)phenyl]-3-[2-chloro-3-(trifluoromethyl)benzyl]-2,4-dioxo-1,2,3,4-tetrahydropyrimidine-5-carboxylate

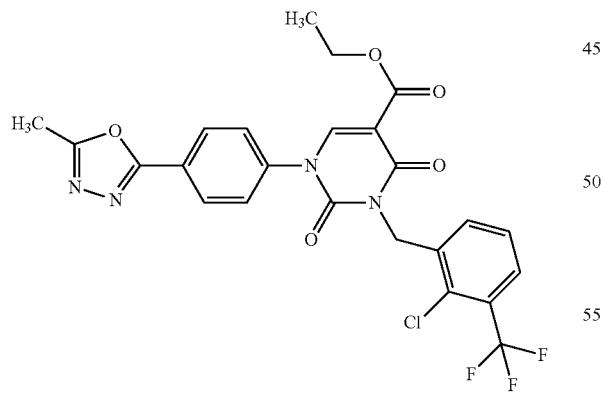

At RT, 42 μl (440 μmol) of acetic anhydride were added to a solution of 45 mg (88 μmol) of the compound from Example 59A in 1.4 ml of dichloromethane, and the mixture was stirred for 1 h. The resulting suspension was freed from the volatile constituents on a rotary evaporator. The residue was taken up in 1 ml of acetonitrile and 3 ml of chloroform, and 123 μl (880 μmol) of triethylamine, 600 μl of carbon tetrachloride and subsequently 69 mg (264 μmol) of triphenylphosphine were then added at RT. The reaction mixture was stirred at 50° C. for 2 h and then allowed to cool to RT and concentrated on a rotary evaporator. The residue was purified by preparative HPLC (Method 8). This gave 34 mg (72% of theory) of the title compound.

LC/MS (Method 1): R_f=1.32 min; m/z=535 (M+H)⁺
¹H-NMR (400 MHz, DMSO-d₆): δ [ppm]=1.24 (t, 3H), 2.61 (s, 3H), 4.22 (q, 2H), 5.16 (s, 2H), 7.52 (t, 1H), 7.63 (d, 1H), 7.75-7.84 (m, 3H), 8.11-8.17 (m, 2H), 8.57 (s, 1H).

Example 97

Ethyl 1-[4-(5-methyl-1,3,4-oxadiazol-2-yl)phenyl]-3-[2-methyl-3-(trifluoromethyl)benzyl]-2,4-dioxo-1,2,3,4-tetrahydropyrimidine-5-carboxylate

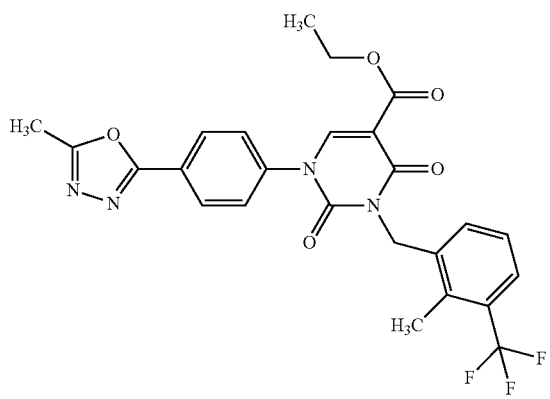

The title compound was prepared analogously to Example 96 from 38 mg (77 μmol) of the compound from Example 60A and 37 μl (387 μmol) of acetic anhydride: yield 30 mg (75% of theory).

LC/MS (Method 3): R_f=1.09 min; m/z=515 (M+H)⁺
¹H-NMR (400 MHz, DMSO-d₆): δ [ppm]=1.24 (t, 3H), 2.61 (s, 3H), 4.21 (q, 2H), 5.09 (s, 2H), 7.35 (t, 1H), 7.42 (d, 1H), 7.60 (d, 1H), 7.78 (d, 2H), 8.13 (d, 2H), 8.54 (s, 1H).

Example 98

Ethyl 3-[2-methyl-3-(trifluoromethyl)benzyl]-2,4-dioxo-1-[4-(5-oxo-4,5-dihydro-1,2,4-oxadiazol-3-yl)phenyl]-1,2,3,4-tetrahydropyrimidine-5-carboxylate

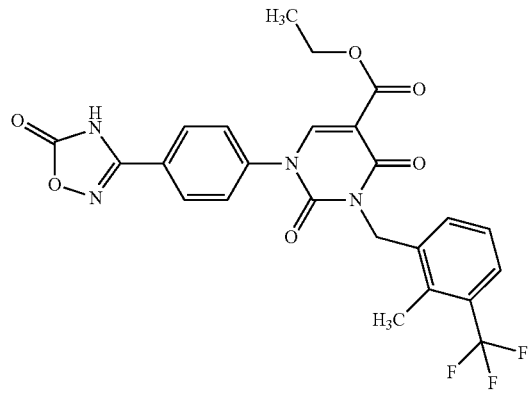 [SMILES: CCOC(=O)c1cn(-c2ccc(-c3noc(=O)[nH]3)cc2)c(=O)n(Cc2cccc(C(F)(F)F)c2C)c1=O]

Under an atmosphere of argon and at RT, first 9 μl (0.11 mmol) of pyridine and then dropwise 13 μl (0.10 mmol) of isobutyl chloroformate were added to 50 mg (0.10 mmol) of the compound from Example 63A in 2 ml of anhydrous DMF. The reaction mixture was stirred at RT for 1 h and then diluted with 30 ml of water. The resulting intermediate (ethyl 1-(4-{N'-[(3-methylbutanoyl)oxy]carbamimidoyl}phenyl)-3-[2-methyl-3-(trifluoromethyl)benzyl]-2,4-dioxo-1,2,3,4-tetrahydropyrimidine-5-carboxylate) was filtered off with suction, washed with a little water and then dried in a vacuum drying cabinet at 50° C. 2 ml of xylene and 100 µl of ionic fluid (1-n-butyl-3-methylimidazolium hexafluorophosphate) were added to the solid, and the mixture was stirred in a microwave (device: Biotage Initiator 60) at 200° C. for 1 h. The mixture was concentrated on a rotary evaporator and the residue was purified by preparative HPLC. This gave 27 mg (51% of theory) of the title compound.

LC/MS (Method 3): $R_t$=1.03 min; m/z=517 (M+H)$^+$ $^1$H-NMR (400 MHz, DMSO-d$_6$): δ [ppm]=1.24 (t, 3H), 2.46 (s, 3H), 4.21 (q, 2H), 5.09 (s, 2H), 7.34 (t, 1H), 7.38-7.44 (m, 1H), 7.60 (d, 1H), 7.77 (d, 2H), 7.96 (d, 2H), 8.54 (s, 1H), 13.10 (br. s., 1H).

Example 99

1-[4-(4-Methyl-5-oxo-4,5-dihydro-1,2,4-oxadiazol-3-yl)phenyl]-3-[2-methyl-3-(trifluoromethyl)benzyl]-2,4-dioxo-1,2,3,4-tetrahydropyrimidine-5-carboxylic acid

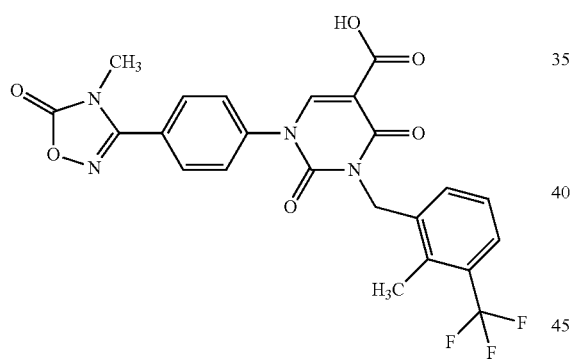

36 µl (73 µmol) of trimethylsilyldiazomethane were added to a solution of 25 mg (48 µmol) of the compound from Example 98 in 1.04 ml of THF, and the mixture was stirred at RT for 2 h. LC-MS (Method 3) showed two main products ($R_t$=1.10 min and $R_t$=1.21 min, both having m/z=531) in a ratio of 1.15:1, which were assigned to the respective N- and O-methylation products. The reaction mixture was concentrated on a rotary evaporator and the residue was directly subjected to ester hydrolysis. To this end, it was heated with 1.5 ml of conc. acetic acid and 0.75 ml of conc. hydrochloric acid at 120° C. for 2 h. After cooling to RT, the mixture was concentrated on a rotary evaporator and the residue was separated by preparative HPLC (Method 8). Two products were isolated: first to elute was the minor product (9 mg, 33% of theory), which is prepared here as Example 100, followed by the desired title compound (10 mg, 33% of theory), for which the following analytical data were measured.

LC/MS (Method 3): $R_t$=1.06 min; m/z=503 (M+H)$^+$.

$^1$H-NMR (400 MHz, DMSO-d$_6$): δ [ppm]=2.47 (s, 3H), 5.12 (s, 2H), 7.32-7.39 (m, 1H), 7.41-7.47 (m, 1H), 7.61 (d, 1H), 7.78-7.84 (m, 2H), 7.88-7.94 (m, 2H), 8.58 (s, 1H), 12.77 (s, 1H).

Example 100

3-[2-Methyl-3-(trifluoromethyl)benzyl]-2,4-dioxo-1-[4-(5-oxo-4,5-dihydro-1,2,4-oxadiazol-3-yl)phenyl]-1,2,3,4-tetrahydropyrimidine-5-carboxylic acid

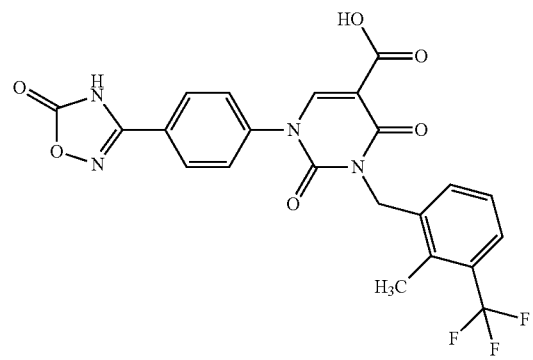 [SMILES: Cc1c(Cn2c(=O)c(C(=O)O)cn(-c3ccc(-c4noc(=O)[nH]4)cc3)c2=O)cccc1C(F)(F)F]

By-product of the preparation of Example 99.

LC/MS (Method 3): $R_t$=1.03 min; m/z=489 (M+H)$^+$ $^1$H-NMR (400 MHz, DMSO-d$_6$): δ [ppm]=2.47 (s, 3H), 5.11 (s, 2H), 7.31-7.38 (m, 1H), 7.40-7.45 (m, 1H), 7.61 (d, 1H), 7.77 (d, 2H), 7.96 (d, 2H), 8.56 (s, 1H), 12.77 (s, 1H), 13.10 (br. s., 1H).

Example 101

Ethyl 3-[(3-chloro-4-methyl-2-thienyl)methyl]-2,4-dioxo-1-[4-(2-oxo-1,3-oxazolidin-3-yl)phenyl]-1,2,3,4-tetrahydropyrimidine-5-carboxylate

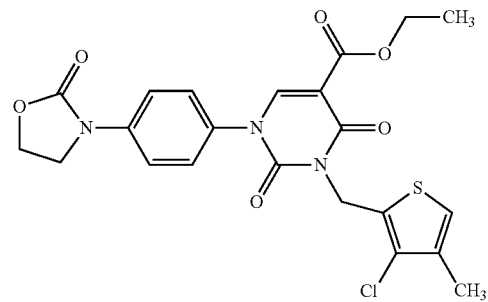 [SMILES: CCOC(=O)c1cn(-c2ccc(N3CCOC3=O)cc2)c(=O)n(Cc2scc(C)c2Cl)c1=O]

Under argon, 44 µl (0.23 mmol) of diisopropyl azodicarboxylate were added dropwise to a solution of 34 mg (0.21 mmol) of the compound from Example 23A and 74 mg (0.28 mmol) of triphenylphosphine in 2.2 ml of THF. After 5 min, 65 mg (0.19 mmol) of the compound from Example 21A were added and the mixture was stirred at RT overnight. 3 drops of 1 N aqueous hydrochloric acid were added, and the entire mixture was separated by preparative HPLC (Method 7a). This gave 21 mg (22% of theory) of the title compound.

LC/MS (Method 3): $R_t$=1.03 min; m/z=490 (M+H)$^+$

¹H-NMR (400 MHz, DMSO-d₆): δ [ppm]=1.24 (t, 3H), 2.12 (s, 3H), 4.11 (t, 2H), 4.20 (q, 2H), 4.48 (t, 2H), 5.18 (s, 2H), 7.28 (s, 1H), 7.53 (d, 3H), 7.70 (d, 3H), 8.36 (s, 1H).

Example 102

Ethyl 3-[(3-chloro-4-methyl-2-thienyl)methyl]-1-(3,4-dimethoxyphenyl)-2,4-dioxo-1,2,3,4-tetrahydropyrimidine-5-carboxylate

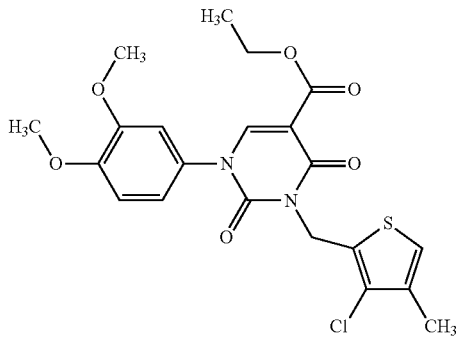

Analogously to Example 101, 36 mg (0.22 mmol) of the compound from Example 23A and 65 mg (0.20 mmol) of the compound from Example 39A gave 35 mg (35% of theory) of the title compound.

LC/MS (Method 3): R$_t$=1.09 min; m/z=465 (M+H)⁺

¹H-NMR (400 MHz, DMSO-d₆): δ [ppm]=1.24 (d, 3H), 2.12 (s, 3H), 3.76 (s, 3H), 3.81 (s, 3H), 4.20 (q, 2H), 5.18 (s, 2H), 6.97-7.09 (m, 2H), 7.16 (d, 1H), 7.28 (s, 1H), 8.32 (s, 1H).

Example 103

1-[4-(5-Amino-1,3,4-oxadiazol-2-yl)phenyl]-3-[2-chloro-3-(trifluoromethyl)benzyl]-2,4-dioxo-1,2,3,4-tetrahydropyrimidine-5-carboxylic acid

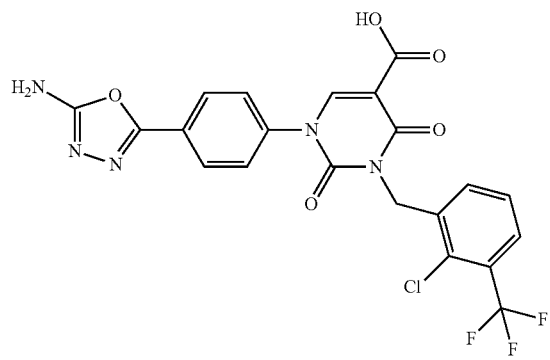

29 mg (0.054 mmol) of the compound from Example 93 with 0.5 ml of a 2:1 (v/v) mixture of conc. acetic acid and conc. hydrochloric acid were heated at 120° C. for 1 h. After cooling to RT, the mixture was diluted with 15 ml of water. The solid formed was filtered off, washed with a little water and dried under high vacuum. This gave 26 mg (90% of theory) of the title compound.

LC/MS (Method 3): R$_t$=0.92 min; m/z=508 (M+H)⁺

¹H-NMR (400 MHz, DMSO-d₆): δ [ppm]=5.17 (s, 2H), 7.35 (s, 2H), 7.52 (t, 1H), 7.64 (d, 1H), 7.70 (d, 2H), 7.81 (d, 1H), 7.93 (d, 2H), 8.56 (s, 1H), 12.76 (br. s., 1H).

Example 104

1-[4-(5-Amino-1,3,4-oxadiazol-2-yl)phenyl]-3-[2-methyl-3-(trifluoromethyl)benzyl]-2,4-dioxo-1,2,3,4-tetrahydropyrimidine-5-carboxylic acid

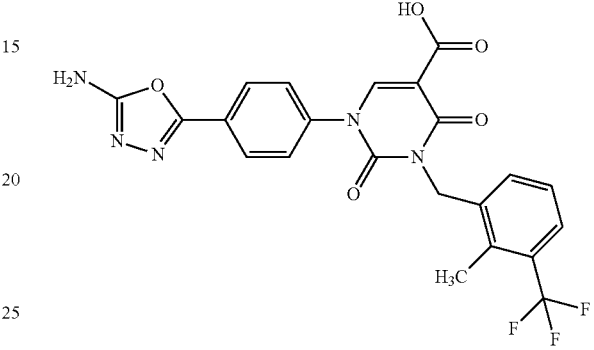

The title compound was prepared analogously to Example 103 from 42 mg (81 μmol) of the compound from Example 94: yield 28 mg (66% of theory).

LC/MS (Method 1): R$_t$=1.29 min; m/z=488 (M+H)⁺

¹H-NMR (400 MHz, DMSO-d₆): δ [ppm]=2.47 (s, 3H), 5.11 (s, 2H), 7.29-7.48 (m, 3H), 7.61 (d, 1H), 7.71 (d, 2H), 7.93 (d, 2H), 8.54 (s, 1H), 12.78 (br. s, 1H).

Example 105

1-[4-(5-Amino-1,3,4-oxadiazol-2-yl)phenyl]-3-(2,3-dichlorobenzyl)-2,4-dioxo-1,2,3,4-tetrahydropyrimidine-5-carboxylic acid

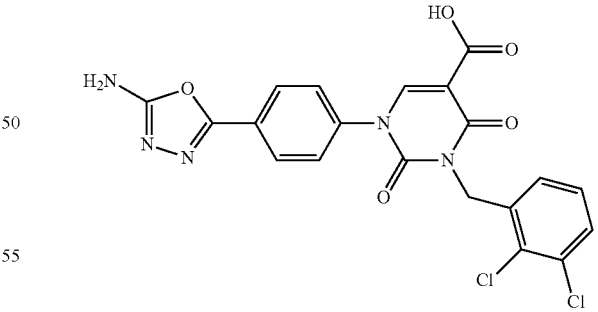

The title compound was prepared analogously to Example 103 from 26 mg (52 μmol) of the compound from Example 95: yield 24 mg (88% of theory).

LC/MS (Method 3): R$_t$=0.89 min; m/z=474 (M+H)⁺

¹H-NMR (400 MHz, DMSO-d₆): δ [ppm]=5.11 (s, 2H), 7.25-7.36 (m, 2H), 7.38 (br. s, 1H), 7.56-7.62 (m, 1H), 7.67-7.73 (m, 2H), 7.90-7.96 (m, 2H), 8.55 (s, 1H), 12.76 (br. s, 1H).

Example 106

3-[(3-Chloro-4-methyl-2-thienyl)methyl]-2,4-dioxo-1-[4-(2-oxo-1,3-oxazolidin-3-yl)phenyl]-1,2,3,4-tetrahydropyrimidine-5-carboxylic acid

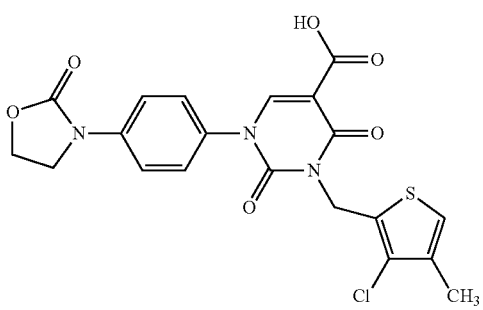 [SMILES: Cc1csc(Cn2c(=O)c(C(=O)O)cn(-c3ccc(N4CCOC4=O)cc3)c2=O)c1Cl]

The title compound was prepared analogously to Example 103 from 15 mg (31 µmol) of the compound from Example 101. For additional purification, the solid obtained was then stirred with diethyl ether, filtered off with suction and dried under high vacuum: yield 8.5 mg (58% of theory).

LC/MS (Method 3): $R_t$=1.00 min; m/z=462 (M+H)$^+$.

$^1$H-NMR (400 MHz, DMSO-d$_6$): δ [ppm]=2.12 (s, 3H), 4.00-4.20 (m, 2H), 4.40-4.55 (m, 2H), 5.20 (s, 2H), 7.29 (s, 1H), 7.53 (d, 2H), 7.70 (d, 2H), 8.37 (s, 1H), 12.74 (br. s, 1H).

Example 107

3-[(3-Chloro-4-methyl-2-thienyl)methyl]-1-(3,4-dimethoxyphenyl)-2,4-dioxo-1,2,3,4-tetrahydropyrimidine-5-carboxylic acid

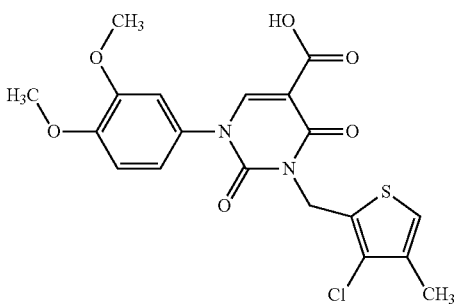

The title compound was prepared analogously to Example 103 from 30 mg (61 µmol) of the compound from Example 102. For additional purification, the solid obtained was then stirred with diethyl ether, filtered off with suction and dried under high vacuum: yield 25 mg (91% of theory).

LC/MS (Method 3): $R_t$=1.05 min; m/z=437 (M+H)$^+$ $^1$H-NMR (400 MHz, DMSO-d$_6$): δ [ppm]=2.12 (s, 3H), 3.76 (s, 3H), 3.78-3.85 (m, 3H), 5.20 (s, 2H), 6.99-7.09 (m, 2H), 7.16 (s, 1H), 7.29 (s, 1H), 8.33 (s, 1H), 12.73 (br. s, 1H).

Example 108

1-[4-(5-Methyl-1,3,4-oxadiazol-2-yl)phenyl]-3-[2-chloro-3-(trifluoromethyl)benzyl]-2,4-dioxo-1,2,3,4-tetrahydropyrimidine-5-carboxylic acid

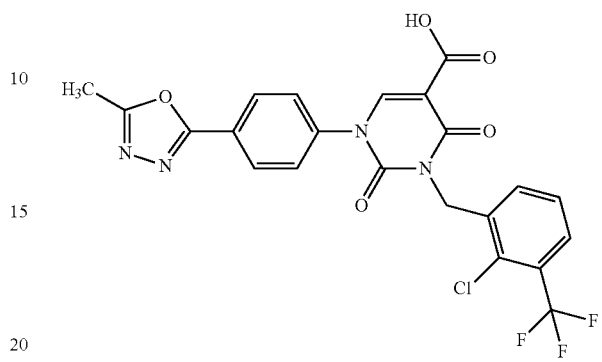

330 µl of a 0.4 N aqueous sodium bicarbonate solution were added to 32 mg (60 µmol) of the compound from Example 96 in 320 µl of acetonitrile, and the mixture was heated at reflux for 1 h. After cooling to RT, the reaction mixture was acidified with 1N aqueous hydrochloric acid and separated by preparative HPLC (Method 7a). The product-containing fraction was concentrated on a rotary evaporator and then dried under high vacuum. The residue was stirred with a little diethyl ether for 10 min, the liquid phase was decanted off and the solid was dried under high vacuum. This gave 9 mg (27% of theory) of the title compound.

LC/MS (Method 3): $R_t$=1.01 min; m/z=507 (M+H)$^+$ $^1$H-NMR (400 MHz, DMSO-d$_6$): δ [ppm]=2.61 (s, 3H), 5.18 (s, 2H), 7.50-7.56 (m, 1H), 7.64 (d, 1H), 7.74-7.84 (m, 3H), 8.13 (d, 2H), 8.58 (s, 1H), 12.77 (br. s., 1H).

Example 109

1-[4-(5-Methyl-1,3,4-oxadiazol-2-yl)phenyl]-3-[2-methyl-3-(trifluoromethyl)benzyl]-2,4-dioxo-1,2,3,4-tetrahydropyrimidine-5-carboxylic acid

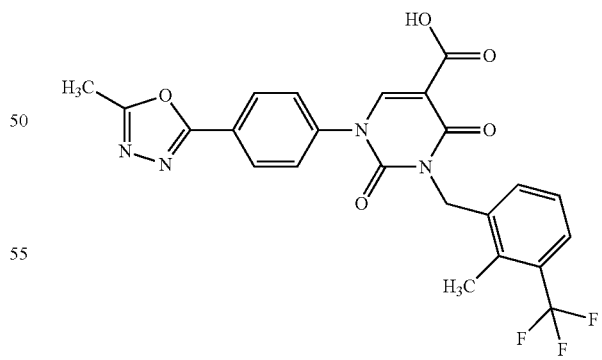

310 µl of a 0.4 N aqueous sodium bicarbonate solution were added to 29 mg (56 µmol) of the compound from Example 97 in 300 µl of acetonitrile, and the mixture was heated at reflux for 1.5 h. After cooling to RT, the reaction mixture was acidified with 1 N aqueous hydrochloric acid and separated by preparative HPLC (Method 7a). The product-containing fraction was freed from the volatile constituents on a rotary evaporator. The residue was dried under high vacuum. This gave 9 mg (33% of theory) of the title compound.

LC/MS (Method 3): $R_t$=1.05 min; m/z=487 (M+H)$^+$
$^1$H-NMR (400 MHz, DMSO-d$_6$): δ [ppm]=2.47 (s, 3H), 2.61 (s, 3H), 5.11 (s, 2H), 7.29-7.40 (m, 1H), 7.41-7.47 (m, 1H), 7.61 (d, 1H), 7.78 (d, 2H), 8.13 (d, 2H), 8.57 (s, 1H), 12.77 (s, 1H).

Example 110

Ethyl 3-[2-chloro-3-(trifluoromethyl)benzyl]-2,4-dioxo-1-[4-(2-oxo-1,3-oxazolidin-3-yl)phenyl]-1,2,3,4-tetrahydropyrimidine-5-carboxylate

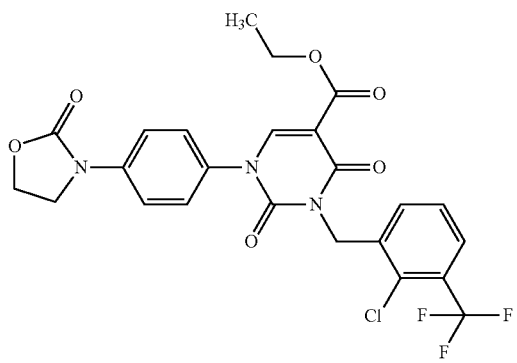 [SMILES: CCOC(=O)c1cn(-c2ccc(N3CCOC3=O)cc2)c(=O)n(Cc2cccc(C(F)(F)F)c2Cl)c1=O]

200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 21A were initially charged in 5 ml of acetonitrile. 158 mg (0.57 mmol) of 2-chloro-3-(trifluoromethyl)benzyl bromide, 160 mg (1.15 mmol) of potassium carbonate and 48 mg (0.29 mmol) of potassium iodide were added and the mixture was stirred at 60° C. for 5 h. Water was then added to the reaction mixture which had cooled to RT, and the solid formed was filtered off, washed with water and dried under reduced pressure. This gave 173 mg (53% of theory) of the title compound.

LC-MS (Method 3): $R_t$=1.09 min; m/z=538 (M+H)$^+$.
$^1$H-NMR (400 MHz, DMSO-d$_6$): δ=1.24 (t, 3H), 4.11 (t, 2H), 4.21 (q, 2H), 4.47 (t, 2H), 5.14 (s, 2H), 7.48-7.61 (m, 4H), 7.68-7.75 (m, 2H), 7.80 (d, 1H), 8.45 (s, 1H).

Example 111

Ethyl 1-{4-[(5S)-5-(acetamidomethyl)-2-oxo-1,3-oxazolidin-3-yl]phenyl}-3-[2-chloro-3-(trifluoromethyl)benzyl]-2,4-dioxo-1,2,3,4-tetrahydropyrimidine-5-carboxylate (S enantiomer)

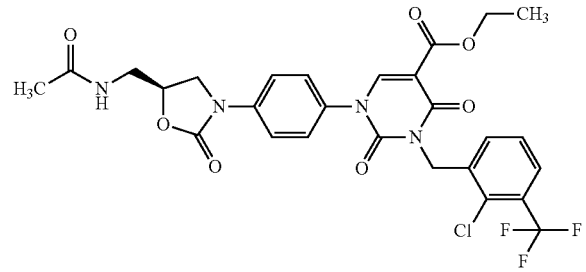 [SMILES: CCOC(=O)c1cn(-c2ccc(N3C[C@H](CNC(C)=O)OC3=O)cc2)c(=O)n(Cc2cccc(C(F)(F)F)c2Cl)c1=O]

Preparation and purification of the title compound were analogous to Example 110. Starting with 156 mg (0.37 mmol) of ethyl 1-{4-[(5S)-5-(acetamidomethyl)-2-oxo-1,3-oxazolidin-3-yl]phenyl}-2,4-dioxo-1,2,3,4-tetrahydropyrimidine-5-carboxylate (S enantiomer) from Example 87A and 102 mg (0.37 mmol) of 2-chloro-3-(trifluoromethyl)benzyl bromide, after additional purification by flash chromatography (dichloromethane/ethanol 40:1) 151 mg (66% of theory) of the title compound were obtained.

LC-MS (Method 2): $R_t$=2.17 min; m/z=609 (M+H)$^+$.
$^1$H-NMR (400 MHz, DMSO-d$_6$): δ=1.24 (t, 3H), 1.84 (s, 3H), 3.44 (t, 2H), 3.75-3.83 (m, 1H), 4.12-4.26 (m, 3H), 4.70-4.81 (m, 1H), 5.14 (s, 2H), 7.48-7.61 (m, 4H), 7.68 (d, 2H), 7.80 (d, 1H), 8.26 (t, 1H), 8.45 (s, 1H).

Example 112

Ethyl 3-[2-chloro-3-(trifluoromethyl)benzyl]-2,4-dioxo-1-[4-(2-oxoimidazolidin-1-yl)phenyl]-1,2,3,4-tetrahydropyrimidine-5-carboxylate

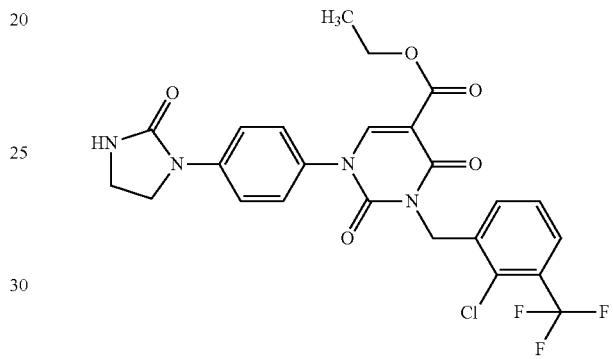

Preparation and purification of the title compound were carried out analogously to Example 110 using a reaction time of 16 h. Starting from 200 mg (0.58 mmol) of ethyl 2,4-dioxo-1-[4-(2-oxoimidazolidin-1-yl)phenyl]-1,2,3,4-tetrahydropyrimidine-5-carboxylate from Example 15A and 175 mg (0.63 mmol) of 2-chloro-3-(trifluoromethyl)benzyl bromide, 232 mg (67% of theory) of the title compound were obtained.

LC-MS (Method 3): $R_t$=1.04 min; m/z=537 (M+H)$^+$.
$^1$H-NMR (400 MHz, DMSO-d$_6$): δ=1.24 (t, 3H), 3.44 (t, 2H), 3.89 (t, 2H), 4.20 (q, 2H), 5.14 (s, 2H), 7.11 (s, 1H), 7.44-7.50 (m, 2H), 7.52 (d, 1H), 7.58 (d, 1H), 7.69 (d, 2H), 7.79 (d, 1H), 8.42 (s, 1H).

Example 113

Ethyl 1-[3-chloro-4-(2-oxo-1,3-oxazolidin-3-yl)phenyl]-3-[2-chloro-3-(trifluoromethyl)benzyl]-2,4-dioxo-1,2,3,4-tetrahydropyrimidine-5-carboxylate

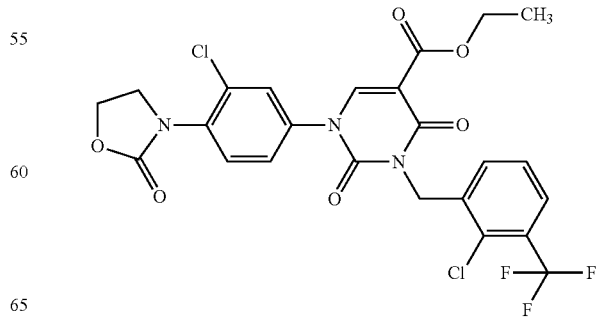

Preparation and purification of the title compound were analogous to Example 110. Starting with 165 mg (0.43 mmol) of ethyl 1-[3-chloro-4-(2-oxo-1,3-oxazolidin-3-yl)phenyl]-2,4-dioxo-1,2,3,4-tetrahydropyrimidine-5-carboxylate from Example 64A and 131 mg (0.47 mmol) of 2-chloro-3-(trifluoromethyl)benzyl bromide, 195 mg (78% of theory) of the title compound were obtained.

LC-MS (Method 1): $R_t$=1.30 min; m/z=572 (M+H)$^+$.

$^1$H-NMR (400 MHz, DMSO-$d_6$): δ=1.24 (t, 3H), 4.00 (t, 2H), 4.20 (q, 2H), 4.53 (t, 2H), 5.14 (s, 2H), 7.52 (t, 1H), 7.57-7.67 (m, 2H), 7.74 (d, 1H), 7.81 (d, 1H), 7.89 (d, 1H), 8.61 (s, 1H).

Example 114

Ethyl 1-[3-chloro-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate

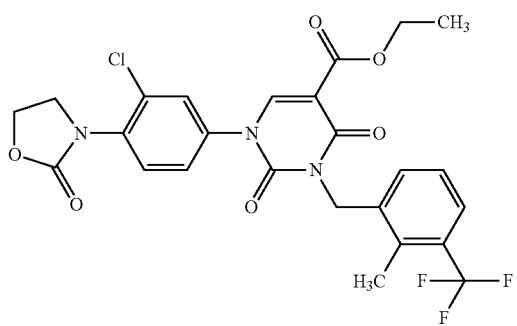 [SMILES: CCOC(=O)c1cn(-c2ccc(N3CCOC3=O)c(Cl)c2)c(=O)n(Cc2cccc(C(F)(F)F)c2C)c1=O]

Preparation and purification of the title compound were analogous to Example 110. Starting with 165 mg (0.43 mmol) of ethyl 1-[3-chloro-4-(2-oxo-1,3-oxazolidin-3-yl)phenyl]-2,4-dioxo-1,2,3,4-tetrahydropyrimidine-5-carboxylate from Example 64A and 121 mg (0.47 mmol) of 2-methyl-3-(trifluoromethyl)benzyl bromide, 162 mg (57% of theory) of the title compound were obtained.

LC-MS (Method 1): $R_t$=1.30 min; m/z=552 (M+H)$^+$.

$^1$H-NMR (400 MHz, DMSO-$d_6$): δ=1.24 (t, 3H), 2.46 (s, 3H), 4.00 (t, 2H), 4.20 (q, 2H), 4.53 (t, 2H), 5.08 (s, 2H), 7.34 (t, 1H), 7.41 (d, 1H), 7.57-7.67 (m, 2H), 7.74 (d, 1H), 7.90 (d, 1H), 8.57 (s, 1H).

Example 115

Ethyl 3-[2-chloro-3-(trifluoromethyl)benzyl]-1-[2-fluoro-4-(2-oxo-1,3-oxazolidin-3-yl)phenyl]-2,4-dioxo-1,2,3,4-tetrahydropyrimidine-5-carboxylate

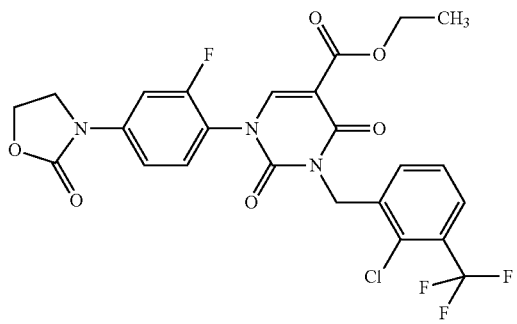 [SMILES: CCOC(=O)c1cn(-c2ccc(N3CCOC3=O)cc2F)c(=O)n(Cc2cccc(C(F)(F)F)c2Cl)c1=O]

250 mg (0.68 mmol) of ethyl 1-[2-fluoro-4-(2-oxo-1,3-oxazolidin-3-yl)phenyl]-2,4-dioxo-1,2,3,4-tetrahydropyrimidine-5-carboxylate from Example 76A were initially charged in 2.5 ml of acetonitrile, 207 mg (0.75 mmol) of 2-chloro-3-(trifluoromethyl)benzyl bromide, 190 mg (1.38 mmol) of potassium carbonate and 11 mg (0.07 mmol) of potassium iodide were then added and the mixture was stirred at 80° C. for 5 h. Water was then added to the reaction mixture which had cooled to RT, and the mixture was extracted twice with ethyl acetate. The collected organic phases were washed with water and saturated aqueous sodium chloride solution, dried over magnesium sulfate, filtered and concentrated. The residue was dried under high vacuum, giving 397 mg (104% of theory, purity 85%) of the title compound.

LC-MS (Method 3): $R_t$=1.11 min; m/z=556 (M+H)$^+$.

$^1$H-NMR (400 MHz, DMSO-$d_6$): δ=1.24 (t, 3H), 4.11 (t, 2H), 4.21 (q, 2H), 4.49 (t, 2H), 5.16 (s, 2H), 7.48-7.57 (m, 3H), 7.66-7.76 (m, 2H), 7.78-7.83 (m, 1H), 8.60 (s, 1H).

Example 116

Ethyl 3-(2,3-dichlorobenzyl)-1-[2-fluoro-4-(2-oxo-1,3-oxazolidin-3-yl)phenyl]-2,4-dioxo-1,2,3,4-tetrahydropyrimidine-5-carboxylate

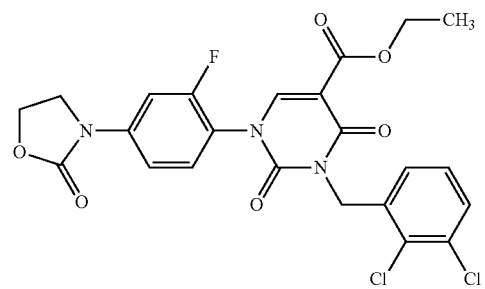 [SMILES: CCOC(=O)c1cn(-c2ccc(N3CCOC3=O)cc2F)c(=O)n(Cc2cccc(Cl)c2Cl)c1=O]

Preparation and purification of the title compound were analogous to Example 115. Starting with 250 mg (0.68 mmol) of ethyl 1-[2-fluoro-4-(2-oxo-1,3-oxazolidin-3-yl)phenyl]-2,4-dioxo-1,2,3,4-tetrahydropyrimidine-5-carboxylate from Example 76A and 182 mg (0.75 mmol) of 2,3-dichlorobenzyl bromide, 359 mg (99% of theory, purity 88%) of the title compound were obtained.

LC-MS (Method 3): $R_t$=1.09 min; m/z=522 (M+H)$^+$.

$^1$H-NMR (400 MHz, DMSO-$d_6$): δ=1.24 (t, 3H), 4.11 (t, 2H), 4.21 (q, 2H), 4.49 (t, 2H), 5.11 (s, 2H), 7.15 (d, 1H), 7.31-7.37 (m, 1H), 7.50 (dd, 1H), 7.59 (d, 1H), 7.67-7.76 (m, 2H), 8.59 (s, 1H).

Example 117

Ethyl 1-[2-fluoro-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate

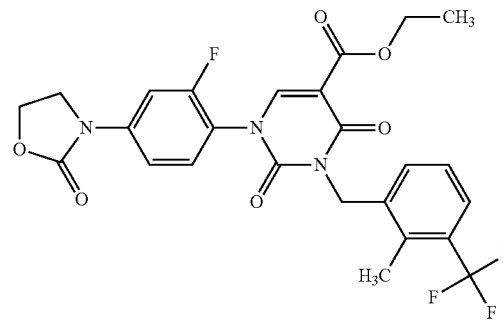

Preparation and purification of the title compound were analogous to Example 110 with a reaction time of 12 h and a reaction temperature of 80° C. Starting with 256 mg (0.70 mmol) of ethyl 1-[2-fluoro-4-(2-oxo-1,3-oxazolidin-3-yl)phenyl]-2,4-dioxo-1,2,3,4-tetrahydropyrimidine-5-carboxylate from Example 76A and 196 mg (0.77 mmol) of 2-methyl-3-(trifluoromethyl)benzyl bromide, 305 mg (78% of theory) of the title compound were obtained.

LC-MS (Method 3): $R_t$=1.11 min; m/z=536 (M+H)$^+$.

$^1$H-NMR (400 MHz, DMSO-d$_6$): δ=1.24 (t, 3H), 2.46 (s, 3H), 4.10 (t, 2H), 4.20 (q, 2H), 4.48 (t, 2H), 5.09 (s, 2H), 7.30 (d, 1H), 7.36 (t, 1H), 7.50 (dd, 1H), 7.60 (d, 1H), 7.68-7.76 (m, 2H), 8.58 (s, 1H).

Example 118

Ethyl 1-[3-methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate

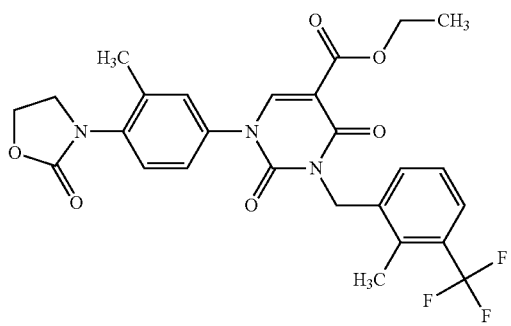 [SMILES: CCOC(=O)c1cn(-c2ccc(N3CCOC3=O)c(C)c2)c(=O)n(Cc2cccc(C(F)(F)F)c2C)c1=O]

Preparation and purification of the title compound were analogous to Example 115 at a reaction temperature of 80° C. Starting with 250 mg (0.69 mmol) of ethyl 1-[3-methyl-4-(2-oxo-1,3-oxazolidin-3-yl)phenyl]-2,4-dioxo-1,2,3,4-tetrahydropyrimidine-5-carboxylate from Example 79A and 194 mg (0.76 mmol) of 2-methyl-3-(trifluoromethyl)benzyl bromide, 349 mg (94% of theory, purity 88%) of the title compound were obtained.

LC-MS (Method 1): $R_t$=1.26 min; m/z=532 (M+H)$^+$.

$^1$H-NMR (400 MHz, DMSO-d$_6$): δ=1.24 (t, 3H), 2.28 (s, 3H), 2.46 (s, 3H), 3.98 (t, 2H), 4.19 (q, 2H), 4.50 (t, 2H), 5.08 (s, 2H), 7.31-7.41 (m, 2H), 7.42-7.47 (m, 1H), 7.49-7.54 (m, 2H), 7.60 (d, 1H), 8.47 (s, 1H).

Example 119

Ethyl 3-[2-chloro-3-(trifluoromethyl)benzyl]-1-[3-methyl-4-(2-oxo-1,3-oxazolidin-3-yl)phenyl]-2,4-dioxo-1,2,3,4-tetrahydropyrimidine-5-carboxylate

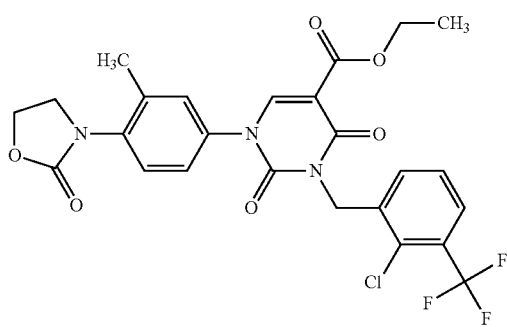 [SMILES: CCOC(=O)c1cn(-c2ccc(N3CCOC3=O)c(C)c2)c(=O)n(Cc2cccc(C(F)(F)F)c2Cl)c1=O]

Preparation and purification of the title compound were analogous to Example 115 at a reaction temperature of 80° C. Starting with 250 mg (0.69 mmol) of ethyl 1-[3-methyl-4-(2-oxo-1,3-oxazolidin-3-yl)phenyl]-2,4-dioxo-1,2,3,4-tetrahydropyrimidine-5-carboxylate from Example 79A and 209 mg (0.76 mmol) of 2-chloro-3-(trifluoromethyl)benzyl bromide, 375 mg (97% of theory, purity 87%) of the title compound were obtained.

LC-MS (Method 1): $R_t$=1.26 min; m/z=552 (M+H)$^+$.

$^1$H-NMR (400 MHz, DMSO-d$_6$): δ=1.24 (t, 3H), 2.28 (s, 3H), 3.98 (t, 2H), 4.20 (q, 2H), 4.50 (t, 2H), 5.15 (s, 2H), 7.43-7.47 (m, 1H), 7.49-7.55 (m, 3H), 7.59 (d, 1H), 7.80 (d, 1H), 8.50 (s, 1H).

Example 120

Ethyl 3-[2-chloro-3-(trifluoromethyl)benzyl]-1-[3,5-dichloro-4-(2-oxo-1,3-oxazolidin-3-yl)phenyl]-2,4-dioxo-1,2,3,4-tetrahydropyrimidine-5-carboxylate

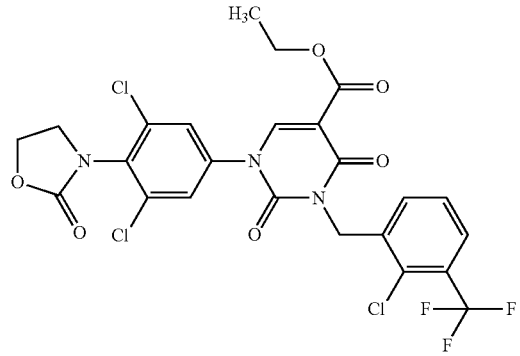 [SMILES: CCOC(=O)c1cn(-c2cc(Cl)c(N3CCOC3=O)c(Cl)c2)c(=O)n(Cc2cccc(C(F)(F)F)c2Cl)c1=O]

200 mg (0.48 mmol) of ethyl 1-[3,5-dichloro-4-(2-oxo-1,3-oxazolidin-3-yl)phenyl]-2,4-dioxo-1,2,3,4-tetrahydropyrimidine-5-carboxylate from Example 86A were initially charged in 6 ml of DMF, 145 mg (0.53 mmol) of 2-chloro-3-(trifluoromethyl)benzyl bromide, 133 mg (0.96 mmol) of potassium carbonate and 8 mg (0.04 mmol) of potassium iodide were then added and the mixture was stirred at 60° C. for 5 h. Water was then added to the reaction mixture which had cooled to RT, and the solid formed was filtered off, washed with water and MTBE and dried under reduced pressure. This gave 194 mg (66% of theory) of the title compound.

LC-MS (Method 3): $R_t$=1.25 min; m/z=606 (M+H)$^+$.

$^1$H-NMR (400 MHz, DMSO-d$_6$): δ=1.25 (t, 3H), 3.93 (t, 2H), 4.21 (q, 2H), 4.62 (t, 2H), 5.15 (s, 2H), 7.52 (t, 1H), 7.59 (d, 1H), 7.81 (d, 1H), 7.95 (s, 2H), 8.70 (s, 1H).

Example 121

Ethyl 1-[3-chloro-4-(2-oxoimidazolidin-1-yl)phenyl]-3-[2-chloro-3-(trifluoromethyl)benzyl]-2,4-dioxo-1,2,3,4-tetrahydropyrimidine-5-carboxylate

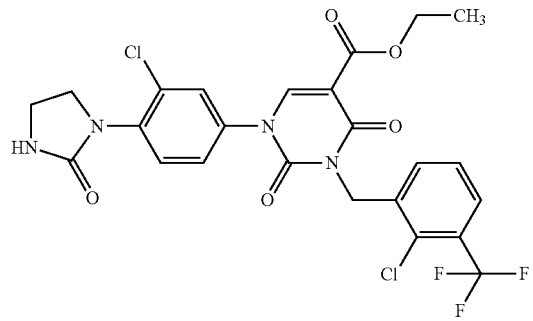 [SMILES: CCOC(=O)c1cn(-c2ccc(N3CCNC3=O)c(Cl)c2)c(=O)n(Cc2cccc(C(F)(F)F)c2Cl)c1=O]

Preparation and purification of the title compound were analogous to Example 120. Starting with 116 mg (0.30 mmol) of ethyl 1-[3-chloro-4-(2-oxoimidazolidin-1-yl)phenyl]-2,4-dioxo-1,2,3,4-tetrahydropyrimidine-5-carboxylate from Example 68A and 92 mg (0.33 mmol) of 2-chloro-3-(trifluoromethyl)benzyl bromide, after additional purification by flash chromatography (cyclohexane/ethyl acetate 98:1→4:1) 98 mg (56% of theory) of the title compound were obtained.

LC-MS (Method 3): $R_t$=1.05 min; m/z=571 (M+H)$^+$.
$^1$H-NMR (400 MHz, DMSO-d$_6$): δ=1.24 (t, 3H), 3.47 (t, 2H), 3.81 (t, 2H), 4.20 (q, 2H), 5.14 (s, 2H), 6.95 (s, 1H), 7.49-7.62 (m, 4H), 7.77-7.83 (m, 2H), 8.56 (s, 1H).

Example 122

Ethyl 1-[3-chloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate

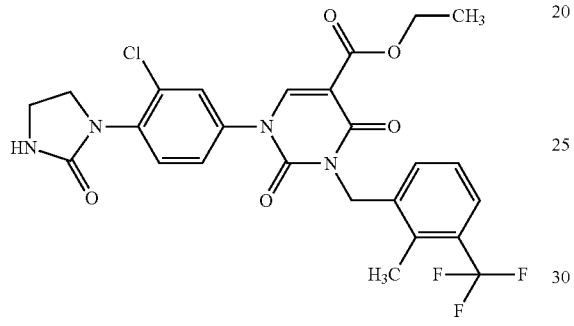

Preparation and purification of the title compound were analogous to Example 120. Starting with 116 mg (0.30 mmol) of ethyl 1-[3-chloro-4-(2-oxoimidazolidin-1-yl)phenyl]-2,4-dioxo-1,2,3,4-tetrahydropyrimidine-5-carboxylate from Example 68A and 85 mg (0.33 mmol) of 2-methyl-3-(trifluoromethyl)benzyl bromide, after additional purification by preparative HPLC (Method 5a) and flash chromatography (cyclohexane/ethyl acetate 98:2→4:1) 87 mg (51% of theory) of the title compound were obtained.

LC-MS (Method 3): $R_t$=1.05 min; m/z=551 (M+H)$^+$.
$^1$H-NMR (400 MHz, DMSO-d$_6$): δ=1.24 (t, 3H), 2.46 (s, 3H), 3.46 (t, 2H), 3.81 (t, 2H), 4.20 (q, 2H), 5.07 (s, 2H), 6.95 (s, 1H), 7.34 (t, 1H), 7.41 (d, 1H), 7.53-7.63 (m, 3H), 7.79-7.84 (m, 1H), 8.52 (s, 1H).

Example 123

Ethyl 1-[2-methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate

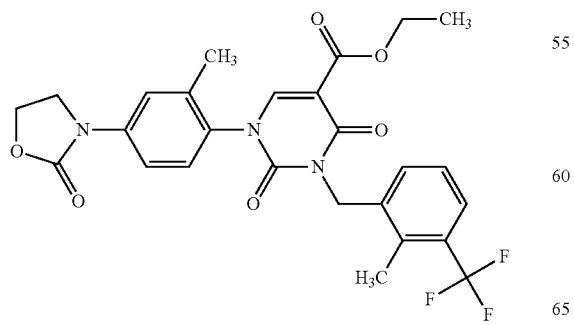

Preparation and purification of the title compound were analogous to Example 110 with a reaction time of 8 h and a reaction temperature of 80° C. Starting with 250 mg (0.69 mmol) of ethyl 1-[2-methyl-4-(2-oxo-1,3-oxazolidin-3-yl)phenyl]-2,4-dioxo-1,2,3,4-tetrahydropyrimidine-5-carboxylate from Example 83A and 194 mg (0.76 mmol) of 2-methyl-3-(trifluoromethyl)benzyl bromide, 338 mg (84% of theory, purity 93%) of the title compound were obtained.

LC-MS (Method 3): $R_t$=1.20 min; m/z=532 (M+H)$^+$.
$^1$H-NMR (400 MHz, DMSO-d$_6$): δ=1.23 (t, 3H), 2.16 (s, 3H), 2.45 (s, 3H), 4.09 (t, 2H), 4.19 (q, 2H), 4.46 (t, 2H), 5.02-5.16 (m, 2H), 7.28-7.39 (m, 2H), 7.49-7.53 (m, 1H), 7.54-7.63 (m, 3H), 8.40 (s, 1H).

Example 124

Ethyl 2-[2-chloro-3-(trifluoromethyl)benzyl]-1-[3-methyl-4-(2-oxo-1,3-oxazolidin-3-yl)phenyl]-2,4-dioxo-1,2,3,4-tetrahydropyrimidine-5-carboxylate

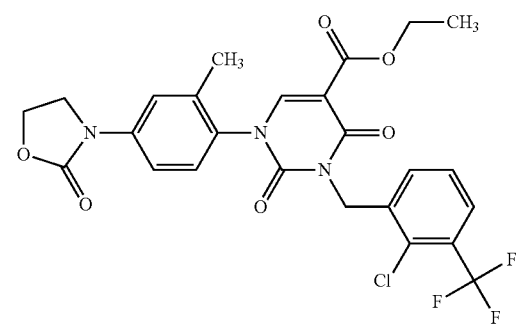 [SMILES: CCOC(=O)c1cn(-c2ccc(N3CCOC3=O)cc2C)c(=O)n(Cc2cccc(C(F)(F)F)c2Cl)c1=O]

Preparation and purification of the title compound were analogous to Example 110 with a reaction time of 8 h and a reaction temperature of 80° C. Starting with 250 mg (0.69 mmol) of ethyl 1-[2-methyl-4-(2-oxo-1,3-oxazolidin-3-yl)phenyl]-2,4-dioxo-1,2,3,4-tetrahydropyrimidine-5-carboxylate from Example 83A and 209 mg (0.76 mmol) of 2-chloro-3-(trifluoromethyl)benzyl bromide, 331 mg (86% of theory, purity 86%) of the title compound were obtained.

LC-MS (Method 3): $R_t$=1.20 min; m/z=552 (M+H)$^+$.
$^1$H-NMR (400 MHz, DMSO-d$_6$): δ=1.24 (t, 3H), 2.18 (br. s., 3H), 4.09 (br. t, 2H), 4.20 (q, 2H), 4.46 (br. t, 2H), 5.15 (br. s., 2H), 7.46-7.61 (m, 5H), 7.76-7.84 (m, 1H), 8.42 (s, 1H).

Example 125

Ethyl 3-[3-(difluoromethyl)-2-methylbenzyl]-1-(3,4-dimethoxyphenyl)-2,4-dioxo-1,2,3,4-tetrahydropyrimidine-5-carboxylate

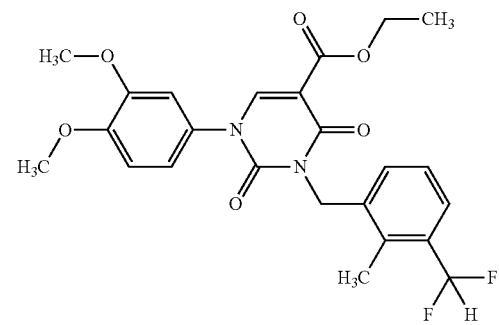 [SMILES: CCOC(=O)c1cn(-c2ccc(OC)c(OC)c2)c(=O)n(Cc2cccc(C(F)F)c2C)c1=O]

200 mg (0.59 mmol) of ethyl 3-[3-(difluoromethyl)-2-methylbenzyl]-2,4-dioxo-1,2,3,4-tetrahydropyrimidine-5-carboxylate from Example 107A, 215 mg (1.18 mmol) of 3,4-dimethoxyphenylboronic acid and 0.14 ml (1.77 mmol) of pyridine were initially charged in 4.8 ml of dichloromethane 527 mg of molecular sieve 3 Å and 161 mg (0.88 mmol) of copper(II) acetate were then added, and at RT the mixture was stirred open exposed to the air for 16 h. The reaction mixture was then diluted with ethyl acetate and washed twice with 1 N aqueous hydrochloric acid and in each case once with saturated aqueous sodium bicarbonate solution and saturated aqueous sodium chloride solution. The organic phase was dried over magnesium sulfate, filtered and concentrated. The residue was stirred in MTBE and the solid formed was filtered off and dried under reduced pressure. This gave 151 mg (53% of theory, purity 80%) of the title compound.

LC-MS (Method 3): $R_t$=1.02 min; m/z=475 $(M+H)^+$.

$^1$H-NMR (400 MHz, DMSO-$d_6$): δ=1.23 (t, 3H), 2.40 (s, 3H), 3.76 (s, 3H), 3.80 (s, 3H), 4.19 (q, 2H), 5.05 (s, 2H), 7.03-7.12 (m, 2H), 7.17-7.31 (m, 4H), 7.44 (d, 1H), 8.37 (s, 1H).

Example 126

Ethyl 3-(2,3-dihydro-1H-inden-1-yl)-1-(3,4-dimethoxyphenyl)-2,4-dioxo-1,2,3,4-tetrahydropyrimidine-5-carboxylate (racemate)

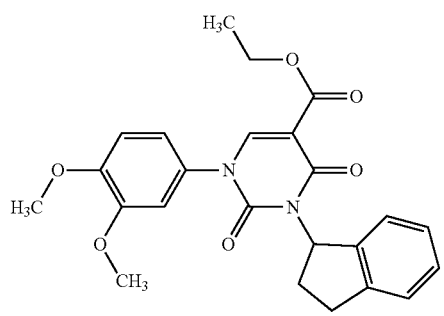 [SMILES: CCOC(=O)c1cn(-c2ccc(OC)c(OC)c2)c(=O)n(C2CCc3ccccc32)c1=O]

Preparation and purification of the title compound were analogous to Example 125. Proceeding from 193 mg (0.64 mmol) of ethyl 3-(2,3-dihydro-1H-inden-1-yl)-2,4-dioxo-1,2,3,4-tetrahydropyrimidine-5-carboxylate from Example 109A and 234 mg (1.28 mmol) of 3,4-dimethoxyphenylboronic acid, 151 mg (53% of theory) of the title compound were obtained.

LC-MS (Method 1): $R_t$=1.22 min; m/z=437 $(M+H)^+$.

$^1$H-NMR (400 MHz, DMSO-$d_6$): δ=1.21 (t, 3H), 2.31-2.43 (m, 2H), 2.86-2.98 (m, 1H), 3.10-3.20 (m, 1H), 3.75 (s, 3H), 3.79 (s, 3H), 4.17 (q, 2H), 6.32-6.48 (m, 1H), 6.99-7.07 (m, 2H), 7.09-7.19 (m, 4H), 7.20-7.25 (m, 1H), 8.27 (s, 1H).

Example 127

Ethyl 3-[2-chloro-3-(trifluoromethyl)benzyl]-1-[3,5-dichloro-4-(2-oxoimidazolidin-1-yl)phenyl]-2,4-dioxo-1,2,3,4-tetrahydropyrimidine-5-carboxylate

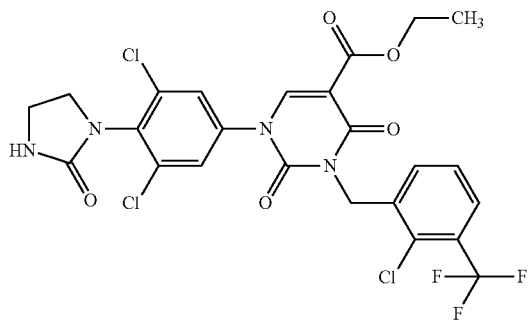 [SMILES: CCOC(=O)c1cn(-c2cc(Cl)c(N3CCNC3=O)c(Cl)c2)c(=O)n(Cc2cccc(C(F)(F)F)c2Cl)c1=O]

Preparation and purification of the title compound were analogous to Example 120. Starting with 200 mg (0.48 mmol) of ethyl 1-[3,5-dichloro-4-(2-oxoimidazolidin-1-yl)phenyl]-2,4-dioxo-1,2,3,4-tetrahydropyrimidine-5-carboxylate from Example 72A and 146 mg (0.53 mmol) of 2-chloro-3-(trifluoromethyl)benzyl bromide, 144 mg (49% of theory) of the title compound were obtained.

LC-MS (Method 3): $R_t$=1.06 min; m/z=605 $(M+H)^+$.

$^1$H-NMR (400 MHz, DMSO-$d_6$): δ=1.24 (t, 3H), 3.53 (t, 2H), 3.72 (t, 2H), 4.20 (q, 2H), 5.14 (s, 2H), 6.91 (s, 1H), 7.52 (t, 1H), 7.60 (d, 1H), 7.80 (d, 1H), 7.87 (s, 2H), 8.66 (s, 1H).

Example 128

Ethyl 1-[3,5-dichloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate

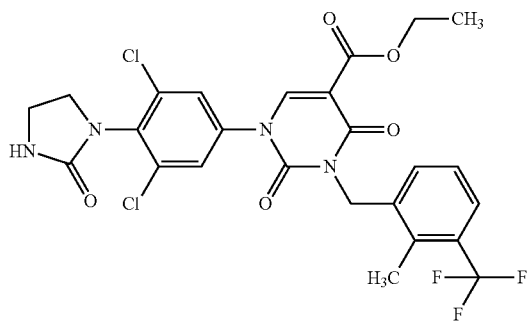 [SMILES: CCOC(=O)c1cn(-c2cc(Cl)c(N3CCNC3=O)c(Cl)c2)c(=O)n(Cc2cccc(C(F)(F)F)c2C)c1=O]

Preparation and purification of the title compound were analogous to Example 120. Starting with 200 mg (0.48 mmol) of ethyl 1-[3,5-dichloro-4-(2-oxoimidazolidin-1-yl)phenyl]-2,4-dioxo-1,2,3,4-tetrahydropyrimidine-5-carboxylate from Example 72A and 135 mg (0.53 mmol) of 2-methyl-3-(trifluoromethyl)benzyl bromide, 145 mg (51% of theory) of the title compound were obtained.

LC-MS (Method 3): $R_t$=1.06 min; m/z=585 $(M+H)^+$.

¹H-NMR (400 MHz, DMSO-d₆): δ=1.24 (t, 3H), 2.46 (s, 3H), 3.53 (t, 2H), 3.72 (t, 2H), 4.20 (q, 2H), 5.07 (s, 2H), 6.91 (s, 1H), 7.34 (t, 1H), 7.40 (d, 1H), 7.60 (d, 1H), 7.89 (s, 2H), 8.62 (s, 1H).

Example 129

Ethyl 3-[2-methyl-3-(trifluoromethyl)benzyl]-2,4-dioxo-1-{4-[(2-oxo-1,3-oxazolidin-3-yl)methyl]phenyl}-1,2,3,4-tetrahydropyrimidine-5-carboxylate

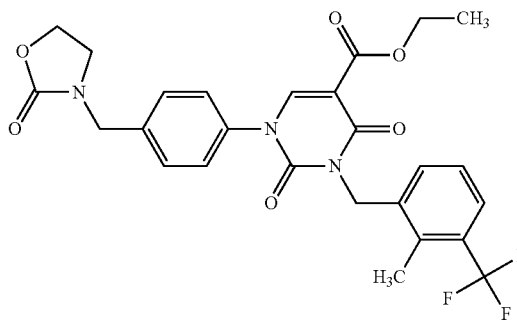

Preparation and purification of the title compound were analogous to Example 110 with a reaction time of 16 h and a reaction temperature of 80° C. Starting with 200 mg (0.55 mmol) of ethyl 2,4-dioxo-1-{4-[(2-oxo-1,3-oxazolidin-3-yl)methyl]phenyl}-1,2,3,4-tetrahydropyrimidine-5-carboxylate from Example 98A and 155 mg (0.61 mmol) of 2-methyl-3-(trifluoromethyl)benzyl bromide, 266 mg (89% of theory) of the title compound were obtained.

LC-MS (Method 3): $R_t$=1.06 min; m/z=532 (M+H)⁺.
¹H-NMR (400 MHz, DMSO-d₆): δ=1.24 (t, 3H), 2.46 (s, 3H), 3.48 (t, 2H), 4.19 (q, 2H), 4.29 (t, 2H), 4.42 (s, 2H), 5.08 (s, 2H), 7.30-7.41 (m, 2H), 7.42-7.47 (m, 2H), 7.52-7.57 (m, 2H), 7.60 (d, 1H), 8.43 (s, 1H).

Example 130

Ethyl 3-[2-chloro-3-(trifluoromethyl)benzyl]-1-[4-(3-methyl-2-oxoimidazolidin-1-yl)phenyl]-2,4-dioxo-1,2,3,4-tetrahydropyrimidine-5-carboxylate

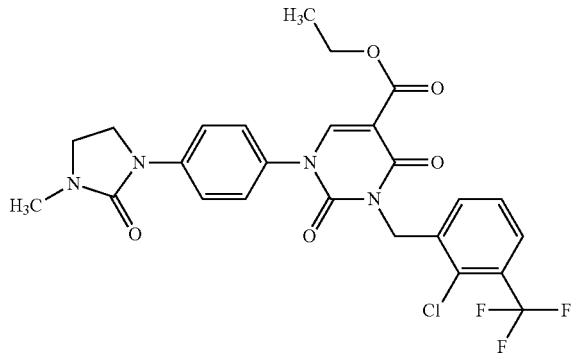 [SMILES: CCOC(=O)c1cn(-c2ccc(N3CCN(C)C3=O)cc2)c(=O)n(Cc2cccc(C(F)(F)F)c2Cl)c1=O]

Preparation and purification of the title compound were analogous to Example 120. Starting with 200 mg (0.55 mmol) of ethyl 1-[4-(3-methyl-2-oxoimidazolidin-1-yl)phenyl]-2,4-dioxo-1,2,3,4-tetrahydropyrimidine-5-carboxylate from Example 92A and 168 mg (0.61 mmol) of 2-chloro-3-(trifluoromethyl)benzyl bromide, 159 mg (51% of theory) of the title compound were obtained.

LC-MS (Method 3): $R_t$=1.07 min; m/z=551 (M+H)⁺.
¹H-NMR (400 MHz, DMSO-d₆): δ=1.24 (t, 3H), 2.79 (s, 3H), 3.47 (t, 2H), 3.83 (t, 2H), 4.20 (q, 2H), 5.14 (s, 2H), 7.48 (d, 2H), 7.53 (d, 1H), 7.58 (d, 1H), 7.70 (d, 2H), 7.80 (d, 1H), 8.43 (s, 1H).

Example 131

Ethyl 3-[2-methyl-3-(trifluoromethyl)benzyl]-2,4-dioxo-1-{4-[2-(2-oxo-1,3-oxazolidin-3-yl)ethyl]phenyl}-1,2,3,4-tetrahydropyrimidine-5-carboxylate

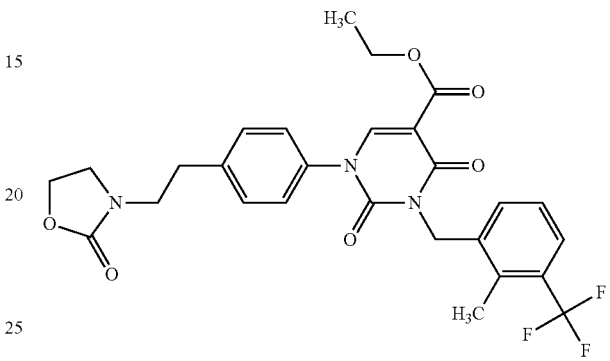

Preparation of the title compound was analogous to Example 110 with a reaction time of 2.5 h and a reaction temperature of 80° C. using 200 mg (0.53 mmol) of ethyl 2,4-dioxo-1-{4-[2-(2-oxo-1,3-oxazolidin-3-yl)ethyl]phenyl}-1,2,3,4-tetrahydropyrimidine-5-carboxylate from Example 97A and 149 mg (0.58 mmol) of 2-methyl-3-(trifluoromethyl)benzyl bromide. For work-up, water was added and the reaction mixture was extracted twice with ethyl acetate. The combined organic phases were dried over magnesium sulfate, filtered and concentrated. The residue was stirred in MTBE and the solid formed was filtered off and dried under reduced pressure. This gave 195 mg (65% of theory) of the title compound.

LC-MS (Method 3): $R_t$=1.04 min; m/z=546 (M+H)⁺.
¹H-NMR (400 MHz, DMSO-d₆): δ=1.23 (t, 3H), 2.46 (s, 3H), 2.88 (t, 2H), 3.43 (t, 2H), 3.53 (t, 2H), 4.16-4.26 (m, 4H), 5.07 (s, 2H), 7.31-7.39 (m, 2H), 7.40-7.44 (m, 2H), 7.46-7.51 (m, 2H), 7.60 (d, 1H), 8.41 (s, 1H).

Example 132

Ethyl 3-[2-chloro-3-(trifluoromethyl)benzyl]-1-[4-(4-methyl-2-oxoimidazolidin-1-yl)phenyl]-2,4-dioxo-1,2,3,4-tetrahydropyrimidine-5-carboxylate (racemate)

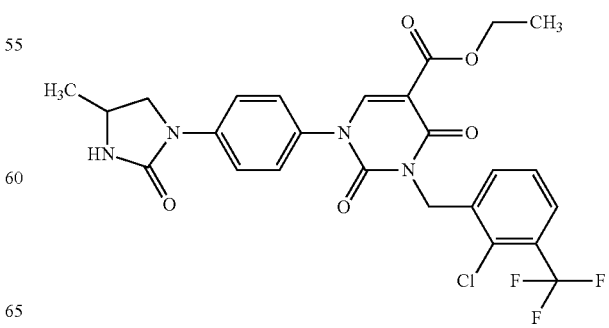

Preparation and purification of the title compound were analogous to Example 120. Starting with 200 mg (0.55 mmol) of ethyl 1-[4-(4-methyl-2-oxoimidazolidin-1-yl)phenyl]-2,4-dioxo-1,2,3,4-tetrahydropyrimidine-5-carboxylate from Example 96A and 168 mg (0.61 mmol) of 2-chloro-3-(trifluoromethyl)benzyl bromide, 251 mg (80% of theory) of the title compound were obtained.

LC-MS (Method 1): $R_t$=1.27 min; m/z=551 (M+H)$^+$.

$^1$H-NMR (400 MHz, DMSO-d$_6$): δ=1.18-1.27 (m, 6H), 3.42 (q, 1H), 3.78-3.88 (m, 1H), 4.00 (t, 1H), 4.20 (q, 2H), 5.14 (s, 2H), 7.27 (s, 1H), 7.43-7.48 (m, 2H), 7.52 (t, 1H), 7.58 (d, 1H), 7.64-7.71 (m, 2H), 7.80 (d, 1H), 8.41 (s, 1H).

Example 133

Ethyl 1-[4-(4,4-dimethyl-2-oxoimidazolidin-1-yl)phenyl]-3-[3-fluoro-2-(trifluoromethyl)benzyl]-2,4-dioxo-1,2,3,4-tetrahydropyrimidine-5-carboxylate

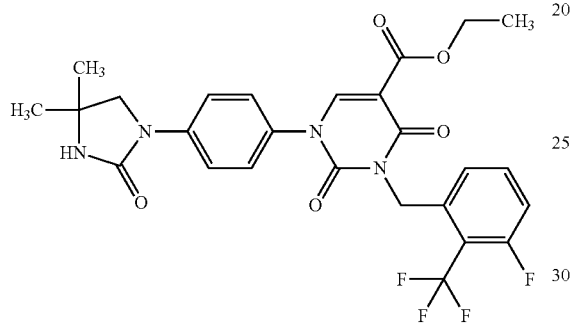

Preparation and purification of the title compound were analogous to Example 120. Starting with 200 mg (0.55 mmol) of ethyl 1-[4-(4,4-dimethyl-2-oxoimidazolidin-1-yl)phenyl]-2,4-dioxo-1,2,3,4-tetrahydropyrimidine-5-carboxylate from Example 91A and 152 mg (0.59 mmol) of 3-fluoro-2-trifluorobenzyl bromide, 230 mg (76% of theory) of the title compound were obtained.

LC-MS (Method 3): $R_t$=1.07 min; m/z=549 (M+H)$^+$.

$^1$H-NMR (400 MHz, DMSO-d$_6$): δ=1.23 (t, 3H), 1.29 (s, 6H), 3.62 (s, 2H), 4.20 (q, 2H), 5.19 (s, 2H), 7.19 (d, 1H), 7.31 (s, 1H), 7.37-7.48 (m, 3H), 7.61-7.70 (m, 3H), 8.41 (s, 1H).

Example 134

Ethyl 1-{4-[(methoxycarbonyl)(methyl)amino]phenyl}-3-[2-methyl-3-(trifluoromethyl)benzyl]-2,4-dioxo-1,2,3,4-tetrahydropyrimidine-5-carboxylate

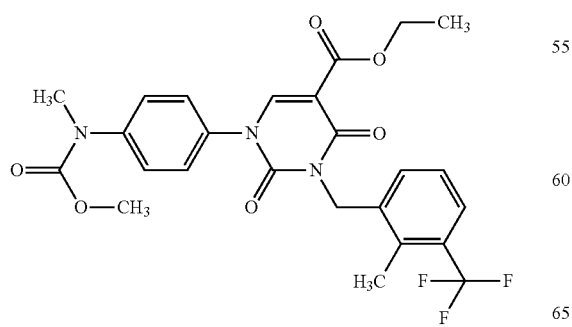

Preparation and purification of the title compound were analogous to Example 120. Starting with 200 mg (0.57 mmol) of ethyl 1-{4-[(methoxycarbonyl)(methyl)amino]phenyl}-2,4-dioxo-1,2,3,4-tetrahydropyrimidine-5-carboxylate from Example 101A and 160 mg (0.63 mmol) of 2-methyl-3-(trifluoromethyl)benzyl bromide, 224 mg (74% of theory) of the title compound were obtained.

LC-MS (Method 3): $R_t$=1.14 min; m/z=520 (M+H)$^+$.

$^1$H-NMR (400 MHz, DMSO-d$_6$): δ=1.24 (t, 3H), 2.46 (s, 3H), 3.26 (s, 3H), 3.64 (s, 3H), 4.20 (q, 2H), 5.08 (s, 2H), 7.31-7.41 (m, 2H), 7.45-7.51 (m, 2H), 7.52-7.57 (m, 2H), 7.60 (d, 1H), 8.46 (s, 1H).

Example 135

Ethyl 3-(3-chloro-2-methylbenzyl)-1-(3,4-dimethoxyphenyl)-2,4-dioxo-1,2,3,4-tetrahydropyrimidine-5-carboxylate

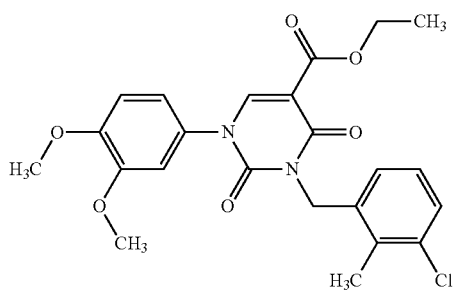 [SMILES: CCOC(=O)c1cn(-c2ccc(OC)c(OC)c2)c(=O)n(Cc2cccc(Cl)c2C)c1=O]

Preparation and purification of the title compound were analogous to Example 125. Starting with 200 mg (0.62 mmol) of ethyl 3-(3-chloro-2-methylbenzyl)-2,4-dioxo-1,2,3,4-tetrahydropyrimidine-5-carboxylate from Example 111A and 226 mg (1.23 mmol) of 3,4-dimethoxyphenylboronic acid, 205 mg (53% of theory, purity 90%) of the title compound were obtained.

LC-MS (Method 3): $R_t$=1.11 min; m/z=459 (M+H)$^+$.

$^1$H-NMR (400 MHz, DMSO-d$_6$): δ=1.23 (t, 3H), 2.41 (s, 3H), 3.76 (s, 3H), 3.80 (s, 3H), 4.19 (q, 2H), 5.04 (s, 2H), 7.04 (d, 1H), 7.07 (s, 2H), 7.15 (t, 1H), 7.21 (s, 1H), 7.32-7.36 (m, 1H), 8.37 (s, 1H).

Example 136

Ethyl 1-(3,4-dimethoxyphenyl)-3-(3-fluoro-2-methylbenzyl)-2,4-dioxo-1,2,3,4-tetrahydropyrimidine-5-carboxylate

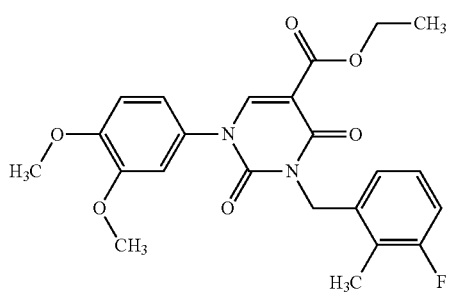 [SMILES: CCOC(=O)c1cn(-c2ccc(OC)c(OC)c2)c(=O)n(Cc2cccc(F)c2C)c1=O]

Preparation and purification of the title compound were analogous to Example 125. Starting with 200 mg (0.65 mmol) of ethyl 3-(3-fluoro-2-methylbenzyl)-2,4-dioxo-1,2,3,4-tetrahydropyrimidine-5-carboxylate from Example 113A and 345 mg (1.30 mmol) of 3,4-dimethoxyphenylboronic acid, 141 mg (48% of theory, purity 90%) of the title compound were obtained.

LC-MS (Method 1): $R_t$=1.29 min; m/z=443 (M+H)$^+$.

$^1$H-NMR (400 MHz, DMSO-d$_6$): δ=1.23 (t, 3H), 2.27 (s, 3H), 3.76 (s, 3H), 3.80 (s, 3H), 4.18 (q, 2H), 5.02 (s, 2H), 6.91 (d, 1H), 7.01-7.10 (m, 3H), 7.12-7.18 (m, 1H), 7.21 (s, 1H), 8.36 (s, 1H).

Example 137

Ethyl 1-(3,4-dimethoxyphenyl)-2,4-dioxo-3-{1-[3-(trifluoromethyl)phenyl]propyl}-1,2,3,4-tetrahydropyrimidine-5-carboxylate (racemate)

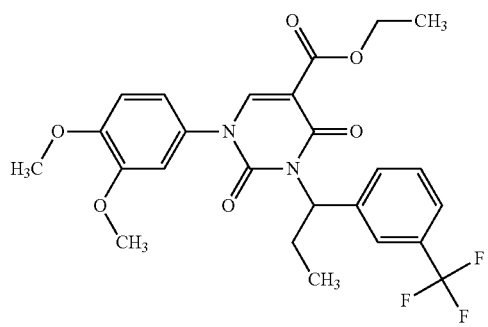 [SMILES: CCOC(=O)c1cn(-c2ccc(OC)c(OC)c2)c(=O)n(C(CC)c2cccc(C(F)(F)F)c2)c1=O]

Preparation and purification of the title compound were analogous to Example 125. Starting with 150 mg (0.40 mmol) of ethyl 2,4-dioxo-3-{1-[3-(trifluoromethyl)phenyl]propyl}-1,2,3,4-tetrahydropyrimidine-5-carboxylate (racemate) from Example 115A and 147 mg (0.81 mmol) of 3,4-dimethoxyphenylboronic acid, after additional purification by preparative HPLC (Method 7a), 111 mg (54% of theory) of the title compound were obtained.

LC-MS (Method 3): $R_t$=1.16 min; m/z=507 (M+H)$^+$.

$^1$H-NMR (400 MHz, DMSO-d$_6$): δ=0.93 (t, 3H), 1.23 (t, 3H), 2.30-2.45 (m, 2H), 3.75 (s, 3H), 3.79 (s, 3H), 4.18 (q, 2H), 5.97 (t, 1H), 6.98-7.06 (m, 2H), 7.16 (d, 1H), 7.53-7.65 (m, 2H), 7.68-7.73 (m, 2H), 8.30 (s, 1H).

Example 138

Ethyl 3-(3-chloro-2-methylbenzyl)-2,4-dioxo-1-[4-(2-oxo-1,3-oxazolidin-3-yl)phenyl]-1,2,3,4-tetrahydropyrimidine-5-carboxylate

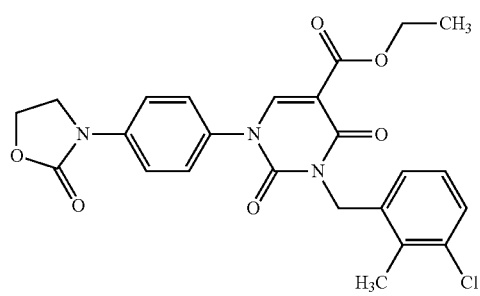 [SMILES: CCOC(=O)c1cn(-c2ccc(N3CCOC3=O)cc2)c(=O)n(Cc2cccc(Cl)c2C)c1=O]

150 mg (0.46 mmol) of ethyl 3-(3-chloro-2-methylbenzyl)-2,4-dioxo-1,2,3,4-tetrahydropyrimidine-5-carboxylate from Example 111A, 269 mg (0.93 mmol) of 3-[4-(4,4,5,5-tetramethyl-1,3,2-dioxaborolan-2-yl)phenyl]-1,3-oxazolidin-2-one from Example 129A and 0.19 ml (1.39 mmol) of triethylamine were initially charged in 4 ml of acetonitrile. 500 mg of molecular sieve 3 Å and 127 mg (0.69 mmol) of copper(II) acetate were then added, and the mixture was stirred under reflux for 3 days. The reaction mixture, cooled to RT, was then diluted with ethyl acetate and washed twice with 1 N aqueous hydrochloric acid and in each case once with saturated aqueous sodium bicarbonate solution and saturated aqueous sodium chloride solution. The organic phase was dried over magnesium sulfate, filtered and concentrated. The residue was purified by preparative HPLC (Method 7a). This gave 49 mg (21% of theory) of the title compound.

LC-MS (Method 1): $R_t$=1.29 min; m/z=484 (M+H)$^+$.

$^1$H-NMR (400 MHz, DMSO-d$_6$): δ=1.23 (t, 3H), 2.41 (s, 3H), 4.10 (t, 2H), 4.20 (q, 2H), 4.47 (t, 2H), 5.03 (s, 2H), 7.05 (d, 1H), 7.15 (t, 1H), 7.34 (d, 1H), 7.56 (d, 2H), 7.70 (d, 2H), 8.41 (s, 1H).

Example 139

Ethyl 3-(4-methyl-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylate (racemate)

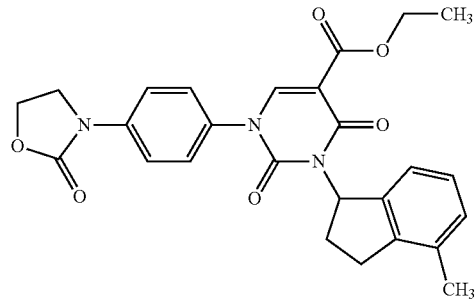 [SMILES: CCOC(=O)c1cn(-c2ccc(N3CCOC3=O)cc2)c(=O)n(C2CCc3c(C)cccc32)c1=O]

69 mg (0.22 mmol) of ethyl 3-(4-methyl-2,3-dihydro-1H-inden-1-yl)-2,4-dioxo-1,2,3,4-tetrahydropyrimidine-5-carboxylate from Example 117A, 127 mg (0.43 mmol) of 3-[4-(4,4,5,5-tetramethyl-1,3,2-dioxaborolan-2-yl)phenyl]-1,3-oxazolidin-2-one from Example 129A and 92 µl (0.65 mmol) of triethylamine were initially charged in 1.5 ml of acetonitrile. 500 mg of molecular sieve 3 Å and 60 mg (0.32 mmol) of copper(II) acetate were then added, and the mixture was stirred under reflux for 16 h. At RT, 0.5 ml of DMSO was added to the cooled reaction mixture, and the mixture was stirred at reflux for a further 16 h. The reaction mixture, cooled to RT, was then diluted with ethyl acetate and washed twice with 1 N aqueous hydrochloric acid and in each case once with saturated aqueous sodium bicarbonate solution and saturated aqueous sodium chloride solution. The organic phase was dried over magnesium sulfate, filtered and concentrated. The residue was purified by preparative HPLC (Method 7a). This gave 60 mg (57% of theory) of the title compound.

LC-MS (Method 3): $R_t$=1.01 min; m/z=476 (M+H)$^+$.

$^1$H-NMR (400 MHz, DMSO-d$_6$): δ=1.22 (t, 3H), 2.21 (s, 3H), 2.31-2.44 (m, 2H), 2.76-2.88 (m, 1H), 2.99-3.12 (m, 1H), 4.08 (t, 2H), 4.18 (q, 2H), 4.46 (t, 2H), 6.29-6.51 (m, 1H), 6.92-7.06 (m, 3H), 7.43-7.58 (m, 2H), 7.63-7.70 (m, 2H), 8.31 (s, 1H).

Example 140

Ethyl 3-(2-chloro-3,6-difluorobenzyl)-2,4-dioxo-1-[4-(2-oxo-1,3-oxazolidin-3-yl)phenyl]-1,2,3,4-tetrahydropyrimidine-5-carboxylate

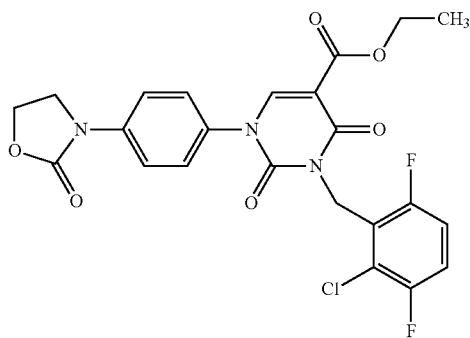 [SMILES: CCOC(=O)c1cn(-c2ccc(N3CCOC3=O)cc2)c(=O)n(Cc2c(F)ccc(F)c2Cl)c1=O]

150 mg (0.43 mmol) of ethyl 3-(2-chloro-3,6-difluorobenzyl)-2,4-dioxo-1,2,3,4-tetrahydropyrimidine-5-carboxylate from Example 119A, 252 mg (0.87 mmol) of 3-[4-(4,4,5,5-tetramethyl-1,3,2-dioxaborolan-2-yl)phenyl]-1,3-oxazolidin-2-one from Example 129A and 182 µl (1.30 mmol) of triethylamine were initially charged in 2 ml of acetonitrile. 500 mg of molecular sieve 3 Å, 119 mg (0.65 mmol) of copper(II) acetate and 0.5 ml of DMSO were then added, and the mixture was shaken at reflux temperature and exposed to the air for 3 days. The reaction mixture, cooled to RT, was then diluted with ethyl acetate and washed twice with 1 N aqueous hydrochloric acid and in each case once with saturated aqueous sodium bicarbonate solution and saturated aqueous sodium chloride solution. The organic phase was dried over magnesium sulfate, filtered and concentrated. The residue was stirred with methanol, and the solid formed was filtered off, washed with methanol and dried under reduced pressure. This gave 135 mg (55% of theory) of the title compound.

LC-MS (Method 2): $R_t$=2.13 min; m/z=506 (M+H)$^+$.

$^1$H-NMR (400 MHz, DMSO-$d_6$): δ=1.22 (t, 3H), 4.10 (t, 2H), 4.19 (q, 2H), 4.47 (t, 2H), 5.21 (s, 2H), 7.23-7.31 (m, 1H), 7.39-7.46 (m, 1H), 7.50 (d, 2H), 7.69 (d, 2H), 8.37 (s, 1H).

Example 141

Ethyl 1-(3,4-dimethoxyphenyl)-2,4-dioxo-3-[4-(trifluoromethyl)-2,3-dihydro-1H-inden-1-yl]-1,2,3,4-tetrahydropyrimidine-5-carboxylate (racemate)

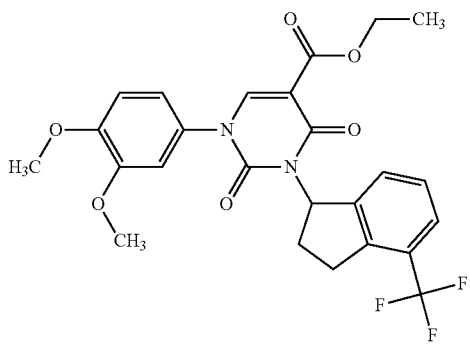 [SMILES: CCOC(=O)c1cn(-c2ccc(OC)c(OC)c2)c(=O)n(C2CCc3c2cccc3C(F)(F)F)c1=O]

Preparation and purification of the title compound were analogous to Example 125. Proceeding from 120 mg (0.32 mmol) of ethyl 2,4-dioxo-3-[4-(trifluoromethyl)-2,3-dihydro-1H-inden-1-yl]-1,2,3,4-tetrahydropyrimidine-5-carboxylate from Example 121A and 119 mg (0.65 mmol) of 3,4-dimethoxyphenylboronic acid, 110 mg (67% of theory) of the title compound were obtained.

LC-MS (Method 1): $R_t$=1.37 min; m/z=505 (M+H)$^+$.

$^1$H-NMR (400 MHz, DMSO-$d_6$): δ=1.22 (t, 3H), 2.32-2.47 (m, 2H), 3.03-3.15 (m, 1H), 3.22-3.30 (m, 1H), 3.75 (s, 3H), 3.80 (s, 3H), 4.17 (q, 2H), 6.34-6.54 (m, 1H), 6.97-7.09 (m, 2H), 7.11-7.22 (m, 1H), 7.36 (t, 1H), 7.45-7.50 (m, 1H), 7.51-7.56 (m, 1H), 8.29 (s, 1H).

Example 142

Ethyl 3-[2,3-bis(trifluoromethyl)benzyl]-2,4-dioxo-1-[4-(2-oxo-1,3-oxazolidin-3-yl)phenyl]-1,2,3,4-tetrahydropyrimidine-5-carboxylate

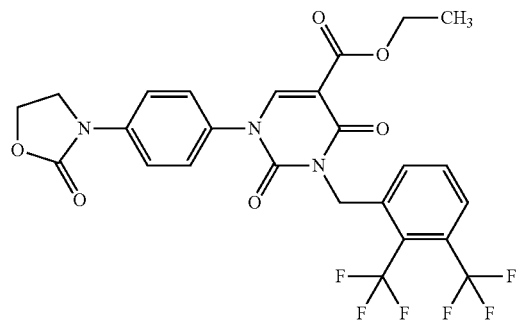 [SMILES: CCOC(=O)c1cn(-c2ccc(N3CCOC3=O)cc2)c(=O)n(Cc2cccc(C(F)(F)F)c2C(F)(F)F)c1=O]

Preparation and purification of the title compound were analogous to Example 140. Starting with 150 mg (0.36 mmol) of ethyl 3-[2,3-bis(trifluoromethyl)benzyl]-2,4-dioxo-1,2,3,4-tetrahydropyrimidine-5-carboxylate from Example 126A and 211 mg (0.73 mmol) of 3-[4-(4,4,5,5-tetramethyl-1,3,2-dioxaborolan-2-yl)phenyl]-1,3-oxazolidin-2-one from Example 129A, after additional purification by preparative HPLC (Method 5a), 94 mg (43% of theory) of the title compound were obtained.

LC-MS (Method 3): $R_t$=1.07 min; m/z=572 (M+H)$^+$.

$^1$H-NMR (400 MHz, DMSO-$d_6$): δ=1.23 (t, 3H), 4.10 (t, 2H), 4.21 (q, 2H), 4.47 (t, 2H), 5.25 (s, 2H), 7.56 (d, 2H), 7.72 (t, 3H), 7.84 (t, 1H), 7.97 (d, 1H), 8.47 (s, 1H).

Example 143

Ethyl 3-(4-chloro-2,3-dihydro-1H-inden-1-yl)-1-(3,4-dimethoxyphenyl)-2,4-dioxo-1,2,3,4-tetrahydropyrimidine-5-carboxylate (racemate)

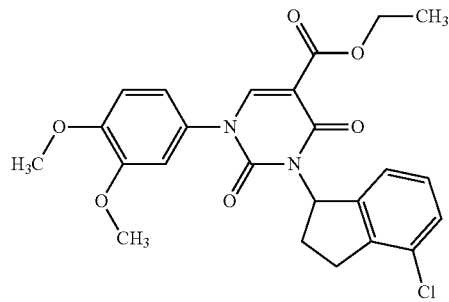 [SMILES: CCOC(=O)c1cn(-c2ccc(OC)c(OC)c2)c(=O)n(C2CCc3c(Cl)cccc32)c1=O]

Preparation and purification of the title compound were carried out analogously to Example 125, with a reaction time of 4 days. Starting with 145 mg (0.43 mmol) of ethyl 3-(4-chloro-2,3-dihydro-1H-inden-1-yl)-2,4-dioxo-1,2,3,4-tetrahydropyrimidine-5-carboxylate from Example 123A and 158 mg (0.86 mmol) of 3,4-dimethoxyphenylboronic acid, after additional purification by flash chromatography (dichloromethane/methanol 98:2), 128 mg (63% of theory) of the title compound were obtained.

LC-MS (Method 3): $R_t$=1.15 min; m/z=471 (M+H)$^+$.

$^1$H-NMR (400 MHz, DMSO-d$_6$): δ=1.23 (t, 3H), 2.32-2.39 (m, 1H), 2.40-2.48 (m, 1H), 2.89-3.00 (m, 1H), 3.07-3.20 (m, 1H), 3.75 (s, 3H), 3.80 (s, 3H), 4.17 (q, 2H), 6.32-6.58 (m, 1H), 6.95-7.08 (m, 2H), 7.10-7.22 (m, 3H), 7.26 (d, 1H), 8.28 (s, 1H).

Example 144

Ethyl 3-(4-chloro-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylate (racemate)

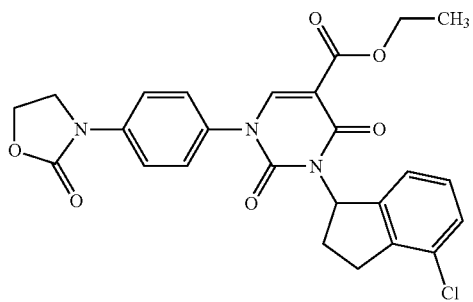 [SMILES: CCOC(=O)c1cn(-c2ccc(N3CCOC3=O)cc2)c(=O)n(C2CCc3c(Cl)cccc32)c1=O]

Preparation and purification of the title compound were analogous to Example 140. Starting with 145 mg (0.43 mmol) of ethyl 3-(4-chloro-2,3-dihydro-1H-inden-1-yl)-2,4-dioxo-1,2,3,4-tetrahydropyrimidine-5-carboxylate from Example 123A and 250 mg (0.86 mmol) of 3-[4-(4,4,5,5-tetramethyl-1,3,2-dioxaborolan-2-yl)phenyl]-1,3-oxazolidin-2-one from Example 129A, after additional purification by flash chromatography (dichloromethane/methanol 98:1), 165 mg (76% of theory, purity 90%) of the title compound were obtained.

LC-MS (Method 3): $R_t$=1.09 min; m/z=496 (M+H)$^+$.

$^1$H-NMR (400 MHz, DMSO-d$_6$): δ=1.23 (t, 3H), 2.32-2.40 (m, 1H), 2.41-2.48 (m, 1H), 2.88-3.00 (m, 1H), 3.06-3.19 (m, 1H), 4.09 (t, 2H), 4.18 (q, 2H), 4.47 (t, 2H), 6.34-6.59 (m, 1H), 7.12-7.21 (m, 2H), 7.26 (d, 1H), 7.43-7.58 (m, 2H), 7.67 (d, 2H), 8.33 (s, 1H).

Example 145

Ethyl 3-[3-chloro-2-(trifluoromethyl)benzyl]-1-[4-(3,5-dimethyl-1H-pyrazol-1-yl)phenyl]-2,4-dioxo-1,2,3,4-tetrahydropyrimidine-5-carboxylate

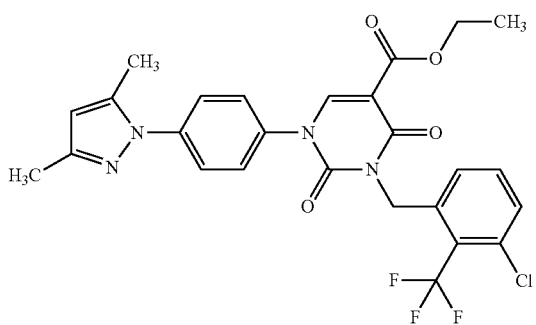 [SMILES: CCOC(=O)c1cn(-c2ccc(-n3nc(C)cc3C)cc2)c(=O)n(Cc2cccc(Cl)c2C(F)(F)F)c1=O]

200 mg (0.56 mmol) of ethyl 1-[4-(3,5-dimethyl-1H-pyrazol-1-yl)phenyl]-2,4-dioxo-1,2,3,4-tetrahydropyrimidine-5-carboxylate from Example 127A were initially charged in DMF (7 ml). 261 mg (0.62 mmol, 65% pure) of 1-(bromomethyl)-3-chloro-2-(trifluoromethyl)benzene (preparation: see WO2004/052858 A2, p. 149, Example 176i), 156 mg (1.12 mmol) of potassium carbonate and 9 mg (0.05 mmol) of potassium iodide were then added, and the reaction mixture was stirred at 80° C. for 2 h. Water was added to the reaction mixture which had cooled to RT, and the solid formed was filtered off, washed with water and dried at 50° C. under reduced pressure. The crude product thus obtained was purified by means of flash chromatography (dichloromethane/methanol 250:1→20:1). This gave 69 mg (21% of theory) of the title compound.

LC-MS (Method 11): $R_t$=1.23 min; m/z=547 (M+H)$^+$.

$^1$H-NMR (400 MHz, DMSO-d$_6$): δ=1.25 (t, 3H), 2.19 (s, 3H), 2.35 (s, 3H), 4.21 (q, 2H), 5.22 (s, 2H), 6.11 (s, 1H), 7.37 (d, 1H), 7.58 (t, 1H), 7.63-7.70 (m, 5H), 8.55 (s, 1H).

Example 146

Ethyl 2,4-dioxo-1-[4-(2-oxo-1,3-oxazolidin-3-yl)phenyl]-3-[(1R)-4-(trifluoromethyl)-2,3-dihydro-1H-inden-1-yl]-1,2,3,4-tetrahydropyrimidine-5-carboxylate (R enantiomer)

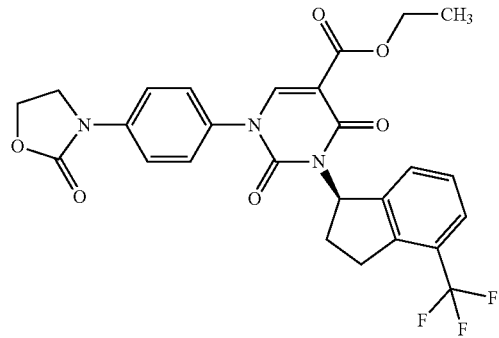 [SMILES: CCOC(=O)c1cn(-c2ccc(N3CCOC3=O)cc2)c(=O)n([C@@H]2CCc3c2cccc3C(F)(F)F)c1=O]

Under argon, 9.00 g (26.1 mmol) of the compound from Example 21A, 6.85 g (33.9 mmol) of the compound from Example 128A and 12.31 g (46.9 mmol) of triphenylphosphine were initially charged in a mixture of 359 ml of anhydrous THF and 359 ml of anhydrous DMF and cooled to 0° C. 8.43 g (41.7 mmol) of diisopropyl azodicarboxylate were added dropwise, and the reaction mixture was allowed to warm to RT and stirred at RT for 1 h. 100 ml of 1 N aqueous hydrochloric acid were added. The mixture was stirred for another 15 min and diluted with 1 l of ethyl acetate. The organic phase was separated off, washed three times with in each case 800 ml of 1 N aqueous hydrochloric acid, then twice with in each case 300 ml of 1 N aqueous sodium carbonate solution and once with 400 ml of saturated aqueous sodium chloride solution, dried over sodium sulfate and concentrated on a rotary evaporator. The solid that remained was stirred in a mixture of 300 ml of MTBE and 200 ml of 2-propanol, isolated by filtration, washed with 100 ml of MTBE and dried under high vacuum. This gave 8.2 g (54% of theory, purity 91%; with 6% of triphenylphosphine oxide as main impurity).

LC-MS (Method 3): $R_t$=1.11 min; MS (ESIpos): m/z=530 (M+H)$^+$.

$^1$H-NMR (400 MHz, CD$_2$Cl$_2$): [ppm]=1.23 (t, 3H), 2.29-2.41 (m, 1H), 2.50 (dtd, 1H), 3.00-3.12 (m, 1H), 3.33-3.45 (m, 1H), 3.93-4.02 (m, 2H), 4.20 (q, 2H), 4.35-4.45 (m, 2H), 6.53 (br. t, 1H), 7.15-7.33 (m, 4H), 7.41 (d, 1H), 7.59 (d, 2H), 8.21 (s, 1H).

Example 147

Ethyl 1-[3-chloro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylate (R enantiomer)

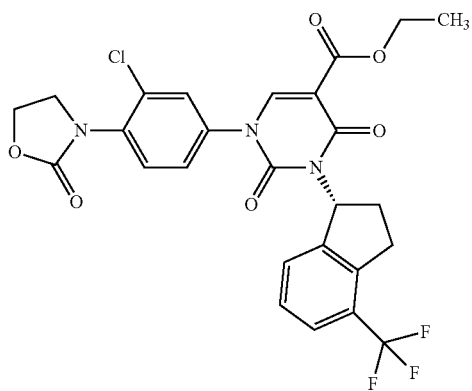 [SMILES: CCOC(=O)c1cn(-c2ccc(N3CCOC3=O)c(Cl)c2)c(=O)n([C@@H]2CCc3c2cccc3C(F)(F)F)c1=O]

Under argon, 250 mg (0.65 mmol) of ethyl-1-[3-chloro-4-(2-oxo-1,3-oxazolidin-3-yl)phenyl]-2,4-dioxo-1,2,3,4-tetrahydropyrimidine-5-carboxylate from Example 64A and 518 mg (1.97 mmol) of triphenylphosphine were initially charged in 12 ml of THF/DMF (1:1). 0.26 ml (1.32 mmol) of diisopropyl azodicarboxylate was then added dropwise, followed by the addition of 160 mg (0.79 mmol) of (1S)-4-(trifluoromethyl)indan-1-ol from Example 128A, and the mixture was stirred at RT for 3 h. 1 ml of 1 M aqueous hydrochloric acid was added and the reaction mixture was diluted with 50 ml of ethyl acetate and washed twice with 20 ml of 1 M aqueous hydrochloric acid and once with 20 ml of saturated aqueous sodium chloride solution. The organic phase was dried over magnesium sulfate, filtered and concentrated. The solid was separated by flash chromatography (dichloromethane/methanol 99.4:0.6). The resulting crude product was stirred in MTBE/cyclohexane and the solid formed was filtered off, washed with a little MTBE and dried under reduced pressure. The filtrate was concentrated again and the residue was dried under reduced pressure. This gave a total of 111 mg (29% of theory) of the title compound.

LC-MS (Method 3): R$_t$=1.10 min; m/z=564 (M+H)$^+$.

$^1$H-NMR (400 MHz, CDCl$_3$): δ=1.36 (t, 3H), 2.37-2.49 (m, 1H), 2.54-2.61 (m, 1H), 3.09-3.20 (m, 1H), 3.46-3.58 (m, 1H), 4.03 (t, 2H), 4.36 (q, 2H), 4.57 (t, 2H), 6.59-6.74 (m, 1H), 7.21-7.29 (m, 2H, hidden by CDCl$_3$ signal), 7.34 (d, 1H), 7.44-7.53 (m, 2H), 7.57 (d, 1H), 8.27 (s, 1H).

[α]$_D^{21}$=+105°, c=0.42, chloroform.

Example 148

3-[2-Chloro-3-(trifluoromethyl)benzyl]-2,4-dioxo-1-[4-(2-oxo-1,3-oxazolidin-3-yl)phenyl]-1,2,3,4-tetrahydropyrimidine-5-carboxylic acid

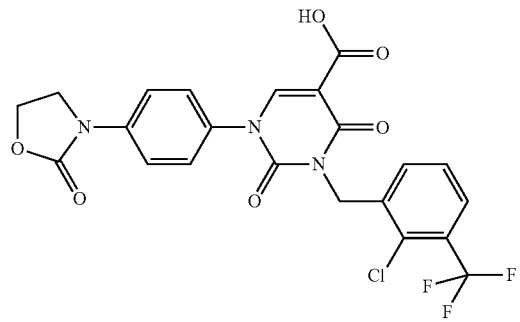 [SMILES: O=C(O)c1cn(-c2ccc(N3CCOC3=O)cc2)c(=O)n(Cc2cccc(C(F)(F)F)c2Cl)c1=O]

140 mg (0.26 mmol) of ethyl 3-[2-chloro-3-(trifluoromethyl)benzyl]-2,4-dioxo-1-[4-(2-oxo-1,3-oxazolidin-3-yl)phenyl]-1,2,3,4-tetrahydropyrimidine-5-carboxylate from Example 110 were stirred in 1.9 ml of glacial acetic acid and 0.9 ml of conc. hydrochloric acid at 120° C. for 1 h. 5 ml of water were then added to the reaction mixture which had cooled to RT, and the solid formed was filtered off, washed with water and MTBE and dried under reduced pressure. This gave 115 mg (84% of theory) of the title compound.

LC-MS (Method 3): R$_t$=1.07 min; m/z=510 (M+H)$^+$.

$^1$H-NMR (400 MHz, DMSO-d$_6$): δ=4.07-4.14 (m, 2H), 4.43-4.50 (m, 2H), 5.17 (s, 2H), 7.49-7.63 (m, 4H), 7.69-7.74 (m, 2H), 7.78-7.83 (m, 1H), 8.47 (s, 1H), 12.72 (br. s., 1H).

Example 149

1-{4-[(5S)-5-(Acetamidomethyl)-2-oxo-1,3-oxazolidin-3-yl]phenyl}-3-[2-chloro-3-(trifluoromethyl)benzyl]-2,4-dioxo-1,2,3,4-tetrahydropyrimidine-5-carboxylic acid (S enantiomer)

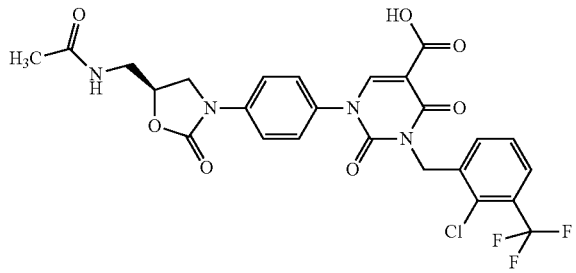 [SMILES: CC(=O)NC[C@H]1CN(c2ccc(-n3cc(C(=O)O)c(=O)n(Cc4cccc(C(F)(F)F)c4Cl)c3=O)cc2)C(=O)O1]

Preparation and purification were carried out analogously to Example 148 using 120 mg (0.20 mmol) of ethyl 1-{4-[(5S)-5-(acetamidomethyl)-2-oxo-1,3-oxazolidin-3-yl]phenyl}-3-[2-chloro-3-(trifluoromethyl)benzyl]-2,4-dioxo-1,2,3,4-tetrahydropyrimidine-5-carboxylate (S) enantiomer from Example 111. Yield: 90 mg (78% of theory).

LC-MS (Method 3): R$_t$=0.98 min; m/z=581 (M+H)$^+$.

$^1$H-NMR (400 MHz, DMSO-d$_6$): δ=1.84 (s, 3H), 3.44 (t, 2H), 3.79 (dd, 1H), 4.17 (t, 1H), 4.72-4.79 (m, 1H), 5.16 (s,

2H), 7.49-7.63 (m, 4H), 7.66-7.72 (m, 2H), 7.80 (d, 1H), 8.26 (t, 1H), 8.46 (s, 1H), 12.74 (br. s., 1H).

Example 150

3-[2-Chloro-3-(trifluoromethyl)benzyl]-2,4-dioxo-1-[4-(2-oxoimidazolidin-1-yl)phenyl]-1,2,3,4-tetrahydropyrimidine-5-carboxylic acid

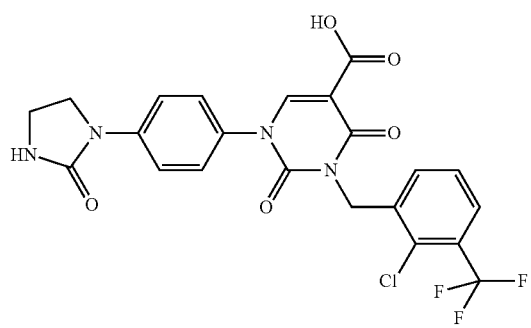 [SMILES: O=C(O)c1cn(-c2ccc(N3CCNC3=O)cc2)c(=O)n(Cc2cccc(C(F)(F)F)c2Cl)c1=O]

Preparation and purification were carried out analogously to Example 148 using 198 mg (0.37 mmol) of ethyl 3-[2-chloro-3-(trifluoromethyl)benzyl]-2,4-dioxo-1-[4-(2-oxoimidazolidin-1-yl)phenyl]-1,2,3,4-tetrahydropyrimidine-5-carboxylate from Example 112. The crude product was dissolved in DMSO and chromatographed using preparative HPLC (Method 7a), and the product fractions were concentrated under reduced pressure. Yield: 115 mg (58% of theory).

LC-MS (Method 1): $R_t$=1.20 min; m/z=509 (M+H)$^+$.
$^1$H-NMR (400 MHz, DMSO-d$_6$): δ=3.39-3.46 (m, 2H), 3.84-3.93 (m, 2H), 5.16 (s, 2H), 7.11 (s, 1H), 7.44-7.49 (m, 2H), 7.50-7.55 (m, 1H), 7.58-7.62 (m, 1H), 7.66-7.72 (m, 2H), 7.78-7.83 (m, 1H), 8.43 (s, 1H), 12.70 (br. s., 1H).

Example 151

1-[3-Chloro-4-(2-oxo-1,3-oxazolidin-3-yl)phenyl]-3-[2-chloro-3-(trifluoromethyl)benzyl]-2,4-dioxo-1,2,3,4-tetrahydropyrimidine-5-carboxylic acid

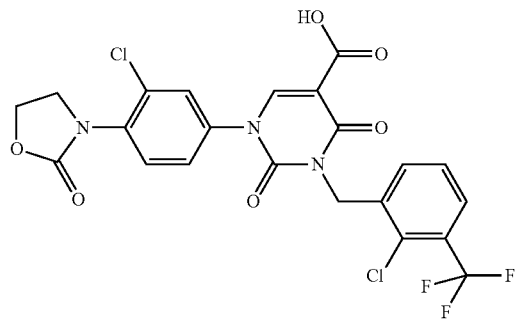 [SMILES: O=C(O)c1cn(-c2ccc(N3CCOC3=O)c(Cl)c2)c(=O)n(Cc2cccc(C(F)(F)F)c2Cl)c1=O]

Preparation and purification were carried out analogously to Example 150 using 150 mg (0.26 mmol) of ethyl 1-[3-chloro-4-(2-oxo-1,3-oxazolidin-3-yl)phenyl]-3-[2-chloro-3-(trifluoromethyl)-benzyl]-2,4-dioxo-1,2,3,4-tetrahydropyrimidine-5-carboxylate from Example 113. Yield: 107 mg (75% of theory).

LC-MS (Method 3): $R_t$=1.08 min; m/z=544 (M+H)$^+$.
$^1$H-NMR (400 MHz, DMSO-d$_6$): δ=4.00 (t, 2H), 4.52 (t, 2H), 5.16 (s, 2H), 7.52 (t, 1H), 7.59-7.66 (m, 2H), 7.74 (d, 1H), 7.81 (d, 1H), 7.88 (d, 1H), 8.59 (s, 1H), 12.76 (br. s., 1H).

Example 152

1-[3-Chloro-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylic acid

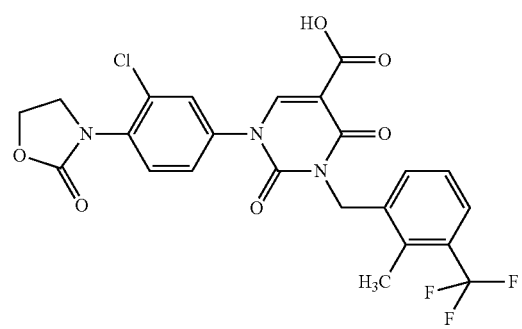 [SMILES: Cc1c(Cn2c(=O)c(C(=O)O)cn(-c3ccc(N4CCOC4=O)c(Cl)c3)c2=O)cccc1C(F)(F)F]

The preparation and purification were carried out analogously to Example 150 using 120 mg (0.217 mmol) of ethyl 1-[3-chloro-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate from Example 114. Yield: 79 mg (69% of theory).

LC-MS (Method 3): $R_t$=1.08 min; m/z=524 (M+H)$^+$.
$^1$H-NMR (400 MHz, DMSO-d$_6$): δ=2.47 (s, partially hidden by DMSO signal), 3.97-4.04 (m, 2H), 4.49-4.56 (m, 2H), 5.10 (s, 2H), 7.32-7.38 (m, 1H), 7.40-7.44 (m, 1H), 7.58-7.66 (m, 2H), 7.72 (d, 1H), 7.89 (d, 1H), 8.58 (s, 1H), 12.74 (br. s., 1H).

Example 153

1-[3-Methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylic acid

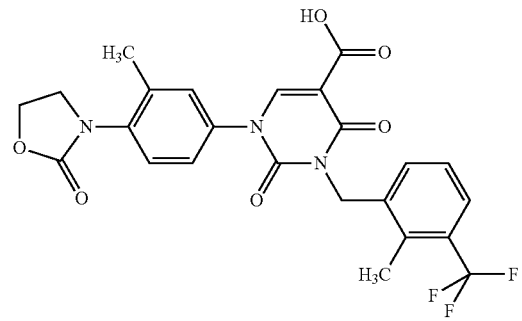 [SMILES: Cc1cc(-n2cc(C(=O)O)c(=O)n(Cc3cccc(C(F)(F)F)c3C)c2=O)ccc1N1CCOC1=O]

Preparation and purification were carried out analogously to Example 148 using 348 mg (0.557 mmol, purity 85%) of ethyl 1-[3-methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate from Example 118. The crude product was dissolved in DMSO and chromatographed using preparative HPLC (Method 7a), and the product fractions were partially concentrated under reduced pressure. The solid formed was filtered off, washed with water and ethyl acetate and dried under reduced pressure. Yield: 145 mg (52% of theory).

LC-MS (Method 3): $R_t$=1.04 min; m/z=504 (M+H)$^+$.

$^1$H-NMR (400 MHz, DMSO-$d_6$): δ=2.28 (s, 3H), 2.47 (s, partially hidden by DMSO signal), 3.94-4.04 (m, 2H), 4.45-4.54 (m, 2H), 5.10 (s, 2H), 7.31-7.48 (m, 3H), 7.48-7.55 (m, 2H), 7.57-7.64 (m, 1H), 8.48 (s, 1H), 12.72 (br. s., 1H).

Example 154

3-[2-Chloro-3-(trifluoromethyl)benzyl]-1-[3-methyl-4-(2-oxo-1,3-oxazolidin-3-yl)phenyl]-2,4-dioxo-1,2,3,4-tetrahydropyrimidine-5-carboxylic acid

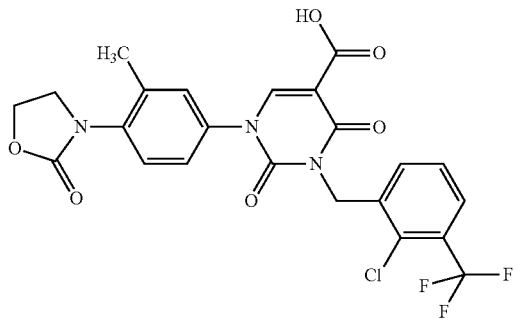 [SMILES: Cc1cc(-n2cc(C(=O)O)c(=O)n(Cc3cccc(C(F)(F)F)c3Cl)c2=O)ccc1N1CCOC1=O]

The preparation and purification were carried out analogously to Example 150 using 374 mg (0.58 mmol) of ethyl 3-[2-chloro-3-(trifluoromethyl)benzyl]-1-[3-methyl-4-(2-oxo-1,3-oxazolidin-3-yl)phenyl]-2,4-dioxo-1,2,3,4-tetrahydropyrimidine-5-carboxylate from Example 119. Yield: 136 mg (44% of theory).

LC-MS (Method 3): $R_t$=1.04 min; m/z=504 (M+H)$^+$.

$^1$H-NMR (400 MHz, DMSO-$d_6$): δ=2.28 (s, 3H), 2.47 (s, partially hidden by DMSO signal), 3.94-4.04 (m, 2H), 4.45-4.54 (m, 2H), 5.10 (s, 2H), 7.31-7.48 (m, 3H), 7.48-7.55 (m, 2H), 7.57-7.64 (m, 1H), 8.48 (s, 1H), 12.72 (br. s., 1H).

Example 155

3-(2,3-Dichlorobenzyl)-1-[2-fluoro-4-(2-oxo-1,3-oxazolidin-3-yl)phenyl]-2,4-dioxo-1,2,3,4-tetrahydropyrimidine-5-carboxylic acid

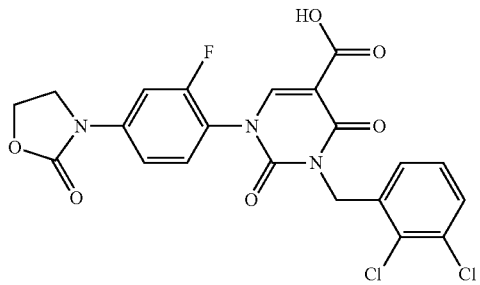 [SMILES: O=C(O)c1cn(-c2ccc(N3CCOC3=O)cc2F)c(=O)n(Cc2cccc(Cl)c2Cl)c1=O]

358 mg (0.60 mmol, purity 87%) of ethyl 3-(2,3-dichlorobenzyl)-1-[2-fluoro-4-(2-oxo-1,3-oxazolidin-3-yl)phenyl]-2,4-dioxo-1,2,3,4-tetrahydropyrimidine-5-carboxylate from Example 116 were stirred in 4 ml of glacial acetic acid and 2 ml of conc. hydrochloric acid at 120° C. for 1 h. 5 ml of water were then added to the reaction mixture which had cooled to RT, and the solid formed was filtered off, washed with water and ethyl acetate and dried under reduced pressure. This gave 237 mg (80% of theory) of the title compound.

LC-MS (Method 3): $R_t$=1.10 min; m/z=495 (M+H)$^+$.

$^1$H-NMR (400 MHz, DMSO-$d_6$): δ=4.10 (t, 2H), 4.48 (t, 2H), 5.13 (s, 2H), 7.17 (d, 1H), 7.34 (t, 1H), 7.46-7.53 (m, 1H), 7.59 (d, 1H), 7.65-7.75 (m, 2H), 8.59 (s, 1H), 12.78 (br. s., 1H).

Example 156

3-[2-Chloro-3-(trifluoromethyl)benzyl]-1-[2-fluoro-4-(2-oxo-1,3-oxazolidin-3-yl)phenyl]-2,4-dioxo-1,2,3,4-tetrahydropyrimidine-5-carboxylic acid

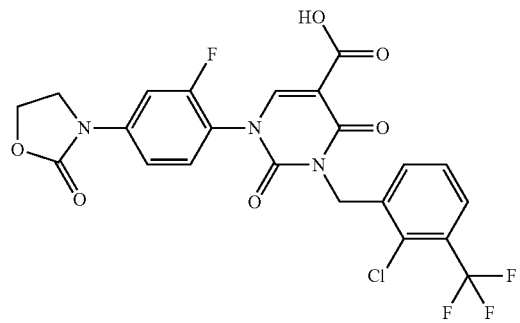 [SMILES: O=C(O)c1cn(-c2ccc(N3CCOC3=O)cc2F)c(=O)n(Cc2cccc(C(F)(F)F)c2Cl)c1=O]

Preparation and purification were carried out analogously to Example 155 using 397 mg (0.61 mmol, purity 85%) of ethyl 3-[2-chloro-3-(trifluoromethyl)benzyl]-1-[2-fluoro-4-(2-oxo-1,3-oxazolidin-3-yl)phenyl]-2,4-dioxo-1,2,3,4-tetrahydropyrimidine-5-carboxylate from Example 115. Yield: 263 mg (82% of theory).

LC-MS (Method 3): $R_t$=1.10 min; m/z=495 (M+H)$^+$.

$^1$H-NMR (400 MHz, DMSO-$d_6$): δ=4.10 (t, 2H), 4.48 (t, 2H), 5.13 (s, 2H), 7.17 (d, 1H), 7.34 (t, 1H), 7.46-7.53 (m, 1H), 7.59 (d, 1H), 7.65-7.75 (m, 2H), 8.59 (s, 1H), 12.78 (br. s., 1H).

Example 157

1-[2-Fluoro-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylic acid

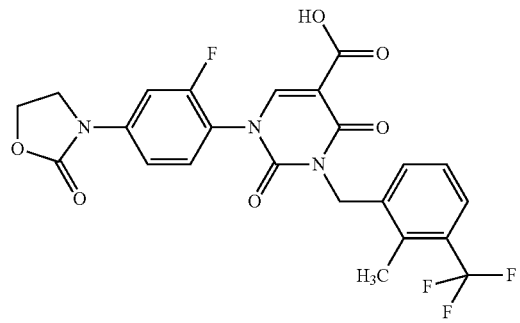 [SMILES: Cc1c(Cn2c(=O)c(C(=O)O)cn(-c3ccc(N4CCOC4=O)cc3F)c2=O)cccc1C(F)(F)F]

Preparation and purification were carried out analogously to Example 150 using 253 mg (0.47 mmol) of ethyl 1-[2-fluoro-4-(2-oxo-1,3-oxazolidin-3-yl)phenyl]-3-[2-methyl- 3-(trifluoromethyl)benzyl]-2,4-dioxo-1,2,3,4-tetrahydropyrimidine-5-carboxylate from Example 117. Yield: 200 mg (82% of theory).

LC-MS (Method 3): $R_t$=1.07 min; m/z=508 (M+H)$^+$.

$^1$H-NMR (400 MHz, DMSO-d$_6$): δ=2.46 (s, partially hidden by DMSO signal), 4.05-4.18 (m, 2H), 4.43-4.54 (m, 2H), 5.11 (br. s., 2H), 7.27-7.41 (m, 2H), 7.46-7.55 (m, 1H), 7.57-7.65 (m, 1H), 7.65-7.78 (m, 2H), 8.59 (br. s., 1H), 12.78 (br. s., 1H).

Example 158

3-[2-Chloro-3-(trifluoromethyl)benzyl]-1-[3,5-dichloro-4-(2-oxo-1,3-oxazolidin-3-yl)phenyl]-2,4-dioxo-1,2,3,4-tetrahydropyrimidine-5-carboxylic acid

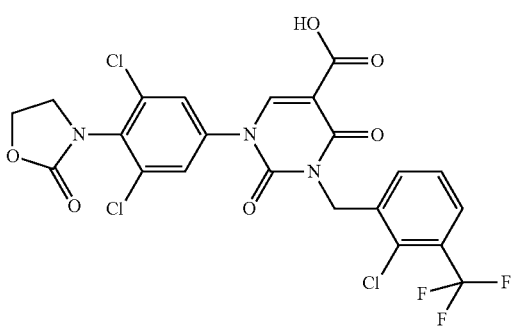 [SMILES: O=C(O)c1cn(-c2cc(Cl)c(N3CCOC3=O)c(Cl)c2)c(=O)n(Cc2cccc(C(F)(F)F)c2Cl)c1=O]

Preparation and purification were carried out analogously to Example 150 using 194 mg (0.32 mmol) of ethyl 3-[2-chloro-3-(trifluoromethyl)benzyl]-1-[3,5-dichloro-4-(2-oxo-1,3-oxazolidin-3-yl)phenyl]-2,4-dioxo-1,2,3,4-tetrahydropyrimidine-5-carboxylate from Example 120. Yield: 71 mg (38% of theory).

LC-MS (Method 3): $R_t$=1.10 min; m/z=578 (M+H)$^+$.

$^1$H-NMR (400 MHz, DMSO-d$_6$): δ=3.89-3.96 (m, 2H), 4.57-4.66 (m, 2H), 5.16 (s, 2H), 7.49-7.56 (m, 1H), 7.58-7.63 (m, 1H), 7.78-7.84 (m, 1H), 7.95 (s, 2H), 8.68 (s, 1H), 12.77 (br. s., 1H).

Example 159

1-[3-Chloro-4-(2-oxoimidazolidin-1-yl)phenyl]-3-[2-chloro-3-(trifluoromethyl)benzyl]-2,4-dioxo-1,2,3,4-tetrahydropyrimidine-5-carboxylic acid

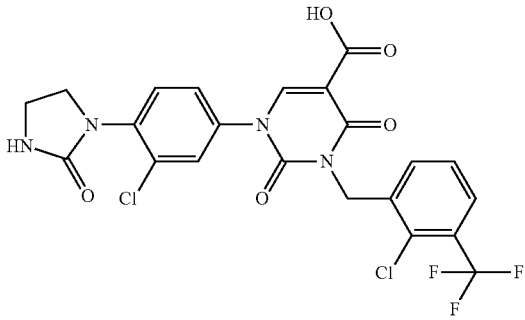 [SMILES: O=C(O)c1cn(-c2ccc(N3CCNC3=O)c(Cl)c2)c(=O)n(Cc2cccc(C(F)(F)F)c2Cl)c1=O]

The preparation and purification were carried out analogously to Example 148 using 97 mg (0.17 mmol) of ethyl 1-[3-chloro-4-(2-oxoimidazolidin-1-yl)phenyl]-3-[2-chloro-3-(trifluoromethyl)benzyl]-2,4-dioxo-1,2,3,4-tetrahydropyrimidine-5-carboxylate from Example 121. Yield: 70 mg (72% of theory).

LC-MS (Method 3): $R_t$=1.02 min; m/z=543 (M+H)$^+$.

$^1$H-NMR (400 MHz, DMSO-d$_6$): δ=3.42-3.50 (m, 2H), 3.77-3.85 (m, 2H), 5.16 (s, 2H), 6.96 (s, 1H), 7.50-7.63 (m, 4H), 7.80 (m, 2H), 8.56 (s, 1H), 12.72 (br. S., 1H).

Example 160

1-[3-Chloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylic acid

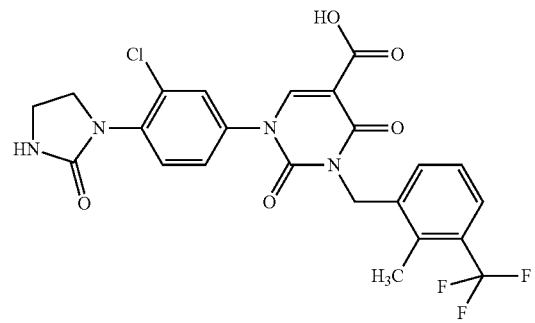 [SMILES: Cc1c(Cn2c(=O)c(C(=O)O)cn(-c3ccc(N4CCNC4=O)c(Cl)c3)c2=O)cccc1C(F)(F)F]

The preparation and purification were carried out analogously to Example 148 using 87 mg (0.16 mmol) of ethyl 1-[3-chloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate from Example 122. Yield: 60 mg (69% of theory).

LC-MS (Method 3): $R_t$=1.01 min; m/z=523 (M+H)$^+$.

$^1$H-NMR (400 MHz, DMSO-d$_6$): δ=2.47 (s, 3H), 3.46 (t, 2H), 3.81 (t, 2H), 5.10 (s, 2H), 6.95 (s, 1H), 7.32-7.38 (m, 1H), 7.39-7.44 (m, 1H), 7.55-7.58 (m, 2H), 7.60 (d, 1H), 7.80-7.83 (m, 1H), 8.54 (s, 1H), 12.72 (br. s., 1H).

Example 161

1-[2-Methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylic acid

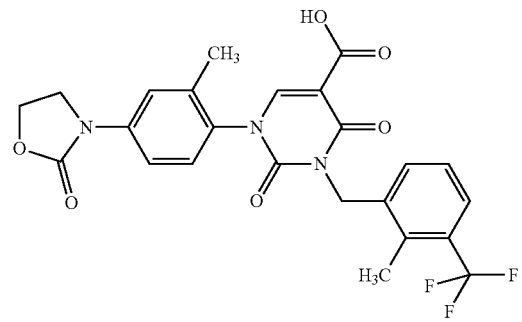 [SMILES: Cc1cc(N2CCOC2=O)ccc1-n1cc(C(=O)O)c(=O)n(Cc2cccc(C(F)(F)F)c2C)c1=O]

298 mg (0.51 mmol, purity 91%) of ethyl 1-[2-methyl-4-(2-oxo-1,3-oxazolidin-3-yl)phenyl]-3-[2-methyl-3-(trifluoromethyl)benzyl]-2,4-dioxo-1,2,3,4-tetrahydropyrimidine-5-carboxylate from Example 123 were initially charged in 3.0 ml of glacial acetic acid and 1.5 ml of conc. hydrochloric acid, and the mixture was stirred at 120° C. for 5 h. 1.0 ml of conc. hydrochloric acid was then added, and the mixture was stirred at 120° C. for a further 4 h. 5 ml of water were then added to the reaction mixture which had cooled to RT, and the solid formed was filtered off, washed with water and ethyl acetate and dried under reduced pressure. This gave 233 mg (88% of theory) of the title compound.

LC-MS (Method 3): $R_t$=1.04 min; m/z=504 (M+H)$^+$.

$^1$H-NMR (400 MHz, DMSO-d$_6$): δ=2.16 (s, 3H), 2.46 (s, partially hidden by DMSO signal), 4.09 (t, 2H), 4.46 (t, 2H), 5.04-5.18 (m, 2H), 7.33-7.38 (m, 2H), 7.48-7.52 (m, 1H), 7.54-7.63 (m, 3H), 8.41 (s, 1H), 12.73 (br. s., 1H).

Example 162

3-[2-Chloro-3-(trifluoromethyl)benzyl]-1-[2-methyl-4-(2-oxo-1,3-oxazolidin-3-yl)phenyl]-2,4-dioxo-1,2,3,4-tetrahydropyrimidine-5-carboxylic acid

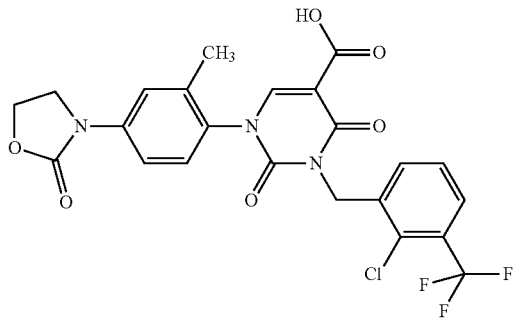 [SMILES: Cc1cc(N2CCOC2=O)ccc1-n1cc(C(=O)O)c(=O)n(Cc2cccc(C(F)(F)F)c2Cl)c1=O]

The preparation and purification were carried out analogously to Example 161 using 331 mg (0.55 mmol, purity 91%) of ethyl 3-[2-chloro-3-(trifluoromethyl)benzyl]-1-[2-methyl-4-(2-oxo-1,3-oxazolidin-3-yl)phenyl]-2,4-dioxo-1,2,3,4-tetrahydropyrimidine-5-carboxylate from Example 124. Yield: 242 mg (82% of theory).

LC-MS (Method 3): $R_t$=1.04 min; m/z=524 (M+H)$^+$.

$^1$H-NMR (400 MHz, DMSO-d$_6$): δ=2.17 (s, 3H), 4.09 (t, 2H), 4.46 (t, 2H), 5.17 (s, 2H), 7.47-7.60 (m, 5H), 7.78-7.83 (m, 1H), 8.42 (s, 1H), 12.73 (br. s., 1H).

Example 163

3-[2,3-Bis(trifluoromethyl)benzyl]-2,4-dioxo-1-[4-(2-oxo-1,3-oxazolidin-3-yl)phenyl]-1,2,3,4-tetrahydropyrimidine-5-carboxylic acid

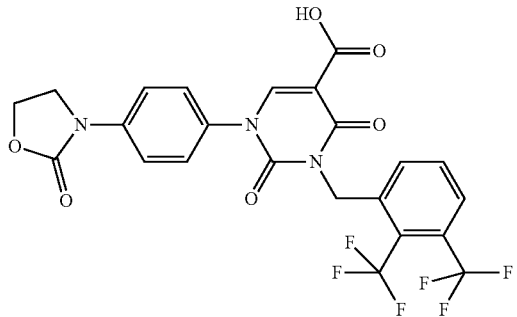 [SMILES: O=C(O)c1cn(-c2ccc(N3CCOC3=O)cc2)c(=O)n(Cc2cccc(C(F)(F)F)c2C(F)(F)F)c1=O]

97 mg (0.17 mmol) of ethyl 3-[2,3-bis(trifluoromethyl)benzyl]-2,4-dioxo-1-[4-(2-oxo-1,3-oxazolidin-3-yl)phenyl]-1,2,3,4-tetrahydropyrimidine-5-carboxylate from Example 142 were stirred in 1.0 ml of glacial acetic acid and 0.5 ml of conc. hydrochloric acid at 120° C. for 45 min 5 ml of water were then added to the reaction mixture which had cooled to RT, and the solid formed was filtered off, washed with water and MTBE and dried under reduced pressure. This gave 69 mg (71% of theory) of the title compound.

LC-MS (Method 3): $R_t$=1.04 min; m/z=544 (M+H)$^+$.

$^1$H-NMR (400 MHz, DMSO-d$_6$): δ=4.07-4.14 (m, 2H), 4.43-4.50 (m, 2H), 5.26 (s, 2H), 7.53-7.59 (m, 2H), 7.69-7.76 (m, 3H), 7.84 (t, 1H), 7.97 (d, 1H), 8.48 (s, 1H), 12.73 (br. s., 1H).

Example 164

3-[3-(Difluoromethyl)-2-methylbenzyl]-1-(3,4-dimethoxyphenyl)-2,4-dioxo-1,2,3,4-tetrahydropyrimidine-5-carboxylic acid

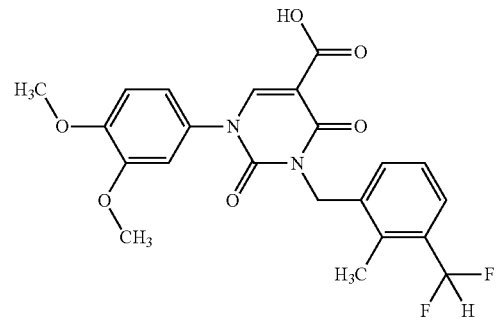 [SMILES: COc1ccc(-n2cc(C(=O)O)c(=O)n(Cc3cccc(C(F)F)c3C)c2=O)cc1OC]

151 mg (0.32 mmol) of ethyl 3-[3-(difluoromethyl)-2-methylbenzyl]-1-(3,4-dimethoxyphenyl)-2,4-dioxo-1,2,3,4-tetrahydropyrimidine-5-carboxylate from Example 125 were stirred in 1.5 ml of glacial acetic acid and 0.8 ml of conc. hydrochloric acid at 120° C. for 1 h. 5 ml of water were then added to the reaction mixture which had cooled to RT, and the solid formed was filtered off, washed with water and ethyl acetate and dried under reduced pressure. The resulting crude product was chromatographed using preparative HPLC (Method 7a, then Method 8), and the product fractions were concentrated under reduced pressure. This gave 22 mg (15% of theory) of the title compound.

LC-MS (Method 3): $R_t$=1.01 min; m/z=447 (M+H)$^+$.

$^1$H-NMR (400 MHz, DMSO-d$_6$): δ=2.41 (s, 3H), 3.77 (s, 3H), 3.80 (s, 3H), 5.08 (s, 2H), 7.03-7.38 (m, 6H), 7.44 (d, 1H), 8.41 (s, 1H), 12.72 (br. s., 1H).

Example 165

3-(2,3-Dihydro-1H-inden-1-yl)-1-(3,4-dimethoxyphenyl)-2,4-dioxo-1,2,3,4-tetrahydropyrimidine-5-carboxylic acid

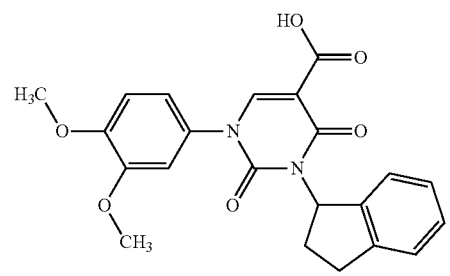 [SMILES: COc1ccc(-n2cc(C(=O)O)c(=O)n(C3CCc4ccccc43)c2=O)cc1OC]

151 mg (0.35 mmol) of ethyl 3-(2,3-dihydro-1H-inden-1-yl)-1-(3,4-dimethoxyphenyl)-2,4-dioxo-1,2,3,4-tetrahydropyrimidine-5-carboxylate from Example 126 were stirred in 1.0 ml of glacial acetic acid and 0.5 ml of conc. hydrochloric acid at 120° C. for 20 min. Water was then added to the reaction mixture which had cooled to RT, and the solid formed was filtered off, washed with water and MTBE/ethyl acetate (10:1) and dried under reduced pressure. The crude product was purified by preparative thin layer chromatography (dichloromethane/methanol 10:1). This gave 19 mg (13% of theory) of the title compound.

LC-MS (Method 1): $R_t$=1.19 min; m/z=431 (M+Na)$^+$.

$^1$H-NMR (400 MHz, DMSO-d$_6$): δ=2.34-2.45 (m, 2H), 2.87-2.98 (m, 1H), 3.12-3.22 (m, partially hidden by water signal), 3.75 (s, 3H), 3.79 (s, 3H), 6.37-6.48 (m, 1H), 6.97-7.07 (m, 2H), 7.09-7.26 (m, 5H), 8.27 (s, 1H), 12.76 (br. s, 1H).

Example 166

Ethyl 1-{4-[(methoxycarbonyl)amino]phenyl}-3-[2-methyl-3-(trifluoromethyl)benzyl]-2,4-dioxo-1,2,3,4-tetrahydropyrimidine-5-carboxylate

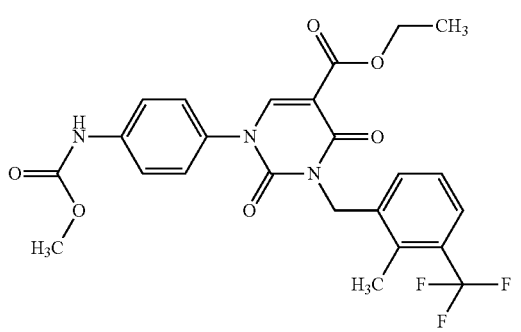 [SMILES: CCOC(=O)c1cn(-c2ccc(NC(=O)OC)cc2)c(=O)n(Cc2cccc(C(F)(F)F)c2C)c1=O]

Under argon, 200 mg (0.44 mmol) of ethyl 1-(4-aminophenyl)-3-[2-methyl-3-(trifluoromethyl)benzyl]-2,4-dioxo-1,2,3,4-tetrahydropyrimidine-5-carboxylate from Example 104A were initially charged in 5 ml of THF and cooled to 0° C. 75 µl (0.54 mmol) of triethylamine were then added, and a solution of 38 µl (0.44 mmol) of methyl chloroformate in 1 ml of THF was added dropwise. The mixture was stirred at 0° C. for 30 min and then at RT for a further 16 h. 1.0 ml of pyridine and a further 75 µl (0.88 mmol) of methyl chloroformate were then added, and the mixture was stirred at RT for 30 min. Water was then added, and the reaction mixture was extracted three times with ethyl acetate. The combined organic phases were washed with saturated aqueous sodium chloride solution, dried over magnesium sulfate, filtered and concentrated. The residue was stirred in ethanol, and the solid formed was filtered off, washed with a little ethanol and dried under reduced pressure. This gave 148 mg (65% of theory) of the title compound.

LC-MS (Method 3): $R_t$=1.07 min; m/z=506 (M+H)$^+$.

$^1$H-NMR (400 MHz, DMSO-d$_6$): δ=1.23 (t, 3H), 2.46 (s, 3H), 3.69 (s, 3H), 4.19 (q, 2H), 5.07 (s, 2H), 7.30-7.40 (m, 2H), 7.42-7.48 (m, 2H), 7.55-7.62 (m, 3H), 8.40 (s, 1H), 9.91 (s, 1H).

Example 167

3-[2-Chloro-3-(trifluoromethyl)benzyl]-1-[3,5-dichloro-4-(2-oxoimidazolidin-1-yl)phenyl]-2,4-dioxo-1,2,3,4-tetrahydropyrimidine-5-carboxylic acid

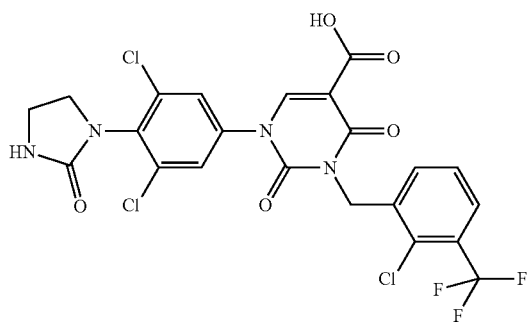 [SMILES: O=C(O)c1cn(-c2cc(Cl)c(N3CCNC3=O)c(Cl)c2)c(=O)n(Cc2cccc(C(F)(F)F)c2Cl)c1=O]

Preparation and purification were carried out analogously to Example 155 using 144 mg (0.24 mmol) of ethyl 3-[2-chloro-3-(trifluoromethyl)benzyl]-1-[3,5-dichloro-4-(2-oxoimidazolidin-1-yl)phenyl]-2,4-dioxo-1,2,3,4-tetrahydropyrimidine-5-carboxylate from Example 127. Yield: 92 mg (65% of theory).

LC-MS (Method 3): $R_t$=1.05 min; m/z=578 (M+H)$^+$.

$^1$H-NMR (400 MHz, DMSO-d$_6$): δ=3.49-3.57 (m, 2H), 3.68-3.75 (m, 2H), 5.16 (s, 2H), 6.91 (s, 1H), 7.49-7.56 (m, 1H), 7.58-7.63 (m, 1H), 7.78-7.83 (m, 1H), 7.87 (s, 2H), 8.65 (s, 1H), 12.75 (br. s., 1H).

Example 168

1-[3,5-Dichloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylic acid

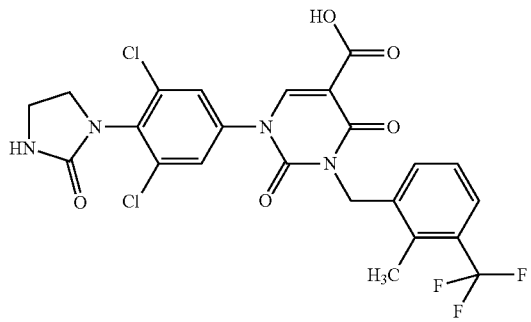 [SMILES: Cc1c(Cn2c(=O)c(C(=O)O)cn(-c3cc(Cl)c(N4CCNC4=O)c(Cl)c3)c2=O)cccc1C(F)(F)F]

Preparation and purification were carried out analogously to Example 155 using 144 mg (0.25 mmol) of ethyl 1-[3,5-dichloro-4-(2-oxoimidazolidin-1-yl)phenyl]-3-[2-methyl-3-(trifluoromethyl)benzyl]-2,4-dioxo-1,2,3,4-tetrahydropyrimidine-5-carboxylate from Example 128. Yield: 101 mg (72% of theory).

LC-MS (Method 3): $R_t$=1.05 min; m/z=558 (M+H)$^+$.

$^1$H-NMR (400 MHz, DMSO-d$_6$): δ=2.47 (s, partially hidden by DMSO signal), 3.50-3.57 (m, 2H), 3.68-3.75 (m, 2H), 5.09 (s, 2H), 6.91 (s, 1H), 7.32-7.38 (m, 1H), 7.39-7.44 (m, 1H), 7.58-7.63 (m, 1H), 7.88 (s, 2H), 8.63 (s, 1H), 12.74 (s, 1H).

Example 169

3-[2-Methyl-3-(trifluoromethyl)benzyl]-2,4-dioxo-1-{4-[(2-oxo-1,3-oxazolidin-3-yl)methyl]phenyl}-1,2,3,4-tetrahydropyrimidine-5-carboxylic acid

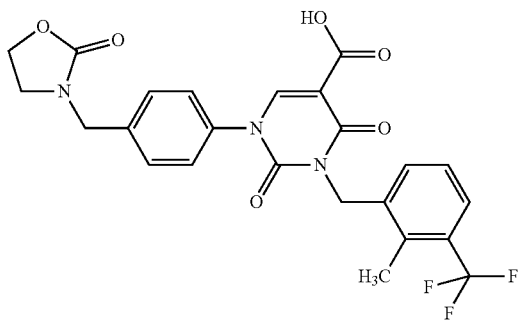 [SMILES: Cc1c(Cn2c(=O)c(C(=O)O)cn(-c3ccc(CN4CCOC4=O)cc3)c2=O)cccc1C(F)(F)F]

265 mg (0.50 mmol) of ethyl 3-[2-methyl-3-(trifluoromethyl)benzyl]-2,4-dioxo-1-{4-[(2-oxo-1,3-oxazolidin-3-yl)methyl]phenyl}-1,2,3,4-tetrahydropyrimidine-5-carboxylate from Example 129 were initially charged in 2.0 ml of glacial acetic acid and 1.0 ml of conc. hydrochloric acid, and the mixture was stirred at 120° C. for 20 min. Water was then added to the reaction mixture which had cooled to RT, and the solid formed was filtered off, washed with water and MTBE and dried under reduced pressure. The crude product was stirred with methanol/DMF/DMSO, filtered off and washed with MTBE, and the solid was dried under reduced pressure. This gave 50 mg (19% of theory) of the title compound.

LC-MS (Method 3): $R_t$=1.02 min; m/z=504 (M+H)$^+$.

$^1$H-NMR (400 MHz, DMSO-d$_6$): δ=2.47 (s, partially hidden by DMSO signal), 3.47 (t, 2H), 4.29 (t, 2H), 4.42 (s, 2H), 5.10 (s, 2H), 7.31-7.37 (m, 1H), 7.38-7.47 (m, 3H), 7.52-7.58 (m, 2H), 7.60 (d, 1H), 8.45 (s, 1H), 12.63 (br. s, 1H).

Example 170

3-[2-Methyl-3-(trifluoromethyl)benzyl]-2,4-dioxo-1-{4-[2-(2-oxo-1,3-oxazolidin-3-yl)ethyl]phenyl}-1,2,3,4-tetrahydropyrimidine-5-carboxylic acid

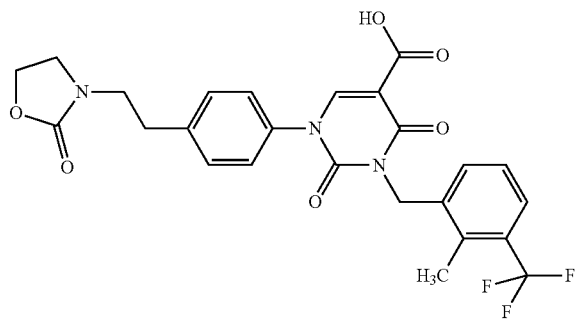 [SMILES: Cc1c(Cn2c(=O)c(C(=O)O)cn(-c3ccc(CCN4CCOC4=O)cc3)c2=O)cccc1C(F)(F)F]

181 mg (0.33 mmol) of ethyl 3-[2-methyl-3-(trifluoromethyl)benzyl]-2,4-dioxo-1-{4-[2-(2-oxo-1,3-oxazolidin-3-yl)ethyl]phenyl}-1,2,3,4-tetrahydropyrimidine-5-carboxylate from Example 131 were initially charged in 2 ml of glacial acetic acid and 1 ml of conc. hydrochloric acid, and the mixture was stirred at 120° C. for 1 h. After cooling to RT, 5 ml of water were added to the reaction mixture, and the solid formed was filtered off, washed with water and dried under reduced pressure. The crude product was chromatographed using preparative HPLC (Method 7a), and the product fractions were concentrated under reduced pressure. This gave 101 mg (59% of theory) of the title compound.

LC-MS (Method 3): $R_t$=1.04 min; m/z=518 (M+H)$^+$.

$^1$H-NMR (400 MHz, DMSO-d$_6$): δ=2.47 (s, partially hidden by DMSO signal), 2.88 (t, 2H), 3.43 (t, 2H), 3.49-3.55 (m, 2H), 4.18-4.25 (m, 2H), 5.10 (s, 2H), 7.32-7.37 (m, 1H), 7.38-7.44 (m, 3H), 7.45-7.50 (m, 2H), 7.60 (d, 1H), 8.43 (s, 1H), 12.72 (br. s., 1H).

Example 171

3-[2-Chloro-3-(trifluoromethyl)benzyl]-1-[4-(3-methyl-2-oxoimidazolidin-1-yl)phenyl]-2,4-dioxo-1,2,3,4-tetrahydropyrimidine-5-carboxylic acid

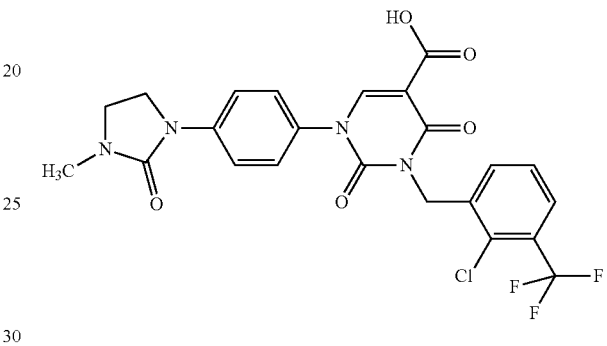

Preparation and purification were carried out analogously to Example 148 using 159 mg (0.29 mmol) of ethyl 3-[2-chloro-3-(trifluoromethyl)benzyl]-1-[4-(3-methyl-2-oxoimidazolidin-1-yl)phenyl]-2,4-dioxo-1,2,3,4-tetrahydropyrimidine-5-carboxylate from Example 130. Yield: 133 mg (88% of theory).

LC-MS (Method 3): $R_t$=1.06 min; m/z=523 (M+H)$^+$.

$^1$H-NMR (400 MHz, DMSO-d$_6$): δ=2.78 (s, 3H), 3.44-3.50 (m, 2H), 3.79-3.86 (m, 2H), 5.16 (s, 2H), 7.45-7.51 (m, 2H), 7.53 (d, 1H), 7.60 (d, 1H), 7.67-7.73 (m, 2H), 7.80 (d, 1H), 8.44 (s, 1H), 12.70 (br. s, 1H).

Example 172

3-[2-Chloro-3-(trifluoromethyl)benzyl]-1-[4-(4-methyl-2-oxoimidazolidin-1-yl)phenyl]-2,4-dioxo-1,2,3,4-tetrahydropyrimidine-5-carboxylic acid (racemate)

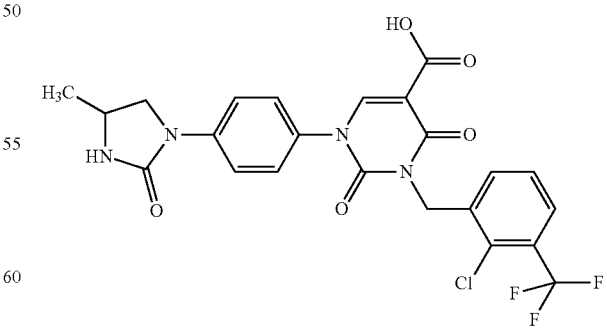

Preparation and purification were carried out analogously to Example 148 using 240 mg (0.44 mmol) of ethyl 3-[2-chloro-3-(trifluoromethyl)benzyl]-1-[4-(4-methyl-2-oxoimidazolidin-1-yl)phenyl]-2,4-dioxo-1,2,3,4-tetrahydropyrimidine-5-carboxylate (racemate) from Example 132. Yield: 194 mg (84% of theory).

LC-MS (Method 3): $R_t$=1.01 min; m/z=523 (M+H)$^+$.

$^1$H-NMR (400 MHz, DMSO-d$_6$): δ=1.21 (d, 3H), 3.42 (dd, 1H), 3.77-3.87 (m, 1H), 4.00 (t, 1H), 5.16 (s, 2H), 7.28 (s, 1H), 7.43-7.49 (m, 2H), 7.52 (t, 1H), 7.60 (d, 1H), 7.65-7.70 (m, 2H), 7.80 (d, 1H), 8.43 (s, 1H), 12.70 (br. s., 1H).

Example 173

1-[4-(4,4-Dimethyl-2-oxoimidazolidin-1-yl)phenyl]-3-[3-fluoro-2-(trifluoromethyl)benzyl]-2,4-dioxo-1,2,3,4-tetrahydropyrimidine-5-carboxylic acid

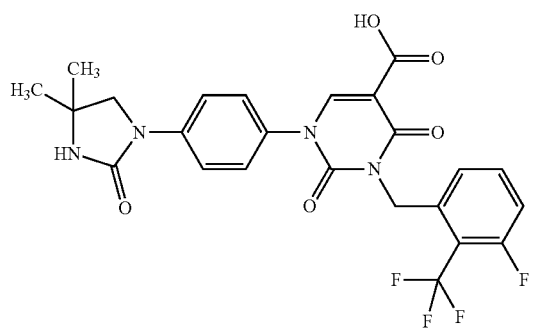 [SMILES: CC1(C)CN(c2ccc(-n3cc(C(=O)O)c(=O)n(Cc4cccc(F)c4C(F)(F)F)c3=O)cc2)C(=O)N1]

The preparation and purification were carried out analogously to Example 148 using 220 mg (0.40 mmol) of ethyl 1-[4-(4,4-dimethyl-2-oxoimidazolidin-1-yl)phenyl]-3-[3-fluoro-2-(trifluoromethyl)benzyl]-2,4-dioxo-1,2,3,4-tetrahydropyrimidine-5-carboxylate from Example 133. Yield: 153 mg (72% of theory).

LC-MS (Method 3): $R_t$=1.00 min; m/z=521 (M+H)$^+$.

$^1$H-NMR (400 MHz, DMSO-d$_6$): δ=1.29 (s, 6H), 3.62 (s, 2H), 5.21 (s, 2H), 7.21 (d, 1H), 7.31 (s, 1H), 7.37-7.42 (m, 1H), 7.43-7.48 (m, 2H), 7.62-7.69 (m, 3H), 8.43 (s, 1H), 12.69 (s, 1H).

Example 174

1-{4-[(Methoxycarbonyl)(methyl)amino]phenyl}-3-[2-methyl-3-(trifluoromethyl)benzyl]-2,4-dioxo-1,2,3,4-tetrahydropyrimidine-5-carboxylic acid

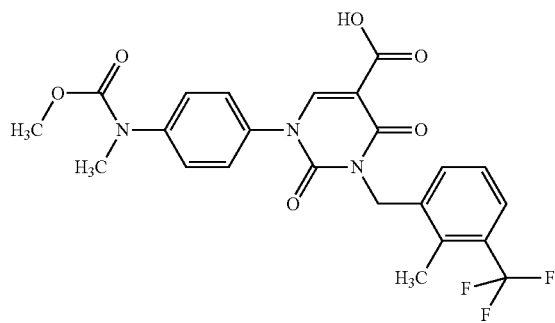 [SMILES: COC(=O)N(C)c1ccc(-n2cc(C(=O)O)c(=O)n(Cc3cccc(C(F)(F)F)c3C)c2=O)cc1]

The preparation and purification were carried out analogously to Example 148 using 220 mg (0.42 mmol) of ethyl 1-{4-[(methoxycarbonyl)(methyl)amino]phenyl}-3-[2-methyl-3-(trifluoromethyl)benzyl]-2,4-dioxo-1,2,3,4-tetrahydropyrimidine-5-carboxylate from Example 134. Yield: 165 mg (78% of theory).

LC-MS (Method 3): $R_t$=1.07 min; m/z=492 (M+H)$^+$.

$^1$H-NMR (400 MHz, DMSO-d$_6$): δ=2.47 (s, partially hidden by DMSO signal), 3.26 (s, 3H), 3.64 (s, 3H), 5.11 (s, 2H), 7.31-7.37 (m, 1H), 7.39-7.43 (m, 1H), 7.45-7.51 (m, 2H), 7.52-7.57 (m, 2H), 7.60 (d, 1H), 8.47 (s, 1H), 12.71 (br. s, 1H).

Example 175

3-(3-Chloro-2-methylbenzyl)-1-(3,4-dimethoxyphenyl)-2,4-dioxo-1,2,3,4-tetrahydropyrimidine-5-carboxylic acid

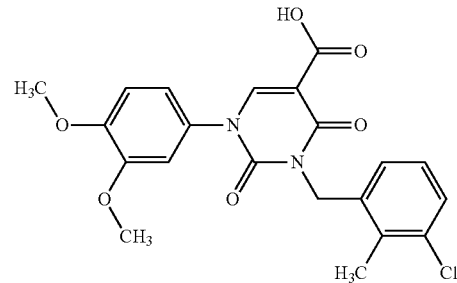 [SMILES: COc1ccc(-n2cc(C(=O)O)c(=O)n(Cc3cccc(Cl)c3C)c2=O)cc1OC]

The preparation and purification were carried out analogously to Example 148 using 205 mg (0.45 mmol) of ethyl 3-(3-chloro-2-methylbenzyl)-1-(3,4-dimethoxyphenyl)-2,4-dioxo-1,2,3,4-tetrahydropyrimidine-5-carboxylate from Example 135. Yield: 151 mg (77% of theory).

LC-MS (Method 3): $R_t$=1.04 min; m/z=431 (M+H)$^+$.

$^1$H-NMR (400 MHz, DMSO-d$_6$): δ=2.41 (s, 3H), 3.76 (s, 3H), 3.80 (s, 3H), 5.07 (s, 2H), 7.04-7.09 (m, 3H), 7.16 (t, 1H), 7.20 (s, 1H), 7.35 (d, 1H), 8.41 (s, 1H), 12.71 (br. s., 1H).

Example 176

1-(3,4-Dimethoxyphenyl)-3-(3-fluoro-2-methylbenzyl)-2,4-dioxo-1,2,3,4-tetrahydropyrimidine-5-carboxylic acid

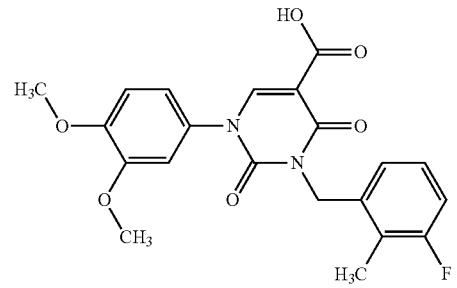 [SMILES: COc1ccc(-n2cc(C(=O)O)c(=O)n(Cc3cccc(F)c3C)c2=O)cc1OC]

141 mg (0.32 mmol) of ethyl 1-(3,4-dimethoxyphenyl)-3-(3-fluoro-2-methylbenzyl)-2,4-dioxo-1,2,3,4-tetrahydropyrimidine-5-carboxylate from Example 136 were stirred in 2 ml of glacial acetic acid and 1 ml of conc. hydrochloric acid at 120° C. for 15 min 5 ml of water were then added to the reaction mixture which had cooled to RT, and the solid formed was filtered off, washed with water and dried under reduced pressure. The crude product was chromatographed using preparative HPLC (Method 7a), and the product fractions were concentrated under reduced pressure. This gave 47 mg (36% of theory) of the title compound.

LC-MS (Method 1): $R_t$=1.33 min; m/z=415 (M+H)$^+$.

$^1$H-NMR (400 MHz, DMSO-d$_6$): δ=2.26-2.29 (m, 3H), 3.76 (s, 3H), 3.80 (s, 3H), 5.05 (s, 2H), 6.94 (d, 1H), 7.03-7.10 (m, 3H), 7.13-7.21 (m, 2H), 8.40 (s, 1H), 12.71 (br. s., 1H).

Example 177

1-(3,4-Dimethoxyphenyl)-2,4-dioxo-3-{1-[3-(trifluoromethyl)phenyl]propyl}-1,2,3,4-tetrahydropyrimidine-5-carboxylic acid

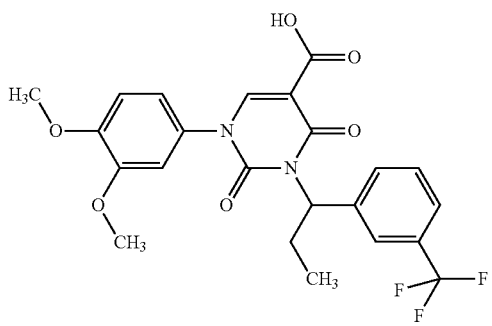 [SMILES: CCC(c1cccc(C(F)(F)F)c1)n1c(=O)c(C(=O)O)cn(-c2ccc(OC)c(OC)c2)c1=O]

110 mg (0.22 mmol) of ethyl 1-(3,4-dimethoxyphenyl)-2,4-dioxo-3-{1-[3-(trifluoromethyl)phenyl]propyl}-1,2,3,4-tetrahydropyrimidine-5-carboxylate from Example 137 were stirred in 2 ml of glacial acetic acid and 1 ml of conc. hydrochloric acid at 120° C. for 30 min 5 ml of water were then added to the reaction mixture which had cooled to RT, and the solid formed was filtered off, washed with water and dried under reduced pressure. This gave 55 mg (50% of theory) of the title compound.

LC-MS (Method 3): R$_t$=1.13 min; m/z=479 (M+H)$^+$.

$^1$H-NMR (400 MHz, DMSO-d$_6$): δ=0.93 (t, 3H), 2.32-2.44 (m, partially hidden by DMSO signal), 3.75 (s, 3H), 3.79 (s, 3H), 5.93-6.04 (m, 1H), 6.97-7.07 (m, 2H), 7.15 (s, 1H), 7.54-7.61 (m, 1H), 7.61-7.67 (m, 1H), 7.69-7.75 (m, 2H), 8.34 (s, 1H), 12.71 (br. s, 1H).

Example 178

3-(3-Chloro-2-methylbenzyl)-2,4-dioxo-1-[4-(2-oxo-1,3-oxazolidin-3-yl)phenyl]-1,2,3,4-tetrahydropyrimidine-5-carboxylic acid

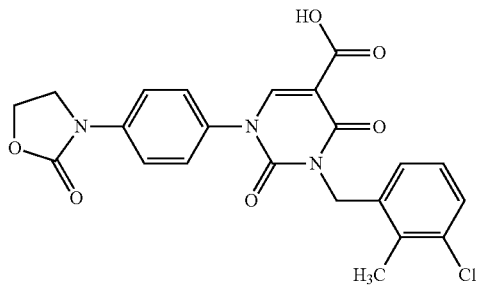 [SMILES: Cc1c(Cl)cccc1Cn1c(=O)c(C(=O)O)cn(-c2ccc(N3CCOC3=O)cc2)c1=O]

48 mg (0.10 mmol) of ethyl 3-(3-chloro-2-methylbenzyl)-2,4-dioxo-1-[4-(2-oxo-1,3-oxazolidin-3-yl)phenyl]-1,2,3,4-tetrahydropyrimidine-5-carboxylate from Example 138 were stirred in 0.8 ml of glacial acetic acid and 0.4 ml of conc. hydrochloric acid at 120° C. for 1 h. 5 ml of water were then added to the reaction mixture which had cooled to RT, and the solid formed was filtered off, washed with water and acetonitrile and dried under reduced pressure. This gave 33 mg (70% of theory) of the title compound.

LC-MS (Method 3): R$_t$=1.02 min; m/z=456 (M+H)$^+$.

$^1$H-NMR (400 MHz, DMSO-d$_6$): δ=2.41 (s, 3H), 4.08-4.13 (m, 2H), 4.43-4.50 (m, 2H), 5.07 (s, 2H), 7.08 (d, 1H), 7.16 (t, 1H), 7.35 (d, 1H), 7.53-7.59 (m, 2H), 7.68-7.73 (m, 2H), 8.44 (s, 1H), 12.72 (br. s., 1H).

Example 179

3-(4-Methyl-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylic acid (racemate)

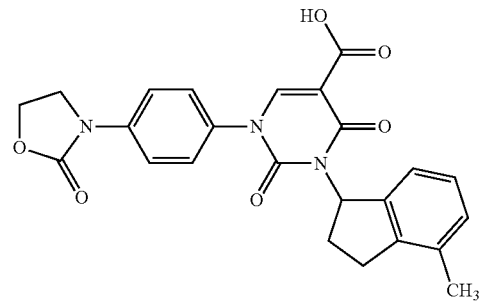 [SMILES: Cc1cccc2c1CCC2n1c(=O)c(C(=O)O)cn(-c2ccc(N3CCOC3=O)cc2)c1=O]

58 mg (0.12 mmol) of ethyl 3-(4-methyl-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylate (racemate) from Example 139 were initially charged in 1.0 ml of glacial acetic acid and 0.5 ml of conc. hydrochloric acid, and the mixture was stirred at 120° C. for 10 min 5 ml of water were then added to the reaction mixture which had cooled to RT, and the solid formed was filtered off, washed with water and dried under reduced pressure. This gave 7 mg (11% of theory) of the title compound.

LC-MS (Method 3): R$_t$=1.00 min; m/z=448 (M+H)$^+$.

$^1$H-NMR (400 MHz, DMSO-d$_6$): δ=2.22 (s, 3H), 2.31-2.46 (m, partially hidden by DMSO signal), 2.77-2.90 (m, 1H), 3.00-3.13 (m, 1H), 4.04-4.14 (m, 2H), 4.42-4.51 (m, 2H), 6.43 (br. s., 1H), 6.96-7.08 (m, 3H), 7.51 (br. s., 2H), 7.61-7.72 (m, 2H), 8.34 (s, 1H), 12.75 (br. s, 1H).

Example 180

3-(2-Chloro-3,6-difluorobenzyl)-2,4-dioxo-1-[4-(2-oxo-1,3-oxazolidin-3-yl)phenyl]-1,2,3,4-tetrahydropyrimidine-5-carboxylic acid

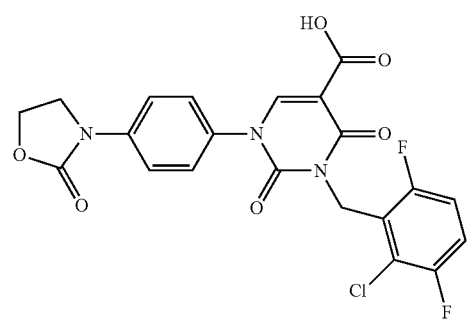 [SMILES: O=C(O)c1cn(-c2ccc(N3CCOC3=O)cc2)c(=O)n(Cc2c(F)ccc(F)c2Cl)c1=O]

133 mg (0.26 mmol) of ethyl 3-(2-chloro-3,6-difluorobenzyl)-2,4-dioxo-1-[4-(2-oxo-1,3-oxazolidin-3-yl)phenyl]-1,2,3,4-tetrahydropyrimidine-5-carboxylate from Example 140 were stirred in 2 ml of glacial acetic acid and 1 ml of conc. hydrochloric acid at 120° C. for 45 min 5 ml of water were then added to the reaction mixture which had cooled to RT, and the solid formed was filtered off, washed with water and diethyl ether/ethyl acetate (1:1) and dried under reduced pressure. This gave 101 mg (81% of theory) of the title compound.

LC-MS (Method 3): $R_t$=0.96 min; m/z=478 (M+H)$^+$.

$^1$H-NMR (400 MHz, DMSO-d$_6$): δ=4.06-4.13 (m, 2H), 4.43-4.51 (m, 2H), 5.23 (s, 2H), 7.24-7.32 (m, 1H), 7.40-7.47 (m, 1H), 7.47-7.53 (m, 2H), 7.66-7.72 (m, 2H), 8.39 (s, 1H), 12.73 (br. s, 1H).

Example 181

1-(3,4-Dimethoxyphenyl)-2,4-dioxo-3-[4-(trifluoromethyl)-2,3-dihydro-1H-inden-1-yl]-1,2,3,4-tetrahydropyrimidine-5-carboxylic acid (racemate)

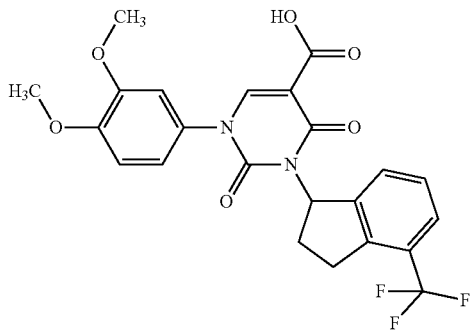 [SMILES: COc1ccc(-n2cc(C(=O)O)c(=O)n(C3CCc4c3cccc4C(F)(F)F)c2=O)cc1OC]

100 mg (0.20 mmol) of ethyl 1-(3,4-dimethoxyphenyl)-2,4-dioxo-3-[4-(trifluoromethyl)-2,3-dihydro-1H-inden-1-yl]-1,2,3,4-tetrahydropyrimidine-5-carboxylate (racemate) from Example 141 were initially charged in 5 ml of acetonitrile/water (1:1), 37 mg (0.44 mmol) of sodium bicarbonate were added and the mixture was stirred at 70° C. overnight. The reaction mixture cooled to RT was acidified with 1 M aqueous hydrochloric acid and extracted twice with ethyl acetate. The combined organic phases were dried over magnesium sulfate, filtered and concentrated under reduced pressure. The residue was chromatographed using preparative HPLC (Method 7a), and the product fractions were partially concentrated under reduced pressure. The precipitate formed was filtered off and dried under reduced pressure. This gave 40 mg (41% of theory) of the title compound.

LC-MS (Method 3): $R_t$=1.09 min; m/z=477 (M+H)$^+$.

$^1$H-NMR (400 MHz, DMSO-d$_6$): δ=2.38-2.49 (m, partially hidden by DMSO signal), 3.04-3.15 (m, 1H), 3.24-3.29 (m, partially hidden by water signal), 3.76 (s, 3H), 3.79 (s, 3H), 6.47 (br. s, 1H), 6.93-7.23 (m, 3H), 7.34-7.41 (m, 1H), 7.48-7.57 (m, 2H), 8.34 (s, 1H), 12.68 (br. s, 1H).

Example 182

Ethyl 3-[2,3-bis(trifluoromethyl)benzyl]-1-(3,4-dimethoxyphenyl)-2,4-dioxo-1,2,3,4-tetrahydropyrimidine-5-carboxylate

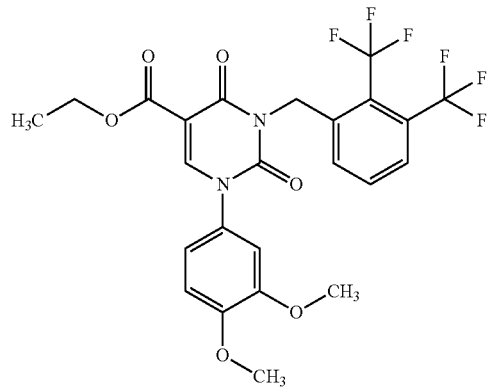 [SMILES: CCOC(=O)c1cn(-c2ccc(OC)c(OC)c2)c(=O)n(Cc2cccc(C(F)(F)F)c2C(F)(F)F)c1=O]

202 mg (0.49 mmol) of ethyl 3-[2,3-bis(trifluoromethyl)benzyl]-2,4-dioxo-1,2,3,4-tetrahydropyrimidine-5-carboxylate from Example 126A and 179 mg (0.99 mmol) of 3,4-dimethoxyphenylboronic acid were initially charged in 3.3 ml of dichloromethane, 439 mg of molecular sieve 3 Å and 134.1 mg (1.48 mmol) of copper(II) acetate were added and the mixture was stirred at RT overnight. The reaction mixture was diluted with ethyl acetate and washed twice with 1N aqueous hydrochloric acid, once with saturated aqueous sodium bicarbonate solution and once with saturated aqueous sodium chloride solution. The organic phase was dried over magnesium sulfate, filtered and concentrated. The residue was stirred in MTBE and the solid was filtered off and dried under reduced pressure. This gave 141 mg (52% of theory) of the target compound.

LC-MS (Method 3): $R_t$=1.16 min; MS (ESIpos): m/z=547 (M+H)$^+$.

$^1$H-NMR (400 MHz, DMSO-d$_6$): δ=1.23 (t, 3H), 3.77 (s, 3H), 3.81 (s, 3H), 4.20 (q, 2H), 5.24 (s, 2H), 7.07 (s, 2H), 7.19 (s, 1H), 7.72 (d, 1H), 7.83 (t, 1H), 7.97 (d, 1H), 8.42 (s, 1H).

Example 183

3-[2,3-Bis(trifluoromethyl)benzyl]-1-(3,4-dimethoxyphenyl)-2,4-dioxo-1,2,3,4-tetrahydropyrimidine-5-carboxylic acid

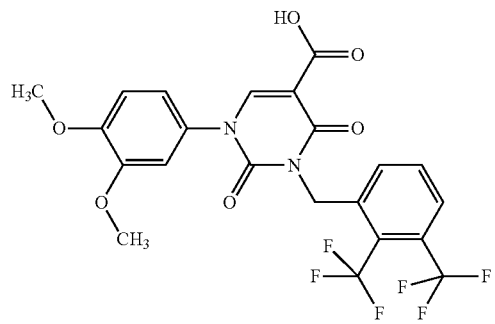 [SMILES: COc1ccc(-n2cc(C(=O)O)c(=O)n(Cc3cccc(C(F)(F)F)c3C(F)(F)F)c2=O)cc1OC]

Preparation and purification were carried out analogously to Example 155 using 141 mg (0.26 mmol) of ethyl 3-[2,3-bis(trifluoromethyl)benzyl]-1-(3,4-dimethoxyphenyl)-2,4-dioxo-1,2,3,4-tetrahydropyrimidine-5-carboxylate from Example 182. Yield: 85 mg (62% of theory).

LC-MS (Method 3): $R_t$=1.09 min; m/z=519 (M+H)$^+$.

$^1$H-NMR (400 MHz, DMSO-d$_6$): δ=3.77 (s, 3H), 3.81 (s, 3H), 5.26 (br. s., 2H), 7.07 (s, 2H), 7.18 (s, 1H), 7.74 (d, 1H), 7.84 (t, 1H), 7.97 (d, 1H), 8.44 (s, 1H), 12.70 (br. s, 1H).

Example 184

3-(4-Chloro-2,3-dihydro-1H-inden-1-yl)-1-(3,4-dimethoxyphenyl)-2,4-dioxo-1,2,3,4-tetrahydropyrimidine-5-carboxylic acid (racemate)

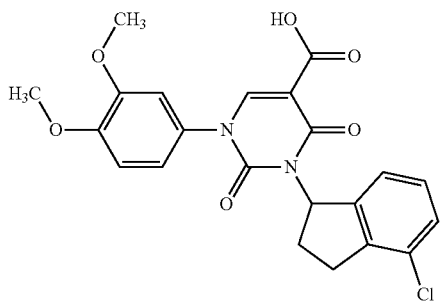 [SMILES: COc1ccc(-n2cc(C(=O)O)c(=O)n(C3CCc4c(Cl)cccc43)c2=O)cc1OC]

Preparation and purification were carried out analogously to Example 181 using 128 mg (0.27 mmol) of ethyl 3-(4-chloro-2,3-dihydro-1H-inden-1-yl)-1-(3,4-dimethoxyphenyl)-2,4-dioxo-1,2,3,4-tetrahydropyrimidine-5-carboxylate from Example 143. Yield: 57 mg (46% of theory).

LC-MS (Method 1): $R_t$=1.30 min; m/z=443 (M+H)$^+$.

$^1$H-NMR (400 MHz, DMSO-d$_6$): δ=2.34-2.50 (m, partially hidden by DMSO signal), 2.89-3.01 (m, 1H), 3.07-3.20 (m, 1H), 3.76 (s, 3H), 3.79 (s, 3H), 6.47 (br. s., 1H), 6.97-7.08 (m, 2H), 7.11-7.22 (m, 3H), 7.24-7.29 (m, 1H), 8.34 (s, 1H), 12.68 (br. s., 1H).

Example 185

3-(4-Chloro-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylic acid (racemate)

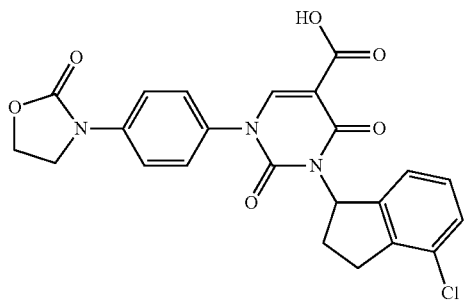 [SMILES: O=C(O)c1cn(-c2ccc(N3CCOC3=O)cc2)c(=O)n(C2CCc3c(Cl)cccc32)c1=O]

164 mg (0.33 mmol) of ethyl 3-(4-chloro-2,3-dihydro-1H-inden-1-yl)-2,4-dioxo-1-[4-(2-oxo-1,3-oxazolidin-3-yl)phenyl]-1,2,3,4-tetrahydropyrimidine-5-carboxylate (racemate) from Example 144 were initially charged in 6 ml of acetonitrile/water (1:1), 61 mg (0.73 mmol) of sodium bicarbonate were added and the mixture was stirred at 70° C. overnight. Subsequently, another 61 mg of sodium bicarbonate were added and the mixture was stirred at 70° C. for a further 2 days. The reaction mixture cooled to RT was acidified with 1 N aqueous hydrochloric acid and the mixture was extracted twice with ethyl acetate. The collected organic phases were dried over magnesium sulfate, filtered and concentrated under reduced pressure. The residue was stirred with acetonitrile and filtered off and the solid was chromatographed using preparative HPLC (Method 7a). The product fractions were partially concentrated under reduced pressure. The precipitate formed was filtered off and dried under reduced pressure. This gave 52 mg (33% of theory) of the title compound.

LC-MS (Method 3): $R_t$=1.07 min; m/z=468 (M+H)$^+$.

$^1$H-NMR (400 MHz, DMSO-d$_6$): δ=2.32-2.50 (m, partially hidden by DMSO signal), 2.90-3.01 (m, 1H), 3.07-3.20 (m, partially hidden by water signal), 4.04-4.15 (m, 2H), 4.41-4.52 (m, 2H), 6.49 (br. s., 1H), 7.14-7.30 (m, 3H), 7.45-7.57 (m, 2H), 7.64-7.72 (m, 2H), 8.38 (s, 1H), 12.70 (br. s, 1H).

Example 186

3-[3-Chloro-2-(trifluoromethyl)benzyl]-1-[4-(3,5-dimethyl-1H-pyrazol-1-yl)phenyl]-2,4-dioxo-1,2,3,4-tetrahydropyrimidine-5-carboxylic acid

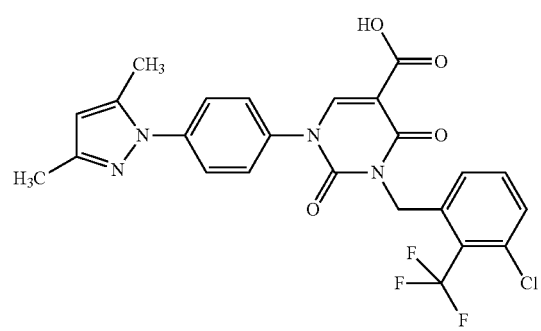 [SMILES: Cc1cc(C)n(-c2ccc(-n3cc(C(=O)O)c(=O)n(Cc4cccc(Cl)c4C(F)(F)F)c3=O)cc2)n1]

The preparation and purification were carried out analogously to Example 179 using 68 mg (0.12 mmol) of ethyl 3-[3-chloro-2-(trifluoromethyl)benzyl]-1-[4-(3,5-dimethyl-1H-pyrazol-1-yl)phenyl]-2,4-dioxo-1,2,3,4-tetrahydropyrimidine-5-carboxylate from Example 145. Yield: 54 mg (79% of theory).

LC-MS (Method 1): $R_t$=1.37 min; m/z=519 (M+H)$^+$.

$^1$H-NMR (400 MHz, DMSO-d$_6$): δ=2.19 (s, 3H), 2.35 (s, 3H), 5.25 (br. s., 2H), 6.12 (s, 1H), 7.38 (d, 1H), 7.60 (t, 1H), 7.63-7.69 (m, 5H), 8.55 (s, 1H), 12.75 (br. s., 1H).

Example 187

2,4-Dioxo-1-[4-(2-oxo-1,3-oxazolidin-3-yl)phenyl]-3-[(1R)-4-(trifluoromethyl)-2,3-dihydro-1H-inden-1-yl]-1,2,3,4-tetrahydropyrimidine-5-carboxylic acid (R enantiomer)

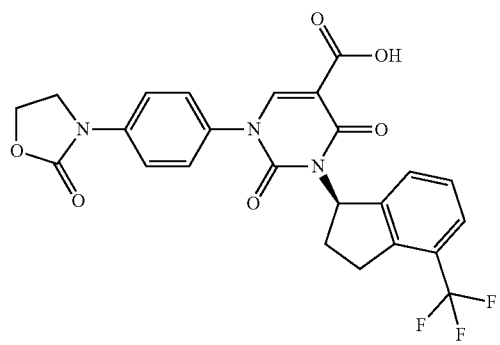 [SMILES: O=C(O)c1cn(-c2ccc(N3CCOC3=O)cc2)c(=O)n([C@@H]2CCc3c2cccc3C(F)(F)F)c1=O]

7.6 g (13.1 mmol) of the compound from Example 146, 82.7 ml of glacial acetic acid and 41.4 ml of conc. hydrochloric acid were heated at reflux for 1 h. After cooling to RT, the reaction mixture was stirred into 1500 ml of water. The solid formed was filtered off with suction, washed with a little water and dried under high vacuum. The residue was then dissolved in a little DMSO and purified by preparative HPLC (Method 8). This gave 4.75 g (72% of theory) of the title compound.

LC-MS (Method 3): $R_t$=1.09 min; MS (ESIpos): m/z=502 (M+H)$^+$.

$^1$H-NMR (400 MHz, $CD_2Cl_2$): δ [ppm]=2.31-2.45 (m, 1H), 2.57 (dtd, 1H), 3.02-3.18 (m, 1H), 3.31-3.50 (m, 1H), 3.88-4.06 (m, 2H), 4.33-4.49 (m, 2H), 6.56 (br. s., 1H), 7.16-7.36 (m, 4H), 7.45 (d, 1H), 7.62 (d, 2H), 8.46 (s, 1H).

Example 188

1-[3-Chloro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylic acid

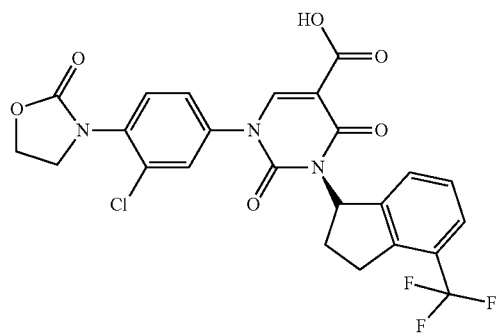

95 mg (0.17 mmol) of ethyl 1-[3-chloro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylate (R enantiomer) from Example 147 were initially charged in 2 ml of glacial acetic acid and 1 ml of conc. hydrochloric acid, and the mixture was stirred at 120° C. for 45 min 20 ml of water were then added to the reaction mixture which had cooled to RT, and the mixture was extracted twice with ethyl acetate. The combined organic phases were dried over magnesium sulfate, filtered and concentrated under reduced pressure. The residue was chromatographed using preparative HPLC (Method 7a), and the product fractions were partially concentrated under reduced pressure. The precipitate formed was filtered off and dried under vacuum. This gave 47 mg (52% of theory) of the title compound.

LC-MS (Method 3): $R_t$=1.10 min; m/z=536 (M+H)$^+$.

$^1$H-NMR (400 MHz, $CD_2Cl_2$): δ=2.32-2.43 (m, 1H), 2.52-2.64 (m, 1H), 3.05-3.16 (m, 1H), 3.37-3.48 (m, 1H), 3.95 (t, 2H), 4.46 (t, 2H), 6.52-6.60 (m, 1H), 7.22-7.31 (m, 3H), 7.42-7.55 (m, 3H), 8.44 (s, 1H), 12.27 (br. s., 1H).

$[α]_D^{21}$=+133° (c=0.42, chloroform).

Example 189

Ethyl 1-[2-fluoro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylate (R enantiomer)

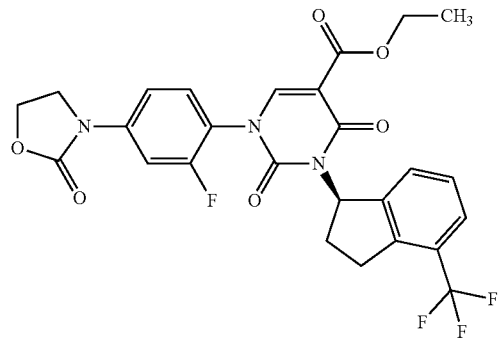 [SMILES: CCOC(=O)c1cn(-c2ccc(N3CCOC3=O)cc2F)c(=O)n([C@@H]2CCc3c2cccc3C(F)(F)F)c1=O]

Under argon, 166.9 mg (0.82 mmol) of ethyl 1-[2-fluoro-4-(2-oxo-1,3-oxazolidin-3-yl)phenyl]-2,4-dioxo-1,2,3,4-tetrahydropyrimidine-5-carboxylate from Example 76A and 541.4 mg (2.06 mmol) of triphenylphosphine were initially charged in THF/DMF 1:1 (8 ml), 270.9 μl (1.37 mmol) of diisopropyl azodicarboxylate and 166.9 mg (0.83 mmol) of (S)-4-(trifluoromethyl)indan-1-ol from Example 128A were added and the mixture was stirred at RT overnight. 1 ml of 1 N aqueous hydrochloric acid was added and the reaction mixture was diluted with 50 ml of ethyl acetate and washed twice with 30 ml of 1 N aqueous hydrochloric acid and once with saturated aqueous sodium chloride solution. The organic phase was dried over magnesium sulfate, filtered and concentrated. The solid was purified by flash chromatography (dichloromethane/methanol 98:2). The product fractions were concentrated, re-purified by preparative HPLC (Method 8) and concentrated. This gave 140.6 mg (35% of theory) of the target compound.

LC-MS (Method 3): $R_t$=1.15 min; MS (ESIpos): m/z=548 (M+H)$^+$.

$^1$H-NMR (400 MHz, $CDCl_3$): δ=1.36 (t, 3H), 2.38-2.50 (m, 1H), 2.52-2.60 (m, 1H), 3.07-3.19 (m, 1H), 3.44-3.56 (m, 1H), 4.06 (t, 2H), 4.35 (q, 2H), 4.53 (t, 2H), 6.58-6.71 (m, 1H), 7.22-7.30 (m, 2H, hidden by $CDCl_3$ signal), 7.31-

7.38 (m, 2H), 7.44-7.49 (m, 1H), 7.62-7.69 (m, 1H), 8.20 (s, 1H).

$[\alpha]_D^{21} = 111.4°$, c=0.39, chloroform.

Example 190

1-[2-Fluoro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

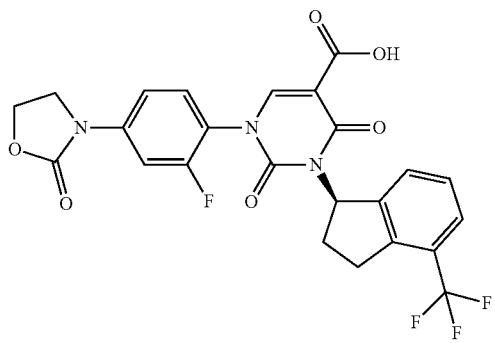 [SMILES: O=C(O)c1cn(-c2ccc(N3CCOC3=O)cc2F)c(=O)n([C@@H]2CCc3c2cccc3C(F)(F)F)c1=O]

114.4 mg (0.21 mmol) of ethyl 1-[2-fluoro-4-(2-oxo-1,3-oxazolidin-3-yl)phenyl]-2,4-dioxo-3-[(1R)-4-(trifluoromethyl)-2,3-dihydro-1H-inden-1-yl]-1,2,3,4-tetrahydropyrimidine-5-carboxylate from Example 189 were initially charged in glacial acetic acid/conc. hydrochloric acid 2:1 (3 ml), and the mixture was stirred at 120° C. for 45 min. The reaction mixture was cooled to RT, 5 ml of water were added and the solid formed was filtered off, washed with water and dried under reduced pressure. This gave 66.4 mg (61% of theory) of the target compound.

LC-MS (Method 3): $R_t$=1.12 min; MS (ESIpos): m/z=520 (M+H)$^+$.

$^1$H-NMR (400 MHz, CD$_2$Cl$_2$): δ=2.32-2.44 (m, 1H), 2.51-2.64 (m, 1H), 3.03-3.15 (m, 1H), 3.33-3.48 (m, 1H), 3.97 (t, 2H), 4.42 (t, 2H), 6.49-6.60 (m, 1H), 7.21-7.34 (m, 4H), 7.42-7.49 (m, 1H), 7.64 (d, 1H), 8.39 (s, 1H).

$[\alpha]_D^{21} = +130.9°$, c=0.37, chloroform.

Example 191

Ethyl 2,4-dioxo-1-[4-(2-oxoimidazolidin-1-yl)phenyl]-3-[(1R)-4-(trifluoromethyl)-2,3-dihydro-1H-inden-1-yl]-1,2,3,4-tetrahydropyrimidine-5-carboxylate (R enantiomer)

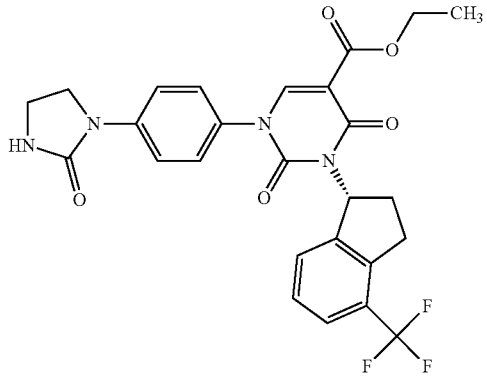 [SMILES: CCOC(=O)c1cn(-c2ccc(N3CCNC3=O)cc2)c(=O)n([C@@H]2CCc3c2cccc3C(F)(F)F)c1=O]

345 mg (0.54 mmol) of ethyl 1-{4-[3-(tert-butoxycarbonyl)-2-oxoimidazolidin-1-yl]phenyl}-2,4-dioxo-3-[(1R)-4-(trifluoromethyl)-2,3-dihydro-1H-inden-1-yl]-1,2,3,4-tetrahydropyrimidine-5-carboxylate (R enantiomer) from Example 133A were initially charged in 2 ml of hydrogen chloride solution (4.0 M in dioxane), and the mixture was stirred at RT for 30 min. The mixture was then neutralized (pH 7) with saturated aqueous sodium bicarbonate solution and extracted twice with ethyl acetate. The combined organic phases were washed twice with saturated aqueous sodium chloride solution, dried over magnesium chloride, filtered and concentrated. The residue was purified by preparative HPLC (Method 8). This gave 191 mg (65% of theory) of the title compound.

LC-MS (Method 11): $R_t$=1.05 min; m/z=529 (M+H)$^+$.

$^1$H-NMR (400 MHz, DMSO-d$_6$): δ=1.22 (t, 3H), 2.37-2.42 (m, 1H), 2.43-2.48 (m, 1H), 3.02-3.14 (m, 1H), 3.21-3.29 (m, 1H), 3.43 (t, 2H), 3.86 (t, 2H), 4.18 (q, 2H), 6.30-6.61 (m, 1H), 7.10 (s, 1H), 7.31-7.45 (m, 3H), 7.48 (d, 1H), 7.53 (d, 1H), 7.66 (d, 2H), 8.31 (s, 1H).

$[\alpha]_D^{21} = +139.7°$, c=0.46, chloroform.

Example 192

2,4-Dioxo-1-[4-(2-oxoimidazolidin-1-yl)phenyl]-3-[(1R)-4-(trifluoromethyl)-2,3-dihydro-1H-inden-1-yl]-1,2,3,4-tetrahydropyrimidine-5-carboxylic acid

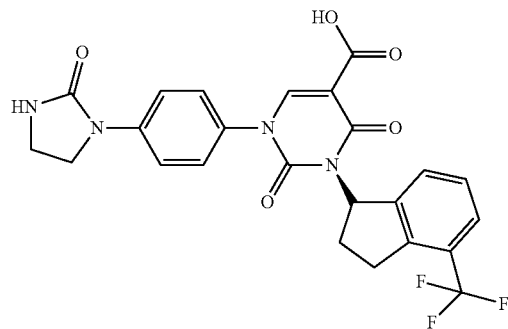

41 mg (0.08 mmol) of ethyl 2,4-dioxo-1-[4-(2-oxoimidazolidin-1-yl)phenyl]-3-[(1R)-4-(trifluoromethyl)-2,3-dihydro-1H-inden-1-yl]-1,2,3,4-tetrahydropyrimidine-5-carboxylate from Example 191 were stirred in 2 ml of glacial acetic acid and 1 ml of conc. hydrochloric acid at 120° C. for 30 min. The reaction mixture, which had cooled to RT, was then added to 20 ml of water, and the solid formed was filtered off, washed with 50 ml of water and dried under reduced pressure. This gave 20 mg (48% of theory) of the title compound.

LC-MS (Method 3): $R_t$=1.01 min; m/z=501 (M+H)$^+$.

$^1$H-NMR (400 MHz, CDCl$_3$): δ=2.41-2.53 (m, 1H), 2.57-2.69 (m, 1H), 3.12-3.23 (m, 1H), 3.49-3.66 (m, 3H), 3.91-4.01 (m, 2H), 4.81 (s, 1H), 6.59-6.69 (m, 1H), 7.25-7.33 (m, partially hidden by CHCl$_3$ signal), 7.50-7.55 (m, 1H), 7.67-7.73 (m, 2H), 8.56 (s, 1H), 12.46 (br. s, 1H).

$[\alpha]_D^{21} = +139°$, c=0.36, chloroform.

Example 193

1-{4-[(Methoxycarbonyl)amino]phenyl}-3-[2-methyl-3-(trifluoromethyl)benzyl]-2,4-dioxo-1,2,3,4-tetrahydropyrimidine-5-carboxylic acid

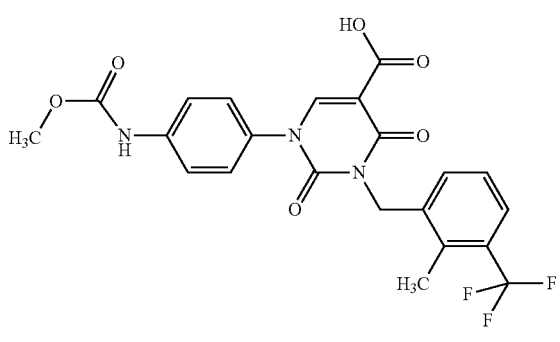 [SMILES: COC(=O)Nc1ccc(-n2cc(C(=O)O)c(=O)n(Cc3cccc(C(F)(F)F)c3C)c2=O)cc1]

Preparation and purification were carried out analogously to Example 155 from 49 mg (0.10 mmol) of ethyl 1-{4-[(methoxycarbonyl)amino]phenyl}-3-[2-methyl-3-(trifluoromethyl)benzyl]-2,4-dioxo-1,2,3,4-tetrahydropyrimidine-5-carboxylate from Example 166. Yield: 23 mg (46% of theory).

LC-MS (Method 3): $R_t$=1.07 min; m/z=478 (M+H)$^+$.

$^1$H-NMR (400 MHz, DMSO-$d_6$): δ=2.46 (s, partially hidden by DMSO signal), 3.69 (s, 3H), 5.10 (s, 2H), 7.31-7.41 (m, 2H), 7.42-7.47 (m, 2H), 7.54-7.62 (m, 3H), 8.43 (s, 1H), 9.91 (s, 1H), 12.71 (br. s., 1H).

Example 194

Ethyl 3-(5-chloro-1,2,3,4-tetrahydronaphthalen-1-yl)-2,4-dioxo-1-[4-(2-oxo-1,3-oxazolidin-3-yl)phenyl]-1,2,3,4-tetrahydropyrimidine-5-carboxylate (racemate)

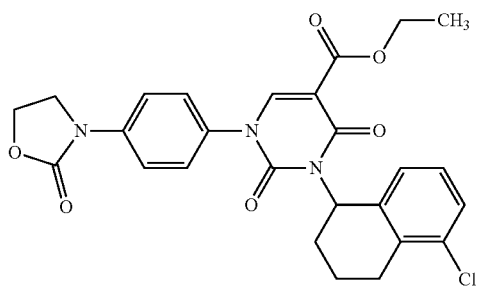 [SMILES: CCOC(=O)c1cn(-c2ccc(N3CCOC3=O)cc2)c(=O)n(C2CCCc3c(Cl)cccc32)c1=O]

Under argon, 150 mg (0.43 mmol) of the compound from Example 21A, 95.2 mg (0.52 mmol) of 5-chloro-1,2,3,4-tetrahydronaphthalen-1-ol (racemate) and 193.7 mg (0.74 mmol) of triphenylphosphine were dissolved in 6 ml of DMF and 3 ml of THF. 137 µl (0.70 mmol) of DIAD were added dropwise and the reaction mixture was stirred at RT for 2 h. After addition of 2 ml of 1N aqueous hydrochloric acid, the entire mixture was purified by preparative HPLC (Method 14). This gave 68 mg (29% of theory) of the title compound.

LC-MS (Method 3): $R_t$=1.12 min; m/z=510 (M+H)$^+$.

$^1$H-NMR (500 MHz, CD$_2$Cl$_2$): δ [ppm]=1.36 (t, 3H), 1.78-1.91 (m, 1H), 2.07-2.14 (m, 1H), 2.14-2.23 (m, 1H), 2.38-2.54 (m, 1H), 2.68-2.83 (m, 1H), 3.07 (d, 1H), 4.03-4.16 (m, 2H), 4.26-4.40 (m, 2H), 4.49-4.56 (m, 2H), 6.28 (br. s, 1H), 6.96 (d, 1H), 7.09 (t, 1H), 7.25 (d, 1H), 7.28-7.49 (m, 2H), 7.61-7.80 (m, 2H), 8.36 (s, 1H).

Example 195

3-(5-Chloro-1,2,3,4-tetrahydronaphthalen-1-yl)-2,4-dioxo-1-[4-(2-oxo-1,3-oxazolidin-3-yl)phenyl]-1,2,3,4-tetrahydropyrimidine-5-carboxylic acid (racemate)

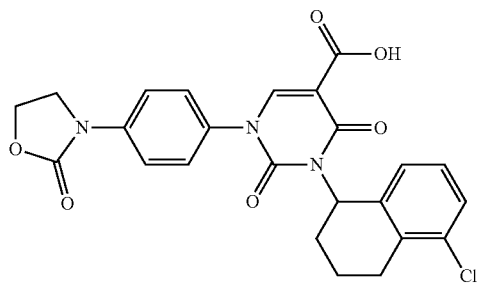 [SMILES: O=C(O)c1cn(-c2ccc(N3CCOC3=O)cc2)c(=O)n(C2CCCc3c(Cl)cccc32)c1=O]

62 mg (0.113 mmol) of the compound from Example 194 in 2 ml of glacial acetic acid/conc. hydrochloric acid 2:1 (v/v) were heated at reflux temperature for 30 min. After cooling to RT, the mixture was diluted with acetonitrile (about 2 ml) and purified by preparative HPLC (Method 14). This gave 41 mg (54% of theory) of the title compound.

LC-MS (Method 3): $R_t$=1.11 min; m/z=482 (M+H)$^+$.

$^1$H-NMR (500 MHz, CD$_2$Cl$_2$): δ [ppm]=1.75-1.89 (m, 1H), 2.06-2.24 (m, 2H), 2.42 (q, 1H), 2.63-2.80 (m, 1H), 3.05 (d, 1H), 4.06 (t, 2H), 4.49 (t, 2H), 6.26 (br. s., 1H), 6.90 (d, 1H), 7.08 (t, 1H), 7.25 (d, 1H), 7.35 (br. s., 2H), 7.70 (d, 2H), 8.56 (s, 1H), 12.44 (br. s, 1H).

Example 196

Ethyl 2,4-dioxo-1-[4-(2-oxo-1,3-oxazolidin-3-yl)phenyl]-3-[5-(trifluoromethyl)-1,2,3,4-tetrahydronaphthalen-1-yl]-1,2,3,4-tetrahydropyrimidine-5-carboxylate (racemate)

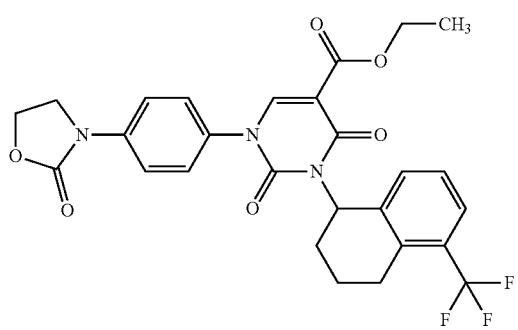 [SMILES: CCOC(=O)c1cn(-c2ccc(N3CCOC3=O)cc2)c(=O)n(C2CCCc3c2cccc3C(F)(F)F)c1=O]

Under argon, 150 mg (0.43 mmol) of the compound from Example 21A, 113 mg (0.52 mmol) of 5-(trifluoromethyl)-1,2,3,4-tetrahydronaphthalen-1-ol (racemate) and 193.7 mg (0.74 mmol) of triphenylphosphine were dissolved in 6 ml of DMF and 3 ml of THF. 137 µl (0.70 mmol) of DIAD were added dropwise and the reaction mixture was stirred at RT for 2 h. After addition of 2 ml of 1N aqueous hydrochloric acid, the entire mixture was separated by preparative HPLC (Method 14). This gave 68 mg (29% of theory) of the title compound.

LC-MS (Method 3): $R_t$=1.15 min; m/z=544 (M+H)$^+$.

$^1$H-NMR (400 MHz, CD$_2$Cl$_2$): δ [ppm]=1.23 (t, 3H), 1.65-1.80 (m, 1H), 1.97-2.11 (m, 2H), 2.24-2.40 (m, 1H), 2.75-2.91 (m, 1H), 2.93-3.05 (m, 1H), 3.97 (t, 2H), 4.21 (q, 2H), 4.40 (t, 2H), 6.20 (br. s., 1H), 7.12 (d, 2H), 7.26 (br. s., 2H), 7.40 (t, 1H), 7.59 (d, 2H), 8.23 (s, 1H).

Example 197

2,4-Dioxo-1-[4-(2-oxo-1,3-oxazolidin-3-yl)phenyl]-3-[5-(trifluoromethyl)-1,2,3,4-tetrahydronaphthalen-1-yl]-1,2,3,4-tetrahydropyrimidine-5-carboxylic acid (racemate)

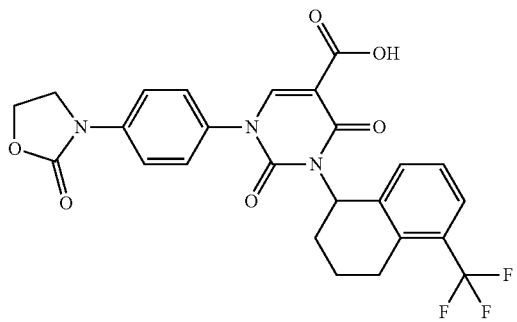 [SMILES: O=C(O)c1cn(-c2ccc(N3CCOC3=O)cc2)c(=O)n(C2CCCc3c2cccc3C(F)(F)F)c1=O]

50 mg (92 µmol) of the compound from Example 196 in 2 ml of glacial acetic acid/conc. hydrochloric acid 2:1 (v/v) were heated at reflux temperature for 30 min. After cooling to RT, the mixture was diluted with acetonitrile (about 2 ml) and separated by preparative HPLC (Method 14). This gave 25 mg (53% of theory) of the title compound.

LC-MS (Method 3): $R_t$=1.13 min; m/z=516 (M+H)$^+$.

$^1$H-NMR (400 MHz, CD$_2$Cl$_2$): δ [ppm]=1.81-1.93 (m, 1H), 2.17-2.27 (m, 2H), 2.40-2.51 (m, 1H), 2.91-3.02 (m, 1H), 3.14 (br. d, 1H), 4.10 (t, 2H), 4.49-4.57 (m, 2H), 6.36 (br. s., 1H), 7.23 (d, 1H), 7.28 (t, 1H), 7.39 (br. s, 2H), 7.56 (d, 1H), 7.74 (d, 2H), 8.61 (s, 1H), 12.42 (br. s, 1H).

Example 198

3-(2,3-Dichlorobenzyl)-2,4-dioxo-1-[4-(4-oxoimidazolidin-1-yl)phenyl]-1,2,3,4-tetrahydropyrimidine-5-carboxylic acid

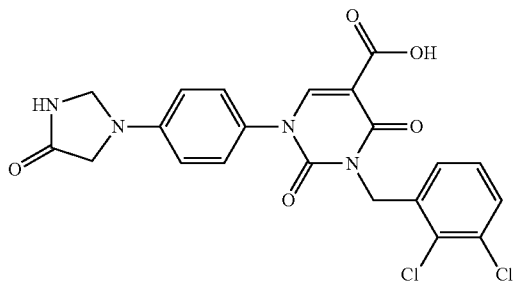 [SMILES: O=C1CN(c2ccc(-n3cc(C(=O)O)c(=O)n(Cc4cccc(Cl)c4Cl)c3=O)cc2)CN1]

40 mg (79 µmol) of the compound from Example 6 in 1 ml of glacial acetic acid/conc. hydrochloric acid/water 4:1:1 (v/v/v) were heated at 70° C. for 3 h. After cooling to RT, the mixture was diluted with 50 ml of water. The solid formed was filtered off with suction, washed with a little water and cyclohexane and dried under high vacuum. This gave 24 mg of the title compound, which was contaminated with a by-product. This solid was purified by thin-layer chromatography (silica gel, methanol/dichloromethane 1:1). This gave 4.5 mg (12% of theory) of the title compound.

LC-MS (Method 1): $R_t$=1.14 min; m/z=475 (M+H)$^+$.

$^1$H-NMR (400 MHz, DMSO-d$_6$): δ [ppm]=3.78 (s, 2H), 4.70 (s, 2H), 5.07 (s, 2H), 6.64 (d, 2H), 7.02-7.09 (m, 1H), 7.27-7.37 (m, 3H), 7.55 (d, 1H), 7.86-7.96 (m, 1H), 8.67 (s, 1H).

Example 199

3-[2-Methyl-3-(trifluoromethyl)benzyl]-2,4-dioxo-1-[4-(4-oxoimidazolidin-1-yl)phenyl]-1,2,3,4-tetrahydropyrimidine-5-carboxylic acid

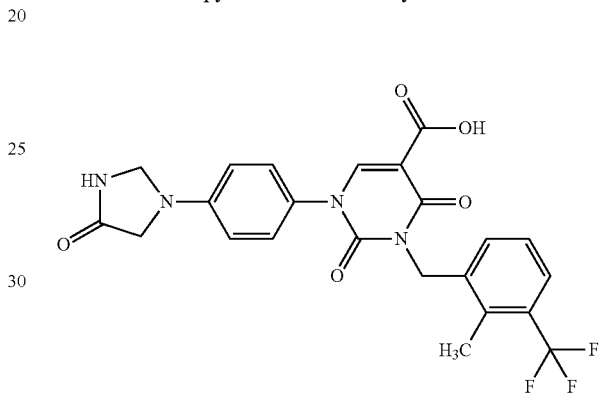

65 mg (126 µmol) of the compound from Example 8 in 1.65 ml of glacial acetic acid/conc. hydrochloric acid/water 4:1:1 (v/v/v) were heated at 70° C. for 7 h. After cooling to RT, the mixture was diluted with 50 ml of water. The solid formed was purified by preparative HPLC (Method 5a). This gave 15 mg (25% of theory) of the title compound.

LC-MS (Method 1): $R_t$=1.16 min; m/z=489 (M+H)$^+$.

$^1$H-NMR (400 MHz, DMSO-d$_6$): δ [ppm]=2.46 (s, 3H), 3.77 (s, 2H), 4.70 (s, 2H), 5.03 (s, 2H), 6.64 (d, 2H), 7.20-7.25 (m, 1H), 7.27-7.38 (m, 3H), 7.57 (d, 1H), 7.78 (d, 1H), 8.66 (s, 1H).

B. ASSESSMENT OF PHARMACOLOGICAL EFFICACY

B. Assessment of Pharmacological Efficacy

The pharmacological activity of the compounds according to the invention can be shown in the assays described below:

Abbreviations:

| | |
|---|---|
| Abz-HPFHL-Lys(Dnp)-NH$_2$ | 1-[N-(3-aminobenzoyl)histidylprolylphenyl-alanylhistidylleucyl-N$^6$-(2,4-dinitrophenyl)lysine |
| AMC | 7-amido-4-methylcoumarin |
| BNP | brain natriuretic peptide |
| BSA | bovine serum albumin |
| CHAPS | 3-[(3-cholamidopropyl)dimethylammonio]-1-propanesulfonate |
| HEPES | N-(2-hydroxyethyl)piperazine-N'-2-ethanesulfonic acid |
| IC | inhibition concentration |

-continued

| | |
|---|---|
| MeOSuc | methoxysuccinyl |
| NADP | nicotinamide adenine dinucleotide phosphate |
| PBS | phosphate-buffered saline solution |
| PEG | polyethylene glycol |
| v/v | volume to volume ratio (of a solution) |
| w/v | weight to volume ratio (of a solution) |

B-1. Enzymatic Chymase Assay

The enzyme source used is recombinant human chymase (expressed in HEK293 cells) or chymase purified from hamsters' tongues. The substrate used for chymase is Abz-HPFHL-Lys(Dnp)-$NH_2$. For the assay, 1 µl of a 50-fold concentrated solution of test substance in DMSO, 24 al of enzyme solution (dilution 1:80 000 human or 1:4000 hamster) and 25 al of substrate solution (final concentration 10 µM) in assay buffer (Tris 50 mM (pH 7.5), sodium chloride 150 mM, BSA 0.10%, Chaps 0.10%, glutathione 1 mM, EDTA 1 mM) are combined in a white 384-hole microtiter plate (Greiner Bio-One, Frickenhausen, Germany). The reaction is incubated at 32 degrees for 60 min and the fluorescence emission at 465 nm after excitation at 340 nm is measured in a fluorescence reader, for example Tecan Ultra (Tecan, Männedorf, Switzerland).

One test compound is tested on the same microtiter plate in 10 different concentrations from 30 µM to 1 nM in a double determination. The data are normalized (enzyme reaction without inhibitor=0% inhibition, all assay components without enzyme=100% inhibition) and $IC_{50}$ values are calculated using in-house software. Compounds in the context of the invention which were tested in this assay inhibited chymase activity with an $IC_{50}$ of less than 10 µM.

$IC_{50}$ values representative of the compounds of the invention are shown in Table 1 below:

| Example No.: | hamster chymase $IC_{50}$ [nM] |
|---|---|
| 3 | 186 |
| 4 | 348 |
| 5 | 522 |
| 6 | 279 |
| 7 | 171 |
| 8 | 79 |
| 11 | 263 |
| 18 | 171 |
| 19 | 591 |
| 20 | 435 |
| 22 | 189 |
| 23 | 205 |
| 24 | 625 |
| 25 | 290 |
| 26 | 593 |
| 31 | 207 |
| 32 | 271 |
| 42 | 109 |
| 44 | 241 |
| 46 | 227 |
| 48 | 396 |
| 49 | 78 |
| 50 | 423 |
| 51 | 45 |
| 52 | 138 |
| 53 | 98 |
| 54 | 419 |
| 55 | 222 |
| 56 | 110 |
| 57 | 67 |
| 58 | 24 |
| 59 | 217 |
| 60 | 68 |
| 61 | 433 |
| 62 | 145 |
| 63 | 74 |
| 64 | 59 |
| 65 | 21 |
| 66 | 88 |
| 67 | 252 |
| 68 | 56 |
| 69 | 289 |
| 70 | 225 |
| 71 | 427 |
| 72 | 632 |
| 73 | 61 |
| 74 | 210 |
| 75 | 106 |
| 76 | 642 |
| 77 | 97 |
| 78 | 92 |
| 79 | 362 |
| 80 | 297 |
| 81 | 28 |
| 82 | 54 |
| 83 | 133 |
| 84 | 143 |
| 85 | 99 |
| 86 | 127 |
| 87 | 79 |
| 88 | 368 |
| 89 | 176 |
| 90 | 231 |
| 91 | 392 |
| 92 | 21 |
| 93 | 700 |
| 94 | 580 |
| 95 | 2200 |
| 96 | 2000 |
| 97 | 3000 |
| 98 | 1000 |
| 99 | 230 |
| 100 | 1700 |
| 101 | 560 |
| 102 | 510 |
| 103 | 151 |
| 104 | 213 |
| 105 | 297 |
| 106 | 74 |
| 107 | 120 |
| 108 | 815 |
| 109 | 680 |
| 110 | 38 |
| 111 | 540 |
| 112 | 160 |
| 114 | 76 |
| 117 | 72 |
| 120 | 140 |
| 122 | 81 |
| 123 | 230 |
| 127 | 49 |
| 128 | 54 |
| 131 | 340 |
| 132 | 560 |
| 133 | 1900 |
| 134 | 630 |
| 146 | 80 |
| 147 | 220 |
| 148 | 18 |
| 149 | 170 |
| 150 | 60 |
| 151 | 17 |
| 152 | 16 |
| 153 | 38 |
| 154 | 31 |
| 155 | 55 |
| 156 | 58 |
| 157 | 31 |
| 158 | 37 |
| 159 | 13 |

-continued

| Example No.: | hamster chymase IC$_{50}$ [nM] |
|---|---|
| 160 | 12 |
| 161 | 60 |
| 162 | 58 |
| 163 | 19 |
| 164 | 110 |
| 165 | 500 |
| 167 | 16 |
| 168 | 11 |
| 169 | 80 |
| 170 | 71 |
| 171 | 370 |
| 172 | 170 |
| 173 | 490 |
| 174 | 240 |
| 175 | 82 |
| 176 | 128 |
| 177 | 410 |
| 178 | 63 |
| 179 | 180 |
| 180 | 290 |
| 181 | 18 |
| 183 | 24 |
| 184 | 64 |
| 185 | 56 |
| 186 | 260 |
| 187 | 17 |
| 188 | 66 |
| 189 | 62 |
| 190 | 13 |
| 191 | 120 |
| 192 | 54 |
| 193 | 210 |
| 194 | 90 |
| 195 | 43 |
| 196 | 22 |
| 197 | 10 |
| 198 | 92 |
| 199 | 31 |

B-2. Measurement of Contraction on Isolated Aorta Rings of Hamsters

Male Syrian hamsters (120-150 g) were euthanized with carbon dioxide. The aorta was prepared and placed into ice-cold Krebs-Henseleit buffer. (Composition in mmol/l: sodium chloride 112, potassium chloride 5.9, calcium chloride 2.0, magnesium chloride 1.2, sodium dihydrogenphosphate 1.2, sodium bicarbonate 25, glucose 11.5). The aorta was cut into rings of length 2 mm, transferred to an organ bath filled with 5 ml of Krebs-Henseleit buffer and connected to a myograph (DMT, Denmark). The buffer was warmed to 37° C. and sparged with 95% oxygen, 5% carbon dioxide. In order to measure the isometric muscle contraction, the aorta rings were mounted between two hooks. One of the hooks was connected to a pressure transducer. The second hook was movable and allowed precise setting of the initial load by a protocol described by Mulvany and Halpern (Circulation Research 1977; 41:19-26).

Before each experiment, the responsiveness of the preparation was tested by adding potassium-containing Krebs-Henseleit solution (50 mmol/l KCl). A synthetic peptide, angiotensin 1-18, was used to induce contraction of the aorta rings. The angiotensin 1-18 is converted to angiotensin II independently of ACE. Subsequently, the aorta rings were incubated with the test substance for 20 min and the contraction measurement was repeated. Chymase inhibition is shown as a reduction in the contraction induced by angiotensin 1-18.

B-3. Isoprenaline-Induced Cardiac Fibrosis Model in Hamsters

For the experiments, male Syrian hamsters having a body weight of 130-160 g were used. Cardiac hypertrophy and cardiac fibrosis were induced by a daily subcutaneous injection of 20 mg/kg isoprenaline over 7 days. The test substance was administered orally to the animals 2 hours before the injection of the isoprenaline. Control groups were treated subcutaneously and orally with solvents in a corresponding manner. At the end of the experiment, the hearts were removed, weighed and fixed. The fibrotic tissue on the histological sections from the hearts was marked with the aid of Sirius Red staining Subsequently, the fibrotic area was determined by planimetry.

C. WORKING EXAMPLES FOR PHARMACEUTICAL COMPOSITIONS

The compounds of the invention can be converted to pharmaceutical formulations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h before swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:
1. A compound of the formula (I)

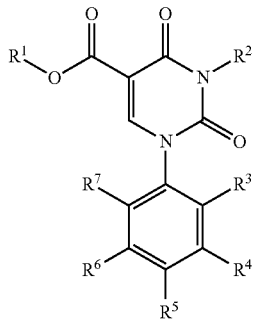

in which
R¹ represents hydrogen or $(C_1-C_4)$-alkyl,
R² represents a group of the formula

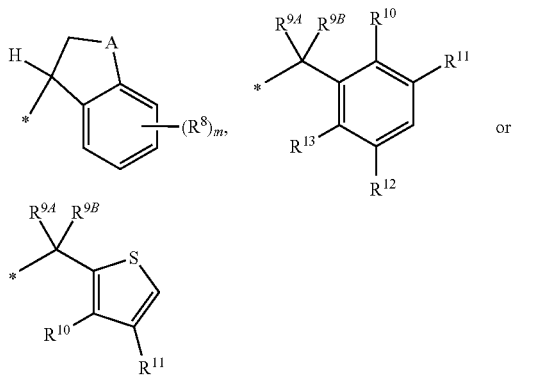

where
* represents the point of attachment to the uracil nitrogen atom,
A represents —$CH_2$—, —$CH_2$—$CH_2$—, —O—$CH_2$-## or oxygen, in which ## represents the point of attachment to the phenyl ring,
m represents a number 0, 1 or 2,
R⁸ represents hydrogen, halogen, difluoromethyl, trifluoromethyl, $(C_1-C_4)$-alkyl, difluoromethoxy, trifluoromethoxy or $(C_1-C_4)$-alkoxy,
$R^{9A}$ represents hydrogen or deuterium,
$R^{9B}$ represents hydrogen, deuterium or $(C_1-C_4)$-alkyl,
R¹⁰ represents hydrogen, halogen, $(C_1-C_4)$-alkyl, difluoromethyl, trifluoromethyl, nitro or $(C_1-C_4)$-alkylthio,
R¹¹ represents hydrogen, halogen, $(C_1-C_4)$-alkyl, difluoromethyl, trifluoromethyl, nitro or $(C_1-C_4)$-alkylthio,
R¹² represents hydrogen or halogen,
R¹³ represents hydrogen or halogen,
R³ represents hydrogen,
R⁴ represents hydrogen, halogen, $(C_1-C_4)$-alkyl or $(C_1-C_4)$-alkoxy,
R⁵ represents $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl or —$N(R^{14}R^{15})$,
where $(C_1-C_4)$-alkyl may be substituted by 1 or 2 substituents independently of one another selected from the group consisting of halogen, hydroxy, 4- to 7-membered heterocyclyl, $(C_1-C_4)$-alkoxy, hydroxycarbonyl, $(C_1-C_4)$-alkoxycarbonyl, aminocarbonyl, mono-$(C_1-C_4)$-alkylaminocarbonyl and di-$(C_1-C_4)$-alkylaminocarbonyl,
in which 4- to 7-membered heterocyclyl may be substituted by 1 or 2 halogen or oxo substituents,
where $(C_1-C_4)$-alkoxy may be substituted by a substituent independently of one another selected from the group consisting of hydroxy, $(C_1-C_4)$-alkoxycarbonyl, amino, mono-$(C_1-C_4)$-alkylamino, di-$(C_1-C_4)$-alkylamino, aminocarbonyl, mono-$(C_1-C_4)$-alkylaminocarbonyl and di-$(C_1-C_4)$-alkylaminocarbonyl,
where
R¹⁴ represents $(C_1-C_4)$-alkyl, $(C_1-C_4)$-alkoxycarbonyl or $(C_1-C_4)$-alkylaminocarbonyl,
in which $(C_1-C_4)$-alkyl may be substituted by hydroxy or $(C_1-C_4)$-alkoxy,
and
in which $(C_1-C_4)$-alkylaminocarbonyl may be substituted by hydroxy or $(C_1-C_4)$-alkoxy,
R¹⁵ represents hydrogen or $(C_1-C_4)$-alkyl,
or
R⁵ represents 4- to 7-membered heterocyclyl or 5- to 6-membered heteroaryl,
where 4- to 7-membered heterocyclyl may be substituted by 1 to 3 substituents independently of one another selected from the group consisting of halogen, trifluoromethyl, $(C_1-C_4)$-alkyl, hydroxy, oxo, amino and $(C_1-C_4)$-alkoxycarbonyl,
in which $(C_1-C_4)$-alkyl may be substituted by 1 or 2 substituents independently of one another selected from the group consisting of halogen, hydroxy and —$N(R^{16}R^{17})$,
in which R⁶ represents hydrogen, $(C_1-C_4)$-alkyl or $(C_1-C_4)$-alkylcarbonyl,
in which R¹⁷ represents hydrogen or $(C_1-C_4)$-alkyl,
where 5- to 6-membered heteroaryl may be substituted by 1 or 2 substituents independently of one another selected from the group consisting of halogen, trifluoromethyl, $(C_1-C_4)$-alkyl, hydroxy, amino and $(C_1-C_4)$-alkoxycarbonyl,
in which $(C_1-C_4)$-alkyl may be substituted by 1 or 2 substituents independently of one another selected from the group consisting of halogen, hydroxy and —$N(R^{16}R^{17})$,
in which R¹⁶ represents hydrogen, $(C_1-C_4)$-alkyl or $(C_1-C_4)$-alkylcarbonyl,
in which R¹⁷ represents hydrogen or $(C_1-C_4)$-alkyl,
R⁶ represents hydrogen, halogen, cyano, $(C_1-C_4)$-alkyl or $(C_1-C_4)$-alkoxy,
R⁷ represents hydrogen, halogen, $(C_1-C_4)$-alkyl or $(C_1-C_4)$-alkoxy, a salt or a solvate thereof, or a solvate of the salt.

2. The compound of claim 1 in which
R¹ represents hydrogen, methyl or ethyl,
R² represents a group of the formula

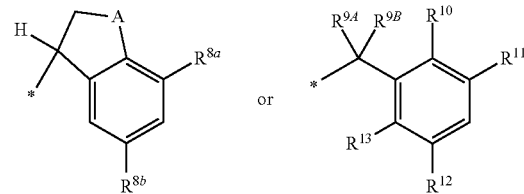

where
* represents the point of attachment to the uracil nitrogen atom,
A represents —$CH_2$—, —$CH_2$—$CH_2$— or oxygen,
$R^{8a}$ represents hydrogen, fluorine, chlorine, trifluoromethyl or methyl,
$R^{8b}$ represents hydrogen, fluorine, chlorine, trifluoromethyl or methyl,
$R^{9A}$ represents hydrogen,
$R^{9B}$ represents hydrogen, methyl or ethyl,
$R^{10}$ represents hydrogen, fluorine, chlorine, difluoromethyl, trifluoromethyl or methyl,
$R^{11}$ represents hydrogen, fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine, chlorine or methoxy,
$R^5$ represents ($C_1$-$C_4$)-alkoxy, 5- or 6-membered heterocyclyl or 5-membered heteroaryl,
where 5- to 6-membered heterocyclyl may be substituted by 1 or 2 substituents independently of one another selected from the group consisting of trifluoromethyl, methyl, ethyl, hydroxy, oxo and ($C_1$-$C_4$)-alkoxycarbonyl,
in which methyl and ethyl may be substituted by —N($R^{16}R^{17}$),
in which $R^{16}$ represents ($C_1$-$C_4$)-alkylcarbonyl,
in which $R^{17}$ represents hydrogen,
where 5-membered heteroaryl may be substituted by fluorine, chlorine, trifluoromethyl, methyl, hydroxy, amino or ($C_1$-$C_4$)-alkoxycarbonyl,
in which methyl may be substituted by hydroxy,
$R^6$ represents hydrogen, fluorine, chlorine or methyl,
$R^7$ represents hydrogen, fluorine, chlorine or methyl, a salt or a solvate thereof, or a solvate of the salt.

3. The compound of claim 1 in which
$R^1$ represents hydrogen, methyl or ethyl,
$R^2$ represents a group of the formula

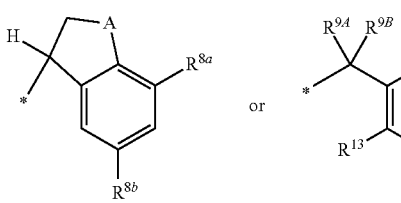 or 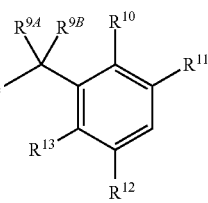

where
* represents the point of attachment to the uracil nitrogen atom,
A represents —$CH_2$— or —$CH_2$—$CH_2$—,
$R^{8a}$ represents hydrogen, chlorine, trifluoromethyl or methyl,
$R^{8b}$ represents hydrogen,
$R^{9A}$ represents hydrogen,
$R^{9B}$ represents hydrogen, methyl or ethyl,
$R^{10}$ represents hydrogen, chlorine, trifluoromethyl or methyl,
$R^{11}$ represents fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine, chlorine or methoxy,
$R^5$ represents 5- or 6-membered heterocyclyl or 5-membered heteroaryl,
where 5- to 6-membered heterocyclyl may be substituted by 1 or 2 methyl, ethyl or oxo substituents,
where 5-membered heteroaryl may be substituted by methyl or amino, in which methyl may be substituted by hydroxy,
$R^6$ represents hydrogen, fluorine, chlorine or methyl,
$R^7$ represents hydrogen, fluorine or methyl, a salt or a solvate thereof, or a solvate of the salt.

4. The compound of claim 1 in which
$R^1$ represents hydrogen, methyl or ethyl,
$R^2$ represents a group of the formula

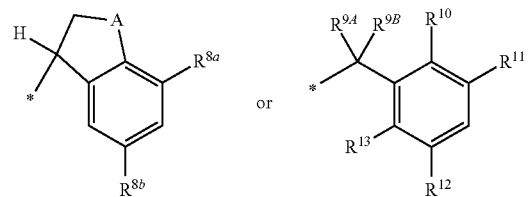

where
* represents the point of attachment to the uracil nitrogen atom,
A represents —$CH_2$— or —$CH_2$—$CH_2$—,
$R^{8a}$ represents chlorine or trifluoromethyl,
$R^{8b}$ represents hydrogen,
$R^{9A}$ represents hydrogen,
$R^{9B}$ represents hydrogen,
$R^{10}$ represents chlorine, trifluoromethyl or methyl,
$R^{11}$ represents fluorine, chlorine, difluoromethyl, trifluoromethyl or methyl,
$R^{12}$ represents hydrogen,
$R^{13}$ represents hydrogen,
$R^3$ represents hydrogen,
$R^4$ represents hydrogen, fluorine or chlorine,
$R^5$ represents a group of the formula

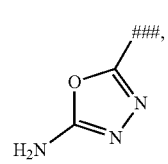 (a-1)

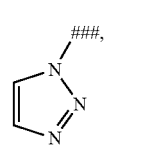 (b-1)

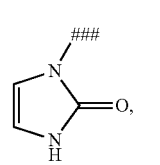 (c-1)

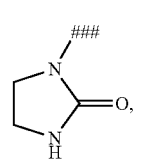 (d-1)

-continued

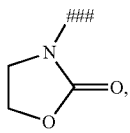 (e-1)

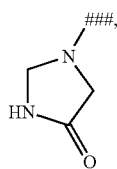 (f-1)

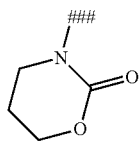 (g-1)

or

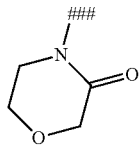 (h-1)

in which
represents the point of attachment to the phenyl ring,
$R^6$ represents hydrogen, fluorine, chlorine or methyl,
$R^7$ represents hydrogen, fluorine or methyl, a salt or a solvate thereof, or a solvate of the salt.

5. The compound of claim 1 in which
$R^1$ represents hydrogen, methyl or ethyl,
$R^2$ represents a group of the formula

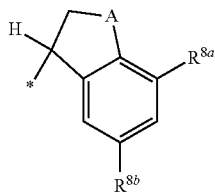

where
* represents the point of attachment to the uracil nitrogen atom,
A represents —CH$_2$— or —CH$_2$—CH$_2$—,
$R^{8a}$ represents chlorine or trifluoromethyl,
$R^{8b}$ represents hydrogen,
$R^3$ represents hydrogen,
$R^4$ represents hydrogen,
$R^5$ represents a group of the formula

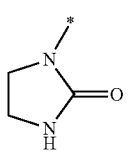 (d-1)

or

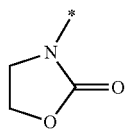 (e-1)

$R^6$ represents hydrogen,
$R^7$ represents hydrogen, a salt or a solvate thereof, or a solvate of the salt.

6. A method of making compounds of the formula (I) according to claim 1, in which

[A] a compound of the formula (II)

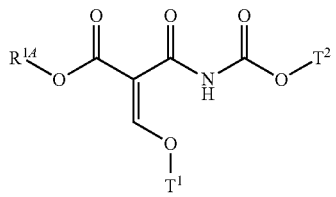 (II)

in which
$R^{1a}$ represents (C$_1$-C$_4$)-alkyl,
$T^1$ represents (C$_1$-C$_4$)-alkyl,
$T^2$ represents (C$_1$-C$_4$)-alkyl,
is reacted in an inert solvent, optionally in the presence of a suitable base, with a compound of the formula (III)

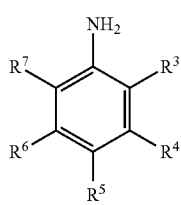 (III)

in which $R^3$, $R^4$, $R^5$, $R^6$ and $R^7$ are as defined in claim 1,
to give a compound of the formula (IV)

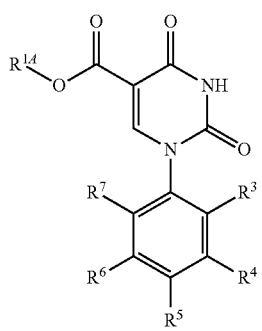 (IV)

in which $R^{1A}$, $R^3$, $R^4$, $R^5$, $R^6$ and $R^7$ each have the meanings given above, this is then reacted in an inert solvent, in the presence of a suitable base, with a compound of the formula (V)

$X^1$—$R^2$ (V)

in which $R^2$ is as defined in claim 1 and
$X^1$ represents hydroxy or a suitable leaving group, selected from chlorine, bromine or iodine,
to give a compound of the formula (I-1)

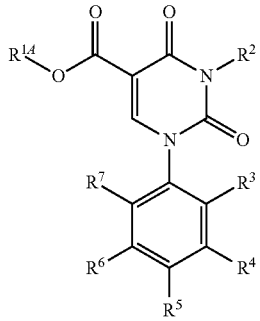

(I-1)

in which $R^{14}$, $R^2$, $R^3$, $R^4$, $R^5$, $R^6$ and $R^7$ each have the meanings given above,
or
[B] a compound of the formula (VI)

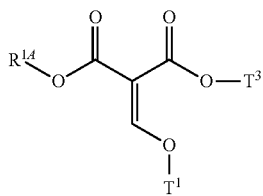

(VI)

in which $R^{14}$ and $T^1$ each have the meanings mentioned above and
$T^3$ represents $(C_1$-$C_4)$-alkyl,
is converted in an inert solvent or else without solvent with a compound of the formula (III) to a compound of the formula (VII)

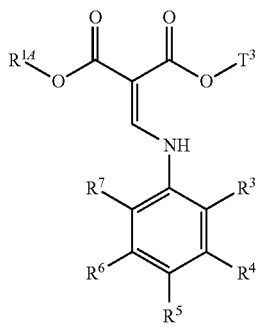

(VII)

in which $R^{14}$, $R^3$, $R^4$, $R^5$, $R^6$, $R^7$ and $T^3$ each have the meanings given above, this is subsequently reacted in an inert solvent with chlorosulfonyl isocyanate to give a compound of the formula (IV) and this is subsequently converted analogously to process [A] to a compound of the formula (I-1),
or
[C] a compound of the formula (VIII)

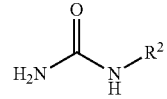

(VIII)

in which $R^2$ is as defined above
is reacted in an inert solvent with a compound of the formula (IX)

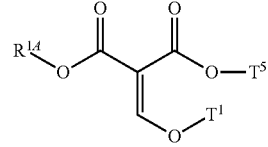

(IX)

in which $R^{14}$ and $T^1$ each have the meanings given above and
$T^5$ represents $(C_1$-$C_4)$-alkyl,
and cyclized in the presence of a suitable base to give a compound of the formula (X)

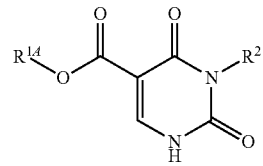

(X)

in which $R^{14}$ and $R^2$ each have the meanings mentioned above, and this is then reacted in an inert solvent in the presence of a suitable catalyst and a suitable base with a compound of the formula (XI)

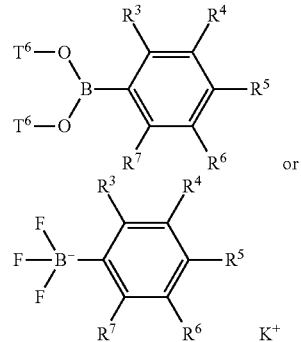

(XI)

in which $R^3$, $R^4$, $R^5$, $R^6$ and $R^7$ have the meaning given above and
$T^6$ represents hydrogen, $(C_1$-$C_4)$-alkyl or the two radicals $T^6$ together form a —$C(CH_3)_2$—$C(CH_3)_2$— bridge,
to give a compound of the formula (I-1),
or
[D] a compound of the formula (I-1) is hydrolyzed in an inert solvent in the presence of a suitable acid or base to give a compound of the formula (I-2)

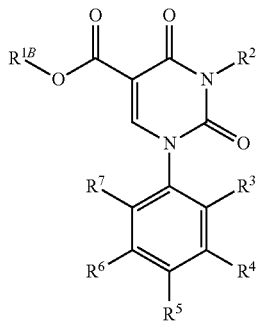

(I-2)

in which R², R³, R⁴, R⁵, R⁶ and R⁷ each have the meanings mentioned above
and
$R^{1B}$ represents hydrogen,
any protecting groups are detached and/or the compounds of the formulae (I-1) and (I-2) are, where appropriate, converted with the appropriate (i) solvents and/or (ii) bases or acids to the solvates, salts and/or solvates of the salts thereof.

7. A medicament comprising the compound of claim 1 in combination with one or more inert, nontoxic, pharmaceutically suitable excipients.

8. A medicament comprising the compound of claim 1 in combination with one or more further active ingredients selected from the group consisting of calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, rho-kinase inhibitors, diuretics, kinase inhibitors, matrix metalloprotease inhibitors, stimulators and activators of soluble guanylate cyclase and phosphodiesterase inhibitors.

9. A method for treatment of heart failure, cardiac fibrosis or dermatological fibroses in a human or an animal in need thereof comprising administering to the human or the animal an effective amount of the compound of claim 1, a salt, or a solvate thereof, or a solvate of the salt.

10. A method for treatment of heart failure, cardiac fibrosis or dermatological fibroses in a human or an animal in need thereof comprising administering to the human or the animal an effective amount of the medicament of claim 7.

* * * * *